(12) United States Patent
Adam et al.

(10) Patent No.: US 8,138,175 B2
(45) Date of Patent: Mar. 20, 2012

(54) HETEROCYCLYL COMPOUNDS

(75) Inventors: Jean-Michel Adam, Rosenau (FR); Johannes Aebi, Binningen (CH); Alfred Binggeli, Binningen (CH); Luke Green, Basel (CH); Guido Hartmann, Loerrach (DE); Hans P. Maerki, Basel (CH); Patrizio Mattei, Riehen (CH); Fabienne Ricklin, Hombourg (FR); Olivier Roche, Folgensbourg (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 293 days.

(21) Appl. No.: 12/507,858

(22) Filed: Jul. 23, 2009

(65) Prior Publication Data

US 2010/0022518 A1 Jan. 28, 2010

(30) Foreign Application Priority Data

Jul. 28, 2008 (EP) .................... 08161278

(51) Int. Cl.
*C07D 241/08* (2006.01)
*C07D 243/08* (2006.01)
*C07D 401/06* (2006.01)
*C07D 401/14* (2006.01)
*C07D 413/06* (2006.01)
*A61K 31/551* (2006.01)
*A61K 31/4965* (2006.01)

(52) U.S. Cl. ........................ 514/218; 540/492
(58) Field of Classification Search .................. 540/492; 514/218
See application file for complete search history.

(56) References Cited

U.S. PATENT DOCUMENTS

| 6,645,958 B2 * | 11/2003 | Weikert et al. | 514/211.03 |
| 6,730,681 B2 * | 5/2004 | Chambers et al. | 514/262.1 |
| 7,144,887 B2 * | 12/2006 | Bryant et al. | 514/257 |
| 2003/0144277 A1 | 7/2003 | DeLucca | |
| 2007/0238723 A1 | 10/2007 | Goble et al. | |
| 2007/0249589 A1 | 10/2007 | Aebi et al. | |

FOREIGN PATENT DOCUMENTS

| WO | WO 01/90081 | 11/2001 |
| WO | WO 2007/122103 | 11/2007 |
| WO | WO 2008/060621 | 5/2008 |

OTHER PUBLICATIONS

Uchida Hiroaki et al: *Bulletin of the Chemical Society of Japan*, 46(11), 3612-13, 1973, XP002549406.
Radosevich et al., J. Am. Chem. Soc., 127, pp. 1090-1091 (2005).
Vice et al., J. Org. Chem., 66, pp. 2487-2492 (2001).
Ripin et al., Tetrahedron Lett., 41, pp. 5817-5819 (2000).
Mori, K., Tetrahedron, 39, pp. 3107-3109 (1983).
Avenoza et al., Synthesis, 10, pp. 1146-1150 (1997).
McManus et al., J. Med. Chem., 8, pp. 766-776 (1965).
Okawara et al., Chem. Pharm. Bull., 30, pp. 1225-1233 (1982).
Phillips et al., J. Heterocyclic Chem., 795-799 (1973).
Hanessian et al., J. Org. Chem., 58, pp. 7768-7781 (1993).
Sugiyama et al., J. Am. Chem. Soc., 129, pp. 14811-14817 (2007).
Schuda et al., Synthesis, pp. 309-312 (1986).

* cited by examiner

*Primary Examiner* — Bruck Kifle
(74) *Attorney, Agent, or Firm* — George W. Johnston; Patricia S. Rocha-Tramaloni; Gene J. Yao

(57) ABSTRACT

The invention is concerned with novel heterocyclyl compounds of formula (I):

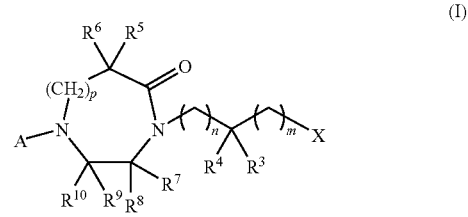

wherein A, X, $R^3$, $R^4$, $R^5$, $R^6$, $R^7$, $R^8$, $R^9$, $R^{10}$, m, n and p are as defined in the description and in the claims, as well as physiologically acceptable salts thereof. These compounds are antagonists of CCR2 receptor, CCR5 receptor and/or CCR3 receptor and may be used as medicaments.

23 Claims, No Drawings

US 8,138,175 B2

HETEROCYCLYL COMPOUNDS

PRIORITY TO RELATED APPLICATION(S)

This application claims the benefit of European Patent Application No. 08161278.0, filed Jul. 28, 2008, which is hereby incorporated by reference in its entirety.

BACKGROUND OF THE INVENTION

Chemokines are a family of small, secreted proinflammatory cytokines functioning as chemoattractants for leukocytes. They promote trafficking of leukocytes from vascular beds into surrounding tissues in response to inflammatory signals. Chemotaxis starts upon chemokine binding to receptors (GPCRs) by initiating signaling pathways involving increased Ca-flux, inhibition of cAMP production, rearrangements of the cytoskeleton, activation of integrins and of cell motility processes and an increase in the expression of adhesion proteins.

Proinflammatory chemokines are considered to be involved in the development of atherosclerosis and other important diseases with inflammatory components like rheumatoid arthritis, asthma, multiple sclerosis, transplant rejection and ischemia reperfusion injury with specific prominent effects in nephropathy and peripheral vascular diseases. Monocyte Chemotactic protein 1 is considered to be the major stimulated chemokine mediating inflammatory processes in these diseases through the CCR2 receptor on monocytes and on some T lymphocytes. In addition MCP-1/CCR2 are in discussion to be related to the progression of the metabolic syndrome to more severe stages of obese and diabetic diseases. CCR2 has also been linked to HIV infection, and consequently the course of autoimmune diseases, through its heterodimerization with CCR5 which has a role as coreceptor for viral entry into host cells.

Thus, CCR2 can be a target of a new medicine for treatment of peripheral vascular diseases, and more specifically for treatment of patients with critical limb ischemia. Furthermore, study results and experiences from the development of a new CCR2 medicine for this indication may facilitate a follow-up development for treatment of atherosclerosis. There is a large body of information from animal models of MCP-1 and CCR2 ko mice in wt or apoE−/− or LDL-R−/− backgrounds showing that the MCP-1/CCR2 pathway is essential for monocyte/macrophage recruitment, and also for intimal hyperplasia and the formation and stability of atherosclerotic lesions. In addition, numerous reports describe involvement of the MCP-1/CCR2 pathway in man post injury and in various inflammatory processes, including such in vascular beds.

SUMMARY OF THE INVENTION

The invention is concerned with novel heterocyclyl compounds of formula (I):

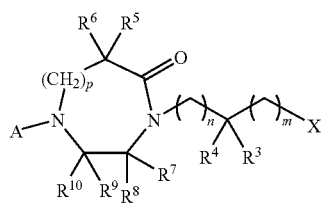

(I)

and pharmaceutically acceptable salts, prodrugs, or esters thereof, wherein A, X, $R^3$-$R^{10}$, n, m, and p are as defined in the detailed description and claims.

The compounds of formula (I) are CCR2 receptor (Chemokine Receptor 2/Monocyte chemotactic protein 1 receptor) antagonists and also CCR5 receptor (Chemokine Receptor 5) and/or CCR3 receptor (Chemokine Receptor 3) antagonists which may be useful in the treatment of diseases or disorders associated with such receptors. Further, the invention is concerned with a process and an intermediate for the manufacture of such compounds and pharmaceutical compositions which contain such compounds.

DETAILED DESCRIPTION OF THE INVENTION

Unless otherwise indicated, the following definitions are set forth to illustrate and define the meaning and scope of the various terms used to describe the invention herein.

The term "hydrogen" or "hydro" refers to the moiety of a hydrogen atom (—H) and not $H_2$.

The term "halogen" or "halo" means fluoro, chloro, bromo or iodo. Preferred "halogen" groups are fluoro or chloro.

The term "$C_{1-6}$ alkyl," alone or in combination with other groups, means a branched or straight-chain monovalent alkyl radical, having one to six carbon atoms. This term is further exemplified by such radicals as methyl, ethyl, n-propyl, iso-propyl, n-butyl, s-butyl, t-butyl. $C_{1-4}$ alkyl or $C_{1-3}$ alkyl is more preferred. The term "$C_{2-6}$ alkyl" means the same as a "$C_{1-6}$ alkyl", except that the $C_{2-6}$ alkyl has two to six carbon atoms.

The term "hydroxy $C_{1-6}$ alkyl" means a $C_{1-6}$ alkyl substituted by one or more hydroxy group(s).

The term "halo $C_{1-6}$ alkyl" means a $C_{1-6}$ alkyl substituted by one or more of the same or different halogen atoms. Examples are 1-fluoromethyl, difluoromethyl, trifluoromethyl, 1-fluoroethyl, 2-fluoroethyl and 2,2,2-trifluoroethyl. The most preferred "halo $C_{1-6}$ alkyl" is trifluoromethyl.

The term "$C_{3-7}$ cycloalkyl," alone or in combination with other groups, means a saturated monovalent mono-cyclic hydrocarbon radical of three to seven ring carbons (e.g., cyclopropyl, cyclobutyl, or cyclohexyl).

The term "$C_{3-7}$ cycloalkyl $C_{1-6}$ alkyl" means a $C_{1-6}$ alkyl substituted by one or more $C_{3-7}$ cycloalkyl groups, as defined herein.

The term "$C_{7-10}$ bicycloalkyl," alone or in combination with other groups, means a saturated monovalent cyclic hydrocarbon radical of seven to ten ring carbons, having two rings, in which two or more ring carbon atoms of one ring are ring carbon atoms of the other ring (e.g., bicyclo[2.2.1]heptyl).

The term "$C_{1-6}$ alkoxy," alone or in combination with other groups, means the group R'—O—, wherein R' is a $C_{1-6}$ alkyl.

The term "$C_{1-6}$ alkoxy-carbonyl" refers to the group $R^{a1}$—C(O)—, wherein $R^{a1}$ is a $C_{1-6}$ alkoxy as defined above.

The term "$C_{1-6}$ alkoxy-$C_{1-6}$ alkyl" means a $C_{1-6}$ alkyl substituted by a $C_{1-6}$ alkoxy group, as defined herein.

The term "halo $C_{1-6}$ alkoxy," alone or in combination with other groups, means a $C_{1-6}$ alkoxy substituted by one or more halogens. In particular embodiments the $C_{1-6}$ alkoxy is substituted by one to three halogens.

The term "$C_{1-6}$ alkylenedioxy" means —O—$C_{1-6}$ alkyl-O—. When a group is substituted by a $C_{1-6}$ alkylenedioxy, each end of the $C_{1-6}$ alkylenedioxy replaces a hydrogen atom of that group. Methylenedioxy or 1,2-ethylenedioxy are preferred examples.

The term "$C_{3-6}$ alkenyl," alone or in combination with other groups, means a straight-chain or branched hydrocarbon residue comprising a carbon-carbon double bond, having three to six carbon atoms, provided that the carbon atom of the attachment point of the $C_{3-6}$ alkenyl to the rest of the molecule is not bonded to another carbon atom of the $C_{3-6}$ alkenyl by a carbon-carbon double bond. An example of a $C_{3-6}$ alkenyl is 2-propenyl.

The term "$C_{3-6}$-alkynyl," alone or in combination with other groups, means a straight-chain or branched hydrocarbon residue comprising a carbon-carbon triple bond, having three to six carbon atoms, provided that the carbon atom of the attachment point of the $C_{3-6}$ alkynyl to the rest of the molecule is not bonded to another carbon atom of the $C_{3-6}$ alkynyl by a carbon-carbon triple bond. An example of a $C_{3-6}$ alkynyl is 2-propynyl.

The term "acyl" means R—C(O)—, in which R is a $C_{1-6}$ alkyl, halo $C_{1-6}$ alkyl, $C_{3-7}$ cycloalkyl or $C_{3-7}$ cycloalkyl $C_{1-6}$ alkyl.

The term "heterocyclyl," alone or in combination with other groups, means a non-aromatic mono- or bi-cyclic radical of four to nine ring atoms in which one to three ring atoms are heteroatoms independently selected from N, O and $S(O)_n$ (where n is an integer from 0 to 2), with the remaining ring atoms being C. The more preferred heterocyclyls are piperidyl or 6-aza-spiro[2,5]oct-6yl.

The term "heterocyclyl-$C_{1-3}$alkyl" means a $C_{1-3}$ alkyl, substituted by one heterocyclyl, as defined herein.

The term "optionally substituted heterocyclyl-carbonyl" refers to the group $R^{v1}$—C(O)—, wherein $R^{v1}$ is a heterocyclyl as defined herein, optionally substituted by one or more substituents independently selected from the group consisting of $C_{1-4}$ alkyl, halo $C_{1-4}$ alkyl and halogen. In particular embodiments, the "optionally substituted heterocyclyl-carbonyl" is pyrrolidinyl-carbonyl or di-fluoro-azetidinyl-carbonyl.

The term "aryl," alone or combination with other groups, means phenyl or naphthyl. The term "arylmethyl" means a phenyl-CH$_2$— or a naphthyl-CH$_2$ radical.

The term "phenyl-$C_{1-3}$alkyl" means a $C_{1-3}$ alkyl, as defined herein, substituted by phenyl.

The term "arylcarbonyloxy-$C_{1-6}$ alkyl" refers to the group $R^{c1}$—C(O)—O—$R^{c2}$—, wherein $R^{c2}$ is a $C_{1-6}$ alkylene and $R^{c1}$ is an aryl, as defined above The term "heteroaryl," alone or combination with other groups, means an aromatic monocyclic- or bicyclic-aromatic radical of 5 to 10 ring atoms having one to three ring heteroatoms independently selected from N, O, and S, with the remaining ring atoms being C.

The term "heteroaryl-$C_{1-3}$alkyl" means a $C_{1-3}$ alkyl substituted by a heteroaryl, as defined herein.

The term "$C_{1-6}$ alkoxy-carbonyloxy" refers to the group $R^{a2}$—C(O)—O—, wherein $R^{a2}$ is a $C_{1-6}$ alkoxy as defined above.

The term "bicyclic radicals" means radicals having two rings, in which two or more ring atoms of one ring are ring carbon atoms of the other ring.

The terms "$C_{1-6}$ alkylsulfonyl", "$C_{1-6}$ alkylsulfinyl" and "$C_{1-6}$ alkylthio" means a $C_{1-6}$ alkyl-SO$_2$—, a $C_{1-6}$ alkyl-SO— and a $C_{1-6}$ alkyl-S—, respectively.

Preferred radicals for the chemical groups whose definitions are given above are those specifically exemplified in the Examples.

Compounds of formula (I) can form pharmaceutically acceptable acid addition salts. Examples of such pharmaceutically acceptable salts are salts of compounds of formula (I) with physiologically compatible mineral acids, such as hydrochloric acid, hydrobromic acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts.

Unless otherwise indicated, in reference to a particular group or molecule, the term "substituted" refers to the fact that at least one of the hydrogen atoms of that group or molecule is replaced by some other substituent.

"Optional" or "optionally" means that the subsequently described event or circumstance may but need not occur, and that the description includes instances where the event or circumstance occurs and instances in which it does not. For example, an "aryl group optionally substituted with an alkyl group" means that the alkyl may but need not be present, and the description includes situations where the aryl group is substituted with an alkyl group and situations where the aryl group is not substituted with the alkyl group.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, preferably from about 0.1 mg to about 1,000 mg, more preferably from about 0.5 to 500 mg, and more preferably from about 1 mg to 100 mg, should be appropriate, although the upper limit may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

Unless otherwise indicated, the term "a compound of the formula" or "a compound of formula" or "compounds of the formula" or "compounds of formula" refers to any compound selected from the genus of compounds as defined by the formula.

The invention is directed to compounds of formula (I):

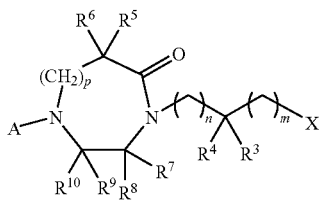

(I)

or pharmaceutically acceptable salts or esters thereof, wherein:

A is aryl, heteroaryl, arylmethyl or heteroarylmethyl, wherein said aryl or heteroaryl portion of A is optionally substituted by one to three substituents independently selected from the group consisting of halogen, aryl, heteroaryl, $C_{1-6}$ alkyl, halo $C_{1-6}$ alkyl, $C_{1-6}$ alkoxy, halo $C_{1-6}$ alkoxy, and $C_{1-6}$ alkylenedioxy;

X is —N($R^1$)($R^2$);

$R^1$ and $R^2$ are independently selected from the group consisting of:
(1) hydrogen,
(2) $C_{1-6}$ alkyl,
(3) $C_{3-6}$ alkenyl,
(4) $C_{3-6}$ alkynyl,
(5) hydroxy $C_{2-6}$ alkyl,
(6) $C_{1-6}$ alkoxy $C_{2-6}$ alkyl,
(7) $C_{3-7}$ cycloalkyl, which is optionally substituted one to three times by $R^d$,
(8) $C_{3-7}$ cycloalkyl $C_{1-6}$ alkyl, wherein the $C_{3-7}$ cycloalkyl portion of said $C_{3-7}$ cycloalkyl $C_{1-6}$ alkyl is optionally substituted one to three times by $R^d$,
(9) $C_{7-10}$ bicycloalkyl,
(10) phenyl $C_{1-3}$ alkyl, wherein the phenyl portion of said phenyl $C_{1-3}$ alkyl is optionally substituted one to three times by $R^d$.
(11) heteroaryl $C_{1-3}$ alkyl, wherein the heteroaryl portion of said heteroaryl $C_{1-3}$ alkyl is optionally substituted one to three times by $R^d$.
(12) heterocyclyl, which is optionally substituted one to three times by $R^d$, and
(13) heterocyclyl $C_{1-6}$ alkyl, wherein the heterocyclyl portion of said heterocyclyl $C_{1-6}$ alkyl is optionally substituted one to three times by $R^d$;
provided that at least one of $R^1$ and $R^2$ is not hydrogen; or alternatively, $R^1$ and $R^2$, together with the nitrogen atom to which they are attached, form a heterocyclyl optionally substituted one to three times by $R^d$, and wherein: (a) one of the ring carbon atoms of said heterocyclyl formed by $R^1$ and $R^2$ is optionally replaced with a carbonyl group; and/or (b) one of the ring carbon atoms of said heterocyclyl formed by $R^1$ and $R^2$ is also a ring carbon atom of another ring which is a $C_{3-7}$ cycloalkyl or heterocyclyl, which is optionally substituted by a $C_{1-6}$ alkyl, and wherein one or two ring carbon atoms of said $C_{3-7}$ cycloalkyl or heterocyclyl is optionally replaced by a carbonyl group;

$R^3$ and $R^4$ are independently selected from the group consisting of:
(1) hydrogen,
(2) hydroxy,
(3) $C_{1-6}$ alkyl,
(4) $C_{1-6}$ alkoxy,
(5) $C_{3-7}$ cycloalkyl,
(6) $C_{3-7}$ cycloalkyl $C_{1-6}$ alkyl,
(7) $C_{1-6}$ alkoxycarbonyl,
(8) carboxyl,
(9) carbamoyl,
(10) mono or di-$C_{1-6}$ alkyl substituted carbamoyl,
(11) $C_{1-6}$ alkoxycarbonyloxy,
(12) mono or di-$C_{1-6}$ alkyl substituted aminocarbonyloxy,
(13) hydroxy-$C_{1-6}$ alkyl,
(14) $C_{1-6}$ alkoxy-$C_{1-6}$ alkyl,
(15) halogen or halo $C_{1-6}$ alkyl,
(16) optionally substituted heterocyclyl-carbonyl, and
(17) $R^{aa}R^{bb}$N—C(O)— wherein $R^{aa}$ and $R^{bb}$ are independently selected from the group consisting of hydrogen, $C_{1-6}$ alkyl, hydroxy-$C_{1-6}$ alkyl and $C_{3-7}$ cycloalkyl; or alternatively, $R^3$ and $R^4$, together with the carbon atom to which they are attached, form $C_{3-7}$ cycloalkyl or heterocyclyl optionally substituted by one to three substituents independently selected from the group consisting of $C_{1-4}$ alkyl, halo $C_{1-4}$ alkyl and halogen;

$R^5$ and $R^6$ are independently hydrogen, $C_{1-6}$ alkyl or $C_{3-7}$ cycloalkyl, wherein said $C_{1-6}$ alkyl and said $C_{3-7}$ cycloalkyl are optionally substituted by one to three substituents independently selected from the group consisting of: (1) amino, (2) hydroxy, (3) carboxyl, (4) carbamoyl, (5) mono or di-$C_{1-6}$ alkyl substituted carbamoyl and (6) $C_{1-6}$ alkoxycarbonyl; or alternatively $R^5$ and $R^6$, together with the carbon atom to which they are attached, form $C_{3-7}$ cycloalkyl or heterocyclyl;

$R^7$, $R^8$, $R^9$ and $R^{10}$ are independently hydrogen, $C_{1-6}$ alkyl, $C_{3-7}$ cycloalkyl, or aryl; wherein said $C_{1-6}$ alkyl is optionally substituted by one to three substituents independently selected from the group consisting of:
(1) hydroxy,
(2) $C_{1-6}$ alkoxy,
(3) carboxyl,
(4) carbamoyl,
(5) mono or di-$C_{1-6}$ alkyl substituted carbamoyl,
(6) $C_{1-6}$ alkoxycarbonyl,
(7) aryl, optionally substituted by one to three substituents independently selected from the group consisting of halogen, $C_{1-6}$ alkyl, halo $C_{1-6}$ alkyl, $C_{1-6}$ alkoxy and halo $C_{1-6}$ alkoxy, and
(8) heteroaryl, optionally substituted by one to three substituents independently selected from the group consisting of halogen, $C_{1-6}$ alkyl, halo $C_{1-6}$ alkyl, $C_{1-6}$ alkoxy and halo $C_{1-6}$ alkoxy;

$R^d$ is selected from the group consisting of:
(1) hydroxy,
(2) cyano,
(3) $NR^aR^b$,
(4) halogen,
(5) $C_{1-6}$ alkyl,
(6) halo $C_{1-6}$ alkyl,
(7) hydroxy $C_{1-6}$ alkyl,
(8) $C_{1-6}$ alkoxy,
(9) $C_{1-6}$ alkoxy $C_{1-6}$ alkyl,
(10) $C_{3-7}$ cycloalkyl,
(11) $C_{1-6}$ alkoxycarbonyl,
(12) acyl,
(13) —C(O)$NR^aR^b$,
(14) —$NR^a$—C(O)—$R^b$,
(15) —$NR^a$—C(O)—$OR^b$,
(16) —$NR^a$—C(O)—$NR^b$,
(17) —$NR^a$—$SO_2$—$R^b$,
(18) —$NR^a$—$SO_2$—$NR^bR^c$,
(19) —OC(O)$NR^aR^b$,

(20) —OC(O)OR$^a$,
(21) $C_{1-6}$ alkylsulfonyl,
(22) $C_{1-6}$ alkylsulfinyl,
(23) $C_{1-6}$ alkylthio,
(24) phenyl or phenyl $C_{1-3}$ alkyl, wherein the phenyl or phenyl portion of said phenyl $C_{1-3}$ alkyl is optionally substituted one to three times by a substituent independently selected from the group consisting of hydroxy, cyano, NR$^a$R$^b$, halogen, $C_{1-6}$ alkyl, halo $C_{1-6}$ alkyl, hydroxy $C_{1-6}$ alkyl, $C_{1-6}$ alkoxycarbonyl, acyl, —C(O)NR$^a$R$^b$, —NR$^a$—C(O)—R$^b$, —NR$^a$—C(O)—OR$^b$, —NR$^a$—C(O)—NR$^b$, —NR$^a$—SO$_2$—R$^b$, —NR$^a$—SO$_2$—NR$^b$R$^c$, —OC(O)NR$^a$R$^b$, —OC(O)OR$^a$, $C_{1-6}$ alkylsulfonyl, $C_{1-6}$ alkylsulfinyl, and $C_{1-6}$ alkylthio;
(25) heteroaryl or heteroaryl $C_{1-3}$ alkyl, wherein the heteroaryl or heteroaryl portion of said heteroaryl $C_{1-3}$ alkyl is optionally substituted one to three times by a substituent independently selected from the group consisting of hydroxy, cyano, NR$^a$R$^b$, halogen, $C_{1-6}$ alkyl, halo $C_{1-6}$ alkyl, hydroxy $C_{1-6}$ alkyl, $C_{1-6}$ alkoxycarbonyl, acyl, —C(O)NR$^a$R$^b$, —NR$^a$—C(O)—R$^b$, —NR$^a$C(O)—OR$^b$, —NR$^a$—C(O)—NR$^b$, —NR$^a$—SO$_2$—R$^b$, —NR$^a$—SO$_2$—NR$^b$R$^c$, —OC(O)NR$^a$R$^b$, —OC(O)OR$^a$, $C_{1-6}$ alkylsulfonyl, $C_{1-6}$ alkylsulfinyl, and $C_{1-6}$ alkylthio; and
(26) heterocyclyl, which is optionally substituted one to three times by a substituent independently selected from the group consisting of hydroxy, cyano, NR$^a$R$^b$, halogen, $C_{1-6}$ alkyl, halo $C_{1-6}$ alkyl, hydroxy $C_{1-6}$ alkyl, $C_{1-6}$ alkoxycarbonyl, acyl, —C(O)NR$^a$R$^b$, —NR$^a$—C(O)—R$^b$, —NR$^a$—C(O)—OR$^b$, —NR$^a$—C(O)—NR$^b$, —NR$^a$—SO$_2$—R$^b$, —NR$^a$—SO$_2$—NR$^b$R$^c$, —OC(O)NR$^a$R$^b$, —OC(O)OR$^a$, $C_{1-6}$ alkylsulfonyl, $C_{1-6}$ alkylsulfinyl, and $C_{1-6}$ alkylthio, and wherein one or two ring carbon atoms of the heterocyclyl is optionally replaced with a carbonyl group;

R$^a$, R$^b$ and R$^c$ are independently hydrogen or $C_{1-6}$ alkyl;
m is an integer of 0 to 3; n is an integer of 0 to 3; m+n is an integer of 1 to 5; and
p is 0 or 1.

Compounds that have the same molecular Formula but differ in the nature or sequence of bonding of their atoms or the arrangement of their atoms in space are termed "isomers." Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of formula (I) can possess one or more asymmetric centers. Unless indicated otherwise, the description or naming of a particular compound in the specification and claims is intended to include both individual enantiomers and mixtures, racemic or otherwise, thereof, as well as individual epimers and mixture thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

The compounds of formula (I) are CCR2 receptor antagonists, with some antagonist activity also at CCR3 and CCR5.

While the broadest definition of this invention is described before, certain compounds of formula (I) are preferred.

i) In the compounds of formula (I), A is preferably phenyl or naphthyl, said phenyl and said naphthyl being optionally substituted by one to three substituents independently selected from the group consisting of halogen, halo $C_{1-6}$ alkyl, halo $C_{1-6}$ alkoxy and aryl. More preferably, A is phenyl substituted by one or two substituents independently selected from the group consisting of halogen, halo $C_{1-6}$ alkyl and halo $C_{1-6}$ alkoxy, most preferably selected from the group consisting of chloro, trifluoromethyl, trifluoromethoxy. A is especially 3,4-dichlorophenyl, 3-chlorophenyl, 3-trifluoromethylphenyl, 3-Chloro-4 trifluoromethylphenyl or 3-trifluoromethoxylphenyl.

ii) In the compounds of formula (I), X is preferably —N(R$^1$)(R$^2$) and R$^1$ and R$^2$, together with the nitrogen atom to which they are attached, form heterocyclyl optionally substituted by one to three substituents independently selected from the group consisting of hydroxy, $C_{1-6}$ alkyl and hydroxy $C_{1-6}$ alkyl; and/or one of the ring carbon atoms of the heterocyclyl formed by R$^1$ and R$^2$ may be a ring carbon atom of another ring which is $C_{3-7}$ cycloalkyl. The heterocyclyl formed by R$^1$ and R$^2$, together with the nitrogen atom to which they are attached, is preferably piperidyl or pyrrolidinyl, and said piperidyl and pyrrolidinyl being optionally substituted by one or two substituents independently selected from the group consisting of hydroxy, $C_{1-5}$ alkyl and hydroxy $C_{1-6}$ alkyl, and/or one of the ring carbon atoms of said piperidyl and pyrrolidinyl formed by R$^1$ and R$^2$ may be shared by $C_{3-7}$ cycloalkyl, most preferably by a cyclopropyl ring.

More preferably, in the compounds of formula (I), X is a mono spiro-heterocyclyl such as 6-aza-spiro[2,5]oct-6-yl, 5-azaspiro[2.5]oct-5-yl, 7-aza-spiro[3.5]non-7-yl, 8-aza-spiro[4.5]dec-8-yl, 1,8-diaza-spiro[4.5]dec-8-yl, 1,3,8-triaza-spiro[4.5]dec-8-yl, 2,8-diaza-spiro[4.5]dec-8-yl, 1-oxa-3,8-diaza-spiro[4.5]dec-8-yl, 1-oxa-8-aza-spiro[4.5]dec-8-yl, 2-oxa-8-aza-spiro[4.5]dec-8-yl, 2-oxa-7-aza-spiro[3.5]non-7-yl, 1-oxa-7-aza-spiro[3.5]non-7-yl, 9-aza-spiro[5.5]undec-9-yl, 1-oxa-4,9-diaza-spiro[5.5]undec-9-yl, wherein the spiro-heterocyclyl ring is optionally substituted by one to three substituents independently selected from the group consisting of hydroxy, oxo, alkoxy, fluoro or $C_{1-6}$ alkyl. Most preferably the spiro heterocyclyl is 6-aza-spiro[2,5]oct-6-yl wherein the spiro-heterocyclyl ring is optionally substituted by one to two hydroxy.

In the compounds of formula (I), X is especially (S)-4-hydroxy-6-aza-spiro[2.5]oct-6-yl.

iii) In the compounds of formula (I), m+n is an integer of 1, 2 or 3, more preferably m+n is an integer of 2 or 3, most preferably m+n is 2.

iv) In the compounds of formula (I), one of R$^3$ and R$^4$ is preferably hydrogen and the other is hydrogen, hydroxy, $C_{1-6}$ alkoxycarbonyl, di-$C_{1-6}$ alkyl substituted carbamoyl, hydroxy-$C_{1-6}$ alkyl, $C_{1-6}$ alkoxy-$C_{1-6}$ alkyl, N,N,Hydroxy-$C_{1-6}$ alkyl-$C_{1-6}$ alkyl-carbamoyl or N,N—$C_{3-7}$ cycloalkyl, $C_{1-6}$ alkyl-carbamoyl.

v) The compounds of formula (I), wherein n is 0, m is 2 and one of R$^3$ and R$^4$ is hydrogen, and the other is hydrogen, $C_{1-6}$ alkoxycarbonyl, hydroxy-$C_{1-6}$ alkyl, $C_{1-6}$ alkoxy-$C_{1-6}$ alkyl, carboxyl or mono or di-$C_{1-6}$ alkyl substituted carbamoyl, are preferred.

vi) In the compounds of formula (I), preferably, one or two of $R^5$, $R^6$, $R^7$, $R^8$, $R^9$ and $R^{10}$ are independently hydrogen, $C_{1-6}$ alkyl, phenyl or optionally trifluoromethyl substituted phenyl-$C_{1-6}$ alkyl and the others are hydrogen. More preferably, one of $R^5$ and $R^6$ is hydrogen or $C_{1-6}$ alkyl, the other is hydrogen, on of $R^9$ and $R^{10}$ is hydrogen or $C_{1-6}$ alkyl (preferably methyl), the other is hydrogen, and $R^7$, $R^8$, are hydrogen. Even more preferably, one of $R^5$ and $R^6$ is hydrogen or $C_{1-6}$ alkyl, the other is hydrogen, and $R^7$, $R^8$, $R^9$ and $R^{10}$ are hydrogen.

Furthermore preferably, one of $R^5$ and $R^6$ is methyl, the other is hydrogen, and $R^7$, $R^8$, $R^9$ and $R^{10}$ are hydrogen.

vii) Preferred compounds of the invention are compounds of formula (I), such as:

1-(3,4-Dichloro-phenyl)-4-[(S)-3-((S)-4-hydroxy-6-aza-spiro[2.5]oct-6-yl)-1-hydroxymethyl-propyl]-[1,4]diazepan-5-one, 1-(3-Chloro-phenyl)-4-[(S)-3-((S)-4-hydroxy-6-aza-spiro[2.5]oct-6-yl)-1-hydroxymethyl-propyl]-[1,4]diazepan-5-one, 4-[(S)-3-((S)-4-Hydroxy-6-aza-spiro[2.5]oct-6-yl)-1-hydroxymethyl-propyl]-1-(3-trifluoromethyl-phenyl)-[1,4]diazepan-5-one, (S)-4-((S)-4-Hydroxy-6-aza-spiro[2.5]oct-6-yl)-N,N-dimethyl-2-[7-oxo-4-(3-trifluoromethyl-phenyl)-[1,4]diazepan-1-yl]-butyramide, 4-[(S)-3-((S)-4-Hydroxy-6-aza-spiro[2.5]oct-6-yl)-1-methoxymethyl-propyl]-1-(3-trifluoromethyl-phenyl)-[1,4]diazepan-5-one, (S)-1-[3-((S)-4-Hydroxy-6-aza-spiro[2.5]oct-6-yl)-propyl]-3-methyl-4-(3-triflouromethoxy-phenyl)-piperazin-2-one, 4-((S)-4-Hydroxy-6-aza-spiro[2.5]oct-6-yl)-2-[3-methyl-2-oxo-4-(3-trifluoromethoxy-phenyl)-piperazin-1-yl]-butyric acid, 1-[3-((S)-4-Hydroxy-6-aza-spiro[2.5]oct-6-yl)-1-hydroxymethyl-propyl]-3-methyl-4-(3-trifluoromethoxy-phenyl)-piperazin-2-one, 4-((S)-4-Hydroxy-6-aza-spiro[2.5]oct-6-yl)-N,N-dimethyl-2-[3-methyl-2-oxo-4-(3-trifluoromethoxy-phenyl)-piperazin-1-yl]-butyramide, 1-[3-((S)-4-Hydroxy-6-aza-spiro[2.5]oct-6-yl)-1-methoxymethyl-propyl]-3-methyl-4-(3-trifluoromethyl-phenyl)-piperazin-2-one, (R)-1-(3,4-Dichloro-phenyl)-4-[(S)-3-((S)-4-hydroxy-6-aza-spiro[2.5]oct-6-yl)-1-hydroxymethyl-propyl]-2-methyl-[1,4]diazepan-5-one, (S)-4-(3,4-Dichloro-phenyl)-1-[3-((S)-4-hydroxy-6-aza-spiro[2.5]oct-6-yl)-propyl]-3-methyl-piperazin-2-one, (S)-4-(3-Chloro-4-trifluoromethyl-phenyl)-1-[3-((S)-4-hydroxy-6-aza-spiro[2.5]oct-6-yl)-propyl]-3-methyl-piperazin-2-one or (S)-4-(3,4-Dichloro-phenyl)-1-[4-((S)-4-hydroxy-6-aza-spiro[2.5]oct-6-yl)-butyl]-3-methyl-piperazin-2-one.

General Synthetic Procedures

Compounds of formula (I) can be produced as outlined in scheme 1. LG is a leaving group, e.g., chloro, bromo, iodo, or methanesulfonyloxy.

Thus, heterocycle 1 is reacted with alkylating agent 2 in the presence of a base, e.g., sodium hydride or potassium tert-butylate, in a solvent such as N,N-dimethylformamide, N,N-dimethylacetamide or tetrahydrofuran, at temperatures between 0° C. and 100° C., thus leading to (I).

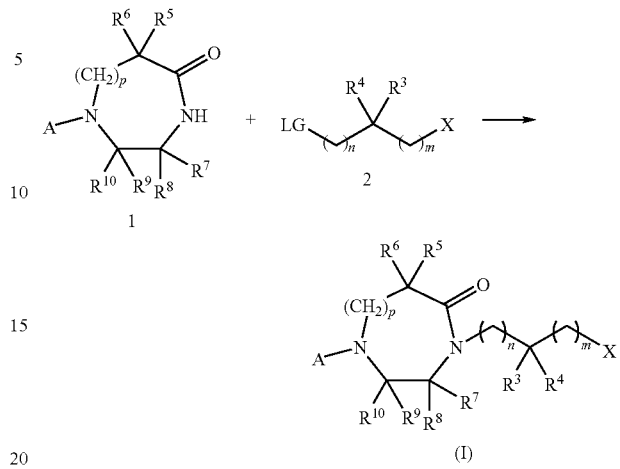

Scheme 1

In Scheme 1, A, X, $R^3$, $R^4$, $R^5$, $R^6$, $R^7$, $R^8$, $R^9$, $R^{10}$, m, n and p are as defined before.

Substituents $R^3$ and/or $R^4$ in (I) or in any synthetic intermediate can be interconverted using reagents and methods known in the art. For instance, esters ($R^3$ and/or $R^4$=$C_{1-6}$ alkoxycarbonyl) can be reduced to the corresponding alcohols ($R^3$ and/or $R^4$=hydroxymethyl), e.g., with lithium borohydride in ethanol. These alcohols can further be transformed to ethers ($R^3$ and/or $R^4$=$CH_2OC_{1-6}$ alkyl), e.g., with an alkyl halide in solvents such as tetrahydrofuran, N,N-dimethylformamide or N,N-dimethylacetamide with sodium hydride as base, or with an alkyl halide in the presence of silver(I) oxide. Similarly, esters ($R^3$ and/or $R^4$=$C_{1-6}$ alkoxycarbonyl) can be hydrolyzed to the corresponding carboxylic acids, ($R^3$ and/or $R^4$=COOH), e.g., through base-mediated hydrolysis using bases such as lithium hydroxide or sodium hydroxide in solvents such as water, methanol, tetrahydrofuran, or mixtures thereof. These acids can then be elaborated to the corresponding amides ($R^3$ and/or $R^4$=mono- or di-$C_{1-6}$ alkyl substituted aminocarbonyloxy), as described in scheme 8, step b.

Compounds of formula (I) can also be synthesized as described in scheme 2. $PG^2$ is a protective group, e.g., benzyl, tetrahydropyran-2-yl, tert-butyldimethylsilyl or tert-butyldiphenylsilyl, LG is a leaving group such as chloro, bromo, iodo, or methanesulfonyloxy.

In step a, scheme 2, heterocycle 1 is reacted with alkylating agent 3, leading to 4. The reaction is performed in analogy with scheme 1.

In step b, scheme 2, the protective group of the hydroxyl of 4, $PG^2$, is removed, using methods and reagents known in the art, leading to 5. In the case where $PG^2$ is benzyl, the protective group is removed, e.g., by hydrogenation at pressures between 1 bar and 100 bar, in the presence of a suitable catalyst, e.g., palladium on activated charcoal, in solvents such as methanol, ethanol, ethyl acetate, acetic acid, or mixtures thereof, at temperatures between 20° C. and 150° C. In the case where $PG^2$ is tetrahydropyran-2-yl, the protective group is removed under acidic conditions, e.g., with toluene-4-sulfonic acid, pyridinium toluene-4-sulfonate, or hydrochloric acid, in solvents such as methanol, ethanol, water, or mixtures thereof, at temperatures between 20° C. and 100° C. In the case where $PG^2$ is a silyl group, e.g., tert-butyldimethylsilyl or tert-butyldiphenylsilyl, the protective group is removed with a fluoride reagent, e.g., tetrabutylammonium fluoride, in a solvent such as tetrahydrofuran, at temperatures between 0° C. and 50° C. In the case where $PG^2$ is a silyl group, e.g., tert-butyldimethylsilyl or tert-butyldiphenylsilyl, and $R^3$ and/or $R^4$ is $C_{1-6}$ alkoxycarbonyl, the protective group is preferably removed by reaction with boron trichloride or boron tribromide in a solvent such as dichloromethane, at temperatures between −78° C. and 40° C.

In step c, scheme 2, alcohol 5 is oxidized to aldehyde 6 using reagents and method known in the art. For instance, the oxidation is carried out with sodium hypochlorite, in a two-phase mixture of water and dichloromethane, in the presence of sodium hydrogencarbonate and catalytic amounts of sodium bromide or potassium bromide and 2,2,6,6-tetramethylpiperidin-1-oxyl radical, at temperatures between 0° C. and 25° C. Alternatively, the oxidation may be performed with catalytic amounts of tetrapropylammonium perruthenate in the presence of stoichoimetric amounts of a co-oxidant such as 4-methylmorpholine-4-oxide and molecular sieves, at temperatures between 0° C. and 40° C., in solvents such as dichloromethane, acetonitrile or mixtures thereof. Alternatively, dimethyl sulfoxide-based reagents can be employed, such as dimethyl sulfoxide-oxalyl chloride, or dimethyl sulfoxide-trifluoroacetic anhydride, in the presence of an organic base such as triethylamine in a solvent such as dichloromethane, at temperatures below 0° C., typically between −78° C. and −60° C. Alternatively, pyridine-sulfur trioxide can be employed in dimethyl sulfoxide or dimethylsulfoxide-dichloromethane solvent mixture in the presence of an organic base such as triethylamine, at temperatures between 0° C. and 25° C.

In step d, scheme 2, aldehyde 6 is transformed into (I) by reaction with amine $HN(R^1)(R^2)$, using methods well known in the art, e.g., reductive amination. The reaction is carried out using a suitable reducing agent, e.g., sodium borohydride, sodium triacetoxyborohydride, sodium cyanoborohydride, or borane pyridine complex, in solvents such as methanol, ethanol, acetic acid, 1,2-dichloroethane, or mixtures thereof, optionally in the presence of a dehydrating agent such as magnesium sulfate, at temperatures between 0° C. and 80° C.

Amines of formula $HN(R^1)(R^2)$ are either commercially available or can be synthesized as described in the experimental section.

Scheme 2

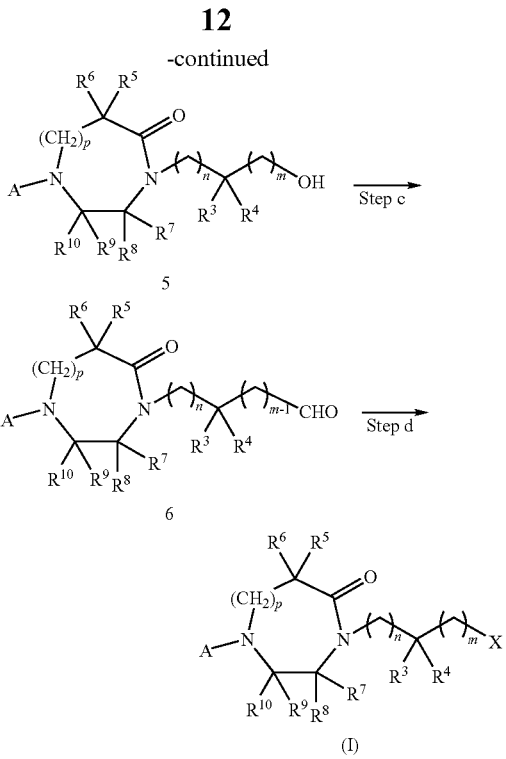

In Scheme 2, A, X, $R^3$, $R^4$, $R^5$, $R^6$, $R^7$, $R^8$, $R^9$, $R^{10}$, m, n and p are as defined before.

Compounds of formula (I) can be produced as outlined in scheme 3. A' is aryl or heteroaryl, $PG^1$ is a suitable protective group such as tert-butoxycarbonyl or benzyloxycarbonyl, $LG^1$ and $LG^2$ are leaving groups such as fluoro, chloro, bromo, iodo, or trifluoromethanesulfonyloxy.

In step a, scheme 3, protected heterocycle 7 is reacted with alkylating agent 2, leading to 8. The reaction is performed in analogy with scheme 1.

In step b, scheme 3, the protective group of 8, $PG^1$, is removed using methods known in the art, leading to secondary amine 9. In the case where $PG^1$ is tert-butoxycarbonyl, suitable deprotection reagents and conditions are strong acids such as hydrogen chloride or trifluoroacetic acid in a solvent such as 1,4-dioxane or dichloromethane, at or below room temperature. In the case where $PG^1$ is benzyloxycarbonyl, the protective group is removed by hydrogenation at pressures between 1 and 100 bar, at temperatures between 0° C. and 100° C., in solvents such as methanol, ethanol, or ethyl acetate.

In step c, scheme 3, secondary amine 9 is converted to compound of general formula (I) through reaction with halide or sulfonate 10A, with boronic acid 10B, or with aldehyde 10C using reagents and methods known in the art.

For instance, the reaction can be performed with halide or sulfonate 10A at temperatures between 20° C. and 200° C., in the presence of a base, e.g., potassium carbonate, cesium carbonate or triethylamine, in a solvent such as acetonitrile, N,N-dimethylformamide or N-methylpyrrolidinone, optionally under microwave irradiation.

Alternatively, in the case where A is aryl or heteroaryl, the reaction can be performed with halide or sulfonate 10A in the presence of a copper(I) salt, e.g., copper(I)iodide, and a diol ligand, e.g., 1,2-ethanediol, in a solvent such as 2-propanol, in the presence of a base, e.g., potassium phosphate or cesium carbonate, at temperatures between 60° C. and 90° C.

Alternatively, in the case where A is aryl or heteroaryl, the reaction may be performed with halide or sulfonate 10A in the presence of a palladium salt, e.g., palladium(II)chloride or palladium(II)acetate, a phosphine ligand, e.g., 2,2'-bis(diphenylphosphino)-1,1'-binaphthyl or 2',4',6'-triisopropyl-1,1'-biphenyl-2-yldicyclohexylphosphine, a base, e.g., potassium phosphate, sodium methylate, or cesium carbonate, in a solvent such as toluene or 1,4-dioxane, at temperatures between 20° C. and 110° C.

Alternatively, in the case where A is aryl or heteroaryl, the reaction may be performed with arylboronic acid 10B in the presence of anhydrous copper(II)acetate, in the presence of a base, e.g., triethylamine or pyridine, in a solvent such as dichloromethane, at temperatures between 0° C. and 40° C., optionally in the presence of molecular sieves.

Alternatively, in the case where A is arylmethyl or heteroarylmethyl, the reaction may be performed with aldehyde 10C, in analogy with scheme 2, step d.

butyldiphenylsilyl. LG is a leaving group such as chloro, bromo, iodo, or methanesulfonyloxy.

In step a, scheme 4, heterocycle 7 is reacted with alkylating agent 3, leading to 11. The reaction is performed in analogy with scheme 1.

In step b, scheme 4, the protective group of the hydroxyl of 11, $PG^2$, is removed, leading to 12. This deprotection is performed in analogy with scheme 2, step b.

In step c, scheme 4, alcohol 12 is oxidized to aldehyde 13, in analogy with scheme 2, step c.

In step d, scheme 4, aldehyde 13 is converted to intermediate 8, in analogy with scheme 2, step d.

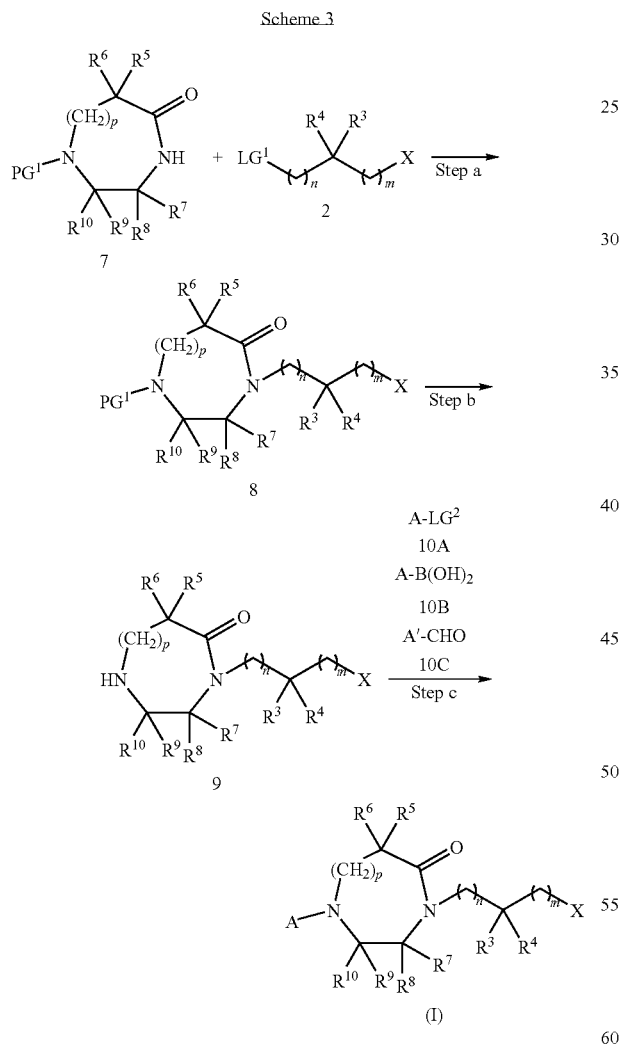

Scheme 3

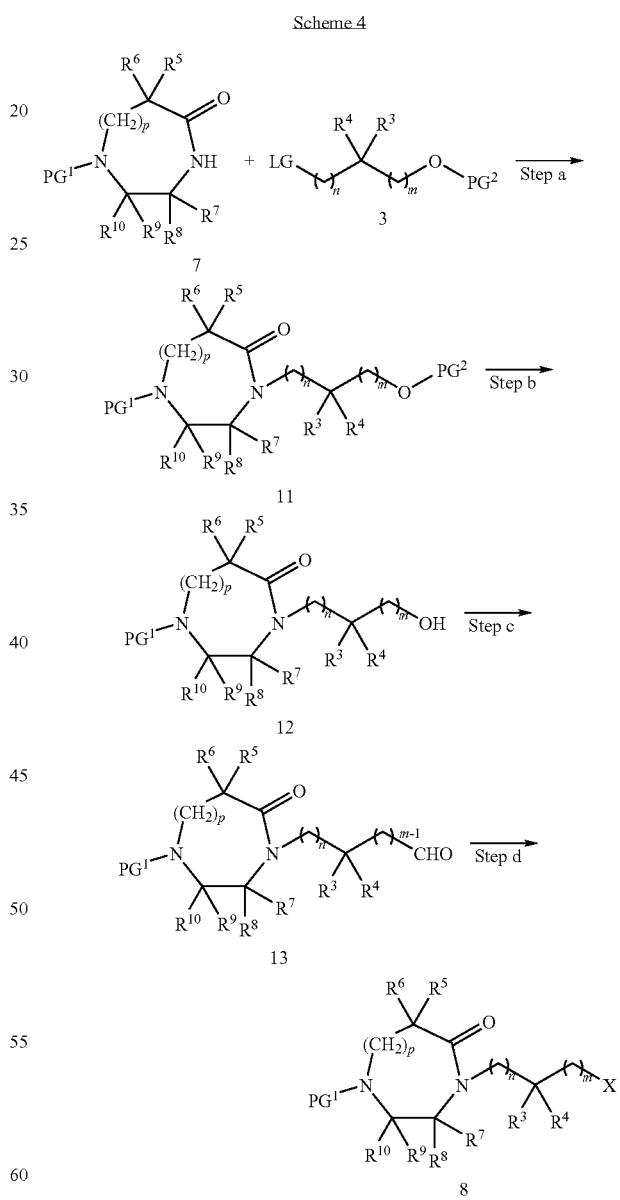

Scheme 4

In Scheme 3, A, X, $R^3$, $R^4$, $R^5$, $R^6$, $R^7$, $R^8$, $R^9$, $R^{10}$, m, n and p are as defined before. A' is aryl or heteroaryl.

Intermediate 8 can also be prepared as outlined in scheme 4. $PG^1$ is a suitable protective group such as tert-butoxycarbonyl or benzyloxycarbonyl, $PG^2$ is a protective group, e.g., benzyl, tetrahydropyran-2-yl, tert-butyldimethylsilyl or tert- In Scheme 4, X, $R^3$, $R^4$, $R^5$, $R^6$, $R^7$, $R^8$, $R^9$, $R^{10}$, m, n and p are as defined before.

Intermediate 4 in which $R^6$, $R^8$ and $R^{10}$ are H and p is 1 is represented by the general formula 4A.

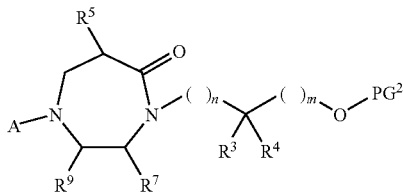

4A

A, $R^3$, $R^4$, $R^5$, $R^7$, $R^9$, $R^{10}$, m and n are as defined before.

Intermediate 4A can be also synthesized as described in scheme 5. $R^e$ is tert-butyl, benzyl, or lower alkyl, e.g., methyl or ethyl, $PG^2$ is a protective group, e.g., benzyl, tetrahydro-pyran-2-yl, tert-butyldimethylsilyl or tert-butyldiphenylsilyl.

In step a, scheme 5, aldehyde or ketone 14 is transformed into 16 by reaction with amine 15, using methods well known in the art, e.g., reductive amination. The reaction is carried out using a suitable reducing agent, e.g., sodium borohydride, sodium triacetoxyborohydride, sodium cyanoborohydride, or borane pyridine complex, in solvents such as methanol, ethanol, acetic acid, 1,2-dichloroethane, or mixtures thereof, at temperatures between 0° C. and 80° C.

Amines of formula 15 are either commercially available or can be synthesized as described in the experimental section.

In step b, scheme 5, ester 16 is deprotected to give acid 17. In the case where $R^e$ is tert-butyl, the deprotection is performed, e.g., with hydrogen chloride, in solvents such as 1,4-dioxane, water, or mixtures thereof, at temperatures between 0° C. and 20° C. In the case where $R^e$ is benzyl, the deprotection is performed, e.g., by hydrogenation at pressures between 1 bar and 10 bar, in solvents such as methanol, ethanol, tetrahydrofuran, ethyl acetate, or mixtures thereof, in the presence of a suitable catalyst, e.g., palladium on activated charcoal. In the case where $R^e$ is lower alkyl, the deprotection is performed, e.g., by base-mediated hydrolysis in solvents such as water, methanol, tetrahydrofuran and mixtures thereof at temperatures between −20° C. and 120° C. Typical reagents are aqueous or lithium hydroxide, sodium hydroxide, potassium hydroxide, sodium hydrogen carbonate, sodium carbonate, potassium hydrogencarbonate and potassium carbonate.

In step c, scheme 5, amino acid 17 is cyclized to 4A using methods well known to someone skilled in the art, e.g., amide formation using a coupling reagent. The reaction is typically carried out in aprotic solvents such as dichloromethane, tetrahydrofuran, N,N-dimethylformamide, N-methylpyrrolidi-none and mixtures thereof in the presence or absence of a base such as triethylamine, diisopropylethylamine, 4-methylmor-pholine, and/or 4-(dimethylamino)pyridine, at temperatures between −30° C. and 60° C. Typically used coupling agents are N,N'-dicyclohexylcarbodiimide, 1-(3-dimethylamino-propyl)-3-ethyl-carbodiimide hydrochloride, O-(benzotria-zol-1-yl)-N,N,N',N'-tetramethyluronium hexafluoro-phosphate or O-(7-azabenzotriazol-1-yl)-N,N,N',N'-tetramethyluronium hexafluoro-phosphate.

Substituents $R^6$ can be introduced in the ring system of 4A via deprotonation of the proton at C(6) of the [1,4]diazepan-5-one ring under suitable conditions (e.g., lithium hexamethyldisilazide or lithium diisopropyl amide in a solvent like tetrahydrofuran at temperatures between −78° C. and 0° C.), followed by selective alkylation with an electrophile of the general formula $R^6$-LG, in which LG is a leaving group such as bromo, iodo, or trifluoromethanesulfonyloxy.

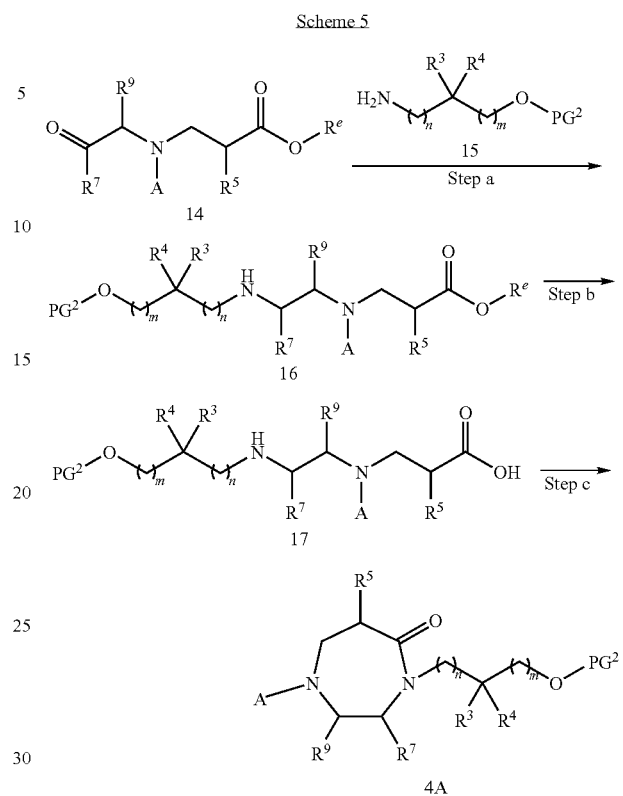

Scheme 5

In Scheme 5, $R^3$, $R^4$, $R^5$, $R^7$, $R^9$, $R^{10}$, m and n are as defined before. $R^e$ is tert-butyl, benzyl, or lower alkyl, e.g., methyl or ethyl.

Intermediate of formula 14 can be synthesized as outlined in scheme 6. $LG^1$ and $LG^2$ are leaving groups, e.g., chloro, bromo, or iodo, $R^e$ is tert-butyl, benzyl, or lower alkyl, e.g., methyl or ethyl.

In step a, scheme 6, aniline 18 is reacted with acrylate 19A or with 3-halopropionate 19B, leading to 20. The reaction with acrylate 19A is either performed neat or in a solvent such as methanol, at temperatures between 0° C. and 100° C. The reaction with 3-halopropionate 19B is preferably performed using a base, e.g., 2,6-lutidine, in a solvent such as toluene or N,N-dimethylformamide, at temperature between 60° C. and the boiling point of the solvent.

In step b, scheme 6, secondary amine 20 is alkylated with 2-halo-N-methoxy-N-methylacetamide 21, leading to 22. The reaction is performed in a solvent such acetonitrile or N,N-dimethylformamide, in the presence of a base, e.g., 2,6-lutidine or potassium carbonate, at temperatures between 50° C. and 150° C.

N-Methoxy-N-methylamides 21 are commercially available or can be synthesized from the corresponding acid by reaction with N,O-dimethyl-hydroxyl-amine hydrochloride in analogy with scheme 8, step b.

In step c, scheme 6, N-methoxy-N-methylamide 22 is converted to ketone 14 using reagents and methods known in the art. For instance, 22 is reacted with the appropriate organo-magnesium ($R^7$—Mg-Hal, with Hal=Cl, Br, I) or organo-lithium ($R^7$—Li) reagent, in a solvent such as tetrahydrofuran, at temperatures between −78° C. and +60° C.

Scheme 6

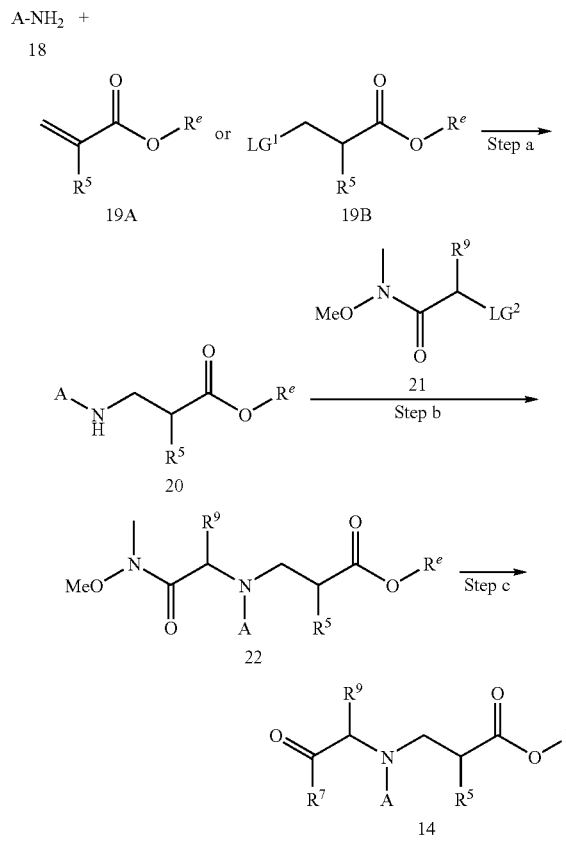

Scheme 7

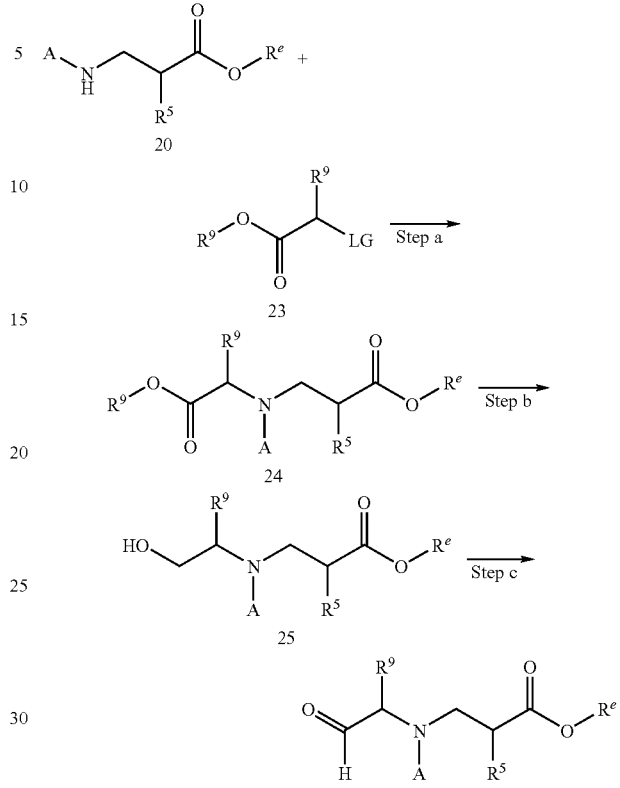

In Scheme 6, $R^5$, $R^7$ and $R^9$ are as defined before. $R^e$ is tert-butyl, benzyl, or lower alkyl, e.g., methyl or ethyl.

Intermediate 14 in which $R^7$ is H is represented by formula 14A.

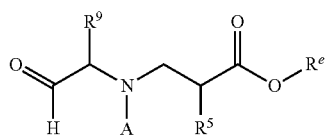

A, $R^5$, $R^9$ are as defined before, and $R^e$ is tert-butyl, benzyl, or lower alkyl, e.g., methyl or ethyl.

Intermediate 14A can be synthesized as outlined in scheme 7. LG is a leaving group, e.g., chloro, bromo, or iodo, $R^e$ is tert-butyl, $R^g$ is lower alkyl, e.g., methyl or ethyl.

In step a, scheme 7, secondary amine is alkylated with 2-haloacetate 23, in analogy with scheme 6, step b, leading to 24.

In step b, scheme 7, the sterically less hindered ester group of 24, C(O)OR$^g$, is selectively reduced, leading to alcohol 25. This conversion is accomplished with a suitable reducing agent, e.g., lithium borohydride, in a solvent such as methanol or ethanol, at temperatures between 0° C. and 40° C.

In step c, scheme 7, alcohol 25 is oxidized to aldehyde 14A, in analogy with scheme 2, step c.

In Scheme 7, $R^5$ and $R^9$ are as defined before. $R^e$ is tert-butyl, $R^g$ is lower alkyl, e.g., methyl or ethyl.

Intermediate 5 in which p is 0, $R^8$ and $R^{10}$ are H is represented by the general formula 5A.

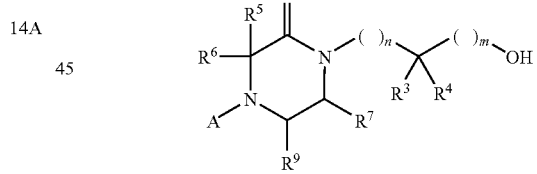

$R^3$, $R^4$, $R^5$, $R^6$, $R^7$, $R^9$, m and n are as defined before.

Intermediate 5A can be also synthesized as described in scheme 8. $R^e$ is lower alkyl, e.g., methyl or ethyl, PG$^2$ is a protective group, e.g., benzyl, tert-butyldimethylsilyl, tert-butyldiphenylsilyl, or tetrahydropyran-2-yl, LG is a leaving group, e.g., chloro or bromo.

In step a, scheme 8, primary amine 15 is converted to secondary amine 27 by reductive amination reaction with carbonyl derivative 26A or by nucleophilic substitution reaction with halide 26B. The reductive amination reaction with 26A is performed in analogy with scheme 5, step a. The nucleophilic substitution reaction with 26B is performed, e.g., in a solvent such as methanol, ethanol, or acetonitrile, at temperatures between 20° C. and the boiling point of the solvent, in the presence of a base, e.g., potassium hydrogencarbonate, potassium carbonate, optionally in the presence of sodium iodide.

In step b, scheme 8, secondary amine 27 is converted to amide of general formula 29 through reaction with N-aryl amino acid 28 using methods well known to someone skilled in the art. For instance, the reaction is carried out in the presence of a coupling agent such as N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine, and/or 4-(dimethylamino)pyridine.

Alternatively, this reaction can be performed in two steps involving first formation of the acyl halide derivative of 28 and subsequent coupling reaction with amine 27 in the presence of a base. Typically employed reagents for the formation of the acyl chloride are thionyl chloride, phosphorus pentachloride, oxalyl chloride or cyanuric chloride, and the reaction is generally conducted in the absence of a solvent or in the presence of an aprotic solvent like dichloromethane, toluene or acetone. A base can optionally be added, like for example pyridine, triethylamine, diisopropylethylamine or 4-methylmorpholine, and catalytic amounts of N,N-dimethylformamide may be used. The obtained acyl chloride can be isolated or reacted as such with amine 27 in an aprotic solvent, like dichloromethane, tetrahydrofuran or acetone, in the presence of a base. Typical bases are triethylamine, 4-methylmorpholine, pyridine, diisopropylethylamine or 4-(dimethylamino) pyridine or mixtures thereof.

Alternatively, such reactions can be performed in two steps involving first formation of a mixed anhydride derivative of 28 obtained by reaction with a reagent such as ethyl chloroformate, isobutyl chloroformate, or acetic anhydride, in a solvent such as dichloromethane or tetrahydrofuran, at temperatures between −30° C. and 20° C., and subsequent reaction with amine 27 as described above.

In the case where the presence of a hydroxy group in $R^3$ or $R^4$ (e.g., $R^3$ or $R^4$=hydroxy or hydroxymethyl) may interfere with the amide coupling reaction of step b, the hydroxyl of 27 may be temporarily protected as the trimethylsilyl ether by reaction with chlorotrimethylsilane, in the presence of a base, e.g., triethylamine of N-methylmorpholine.

N-Aryl amino acids 28 are commercially available or can be synthesized as described in the experimental section.

In step c, scheme 8, cleavage of the acetal and reductive cyclization of 29 leads to piperazinone 5A. This conversion is performed either in one step using an acid, e.g., trifluoroacetic acid or methanesulfonic acid, and a reducing agent such as sodium borohydride or triethylsilane, in solvents such as dichloromethane, 1,4-dioxane, tetrahydrofuran, water, or mixtures thereof. Alternatively, the reaction may be performed in two steps, by first forming a 3,4-dihydro-1H-pyrazin-2-one intermediate in the presence of an acid, e.g., trifluoroacetic acid or methanesulfonic acid, in a solvent such as water or dichloromethane, and subsequent catalytic hydrogenation at pressures between 1 bar and 10 bar, using a suitable catalyst, e.g., palladium on activated charcoal, in solvents such as methanol, ethanol, ethyl acetate, or mixtures thereof, at temperatures between 0° C. and 50° C.

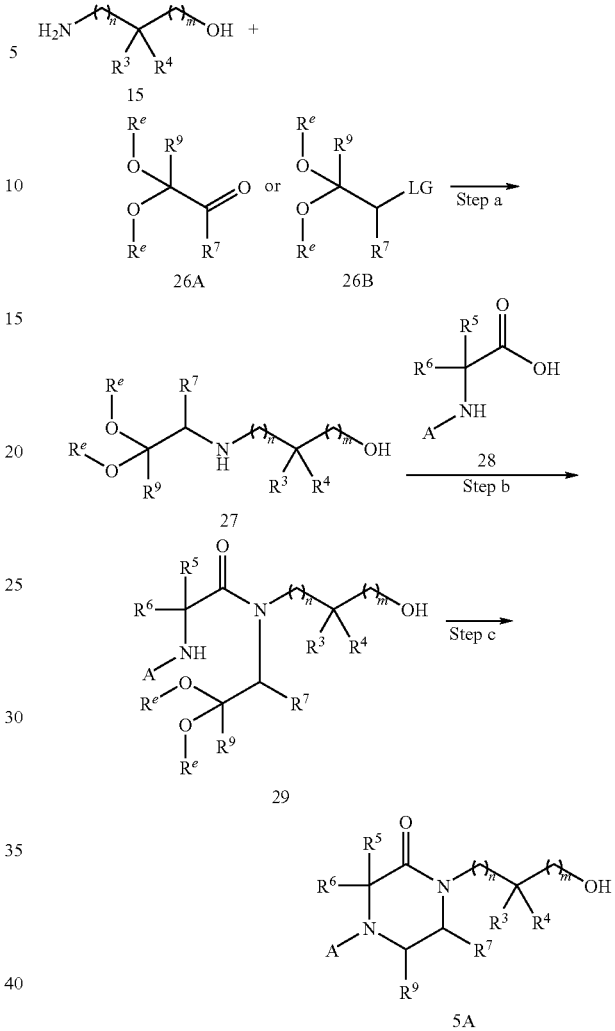

Scheme 8

In Scheme 8, A, $R^3$, $R^4$, $R^5$, $R^6$, $R^7$, $R^9$, m and n are as defined before. $R^e$ is lower alkyl, e.g., methyl or ethyl.

Compound (I) in which p is 0, $R^8$ and $R^{10}$ are H is represented by the general formula (IA).

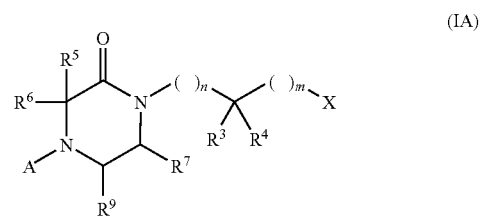

A, X, $R^3$, $R^4$, $R^5$, $R^6$, $R^7$, $R^9$, m and n are as defined before.

Compounds (IA) can be also synthesized as described in scheme 9. $PG^3$ is a suitable protective groups such as tert-butoxycarbonyl or benzyloxycarbonyl, LG is a leaving group, e.g., chloro or bromo, $R^e$ is lower alkyl, e.g., methyl or ethyl.

In step a, scheme 9, alcohol 30A is oxidized to aldehyde 31, in analogy with scheme 2, step c. Alternatively, aldehyde 31 is obtained from alkene 30B, in analogy with scheme 11, step b.

Compounds of formula 30A and 30B are either commercially available or can be synthesized as described in the experimental section.

In step b, scheme 9, aldehyde 31 is reacted with amine of the general formula $HN(R^1)(R^2)$, in analogy with scheme 2, step d, leading to 32.

In step c, the protective group of 32 is removed in analogy with scheme 3, step b, leading to 33.

In step d, scheme 9, primary amine 33 is converted to secondary amine 34 by reaction with 26A or 26B, in analogy with scheme 8, step a.

In step e, scheme 9, N-aryl amino acid 28 is coupled with amine 34 in analogy with scheme 8, step b, leading to 35.

In step f, scheme 9, cleavage of the acetal, and reductive cyclization of 35 leads to piperazinone (IA). This conversion is performed in analogy with scheme 8, step c.

Intermediates 30, 31, and 32 may contain one ore more hydroxy groups. It may be convenient to convert one or more of these hydroxy groups to silyl ethers, e.g., triethylsilyl, tert-butyldimethylsilyl, or tert-butyldiphenylsilyl. This conversion can be performed using methods known in the art, as described in the experimental section. The removal of such protective groups can take place under the acidic reaction conditions of step f. Otherwise, the deprotection reaction is performed using methods and reagents known in the art. Preferred reagents are hydrogen fluoride-pyridine in acetonitrile at 20-80° C., or tetrabutylammonium fluoride in tetrahydrofuran, at 20-60° C.

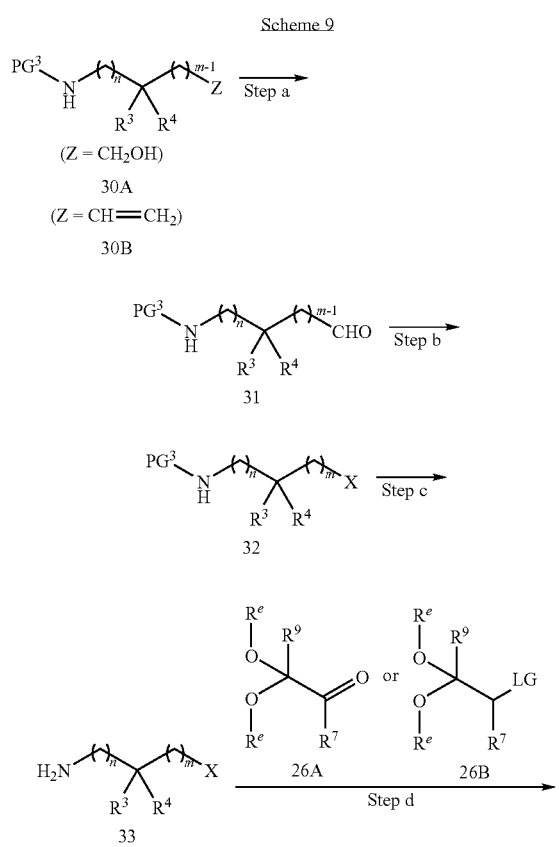

Scheme 9

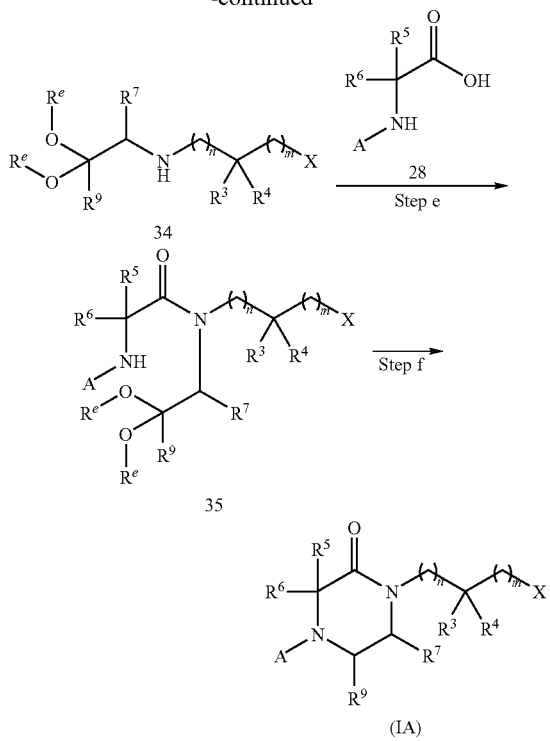

In Scheme 9, A, X, $R^3$, $R^4$, $R^5$, $R^6$, $R^7$, $R^9$, m and n are as defined before. $R^e$ is lower alkyl, e.g., methyl or ethyl.

Intermediate 5 in which $R^3$ is mono- or di-$C_{1-6}$ substituted carbamoyl is represented by formula 5B.

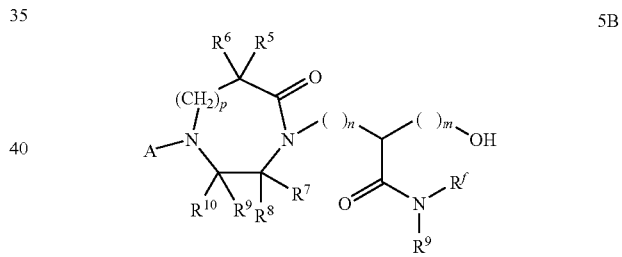

A, $R^5$, $R^6$, $R^7$, $R^8$, $R^9$, $R^{10}$, m, n, p and $PG^2$ are as defined before.

Compounds of formula 5B can also be prepared as described in scheme 10. $R^f$ and $R^g$ are independently hydrogen or $C_{1-6}$ alkyl, $PG^2$ is a protective group, e.g., benzyl, tert-butyl-dimethylsilyl or tert-butyl-diphenylsilyl.

In step a, scheme 10, removal of the protective group, $PG^2$, of 4A and lactonization leads to intermediate 36. This reaction is performed, e.g., in the presence of boron tribromide, in a solvent such as dichlormethane, at temperatures between −78° C. and 20° C. Alternatively, in the case where $PG^2$ is tert-butyl-dimethylsilyl or tert-butyl-diphenylsilyl, fluoride reagents, e.g., tetrabutylammonium fluoride, may be used, in solvents such as tetrahydrofuran, at temperatures between 0° C. and 50° C.

In step b, scheme 10, the lactone ring of 36 is opened with amine of formula $HN(R^f)(R^g)$, leading to hydroxyamide 5B. The reaction is carried out with or without solvent (e.g., water, methanol, ethanol, tetrahydrofuran, toluene, or mixtures thereof), at temperatures between −20° C. and 150° C., optionally in the presence of catalytic amounts of 2-hydroxypyridine. Alternatively, the amines may be substituted by their hydrochloride salts, $HN(R^f)(R^g) \cdot HCl$, and the reaction is carried out as described above and, in addition, in the presence of a base, e.g., triethylamine.

Scheme 10

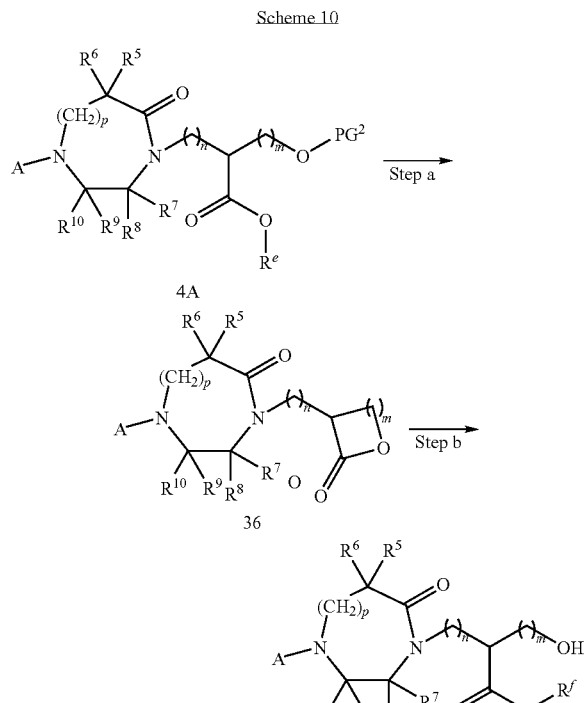

In Scheme 10, A, $R^3$, $R^4$, $R^5$, $R^6$, $R^7$, $R^9$, m, n and p are as defined before. $R^f$ and $R^g$ are independently hydrogen or $C_{1-6}$ alkyl.

Intermediates of formula 6 may also be prepared as outlined in scheme 11. LG is a leaving group, e.g., chloro, bromo, iodo, or methanesulfonyloxy.

In step a, scheme 11, heterocycle 1 is reacted with alkylating agent 37, leading to 38. The reaction is performed in analogy with scheme 1.

In step b, scheme 11, aldehyde 6 is obtained from alkene 38 by oxidation using methods known in the art. Preferably, 38 is reacted with sodium periodate in the presence of catalytic amounts of a suitable osmium source such as osmium(VIII) oxide or potassium osmate(VI) dihydrate, in solvents such as acetone, tert-butylalcohol, water, or mixtures thereof, at temperatures between 0° C. and 30° C.

Scheme 11

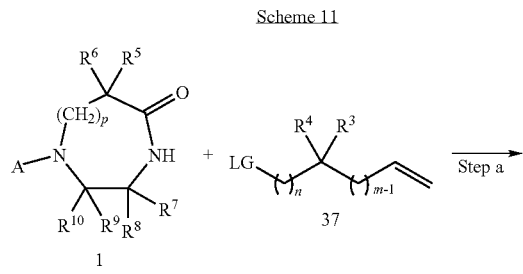

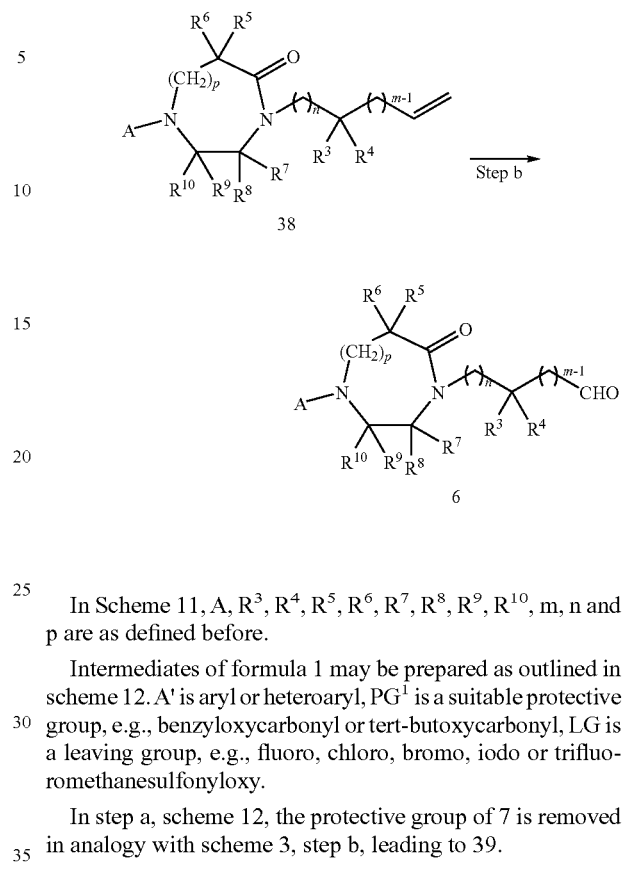

In Scheme 11, A, $R^3$, $R^4$, $R^5$, $R^6$, $R^7$, $R^8$, $R^9$, $R^{10}$, m, n and p are as defined before.

Intermediates of formula 1 may be prepared as outlined in scheme 12. A' is aryl or heteroaryl, $PG^1$ is a suitable protective group, e.g., benzyloxycarbonyl or tert-butoxycarbonyl, LG is a leaving group, e.g., fluoro, chloro, bromo, iodo or trifluoromethanesulfonyloxy.

In step a, scheme 12, the protective group of 7 is removed in analogy with scheme 3, step b, leading to 39.

In step b, scheme 12, heterocycle 39 is reacted with 10A, 10B or 10C in analogy with scheme 3, step c, leading to 1.

Scheme 12

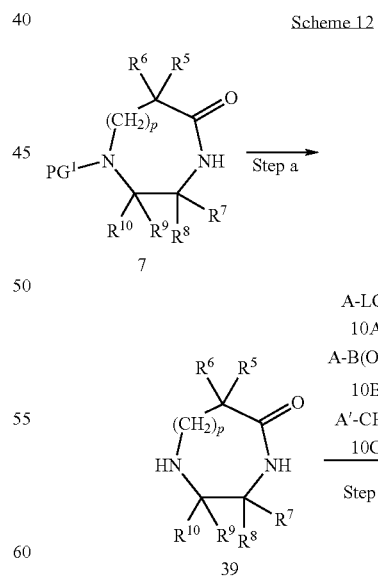

In Scheme 12, A, $R^5$, $R^6$, $R^7$, $R^8$, $R^9$, $R^{10}$ and p are as defined before. A' is aryl or heteroaryl.

Intermediate 7 in which p is 1 is represented by the general formula 7A.

7A

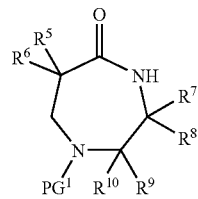

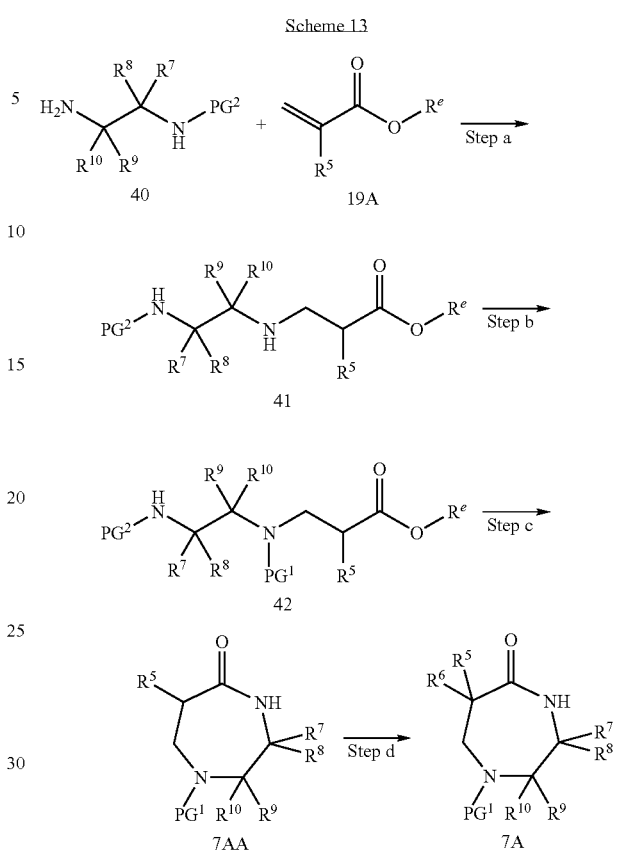

$R^5$, $R^6$, $R^7$, $R^8$, $R^9$ and $R^{10}$ are as defined before.

Intermediates 7A are commercially available or can be synthesized as outlined in scheme 13. $PG^1$ and $PG^2$ are suitable orthogonal protective groups, e.g., benzyloxycarbonyl and tert-butoxycarbonyl, $R^e$ is lower alkyl, e.g., methyl or ethyl.

In step a, scheme 13, protected 1,2-diaminoethane derivative 40 is reacted with acrylate 19A, leading to 41. The reaction is performed either neat or, preferably, in a solvent such as methanol, at temperatures between 0° C. and 50° C.

In step b, scheme 13, the amino group of 41 is protected, using reagents and methods known in the art, thus leading to 42. In the case where $PG^1$ is tert-butoxycarbonyl, the reaction is carried out, e.g., with di-tert-butyl dicarbonate, in a solvent such as dichloromethane or N,N-dimethylformamide, optionally in the presence of a base, e.g., triethylamine. In the case where $PG^1$ is benzyloxycarbonyl, the reaction is performed, e.g., with N-(benzyloxycarbonyloxy)succinimide or with benzyl chloroformate, in solvents such as water, ethyl acetate, acetone, tetrahydrofuran, or mixtures thereof, in the presence of a base, e.g., triethylamine, sodium hydrogencarbonate, or potassium carbonate.

In step c, scheme 13, the protective group of the terminal amino group, $PG^2$, is removed and the resulting aminoester cyclized to [1,4]diazepan-5-one 7AA, using methods and reagents known in the art. In the case where $PG^2$ is tert-butoxycarbonyl, the deprotection is preferably accomplished using concentrated aqueous hydrochloric acid solution, in a solvent such as ethyl acetate, at temperatures between 0° C. and 80° C. The aminoester hydrochloride intermediate is then cyclized under suitable conditions. For instance the reaction is carried out in the presence of an inorganic base, e.g., sodium carbonate, in a solvent such as water or methanol, at temperatures between 20° C. and 80° C. Alternatively, the reaction is performed in the presence of an organic base, e.g., 1,5,7-triaza-bicyclo[4.4.0]dec-5-ene, in a solvent such as dichloromethane or tetrahydrofuran, at temperatures between 0° C. and 40° C.

In optional step d, scheme 13, substituents $R^6$ can be introduced in the ring system of 7AA, leading to 7A. This is accomplished through double deprotonation of the protons at N(4) and C(6) of the [1,4]diazepan-5-one ring under suitable conditions (e.g., lithium hexamethyldisilazide or lithium diisopropyl amide in a solvent like tetrahydrofuran at temperatures between −78° C. and 0° C.), followed by selective alkylation with an electrophile of the general formula $R^6$-LG, in which LG is a leaving group such as bromo, iodo, or trifluoromethanesulfonyloxy, thus leading to 7A.

In Scheme 13, $R^5$, $R^6$, $R^7$, $R^8$, $R^9$ and $R^{10}$ are as defined before. $R^e$ is lower alkyl, e.g., methyl or ethyl.

Compounds of formula 40 are commercially available or can be synthesized as described in the experimental section. In particular, compounds of formula 40 where $R^7$, $R^8$, $R^9$ are H, $R^{10}$ is $CH_3$, and the asymmetric carbon has the (R)-configuration are represented by formula 40A. Compounds of formula 40A may be prepared from commercially available (R)-1,2-diaminopropane dihydrochloride (43) as outlined in scheme 14. $PG^2$ is a suitable protective group, e.g., benzyloxycarbonyl or tert-butoxycarbonyl.

In the case where $PG^2$ is tert-butoxycarbonyl, the reaction is performed using a slight excess, preferably 1.25 equivalents of di-tert-butyl dicarbonate and a slight excess of a base, e.g., sodium hydroxide, preferably ca. 1.3 equivalents. The reaction is carried out in a suitable solvent, e.g., water, methanol, ethanol, or mixtures thereof, preferably in ethanol/water at a ratio between 1:1 and 2:1, at temperatures between 0° C. and 25° C.

Scheme 14

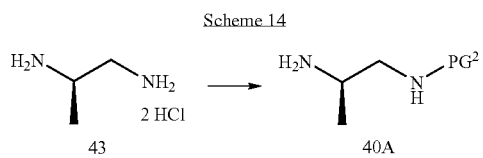

Intermediate 1 in which $R^7$, $R^8$ and $R^{10}$ are H and p is 0 is represented by formula 1A.

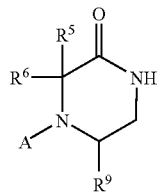
1A

Intermediates 1A can also be synthesized as outlined in scheme 15. LG$^1$ and LG$^2$ are leaving groups, e.g., chloro or bromo.

In step a, scheme 15, aniline 18 is alkylated with haloacetonitrile 44, leading to 45. This reaction is performed in the presence of a base, e.g., sodium carbonate or potassium carbonate, in a solvent such as acetonitrile or N,N-dimethylformamide, optionally in the presence of sodium iodide, at temperatures between 20° C. and 150° C.

In step b, scheme 15, nitrile 45 is reduced to primary amine 46, using reagents and methods known in the art. For instance, the reaction is performed in the presence a suitable reducing agent such as of borane-tetrahydrofuran complex or lithium aluminum hydride, in a solvent such as tetrahydrofuran, at temperatures between −20° C. and 60° C.

In step c, scheme 15, amine 46 is coupled with haloacetic acid 47, in analogy with scheme 8, step b, leading to amide 48.

In step d, scheme 15, compound 48 is cyclized to 1AA, using reagents and methods known in the art. For instance, the reaction is performed in the presence of a base, e.g., sodium hydrogencarbonate or potassium carbonate, in a suitable solvent, e.g., acetone, acetonitrile, methanol, or ethanol, optionally in the presence of sodium iodide, at temperatures between 20° C. and 100° C.

In optional step e, scheme 15, substituents R$^6$ can be introduced in the ring system of 1AA, leading to 1A. This is accomplished through double deprotonation of the protons at N(1) and C(3) of the piperazin-2-one ring under suitable conditions (e.g., lithium hexamethyldisilazide or lithium diisopropyl amide in a solvent like tetrahydrofuran at temperatures between −78° C. and 0° C.), followed by selective alkylation with an electrophile of the general formula R$^6$-LG, in which LG is a leaving group such as bromo, iodo, or trifluoromethanesulfonyloxy.

Scheme 15

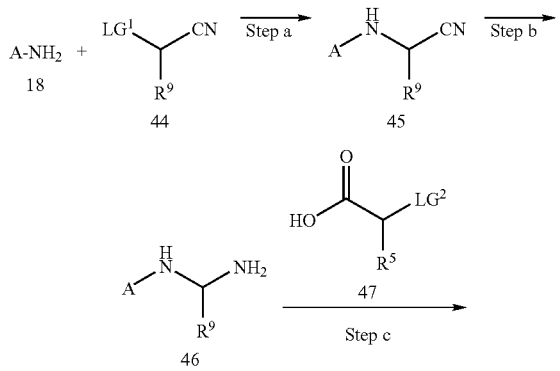

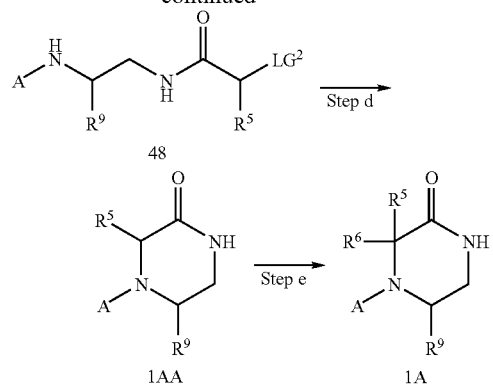

In Scheme 15, A, R$^5$, R$^6$, and R$^9$ are as defined before.

Intermediate 4A in which R$^7$ is H is represented by the general formula 4AA.

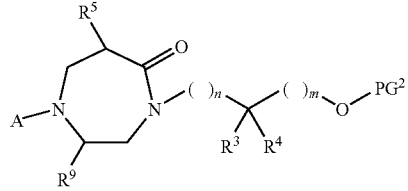
4AA

A, R$^3$, R$^4$, R$^5$, R$^9$, m and n are as defined before.

Intermediate 4AA can be also synthesized as described in scheme 16. R$^e$ is tert-butyl, benzyl, or lower alkyl, e.g., methyl or ethyl, LG$^2$ is a leaving group such as fluoro, chloro, bromo, iodo, or trifluoromethanesulfonyloxy, PG$^2$ is a protective group, e.g., benzyl, tetrahydropyran-2-yl, tert-butyldimethylsilyl or tert-butyldiphenylsilyl.

In step a, scheme 16, halide or sulfonate 10A is transformed into 50 by reaction with amino acid 49, using methods well known in the art, e.g., Ullmann-type coupling reaction. The reaction is carried out using a suitable catalyst, e.g., copper iodide, optionally in the presence of 2-hydroxybenzaldehyde phenylhydrazone with a base like potassium phosphate, in solvents such as N,N-dimethylformamide or N,N-dimethylacetamide, at temperatures between 0° C. and 150° C., preferably at 80-100° C.

Compounds of formula 10A and amino acids 49 are either commercially available or can be synthesized as described in the experimental section.

In step b, scheme 16, acid 50 is reduced to give alcohol 51, e.g., with borane-tetrahydrofuran complex, in solvents such as tetrahydrofuran at temperatures between 0° C. and 20° C.

In step c, scheme 16, alcohol 51 is oxidized to the corresponding aldehyde, as described in scheme 2, step c. The aldehyde intermediate is immediately reacted with amine 15 to give intermediate 52, in analogy to scheme 2, step d.

In step d, scheme 16, secondary amine 52 is converted to amide of general formula 54 through reaction with acid 53 using methods well known to someone skilled in the art. For instance, the reaction is carried out in the presence of a coupling agent such as 2-chloro-1-methylpyridinium iodide in the presence of tributylamine as a base, in aprotic solvents such as dichloromethane, tetrahydrofuran, N,N-dimethylformamide, N-methylpyrrolidinone and mixtures thereof at temperatures between 0° C. and room temperature.

Acids 53 are commercially available or can be synthesized from the corresponding ester or as described in the experimental section.

In step e, scheme 16, cleavage of the acetal and reductive cyclization of 54 leads to ring system 4AA. This conversion is performed in one step using an acid, e.g., trifluoroacetic acid, methanesulfonic acid, and/or boron trifluoride etherate, and a reducing agent such as triethylsilane, in a solvent such as dichloromethane.

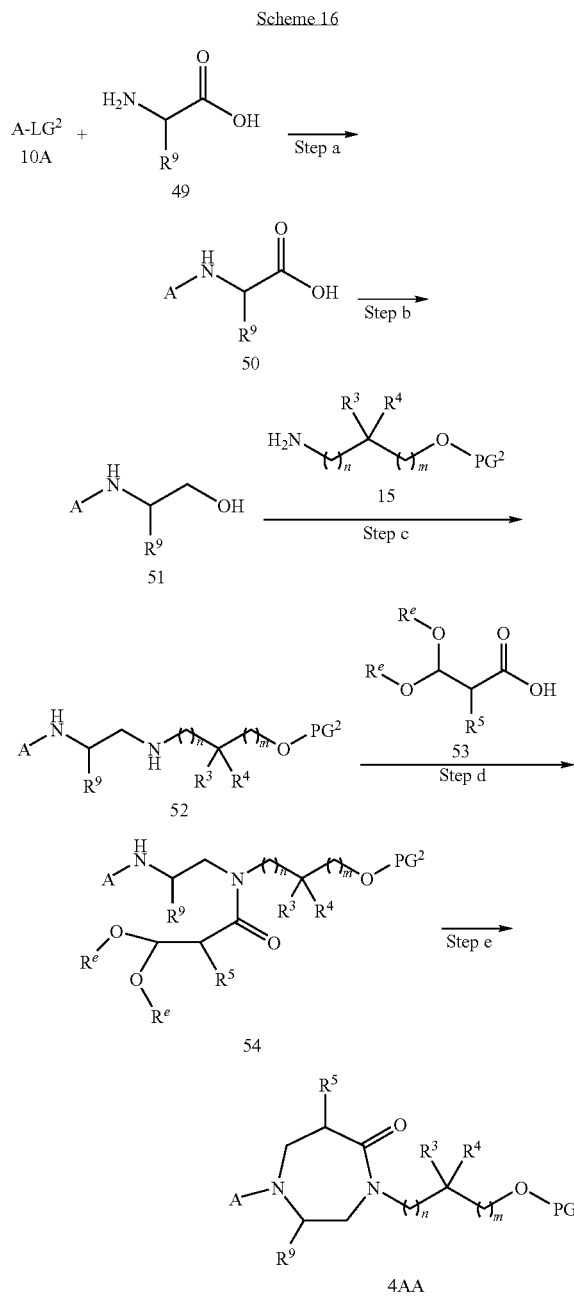

In Scheme 16, A, $R^3$, $R^4$, $R^5$, $R^6$, $R^9$, $R^e$, m and n are as defined before.

Compounds of formula (I) in which $R^3$ is OH, $R^4$ is H, and m is 1 are represented by general formula (IB)

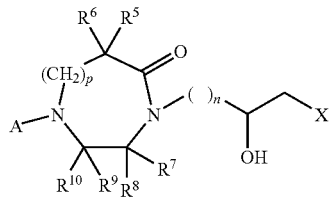

A, $R^5$, $R^6$, $R^7$, $R^8$, $R^9$, $R^{10}$, X, n and p are as defined before.

Compounds of formula (IB) can also be synthesized as described in scheme 17. W is methyl, trifluoromethyl, phenyl, or 4-methylphenyl.

In step a, scheme 17, diol 5C is converted to sulfonate 55 by selective reaction with an appropriate sulfonyl halide, e.g., methanesulfonyl chloride (in the case where W is methyl). This reaction is performed in the presence of a suitable base, e.g., pyridine, 2,4,6-trimethylpyridine or triethylamine, in a solvent such as dichloromethane, tetrahydrofuran, or N,N-dimethylacetamide, at temperatures between −78° C. and 20° C.

In step b, scheme 17, sulfonate 55 is converted to epoxide 56 through intramolecular cyclization. This reaction is performed in the presence of a suitable base, e.g., sodium hydride or lithium bis(trimethylsilyl)amide, in a solvent such as tetrahydrofuran or N,N-dimethylacetamide, at temperatures between −20° C. and 50° C.

In step c, epoxide 56 is converted to (IB) by reaction with an amine of the general formula $HN(R^1)(R^2)$. This reaction is performed in the presence of a suitable base, e.g., potassium carbonate, cesium carbonate and/or N,N-diisopropylethylamine, in a solvent such as tetrahydrofuran or N,N-dimethylacetamide, at temperatures between 0° C. and 150° C.

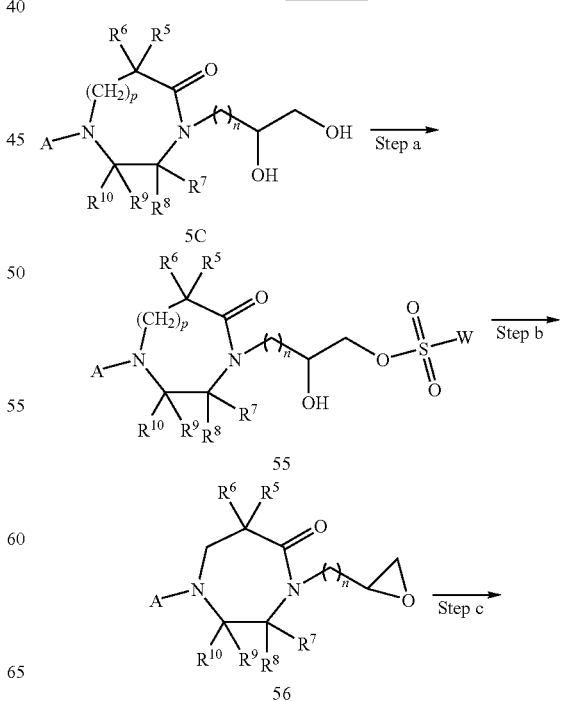

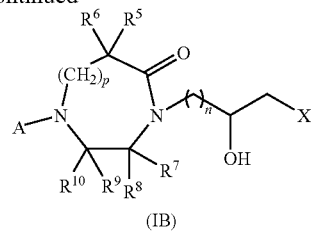

(IB)

In scheme 17, A, $R^5$, $R^6$, $R^7$, $R^8$, $R^9$, $R^{10}$, X, n and p are as defined before.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbent or eluent). The invention embraces all of these forms.

As described above, the compounds of formula (I) are CCR2 receptor antagonists, with some antagonist activity also at CCR3 and CCR5. These compounds consequently prevent migration of various leukocyte populations through the blockade of CCR2 stimulation. They therefore can be used for the treatment and/or prevention of inflammatory and/or allergic diseases, such as peripheral arterial occlusive disease, critical limb ischemia (CLI), vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable bowel syndrome, Crohn's disease, multiple sclerosis, neuropathic pain, atherothrombosis and/or burns/ulcers in diabetes/CLI, and asthma.

Prevention and/or treatment of inflammatory diseases, particularly peripheral arterial occlusive diseases or atherothrombosis is the preferred indication.

The invention therefore also relates to pharmaceutical compositions comprising a compound as defined above and a pharmaceutically acceptable excipient.

The invention likewise embraces compounds as described above for use as therapeutically active substances, especially as therapeutically active substances for the treatment and/or prophylaxis of inflammatory and/or allergic diseases, particularly as therapeutically active substances for the treatment and/or prophylaxis of peripheral arterial occlusive disease, critical limb ischemia, vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable bowel syndrome, Crohn's disease, multiple sclerosis, neuropathic pain, atherothrombosis, burns/ulcers in diabetes/CLI, and allergy, asthma.

The invention also relates to the use of compounds as described above for the preparation of medicaments for the therapeutic and/or prophylactic treatment of inflammatory and/or allergic diseases, particularly for the therapeutic and/or prophylactic treatment of peripheral arterial occlusive disease, critical limb ischemia, vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable bowel syndrome, Crohn's disease, multiple sclerosis, neuropathic pain, atherothrombosis, burns/ulcers in diabetes/CLI, and asthma. Such medicaments comprise a compound as described above.

The invention also relates to the process and the intermediates for manufacturing the compounds of formula (I) as well as the process for manufacturing the intermediates.

CCR2 receptor antagonistic activity by the compounds of the present invention can be demonstrated by the following assays.

Receptor Binding Assays

Binding assays were done with membranes from CHOK1-CCR2B-A5 cells (Euroscreen) stably overexpressing the human CCR2B.

Membranes were prepared by homogenizing the cells in 10 mM Tris pH 7.4, 1 mM EDTA, 0.05 mM benzamidine, leupeptin 6 mg/L and separating the debris at 1000 g. The membranes were then isolated at 100000 g in 50 mM Tris pH 7.4, $MgCl_2$ 10 mM, EGTA 1 mM, glycerol 10%, benzamidine 0.05 mM, leupeptine 6 mg/l.

For binding, CCR2 antagonist compounds were added in various concentrations in 50 mM HEPES pH 7.2, 1 mM $CaCl_2$, 5 mM $MgCl_2$, 0.5% BSA, 0.01% $NaN_3$, together with 100 pM $^{125}$I-MCP-1 (PerkinElmer, 2200 Ci/mmol) to about 5 fMol CCR2 membranes and incubated for 1 hour at room temperature. For unspecific control 57.7 nM MCP-1 (R&D Systems or prepared at Roche) was added. Membranes were harvested through GF/B (glass fiber filter; PerkinElmer) plates, equilibrated with 0.3% polyethylenimine, 0.2% BSA, air dried and binding was determined by counting in a top-counter (NXT Packard). Specific binding was defined as total binding minus nonspecific binding and typically represents about 90-95% of the total binding. Antagonist activity is indicated as inhibitor concentration required for 50% inhibition ($IC_{50}$) of specific binding.

Calcium Mobilization Assay

CHOK1-CCR2B-A5 cells (from Euroscreen) stably overexpressing the human chemokine receptor 2 isoform B were cultured in Nutrient Hams F12 medium supplemented with 5% FBS, 100 U/ml penicillin, 100 µg/ml streptomycin, 400 µg/ml G418 and 5 µg/ml puromycin.

For the assay cells were grown overnight in 384-well black clear flat bottom polystyrene plates (Costar) at 37° C. at 5% $CO_2$. After washing with DMEM, 20 mM Hepes, 2.5 mM probenecid, 0.1% BSA (DMEM assay buffer) cells were loaded with 4 µM Fluo-4 in the same DMEM assay buffer for 2 hours at 30° C. Excess dye was removed and cells were washed with DMEM assay buffer. 384-well compound plates were prepared with DMEM assay buffer/0.5% dimethyl sulfoxide with or without various concentrations of test compounds. Usually compounds were tested for agonist and antagonist activity.

Test compounds were added to the assay plate and agonist activity was monitored as fluorescence for 80 seconds with a FLIPR (488 nm excitation; 510-570 nm emission; Molecular Devices). After 20-30 min. of incubation at 30° C., 20 nM MCP-1 (R&D; Roche) was added and fluorescence was monitored again for 80 seconds. Increases in intracellular calcium are reported as maximum fluorescence after agonist exposure minus basal fluorescence before exposure. Antagonist activity is indicated as inhibitor concentration required for 50% inhibition of specific calcium increases.

The compounds of formula (I) of the present invention exhibit $IC_{50}$ values in the Ca mobilization assay of 1 nM to 10 µM, preferably 1 nM to 1.5 µM for CCR2. The following table shows measured values for some selected compounds of the present invention.

| Example | IC$_{50}$ (μM) | Example | IC$_{50}$ (μM) |
|---|---|---|---|
| 1 | 0.04 | 2 | 0.01 |
| 3 | 0.13 | 4 | 0.06 |
| 5 | 0.02 | 6 | 0.01 |
| 7 | 0.09 | 8 | 0.60 |
| 9 | 0.18 | 11 | 0.40 |
| 12 | 0.12 | 13 | 0.03 |
| 14 | 0.01 | 15 | 0.06 |
| 16 | 0.01 | 17 | 0.14 |
| 18 | 0.65 | 19 | 0.41 |
| 20 | 0.35 | 22 | 0.10 |
| 23 | 0.01 | 24 | 0.09 |
| 25 | 0.20 | 27 | 0.07 |
| 28 | 0.40 | 29 | 0.64 |
| 32 | 0.14 | 34 | 0.93 |
| 41 | 0.58 | 42 | 0.18 |
| 44 | 0.02 | 45 | 0.01 |
| 47 | 0.01 | 48 | 0.03 |
| 49 | 0.005 | 50 | 0.03 |
| 51 | 0.19 | 52 | 0.13 |
| 54 | 0.01 | 55 | 0.01 |
| 56 | 0.01 | 58 | 0.68 |
| 59 | 0.08 | 61 | 0.076 |
| 62 | 0.33 | 64 | 0.663 |
| 65 | 0.016 | 66 | 0.546 |
| 67 | 0.052 | 68 | 0.046 |
| 69 | 0.011 | 70 | 0.579 |
| 71 | 0.226 | 72 | 0.306 |
| 74 | 0.005 | 76 | 0.007 |
| 78 | 0.013 | 79 | 0.029 |
| 80 | 0.318 | 82 | 0.073 |
| 83 | 0.002 | 84 | 0.015 |
| 86 | 0.033 | 87 | 0.053 |
| 88 | 0.325 | 89 | 0.035 |
| 90 | 0.508 | 94 | 0.008 |
| 95 | 0.013 | 96 | 0.026 |
| 99 | 0.008 | 100 | 0.334 |
| 101 | 0.073 | 102 | 0.006 |
| 103 | 0.092 | 104 | 0.203 |
| 105 | 0.027 | 107 | 0.015 |

The compounds of formula (I) and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula (I).

EXAMPLES

The following Examples serve to illustrate the present invention in more detail. They are, however, not intended to limit its scope in any manner.

Abbreviations:

The following are a list of abbreviations and/or acronyms with their corresponding definitions used in the following examples: AcOH=Acetic acid, aq.=aqueous, BuLi=Butyllithium, $CH_2Cl_2$=dichloromethane, $CH_3CN$=acetonitrile, DCE=1,2-dichloroethane, DMA=N,N-Dimethylacetamide, DMAP=4-Dimethylaminopyridine, DMF=N,N-Dimethylformamide, EDCI=N-(3-Dimethylaminopropyl)-N'-ethylcarbodiimide hydrochloride, EtOAc=Ethyl acetate, EtOH=Ethanol, $Et_2O$=Diethyl ether, $Et_3N$=Triethylamine, eq.=Equivalents, FTIR=Fourier transform infrared spectroscopy, GC=gas chromatography, HATU=O-(7-azabenzotriazol-1-yl)-1,1,3,3-tetramethyluronium hexafluorophosphate, HCl=Hydrochloric Acid, HPLC=high-pressure liquid chromatography, IPC=In-process control, ISP=ion spray, $KH_2PO_4$=potassium dihydrogenphosphate, $KHSO_4$=potassium hydrogensulfate, $LiBH_4$=Lithium borohydride, LiOH=lithium hydroxide, MS=mass spectrometry, MeOH=Methanol, NaH=Sodium hydride, NaCl=Sodium chloride, $NaHCO_3$=sodium hydrogencarbonate, NaOMe=Sodium methoxide, NMR=nuclear magnetic resonance spectroscopy, $Pd(OAc)_2$=Palladium (II) acetate, RT=room temperature, SBH=sodium borohydride, sat=saturated, TBME=tert-butyl methyl ether, tBuOH=tert-butylalcohol, TEMPO=2,2,6,6-tetramethylpiperidin-1-oxyl, THF=Tetrahydrofuran, quant.=quantitative and TLC=thin layer chromatography.

Intermediate 1

(rac)-4-(tert-Butyl-dimethyl-silanyloxy)-2-iodo-butyric acid methyl ester

A) (S)-4-(tert-Butyl-dimethyl-silanyloxy)-2-methanesulfonyloxy-butyric acid methyl ester A solution of 2.48 g (10.00 mmol) of methyl (S)-4-(tert-butyldimethylsilyloxy)-2-hydroxybutanoate (*J. Am. Chem. Soc.* 2005 127, 1090-1091) in 50 ml of $CH_2Cl_2$ was treated with 2.09 ml (15.00 mmol, 1.5 eq) of triethylamine and at 0° C. during 5 min with 0.82 ml (10.50 mmol, 1.051 eq) of methanesulfonyl chloride. After 1 h at 0° C. the reaction was partitioned between 10% aq $KH_2PO_4/Et_2O$ (×3), the organic phases were washed with sat. aq. $NaHCO_3$ solution (freshly prepared) and 10% aq. NaCl solution, dried over $Na_2SO_4$ and evaporated to give 2.91 g (89%) of the title compound as yellow oil. MS: 327.1 ($MH^+$).

B) (rac)-4-(tert-Butyl-dimethyl-silanyloxy)-2-iodo-butyric acid methyl ester A solution of 2.89 g (8.85 mmol) of (S)-4-(tert-butyl-dimethyl-silanyloxy)-2-methanesulfonyloxy-butyric acid methyl ester in 90 ml of 2-butanone was treated with 2.65 g (17.70 mmol) of sodium iodide and stirred at 90° C. for 1¼ h. The reaction was cooled, filtered and evaporated. The residue was suspended in $CH_2Cl_2$ treated with $Na_2SO_4$ and filtered to give after evaporation 2.94 g (93%) of the title compound as dark brown oil. MS: 343.0 $(M-CH_3)^+$.

Intermediate 2

(S)-6-Aza-spiro[2.5]octan-4-ol hydrochloride a) 4-Hydroxy-6-aza-spiro[2.5]octane-6-carboxylic acid tert-butyl ester

Method A

To a solution of diethylzinc (1.1 M solution in toluene, 37.5 ml, 0.04 mmol) in DCE (80 ml) at 0° C. was added chloroiodomethane (5.99 ml, 0.08 mmol) under Ar. This mixture was stirred for 15 minutes before a solution of 3-hydroxy-4-methylene-piperidine-1-carboxylic acid tert-butyl ester (*J. Org. Chem.* 2001, 66, 2487) (4.19 g, 19.6 mmol) in DCE (10 ml) was added, after which time the reaction was stirred for 0.5 h at 0° C. and then allowed to reach RT, stirring for a further 1 h. The reaction was then quenched by addition of sat. aq. ammonium chloride solution, separated, and the organic dried ($Na_2SO_4$) and concentrated. Purification by flash column chromatography (EtOAc/heptane 2:8→1:1) afforded the title product (2.4 g, 54%) as a crystalline solid. MS: 228.2 ($MH^+$).

Method B 2 g (9.4 mmol, 1 eq.) 3-hydroxy-4-methylene-piperidine-1-carboxylic acid tert-butyl ester were dissolved in toluene at 25° C. 17.05 ml (2 eq.) 1.1 M diethyl zinc solution in toluene were added at such a rate as to maintain the reaction temperature below 30° C. After 15-30 min at 25° C., 2.29 ml (3 eq.) diiodomethane were added over 2-3 h maintaining the reaction temperature at 25° C. (the reaction is best followed by Tr-Tj measurements and/or in-line FTIR reaction monitoring). After 30-60 min after the end of addition, 4.57 ml 2-ethyl-hexanoic acid were added to the resulting white suspension at such a rate as to maintain the reaction temperature between 25-30° C. The heavy white suspension was stirred for 30 min. 10 ml heptane were added followed by a mixture consisting of 20 ml 25% aq. ammonia solution and 30 ml water. The organic phase was separated and washed with a mixture consisting of 10 ml 25% aq. ammonia solution and 30 ml water. The organic phases were washed with 20 ml half sat. aq. NaCl solution, combined, dried over sodium sulfate, filtered and concentrated under reduced pressure to an oil (may crystallize upon standing). The crude spiro-piperidinol was purified by crystallization in heptane or alternatively in TBME/heptane providing the title product in ca 80% yield as a white powder.

b) (S)-4-Hydroxy-6-aza-spiro[2.5]octane-6-carboxylic acid tert-butyl ester

Method A

The title compound was prepared by chiral separation of (rac)-4-hydroxy-6-aza-spiro[2.5]octane-6-carboxylic acid tert-butyl ester on a Chiralpak® AD column (heptane/2-propanol 95:5).

Method B

4-Hydroxy-6-aza-spiro[2.5]octane-6-carboxylic acid tert-butyl ester (3.00 g; 13.07 mmol) was dissolved in TBME (20.5 ml) and vinyl butyrate (6.5 ml). The solution was heated to 50° C. and the reaction started by the addition of Lipase TL (3.0 g; Meito Sangyo, Tokyo). The solution was stirred at 50° C. for 46 h until the enantiomeric excess of the retained alcohol was >99%. The enzyme was filtered off, the filter cake washed with TBME and the filtrate concentrated in vacuo. The residual oil was chromatographed on silicagel (80 g; 0.040-0.063 mm; $CH_2Cl_2 \to CH_2Cl_2$/acetone 9:1) to separate the formed optically enriched (R)-butyrate from the retained (S)-alcohol (1.18 g white crystals; 40%). Analytics: >99 GC; >99% ee (GC on BGB-176; 30 m×0.25 mm; $H_2$; 1.2 bar; 80° C. to 210° C. with 3° C./min; inj. 200° C.; Det. 215° C.; Retention times: (R)-alcohol 28.58 min, (S)-alcohol 29.00 min). $[\alpha]_D = -43.35°$ (c=1.00, $CHCl_3$).

Method C

Step 1: 4-Oxo-6-aza-spiro[2.5]octane-6-carboxylic acid tert-butyl ester

The title compound was produced from 4-hydroxy-6-aza-spiro[2.5]octane-6-carboxylic acid tert-butyl ester, either by TEMPO/bleach oxidation or by Swern oxidation:

a) TEMPO/Bleach Oxidation

To a solution of 4-hydroxy-6-aza-spiro[2.5]octane-6-carboxylic acid tert-butyl ester (20.0 g, 88.0 mmol) in $CH_2Cl_2$ (170 ml) was added sodium bromide (1.092 g, 10.6 mmol), sodium bicarbonate (2.439 g, 29.0 mmol) and 2,2,6,6-tetramethylpiperidine 1-oxyl (237.1 mg, 1.49 mmol). The mixture was cooled to −5° C. and sodium hypochlorite solution (9.5% in water, 55.16 ml) was added within 10 min resulting in a red coloration and a temperature rise to 9° C. The mixture was stirred for 35 min at 0-5° C. and, as conversion was incomplete (2.5% starting material remaining), additional sodium hypochlorite solution (9.5% in water, 7.0 ml) was added within 30 min and the mixture stirred for another 30 min at 0° C. GC analysis indicated complete conversion (<0.1% starting material remaining). Sodium thiosulfate solution (10% in water, 100 ml) was added within 10 min resulting in decoloration. The organic phase was separated, washed with water (100 ml), dried over sodium sulfate (50 g), filtered and evaporated (15 mbar, 40° C.) to afford 4-oxo-6-aza-spiro[2.5]octane-6-carboxylic acid tert-butyl ester as yellowish powder (19.84 g), GC purity 99a %. The powder was dissolved in warm TBME (20 ml), heptane (60 ml) was added to induce crystallization and the white suspension stirred at 0-5° C. for 1.5 h. Filtration, washing with heptane (20 ml) and drying (10 mbar, 45° C.) afforded 4-oxo-6-aza-spiro[2.5]octane-6-carboxylic acid tert-butyl ester (17.25 g, 87%) as white crystalline material, GC purity 100a %. $^1$H-NMR (CDCl$_3$, 300 MHz): 4.08 (s, CH$_2$ (5)), 3.66 (m, CH$_2$ (7)), 1.88 (m, CH$_2$ (8)), 1.48 (s, tert-Bu), 1.40 (m, 2H), 0.81 (m, 2H).

b) Swern Oxidation

To a solution of oxalyl chloride (42.35 ml, 0.480 mol) in CH$_2$Cl$_2$ (910 ml) was added a solution of dimethylsulfoxide (68.24 ml, 0.961 mol) in CH$_2$Cl$_2$ (910 ml) at −70° C. within 45 min. The solution was stirred for 15 min and a solution of 4-hydroxy-6-aza-spiro[2.5]octane-6-carboxylic acid tert-butyl ester (91.00 g, 0.400 mol) in CH$_2$Cl$_2$ (910 ml) was added within 40 min keeping the internal temperature at below −60° C. The mixture was stirred for 35 min and triethylamine (280.4 ml, 2.00 mol) was added at below −60° C. within 10 min. The cooling bath was removed and the yellow suspension was stirred for 1 h then quenched with water (1.4 l). The organic phase was separated, washed with water (3×1 l) and sat. aq. NaCl solution (3 l) and evaporated. The residual orange powder was dissolved in TBME (1.40 l), the turbid solution filtered (Hyflo Speedex) to remove some insoluble material and the clear filtrate evaporated to provide crude 4-oxo-6-aza-spiro[2.5]octane-6-carboxylic acid tert-butyl ester as yellow powder (91.9 g). The material was re-dissolved in TBME (300 ml) and purified by filtration over silica gel (700 g) using a 3:1 heptane/TBME mixture (6.5 l). Evaporation and drying (10 mbar, 40° C.) afforded 4-oxo-6-aza-spiro[2.5]octane-6-carboxylic acid tert-butyl ester as whitish powder (80.58 g, 89%), GC purity 100a %.

Step 2:
(S)-4-Hydroxy-6-aza-spiro[2.5]octane-6-carboxylic acid tert-butyl ester

D(+)-glucose monoydrate (300 g) and magnesium chloride hexahydrate (1.0 g) were dissolved in 10 mM MES buffer pH 6.5 (2.4 L; Sigma M3671). After addition of 4-oxo-6-aza-spiro[2.5]octane-6-carboxylic acid tert-butyl ester (300 g; 1.33 mmol) and □-NAD (3.0 g; free acid; Roche Diagnostics Cat. No. 10 004 626) the pH was re-adjusted and the suspension heated to 35° C. The reaction was started by adding ketoreductase KRED-NADH-117 (3.0 g; former Biocatalytics, now Codexis) and glucose dehydrogenase GDH-102 (300 mg; Biocatalytics). The suspension was vigorously stirred at 35° C. keeping the pH constant at 6.5 by the controlled addition (pH-stat) of 1.0 M aq. sodium hydroxide solution. After a consumption of 1.307 L (corresponding to 98% conversion; after 17 h) the reaction mixture was extracted with EtOAc (10 L). The organic phase was dried over sodium sulfate and concentrated in vacuo (200 mbar/45° C.) until evaporation fell off. Upon cooling the oily residue (411 g) started to crystallize and was stirred with heptane (1 L) for 2 h. The crystals were filtered off and the filtrate evaporated to dryness, redissolved in EtOAc (150 ml) and concentrated in vacuo as described above. The crystal suspension formed again upon cooling was stirred with heptane (200 ml; 2 h) and the crystals filtered off. Both crops of crystals were washed with heptane and dried under high vacuum to yield the title compound in 93% yield (250.77 g and 34.60 g white crystals), each having a purity of >98.5% GC and 99.8% ee. $[\alpha]_D$=−44.97° (c=1.00, CHCl$_3$).

Method D

Step 1:
(S)-3-hydroxy-4-methylene-piperidine-1-carboxylic acid tert-butyl ester

3-Hydroxy-4-methylene-piperidine-1-carboxylic acid tert-butyl ester (4.50 g; 21.10 mmol) was dissolved in TBME (63 ml) and vinyl butyrate (22.5 ml). The solution was heated to 50° C. and the reaction started by the addition of Lipase TL IM (1.08 g (carrier-fixed); Novozymes, Denmark). The solution was stirred at 50° C. for 20 h until the enantiomeric excess of the retained alcohol was >99%. The enzyme was filtered off, the filter cake washed with TBME and the filtrate concentrated in vacuo. The residual oil was chromatographed on silicagel (100 g; 0.040-0.063 mm; CH$_2$Cl$_2$→CH$_2$Cl$_2$/acetone 9:1) to separate the formed optically enriched (R)-butyrate from the retained (S)-alcohol (1.83 g white crystals; 41%). Analytics: >99 GC; >99% ee (GC on BGB-176; 30 m×0.25 mm; H$_2$; 1.2 bar; 80° C. to 210° C. with 3° C./min; inj. 200° C.; Det. 210° C.; retention times: (R)-alcohol 29.60 min, (S)-alcohol 29.81 min). $[\alpha]_D$=−17.70° (c=1.00, CHCl$_3$).

Step 2:
(S)-4-Hydroxy-6-aza-spiro[2.5]octane-6-carboxylic acid tert-butyl ester

The title compound is produced analogously to intermediate 2a, Method B from (S)-3-hydroxy-4-methylene-piperidine-1-carboxylic acid tert-butyl ester.

c) (S)-6-Aza-spiro[2.5]octan-4-ol; hydrochloride

A solution of (S)-4-hydroxy-6-aza-spiro[2.5]octane-6-carboxylic acid tert-butyl ester (3.26 g, 14.3 mmol) in EtOH (10 ml) was treated at RT with HCl solution (4 M in 1,4-dioxane, 30 ml), then after 1 h TBME (40 ml) was added. The suspension was stirred for 1 h, then the precipitate was collected by filtration to afford the title compound (2.11 g, 90%). White solid, MS: 128.1 (M+H)$^+$.

Alternative Preparation of (S)-6-Aza-spiro[2.5]octan-4-ol; hydrochloride i) Cyclopropanecarboxylic acid tert-butyl ester 219.1 g (1913 mmol, 1 eq.) potassium tert-butylate were suspended in 2.5 L TBME and cooled to 0-5° C. 200 g (1 eq.) cyclopropanecarbonyl chloride were added over 60 min, maintaining the temperature between 0-5° C. (ice-EtOH bath cooling). In-line FTIR reaction monitoring indicates a feed controlled reaction. The reaction mixture was stirred 30 min at 0-5° C. and 1 L of 5% aq. NaHCO$_3$ solution was added. The aqueous phase was separated and extracted with 500 ml TBME. The organic phases were washed with 500 ml half sat. aq. NaCl solution, combined and concentrated under reduced pressure (30° C./150 mbar) to provide 271 g of the title compound (91% yield corrected for 8% residual TBME).

ii) 1-Allyl-cyclopropanecarboxylic acid tert-butyl ester 15.9 ml (1.15 eq.) diisopropylamine were dissolved in 65 ml THF and cooled to ca −10° C. 65 ml (1.08 eq.) 1.6 M BuLi solution in hexane were added over 25 min, maintaining the temperature between −10° C. and 0° C. After 50 min at ca. −5° C., the reaction mixture was cooled to −75° C. A solution of 15 g (96.7 mmol, 1 eq., 92% w/w purity) cyclopropanecarboxylic acid tert-butyl ester in 20 ml THF was added over 15 min keeping the temperature between −75° C. and −70° C. The reaction mixture was stirred 5 h at −75° C. (milky reaction mixture obtained after 2.5 h). A solution of 12.87 g (1.10 eq.) allyl bromide was added over 20 min keeping the temperature between −75° C. and −60° C. The reaction mixture was stirred at −78° C. for 1 h, warmed to RT and stirred overnight. The reaction mixture was cooled to 0° C. 100 ml sat. aq. ammonium chloride solution were added followed by 30 ml water providing a clear biphasic mixture. The mixture was extracted 3 times with 50 ml TBME. The organic phases were combined, dried over sodium sulfate, filtered and concentrated under reduced pressure (40° C./20 mbar) to afford 16.44 g of crude product. The crude product was distilled (2 mbar; ca 40° C. distillation head temperature) to provide the title compound in ca 65% yield.

iii) 1-(2-Oxo-ethyl)-cyclopropanecarboxylic acid tert-butyl ester 6.9 g (36.34 mmol, 1 eq., 96% a % by GC) 1-allyl-cyclopropanecarboxylic acid tert-butyl ester were dissolved in 40 ml $CH_2Cl_2$ and 40 ml MeOH. The solution was cooled to −72° C. and the ozone was bubbled through the reaction mixture until a blue color was obtained. Then nitrogen was bubbled to remove excess ozone until a colorless solution was obtained. 10 ml (3.68 eq.) dimethyl sulfide and 14 ml (2.76 eq.) triethylamine were added. The reaction mixture was warmed to RT and stirred overnight at that temperature (peroxide test negative, pH 7-8). The yellowish reaction mixture was added to 100 ml sat. aq. ammonium chloride solution (exothermic) and extracted 3 times with 70 ml $CH_2Cl_2$. The organic phases were combined, dried over sodium sulfate, filtered and concentrated under reduced pressure to provide the crude aldehyde, which was purified by filtration over $SiO_2$ ($CH_2Cl_2$; TLC:EtOAc/heptane 1:2) to provide 3.90 g (96% GC, 56% yield) of the title compound as an oil.

iv) 1-[2-(Benzyl-tert-butoxycarbonylmethyl-amino)-ethyl]-cyclopropanecarboxylic acid tert-butyl ester 10.5 g (54.7 mmol, 1 eq.) 1-(2-oxo-ethyl)-cyclopropanecarboxylic acid tert-butyl ester and 13.21 g (1.08 eq.) N-benzylglycine tert-butyl ester were dissolved in 140 ml toluene. 21 g (1.63 eq.) sodium triacetoxyborohydride were added (exotherm from 25° C. to 28° C.) and the reaction mixture was stirred 5 h at RT (IPC by GC). A solution of 2 ml (0.64 eq.) AcOH in 15 ml toluene was added. After 30 min at RT, the reaction mixture was cooled to 0° C. and 100 ml sat. aq. $NaHCO_3$ solution was added over 40 min (foaming). 50 ml EtOAc were added. The mixture was stirred for 30 min at RT. The mixture was extracted with 200 ml and a second time with 50 ml EtOAc. The organic phases were washed with 50 ml sat. aq. $NaHCO_3$ solution followed by 50 ml sat. aq. NaCl solution. The organic phases were combined, dried over sodium sulfate, filtered and concentrated under reduced pressure to give 21.5 g of the title compound as an oil (ca. 95% yield, corrected for ca 3% residual toluene and 3% amine starting material).

v) 6-Benzyl-6-aza-spiro[2.5]octan-4-one hydrochloride 10.8 g (24.4 mmol, 1 eq.) 1-[2-(benzyl-tert-butoxycarbonylmethyl-amino)-ethyl]-cyclopropanecarboxylic acid tert-butyl ester were dissolved in 35 ml THF. 50 ml (2.05 eq.) 1 M lithium hexamethyldisilazanide solution in THF were added dropwise over 2.5 h maintaining the temperature between 20° C. and 25° C. After 2 h at RT (IPC by HPLC), the reaction mixture (containing the lithium salt of 6-benzyl-4-hydroxy-6-aza-spiro[2.5]oct-4-enc-5-carboxylic acid tert-butyl ester) was cooled to −10° C. (ice EtOH cooling bath) and 75 ml 1 M aq. sulfuric acid solution were added (temperature increased to 2° C.). The reaction mixture was warmed to RT and the THF removed under reduced pressure at 40° C. The resulting reaction mixture was heated to 40° C. for 1 h, was stirred 15 h at RT and an additional 3 h at 40° C. to complete the reaction (IPC by GC; intermediate 6-benzyl-4-hydroxy-6-aza-spiro[2.5]oct-4-ene-5-carboxylic acid tert-butyl ester is hydrolyzed and decarboxylation follows). The reaction mixture was cooled to 0° C. and was neutralized to pH 7.4 by addition of 10 ml 2 M aq. sodium hydroxide solution and 50 ml 1M aq. $NaHCO_3$ solution were added, setting the pH to 9.4. The crude solution was extracted with TBME and EtOAc. The organic phases were combined, dried over sodium sulfate and filtered over a plug of $SiO_2$. The solution was concentrated under reduced pressure (45° C./20 mbar) to give 4.56 g of the crude product as free base. The crude oil was dissolved in 8 ml EtOAc, cooled to 0° C. and 5.1 ml HCl solution (4.3 M in EtOAc) were added dropwise (exotherm 2° C. to 18° C.). The reaction mixture was stirred overnight at RT (gummy crystals) and filtered. The filter cake was washed with 10 ml EtOAc and dried under reduced pressure until constant weight to give 4.54 g of the title compound as off-white crystals (74% yield).

vi) (S)-6-Benzyl-6-aza-spiro[2.5]octan-4-ol

A mixture of 300 mg of 6-benzyl-6-aza-spiro[2.5]octan-4-one hydrochloride (1.19 mmol, 1 eq.), 1.5 ml of 2-propanol and 28 ml of 30 mM aq. TRIS-HCl buffer (pH 8.1) was heated to 35° C. The pH was re-adjusted to 8.0. The reaction was started by adding β-NAD (1 mg; free acid; Roche Diagnostics Cat. No. 10 004 626) and ketoreductase KRED-NADH-117 (29.3 mg; Codexis [ex. Biocatalytics]). The suspension was stirred at 35° C. keeping the pH constant at 8.0 by the controlled addition (pH-stat) of 1.0 M aq. sodium hydroxide solution. After roughly 80 area % conversion and 1 d, further 2-propanol (0.3 ml), β-NAD (3 mg; free acid; Roche Diagnostics Cat. No. 10 004 626), ketoreductase KRED-NADH-117 (30 mg; Codexis [ex. Biocatalytics]) and magnesium chloride (12.7 mg) were added. After 4 d, 98.5 area % conversion and 5.9 ml consumption of 1.0 M aq. sodium hydroxide solution the reaction mixture was stopped by the addition of NaCl (9 g), EtOAc (30 ml) and filter aid (1 g Dicalite Speedex). The mixture was stirred 30 min. and filtered. The filtrate was extracted 3 times with 30 ml EtOAc. The combined organic phases were dried over sodium sulfate, filtered and concentrated under reduced pressure to provide the crude product in over 99.9% e.e. Purification by flash chromatography provided the title compound as a colorless oil.

vii) (S)-6-Aza-spiro[2.5]octan-4-ol 100 mg (S)-6-benzyl-6-aza-spiro[2.5]octan-4-ol were dissolved in 1 ml MeOH and hydrogenated over palladium on barium sulfate. After de-benzylation (IPC by GC), the catalyst was filtered and the filtrate was concentrated under reduced pressure to provide the title compound. The amino alcohol was treated with di-tert-butyl-dicarbonate in MeOH in the presence of triethylamine. The crude tert-butoxycarbonyl-protected amine product was analyzed by chiral GC (BGB-176; 30 m×0.25 mm; 80° C. to 210° C. in 43 min) and proved to be identical with intermediate 2b.

The hydrochloride salt of the title compound can be obtained by treating the aminoalcohol with HCl in EtOAc.

Preparation of N-benzylglycine tert-butyl ester 40 g (205 mmol, 1 eq.) tert-butyl bromoacetate were dissolved in 200 ml CH$_3$CN. The solution was cooled to 0-5° C. and 47 g benzylamine (2.14 eq.) in solution in 90 ml CH$_3$CN were added over 15 min. After 5 min, the reaction mixture was warmed to RT and stirred for 3 h (IPC by GC). The resulting suspension was filtered and evaporated to constant weight to give 49 g of a yellow oil. The oil was dissolved in 200 ml heptane and washed 3 times with 50 ml aq. NaHCO$_3$ solution. The organic phase was dried over sodium sulfate, filtered and evaporated to give 35.8 g of the crude product. Distillation under high vacuum afforded 27.2 g of the title product (95% pure by GC).

Intermediate 3

(3S,4S)-4-Methyl-piperidin-3-ol; hydrochloride a) (rac, trans)-3-Hydroxy-4-methyl-piperidine-1-carboxylic acid tert-butyl ester (rac, trans)-1-Benzyl-4-methyl-piperidin-3-ol (*Tetrahedron. Lett.* 2000, 41, 5817) (13.0 g, 63 mmol) was dissolved in MeOH with palladium hydroxide (20% on activated charcoal, 4 g) and stirred under a hydrogen atmosphere (balloon) for 16 h after which time di-tert-butyl dicarbonate (13.8 g, 63 mmol) was added, the reaction stirred for 1 h, filtered through Hyflo and concentrated to afford the title product (13.3 g, 98%) as a crystalline solid. MS: 216.2 (MH$^+$).

b) (rac, trans)-4-Methyl-3-(4-nitro-benzoyloxy)-piperidine-1-carboxylic acid tert-butyl ester (rac, trans)-3-Hydroxy-4-methyl-piperidine-1-carboxylic acid tert-butyl ester (6.0 g, 28 mmol) was dissolved in THF (40 ml) with triphenylphosphine (8.9 g, 34 mmol), 4-nitrobenzoic acid (5.7 g, 34 mmol) and cooled to 0° C. before dropwise addition of diisopropyl azodicarboxylate (6.9 g, 34 mmol). The ice bath was removed and the reaction allowed to come to RT, stirring for 16 h. The reaction was then directly absorbed onto silica gel and purified by flash column chromatography (EtOAc/heptane 2:8) to afford the title product (4.0 g, 40%) as a white solid. MS: 365.2 (MH$^+$).

c) (rac, cis)-3-Hydroxy-4-methyl-piperidine-1-carboxylic acid tert-butyl ester (rac, trans)-4-Methyl-3-(4-nitro-benzoyloxy)-piperidine-1-carboxylic acid tert-butyl ester (5.0 g, 14 mmol) was dissolved in MeOH (70 ml) and 6 M aq. sodium hydroxide solution (4.5 ml, 27 mmol) was added. The reaction was stirred for 1 h after which time the solvent removed under vacuum, the residue portioned between water and CH$_2$Cl$_2$ and the organic collected, dried (Na$_2$SO$_4$) and concentrated to afford the title product (2.6 g, 87%) as a crystalline solid. MS: 216.1 (MH$^+$).

d) (3S,4S)-4-Methyl-piperidin-3-ol; hydrochloride (rac, cis)-3-Hydroxy-4-methyl-piperidine-1-carboxylic acid tert-butyl ester was separated on a Chiralpak AD column (Isopropanol/Heptane 5:95) and subsequently, the (−)-enantiomer was deprotected with HCl in dioxane to afford the title compound as a white powder. MS: 116.2 (MH$^+$).

Intermediate 4

(3S,5S)-5-Methyl-piperidin-3-ol; hydrochloride a) (S)-3-(Benzyl-ethoxycarbonylmethyl-amino)-butyric acid ethyl ester To EtOH (55 ml) cooled to 0° C. was added acetyl bromide (41 ml, 0.6 mol) dropwise, followed by a solution of (S)-4-methyl-dihydro-furan-2-one (*Tetrahedron* 1983, 39, 3107; 18.6 g, 0.2 mol) in EtOH (20 ml). The ice bath was removed and the reaction allowed to reach RT. After 2 h of stirring the reaction was concentrated, the residue redissolved in CH$_2$Cl$_2$, washed with sat. aq. NaHCO$_3$ solution, dried (Na$_2$SO$_4$) and concentrated affording (S)-4-bromo-3-methyl-butyric acid ethyl ester (33.6 g, quant). This was redissolved in EtOH (100 ml), cooled to 0° C. and N-benzylglycine ethyl ester (28.2 g, 0.14 mol) and triethylamine (22.4 ml, 0.16 mmol) were added. The reaction was then warmed to 75° C. for 4 d after which time the reaction was concentrated, the residue redissolved in CH$_2$Cl$_2$, washed with sat. aq. NaHCO$_3$ solution, dried (Na$_2$SO$_4$) and concentrated. Purification by flash column chromatography (EtOAc/heptane 5:95) afforded the titled product as a light gold oil (20.3 g, 43%). MS (ISP)=322.2 (M+H)$^+$.

b) (S)-1-Benzyl-5-methyl-piperidin-3-one

To a suspension of NaH (55% dispersion in mineral oil, 6.4 g, 14 mmol) in toluene (90 ml) was added (S)-3-(benzyl-ethoxycarbonylmethyl-amino)-butyric acid ethyl ester (20.3 g, 0.06 mol) in toluene (10 ml), followed by EtOH (1 ml). A vigorous reaction ensued, after 15 minutes the reaction was diluted with EtOAc, washed with 10% aq. citric acid solution, dried (Na$_2$SO$_4$) and concentrated. The residue was purified by flash column chromatography (EtOAc/heptane 1:9) affording a complex mixture of diastereomers (7.2 g, 42%). A portion of this material (3.5 g, 13 mmol) was dissolved in 25% aq. HCl solution (20 ml) and heated in a loosely closed tube at 120° C. for 36 h. The solvent was evaporated, the residue redissolved in CH$_2$Cl$_2$, washed with sat. aq. NaHCO$_3$ solution, dried (Na$_2$SO$_4$) and concentrated. Purification by flash column chromatography (EtOAc/heptane 1:4) afforded the titled product as a crystalline solid (1.1 g, 43%). MS (ISP)=204.3 (M+H)$^+$.

c) (3S,5S)-1-Benzyl-5-methyl-piperidin-3-ol

To a solution of (S)-1-benzyl-5-methyl-piperidin-3-one (1.1 g, 5 mmol) in dry THF (15 ml) at −78° C. was added K-selectride (10.8 ml, 11 mmol, 1 M solution in THF). After 2 h at −78° C. a few drops of water were cautiously added, the reaction allowed to reach RT, the THF removed by evaporation and the residue the residue redissolved in CH$_2$Cl$_2$, washed with sat. aq. NaHCO$_3$ solution, dried (Na$_2$SO$_4$) and concentrated. Purification by flash column chromatography (EtOAc/heptane 1:4) afforded the titled product as a crystalline solid (0.9 g, 43%). MS (ISP)=204.3 (M+H)$^+$.

d) (3S,5S)-5-Methyl-piperidin-3-ol; hydrochloride

To a solution of (S)-1-benzyl-5-methyl-piperidin-3-one (0.9 g, 4 mmol) was dissolved in MeOH, 25% aq. HCl solution added until the pH was acidic, followed by palladium (10% on activated charcoal, 0.2 g). The mixture was stirred under 1 atmosphere of hydrogen (balloon) for 6 h. The reaction was then filtered through Hyflo and concentrated to afford the title product as a white powder (0.66 g, quant). MS (ISP)=116.1 (M+H)$^+$.

Intermediate 5

(S)-2-Amino-4-benzyloxy-butyric acid methyl ester; hydrochloride 15.5 ml of acetyl chloride was added dropwise to 95 ml of MeOH cooled in ice. The solution was stirred for 5 min and 15.47 g (73.91 mmol) O-benzyl-L-homoserine was added in one portion (in analogy to *Synthesis* 1997, 10, 1146). The mixture was stirred at RT for 1 h, and warmed for 2½ h at reflux. The solution was cooled and the solvent removed by evaporation under reduced pressure. The residue was dissolved in CH$_2$Cl$_2$ and evaporated and dried under reduced pressure overnight to give 19.41 g (quantitative) of the title compound as white solid. MS: 224.1 (MH$^+$).

Intermediate 6

4-(3-Piperidin-1-yl-propyl)-[1,4]diazepan-5-one; dihydrochloride

A) 5-Oxo-4-(3-piperidin-1-yl-propyl)-[1,4]diazepane-1-carboxylic acid tert-butyl ester A solution of 8.52 g (39.75 mmol) of 5-oxo-[1,4]diazepane-1-carboxylic acid tert-butyl ester in 200 ml of DMA was treated at 0° C. with 2.60 g (59.6 mmol) of NaH (55% dispersion in oil) in small portions. The reaction was stirred 1 h at this temperature, then the free 1-(3-chloropropyl)piperidine in 200 ml toluene was dropped in [49.62 g (250.42 mmol, 6.3 eq.) 1-(3-chloropropyl)piperidine hydrochloride were dissolved in 262 ml of 1 M aq. NaOH solution and extracted with toluene (200 ml). The organic phase was dried over Na$_2$SO$_4$]. The reaction was warmed up to RT and stirred overnight. After 2 h at 50° C. and cooling to RT, the reaction was neutralized with water (50 ml), evaporated and then dissolved in sat. aq. NaHCO$_3$/Et$_2$O. After reextraction with Et$_2$O, the organic phase was dried (Na$_2$SO$_4$), evaporated and crystallized from pentane to yield 12.08 g (90%) of the title compound as white crystals. MS: 340.2 (MH$^+$).

B) 4-(3-Piperidin-1-yl-propyl)-[1,4]diazepan-5-one; dihydrochloride

A solution of 7.3 g (21.50 mmol) of 5-oxo-4-(3-piperidin-1-yl-propyl)-[1,4]diazepane-1-carboxylic acid tert-butyl ester was dissolved in 140 ml CH$_2$Cl$_2$, cooled to 0° C. and treated with 54 ml (215.03 mmol) of 4 M HCl in dioxane, then warmed to After 3 h, 40 ml of MeOH were added to dissolve the precipitation and stirring was continued over night. The solution was evaporated, dissolved in toluene and evaporated (2×) to yield 7.71 g (quantitative) of the title compound as a white solid. MS: 240.1 (MH$^+$).

Intermediate 7

(R)-2-Amino-4-benzyloxy-butyric acid methyl ester; hydrochloride

In analogy to the procedure described for intermediate 5, O-benzyl-D-homoserine gave the title compound in quantitative yield as white solid. MS: 224.2 (MH$^+$).

Intermediate 8

4-Methyl-piperidin-4-ol

Prepared according to the procedure published in J. Med. Chem. 1965, 8, 766-776.

Intermediate 9

(rac)-2,5-Dibromo-N,N-dimethyl-pentanamide

A) (rac)-2,5-Dibromo-pentanoyl chloride

Prepared according to the procedure published in Chem. Pharm. Bull. 1982, 30, 1225-1233 (and J. *Heterocyclic Chem.* 1973, 795).

B) (rac)-2,5-Dibromo-N,N-dimethyl-pentanamide

To a solution of dimethylamine (0.91 ml, 7.18 mmol; 40% solution in water) and 2.75 ml (19.76 mmol) of Et$_3$N in 6 ml of CH$_2$Cl$_2$ cooled at 0° C. was added dropwise a solution of 2,5-dibromo-pentanoyl chloride (1.00 g, 3.59 mmol) in 4 ml CH$_2$Cl$_2$. After stirring 1 h at RT, the reaction mixture was partitioned between CH$_2$Cl$_2$ and water. The organic phases were washed with water and brine and the aqueous layers extracted twice with CH$_2$Cl$_2$. The organic phases were dried over MgSO$_4$, evaporated and purified by flash silica gel column (EtOAc/n-heptane 1:1) to afford 0.66 g (64%) of the title product as light yellow oil. MS: 288.1 (2Br, MH$^+$).

Intermediate 10

4-(tert-Butyl-dimethyl-silanyloxy)-2-iodo-butyric acid methyl ester

A) 4-(tert-Butyl-diphenyl-silanyloxy)-2-methanesulfonyloxy-butyric acid methyl ester The title compound was produced in analogy to intermediate 1A from methyl 4-(tert-butyldiphenylsilyloxy)-2-hydroxybutanoate (synthesized from DL-malic acid as described in *J. Org. Chem.* 1993, 58, 7768). Orange oil, MS: 468.2 (M+NH$_4$)$^+$.

B) 4-(tert-Butyl-diphenyl-silanyloxy)-2-iodo-butyric acid methyl ester

The title compound was produced in analogy to intermediate 1B from 4-(tert-butyl-diphenyl-silanyloxy)-2-methanesulfonyloxy-butyric acid methyl ester. Dark brown oil, MS: 483.2 (M+H)$^+$.

Intermediate 11

2-(3,4-Dichloro-phenylamino)-propionic acid

A) 2-(3,4-Dichloro-phenylamino)-propionic acid ethyl ester

A mixture of 3,4-dichloroaniline (20.0 g, 120 mmol), ethyl 2-bromopropionate (26.0 g, 144 mmoL), and NaHCO$_3$ (15.1 g, 180 mmol) in EtOH (200 mL) was heated at reflux. After 16 h another portion of ethyl 2-bromopropionate (13.9 g, 96.7 mmol) and NaHCO$_3$ (8.00 g, 95 mmol) was added, and the mixture heated at reflux for an additional 24 h, then evaporated under vacuum. The residue was partitioned between EtOAc and water. The organic layer was washed with brine, dried (MgSO$_4$), filtered, and evaporated. Chromatography (SiO$_2$; heptane/EtOAc 1:1) afforded the title compound (26.1 g, 83%). Yellow oil, MS: 262.0 (M+H)$^+$.

B) 2-(3,4-Dichloro-phenylamino)-propionic acid

A mixture of 2-(3,4-dichloro-phenylamino)-propionic acid ethyl ester (10.0 g, 38.1 mmol) and LiOH (2.74 g, 114 mmol) in THF/MeOH/water 2:1:1 (100 mL) was heated at reflux for 3 h, then after cooling poured onto water and extracted with TBME. The organic phase was extracted twice with 1 M aq. sodium hydroxide solution. The aqueous phases were combined, acidified to pH 2-3 by addition of 37% aq. HCl solution, and extracted with EtOAc. The organic layer was dried (MgSO$_4$), filtered, and evaporated to produce the title compound (7.32 g, 82%). Light yellow solid, MS: 233.9 (M+H)$^+$.

Alternative Preparation of
2-(3,4-dichloro-phenylamino)-propionic acid

A mixture of 1-bromo-3,4-dichlorobenzene (5.10 g, 22.1 mmol), L-alanine (2.96 g, 33.2 mmol) copper(I) iodide (421 mg, 2.21 mmol), tri-potassium phosphate n-hydrate (15.3 g, 66.4 mmol), 2-(dimethylamino)ethanol (5.92 g, 66.4 mmol), and water (22 mL) was heated at 90° C. for 40 h, then poured onto ice water. The pH was set to 6 with 25% aq. HCl solution, and the mixture was extracted with EtOAc. The aqueous phase was acidified to pH 4.5 and extracted with EtOAc. The combined organic layers were dried (MgSO$_4$), filtered, and evaporated. Chromatography (SiO$_2$; EtOAc) afforded the title compound (2.71 g, 53%) as a 60:40 mixture of the (S) and (R) stereoisomers. Light brown solid, MS: 232.1 (M–H)$^-$.

Alternative Preparation of
2-(3,4-dichloro-phenylamino)-propionic acid

A mixture of 3,4-dichloroiodobenzene (1.50 g, 5.50 mmol), L-alanine (734 mg, 8.25 mmol), copper(I) iodide, 2-hydroxybenzaldehyde phenylhydrazone (233 mg, 1.10 mmol), tri-potassium phosphate (3.50 g, 16.5 mmol), and N,N-dimethylformamide (8 mL) was stirred at 80° C. for 40 h, then after cooling diluted with water and acidified to pH 3 by addition of 37% aq. HCl solution. The mixture was extracted with EtOAc, the organic phase was washed with brine, dried (MgSO$_4$), filtered, and evaporated. Chromatography (SiO$_2$; EtOAc) afforded the title compound (1.08 g, 67%) as a 71:29 mixture of the (S) and (R) stereoisomers (accordingly, when D-alanine was used instead of L-alanine as starting material, the title compound was obtained as a 29:71 mixture of the (S) and (R) stereoisomers). Brown solid, MS: 232.1 (M–H)$^-$.

Intermediate 12

2-(4-Chloro-3-trifluoromethyl-phenylamino)-propionic acid

The title compound was produced in analogy with intermediate 11 from 2-chloro-5-iodobenzotrifluoride and L-alanine as a 80:20 mixture of the (S) and (R) stereoisomers. Dark brown oil, MS: 266.2 (M–H)$^-$.

Intermediate 13

2-(4-Fluoro-3-trifluoromethyl-phenylamino)-propionic acid

The title compound was produced in analogy with intermediate 11 from 2-fluoro-5-iodobenzotrifluoride and L-alanine as a 82:18 mixture of the (S) and (R) stereoisomers. Dark brown oil, MS: 250.1 (M–H)$^-$.

Intermediate 14

2-(3-Chloro-4-fluoro-phenylamino)-propionic acid

The title compound was produced in analogy with intermediate 11 from 3-chloro-4-fluoroiodobenzene and L-alanine as a 82:18 mixture of the (S) and (R) stereoisomers. Brown solid, MS: 216.2 (M–H)$^-$.

Intermediate 15

2-(Biphenyl-4-ylamino)-propionic acid

The title compound was produced in analogy with intermediate 11 from 4-bromo-biphenyl and L-alanine as a 82:18 mixture of the (S) and (R) stereoisomers. Light yellow solid, MS: 240.3 (M–H)$^-$.

Intermediate 16

2-(Naphthalen-2-ylamino)-propionic acid

The title compound was produced in analogy with intermediate 11 from 2-bromonaphthalene and L-alanine as a 66:34 mixture of the (S) and (R) stereoisomers. Brown solid.

Intermediate 17

2-(3-Chloro-4-trifluoromethyl-phenylamino)-propionic acid

The title compound was produced in analogy with intermediate 11 from 3-chloro-4-(trifluoromethyl)aniline and ethyl 2-bromopropionate, followed by hydrolysis of the ester intermediate. Light yellow solid, MS: 266.2 (M–H)$^-$.

Intermediate 18

(S)-2-(3-Chloro-4-trifluoromethyl-phenylamino)-propionic acid

A solution of (R)-(+)-1-phenylethylamine (104 mg, 0.86 mmol) in diisopropyl ether/MeOH 20:1 (4.5 mL) was added dropwise at RT to a solution of 2-(3-chloro-4-trifluoromethyl-phenylamino)-propionic acid (417 mg, 1.56 mmol) in diisopropyl ether/MeOH 20:1 (4.5 mL), then after 2 h the precipitate was collected by filtration, washed with diisopropyl ether, and dried under vacuum. This material was digested in chloroform (3 mL) at 50° C. for 18 h, then collected by filtration, and dried under vacuum to afford 2-(3-chloro-4-trifluoromethyl-phenylamino)-propionic acid (R)-(+)-1-phenylethylamine salt (187 mg). This salt was partitioned between 10% aq. KHSO$_4$ solution and EtOAc. The organic layer was dried (MgSO$_4$), filtered, and evaporated to afford the title compound (134 mg, 32%) in an enantiomeric ratio of 98.5:1.5. White solid.

Intermediate 19

(S)-2-(4-Chloro-3-trifluoromethoxy-phenylamino)-propionic acid

A) 2-Chloro-4-iodo-1-trifluoromethyl-benzene

To a solution of 3-chloro-4-(trifluoromethyl)aniline (450 mg, 2.30 mmol) and toluene 4-sulfonic acid (1.19 g, 6.92 mmol) in CH$_3$CN (10 mL) was added a solution of potassium iodide (955 mg, 5.76 mmol) and sodium nitrite (318 mg, 4.61 mmol) in water (1.8 mL) over 15 min at 10° C., then after 20 min the reaction mixture was poured onto water, neutralized with sat. aq. NaHCO$_3$ solution, treated with 2 M aq. sodium thiosulfate solution (6 mL), and extracted with EtOAc. The organic layer was dried (MgSO$_4$), filtered, and evaporated to afford the title compound (517 mg) as a light brown oil, which was directly used in the next step.

B) 2-(4-Chloro-3-trifluoromethoxy-phenylamino)-propionic acid

The title compound was produced in analogy with intermediate 11 from 2-chloro-4-iodo-1-trifluoromethyl-benzene and L-alanine as a 70:30 mixture of the (S) and (R) stereoisomers. Yellow solid, MS: 282.3 (M−H)$^−$.

C) (S)-2-(4-Chloro-3-trifluoromethoxy-phenylamino)-propionic acid

The title compound was produced in analogy with intermediate 18 from 2-(4-chloro-3-trifluoromethoxy-phenylamino)-propionic acid by fractional crystallization with (R)-(+)-1-phenylethylamine and obtained in an enantiomeric ratio of 99:1. White solid, MS: 282.2 (M−H)$^−$.

Intermediate 20

N-(3,4-Dichlorophenyl)glycine

The title compound was produced in analogy with intermediate 11 from 3,4-dichloroaniline and ethyl bromoacetate, followed by hydrolysis of the ester intermediate. Off-white solid.

Intermediate 21

2-(4-Fluoro-3-trifluoromethoxy-phenylamino)-propionic acid

The title compound was produced in analogy with intermediate 11 from 4-fluoro-3-(trifluoromethoxy)aniline and ethyl 2-bromopropionate, followed by hydrolysis of the ester intermediate. Off-white solid, MS: 266.3 (M−H)$^−$.

Intermediate 22

2-(3,4-Dichloro-phenylamino)-butyric acid

The title compound was produced in analogy with intermediate 11 from 3,4-dichloroaniline and ethyl 2-bromobutyrate, followed by hydrolysis of the ester intermediate. Light yellow solid, MS: 246.3 (M−H)$^−$.

Intermediate 23

2-(3-Iodo-phenylamino)-propionic acid

The title compound was produced in analogy with intermediate 11 from 3-iodoaniline and ethyl 2-bromopropionate, followed by hydrolysis of the ester intermediate. Off-white solid, MS: 290.1 (M−H)$^−$.

Intermediate 24

(S)-2-(3,4-Dichloro-phenylamino)-propionic acid

The title compound was produced in analogy with intermediate 18 from 2-(3,4-dichloro-phenylamino)-propionic acid (intermediate 11) by fractional crystallization with (R)-(+)-1-phenylethylamine and obtained in an enantiomeric ratio of 98:2. White solid, MS: 232.1 (M−H)$^−$.

Intermediate 25

(S)-2-(3-Trifluoromethoxy-phenylamino)-propionic acid

A) 2-(3-Trifluoromethoxy-phenylamino)-propionic acid

The title compound was produced in analogy with intermediate 11 from 3-(trifluoro-methoxy)aniline and ethyl 2-bromopropionate, followed by hydrolysis of the ester intermediate. Light yellow solid, MS: 248.2 (M−H)$^−$.

B) (S)-2-(3-Trifluoromethoxy-phenylamino)-propionic acid

The title compound was produced in analogy with intermediate 18 from 2-(3-trifluoromethoxy-phenylamino)-propionic acid by fractional crystallization with (R)-(+)-1-phenylethylamine and obtained in an enantiomeric ratio of 96:4. Light yellow solid, MS: 248.2 (M−H)$^−$.

Intermediate 26

2-(4-Trifluoromethyl-phenylamino)-propionic acid

The title compound was produced in analogy with intermediate 11 from 4-(trifluoro-methyl)aniline and ethyl 2-bromopropionate, followed by hydrolysis of the ester intermediate. Light brown solid, MS: 232.1 (M−H)$^−$.

Intermediate 27

2-(3-Fluoro-4-trifluoromethyl-phenylamino)-propionic acid

The title compound was produced in analogy with intermediate 11 from 3-fluoro-4-(trifluoromethyl)aniline and ethyl 2-bromopropionate, followed by hydrolysis of the ester intermediate. Light yellow solid.

Example 1

(S)-2-[4-(3,4-Dichloro-phenyl)-7-oxo-[1,4]diazepan-1-yl]-4-((S)-4-hydroxy-6-aza-spiro[2.5]oct-6-yl)-butyric acid methyl ester

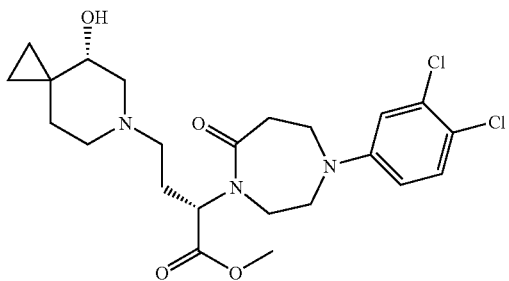

A) 3-(3,4-Dichloro-phenylamino)-propionic acid tert-butyl ester

A solution of 9.61 g (59.33 mmol) of 3,4-dichloro-phenylamine and 10.21 ml (59.33 mmol) of 2,6-lutidine in 55 ml of toluene was treated slowly with 6.50 ml (59.33 mmol) of tert-butyl 3-bromopropionate and stirred 30 h at reflux temperature. The reaction was then partitioned between 10% aq. $KHSO_4$ solution and EtOAc (3×). The organic phases were washed with 10% aq. NaCl solution, dried over $Na_2SO_4$ evaporated and purified by flash silica gel column (n-heptane: EtOAc 9:1) to yield 8.98 g (52%) of the title compound as off-white solid. MS: 290.0 (MH$^+$, 2Cl).

B) 3-[(3,4-Dichloro-phenyl)-methoxycarbonylmethyl-amino]-propionic acid tert-butyl ester A neat solution of 8.82 g (30.39 mmol) of 3-(3,4-dichlorophenylamino)-propionic acid tert-butyl ester, 13.97 ml (151.97 mmol) of methyl bromoacetate and 17.64 ml (151.97 mmol) of 2,6-lutidine was stirred 14 h at 60° C., diluted with 20 ml of $CH_3CN$ and heated at 115° C. for 6 h. The reaction was then partitioned between aq. 10% $KHSO_4$ solution and EtOAc (3×). The organic phases were washed with aq. 10% NaCl solution, dried over $Na_2SO_4$ evaporated and purified by flash silica gel column (n-heptane:EtOAc 95:5 to 9:1) to yield 7.86 g (71%) of the title compound as an yellow oil. MS: 362.0 (MH$^+$, 2Cl).

C) 3-[(3,4-Dichloro-phenyl)-(2-hydroxy-ethyl)-amino]-propionic acid tert-butyl ester A solution of 7.76 g (21.43 mmol) of 3-[(3,4-dichlorophenyl)-methoxycarbonylmethyl-amino]-propionic acid tert-butyl ester in 250 ml of ETOH was treated at 0° C. with 0.98 g (42.86 mmol) of $LiBH_4$. The reaction was stirred 10 min at 0° C. and 15 h at RT. After cooling (0° C.) a second batch of 0.49 g (21.43 mmol) of $LiBH_4$ was added and stirred 6 h at RT. The reaction was cooled (0° C.), neutralized with aq. 10% $KHSO_4$ solution and extracted with EtOAc (3×). The organic phase was dried over $Na_2SO_4$ evaporated and purified by flash silica gel column (n-heptane:EtOAc 9:1 to 1:1) to yield 6.12 g (85%) of the title compound as light yellow oil. MS: 334.2 (MH$^+$, 2Cl).

D) 3-[(3,4-Dichloro-phenyl)-(2-oxo-ethyl)-amino]-propionic acid tert-butyl ester To a solution of 1.91 ml (21.77 mmol) of oxalyl chloride in 64 ml $CH_2Cl_2$ at −50 to −60° C. was added a solution of 3.22 ml (45.42 mmol) dimethylsulfoxide in 12 ml of $CH_2Cl_2$ within 20 min. The solution was stirred for 5 min, then a solution of 6.33 g (18.93 mmol) of 3-[(3,4-dichloro-phenyl)-(2-hydroxy-ethyl)-amino]-propionic acid tert-butyl ester in 43 ml $CH_2Cl_2$ was added within 20 min. The mixture was stirred for 15 min and 13.17 ml (94.63 mmol) of triethylamine were added within 20 min. The suspension was stirred for 3 h and slowly warmed to 0° C. The reaction was neutralized with cold aq. 10% $KH_2PO_4$ solution (adjusted with solid $KH_2PO_4$ to pH 4-5) and extracted with EtOAc (3×). The organic phases were washed with aq. 10% $KH_2PO_4$, solution sat. aq. $NaHCO_3$ solution, aq. 10% NaCl solution, dried over $Na_2SO_4$ evaporated to yield 6.26 g (99.6%) of the title compound as orange oil. MS: 332.0 (MH$^+$, 2Cl).

E) (S)-4-Benzyloxy-2-{2-[(2-tert-butoxycarbonyl-ethyl)-(3,4-dichloro-phenyl)-amino]-ethylamino}-butyric acid methyl ester 6.26 g (18.83 mmol) of 3-[(3,4-dichloro-phenyl)-(2-oxoethyl)-amino]-propionic acid tert-butyl ester and 4.89 g (18.83 mmol) of (S)-2-amino-4-benzyloxy-butyric acid methyl ester; hydrochloride (intermediate 5) were dissolved in DCE:EtOH (1:1, 134 ml) and treated slowly with 3.15 ml (18.83 mmol) of triethylamine, 4.94 ml of AcOH and 4.94 ml (39.55 mmol, 8 M in pyridine) of pyridine-borane complex (cooling with a water bath to RT). The reaction was stirred at RT over 1 h, then partitioned between aq. $NaHCO_3$ solution and EtOAc (3×). The organic phases were washed with aq. sat. $NaHCO_3$ solution, aq. 10% NaCl solution, dried over $Na_2SO_4$ evaporated and purified by flash silica gel column ($CH_2Cl_2$:MeOH 99:1) to yield 9.35 g (92%) of the title compound as yellow oil. MS: 539.5 (MH$^+$, 2Cl).

F) (S)-4-Benzyloxy-2-{2-[(2-carboxy-ethyl)-(3,4-dichloro-phenyl)-amino]-ethylamino}-butyric acid methyl ester; HCl A solution of 8.80 g (16.31 mmol) of (S)-4-benzyloxy-2-{2-[(2-tert-butoxycarbonyl-ethyl)-(3,4-dichloro-phenyl)-amino]-ethylamino}-butyric acid methyl ester in 45 ml of dioxane was cooled (10° C.), treated with 40.78 ml (163.11 mmol) of HCl solution (4 M in dioxane), 0.4 ml of water and stirred at RT for 22 h. The solution was evaporated, suspended in $CH_3CN$ and evaporated (3×) to yield 8.52 g (quantitative) of the title compound as off-white foam. MS: 483.2 (M+H$^+$, 2Cl).

G) (S)-4-Benzyloxy-2-[4-(3,4-dichloro-phenyl)-7-oxo-[1,4]diazepan-1-yl]-butyric acid methyl ester A solution of 8.20 g (15.77 mmol) of (S)-4-benzyloxy-2-{2-[(2-carboxy-ethyl)-(3,4-dichloro-phenyl)-amino]-ethylamino}-butyric acid methyl ester; HCl in 130 ml $CH_2Cl_2$ was treated with 2.20 (15.77 mmol) of triethylamine and at 0° C. with 3.70 g (18.93 mmol) of EDCI. The cooling bath was allowed to come to RT and after 15 h the reaction was extracted with aq. 10% $KHSO_4/Et_2O$ (3×). The organic phases were washed with aq 10% KHSO₄ solution, 10% NaCl and dried over Na₂SO₄ and purified by flash silica gel column (n-heptane:EtOAc 75:25 to 1:1) to yield 5.64 g (77%) of the title compound as a light yellow oil. MS: 465.1 (MH⁺, 2Cl).

H) (S)-2-[4-(3,4-Dichloro-phenyl)-7-oxo-[1,4]diazepan-1-yl]-4-hydroxy-butyric acid methyl ester A solution of 2.05 g (4.40 mmol) of (S)-4-benzyloxy-2-[4-(3,4-dichloro-phenyl)-7-oxo-[1,4]diazepan-1-yl]-butyric acid methyl ester (evaporated with toluene) in 20 ml CH₂Cl₂ was cooled (−20° C.) and treated with 4.62 ml (4.62 mmol, 1M in CH₂Cl₂) of boron tribromide. The solution was warmed in 1 h to 0° C. and kept for 1.5 h at this temperature, additional 0.22 ml (0.22 mmol, 1M in CH₂Cl₂) of boron tribromide was added and stirring was continued for 30 min. The mixture was extracted with cold sat. aq. NaHCO₃ solution and EtOAc (3×). The organic phases were washed with sat. aq. NaHCO₃ solution, aq. 10% NaCl solution, dried over Na₂SO₄ evaporated to give 1.98 g (76%) of the title compound as light yellow foam. MS: 375.2 (MH⁺, 2Cl).

I) (S)-2-[4-(3,4-Dichloro-phenyl)-7-oxo-[1,4]diazepan-1-yl]-4-oxo-butyric acid methyl ester In analogy to the procedure described for example 1D, (S)-2-[4-(3,4-dichloro-phenyl)-7-oxo-[1,4]diazepan-1-yl]-4-hydroxy-butyric acid methyl ester gave the title compound in 97% yield as orange foam. MS: 373.1 (MH⁺, 2Cl).

K) (S)-2-[4-(3,4-Dichloro-phenyl)-7-oxo-[1,4]diazepan-1-yl]-4-((S)-4-hydroxy-6-aza-spiro[2.5]oct-6-yl)-butyric acid methyl ester In analogy to the procedure described for example 1E, (S)-2-[4-(3,4-dichloro-phenyl)-7-oxo-[1,4]diazepan-1-yl]-4-oxo-butyric acid methyl ester and (S)-6-aza-spiro[2.5]octan-4-ol; hydrochloride (intermediate 2) gave the title compound in 60% yield as light yellow foam. MS: 484.3 (MH⁺, 2Cl).

Example 2

1-(3,4-Dichloro-phenyl)-4-[(S)-3-((S)-4-hydroxy-6-aza-spiro[2.5]oct-6-yl)-1-hydroxymethyl-propyl]-[1,4]diazepan-5-one

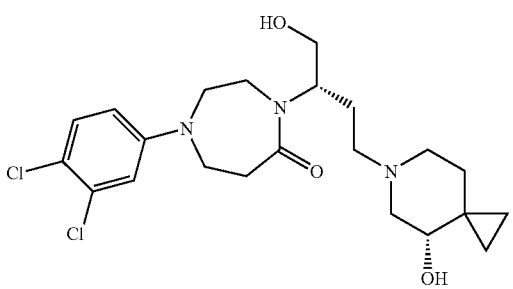

A solution of 0.180 g (0.37 mmol) of (S)-2-[4-(3,4-dichloro-phenyl)-7-oxo-[1,4]diazepan-1-yl]-4-((S)-4-hydroxy-6-aza-spiro[2.5]oct-6-yl)-butyric acid methyl ester in 4 ml of ETOH was treated at 0° C. with 0.017 g (0.74 mmol) of LiBH₄. The reaction was stirred 10 min at 0° C. and 22 h at RT, cooled (0° C.) and treated with 0.009 g (0.37 mmol) of LiBH₄ and after 5 h again cooled (0° C.) and treated with 0.009 g (0.37 mmol) of LiBH₄. After 1 h at RT, the reaction was cooled (0° C.), acidified with 10% aq. KHSO₄ solution and then basified with sat. aq NaHCO₃ solution and extracted with EtOAc (3×). The organic phases were washed with aq. 10% NaCl solution, dried over Na₂SO₄ evaporated and purified by flash silica gel column (CH₂Cl₂:MeOH 95:5 to 9:1) to yield 0.127 g (75%) of the title compound as white foam. MS: 456.2 (MH⁺, 2Cl).

Example 3

(S)-2-[4-(3-Chloro-phenyl)-7-oxo-[1,4]diazepan-1-yl]-4-((S)-4-hydroxy-6-aza-spiro[2.5]oct-6-yl)-butyric acid methyl ester

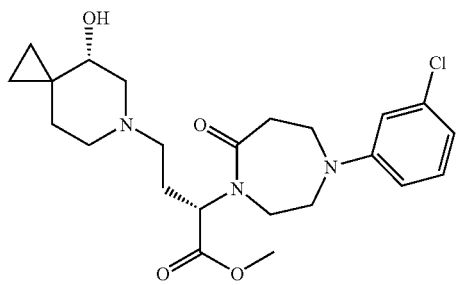

A) 3-[(3-Chloro-phenyl)-(2-oxo-ethyl)-amino]-propionic acid tert-butyl ester

In analogy to the procedure described in example 1A to 1D, 3-chloro-phenylamine gave the title compound as orange oil. MS: 298.1 (MH⁺, 1Cl).

B) (S)-4-Benzyloxy-2-[4-(3-chloro-phenyl)-7-oxo-[1,4]diazepan-1-yl]-butyric acid methyl ester In analogy to the procedure described in example 1E to 1G, 3-[(3-chloro-phenyl)-(2-oxo-ethyl)-amino]-propionic acid tert-butyl ester gave the title compound as off-white gum. MS: 431.3 (MH⁺, 1Cl).

C) (S)-2-[4-(3-Chloro-phenyl)-7-oxo-[1,4]diazepan-1-yl]-4-oxo-butyric acid methyl ester In analogy to the procedure described in example 1H and 1I, (S)-4-benzyloxy-2-[4-(3-chloro-phenyl)-7-oxo-[1,4]diazepan-1-yl]-butyric acid methyl ester gave the title compound as orange oil. MS: 339.1 (MH⁺, 1Cl).

D) (S)-2-[4-(3-Chloro-phenyl)-7-oxo-[1,4]diazepan-1-yl]-4-((S)-4-hydroxy-6-aza-spiro[2.5]oct-6-yl)-butyric acid methyl ester In analogy to the procedure described in example 1K, (S)-2-[4-(3-chloro-phenyl)-7-oxo-[1,4]diazepan-1-yl]-4-oxo-butyric acid methyl ester and (S)-6-aza-spiro[2.5]octan-

Example 4

1-(3-Chloro-phenyl)-4-[(S)-3-((S)-4-hydroxy-6-aza-spiro[2.5]oct-6-yl)-1-hydroxymethyl-propyl]-[1,4]diazepan-5-one

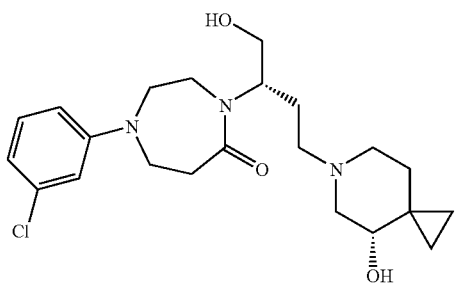

In analogy to the procedure described in example 2, (S)-2-[4-(3-chloro-phenyl)-7-oxo-[1,4]diazepan-1-yl]-4-((S)-4-hydroxy-6-aza-spiro[2.5]oct-6-yl)-butyric acid methyl ester and LiBH$_4$ gave the title compound in 77% yield as a white foam. MS: 421.2 (MH$^+$, 1Cl).

Example 5

(S)-4-((S)-4-Hydroxy-6-aza-spiro[2.5]oct-6-yl)-2-[7-oxo-4-(3-trifluoromethyl-phenyl)-[1,4]diazepan-1-yl]-butyric acid methyl ester

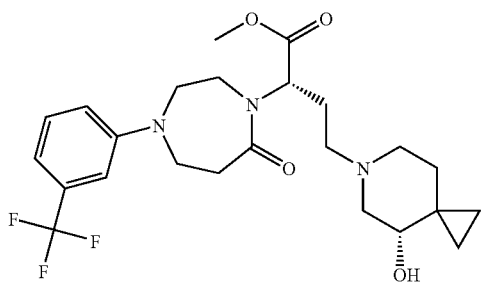

A) 3-[(2-Oxo-ethyl)-(3-trifluoromethyl-phenyl)-amino]-propionic acid tert-butyl ester In analogy to the procedure described in example 1A to 1D, 3-trifluoromethyl-phenylamine gave the title compound as orange oil. MS: 332.1 (MH$^+$).

B) (S)-4-Benzyloxy-2-[7-oxo-4-(3-trifluoromethyl-phenyl)-[1,4]diazepan-1-yl]-butyric acid methyl ester In analogy to the procedure described in example 1E to 1G, 3-[(2-oxo-ethyl)-(3-trifluoromethyl-phenyl)-amino]-propionic acid tert-butyl ester gave the title compound as light yellow oil. MS: 465.2 (MH$^+$).

C) (S)-4-Hydroxy-2-[7-oxo-4-(3-trifluoromethyl-phenyl)-[1,4]diazepan-1-yl]-butyric acid methyl ester A solution of 1.49 g (3.22 mmol) of (S)-4-benzyloxy-2-[7-oxo-4-(3-trifluoromethyl-phenyl)-[1,4]diazepan-1-yl]-butyric acid methyl ester in 50 ml of MeOH was treated with a solution of 3.22 ml of 1 M aq. HCl solution and 0.15 g of palladium on activated charcoal (10%) and was stirred over H$_2$-atmosphere for 1.5 h. After filtration, the solution was evaporated, dissolved in CH$_2$Cl$_2$ and washed with aq. sat. NaHCO$_3$ solution (freshly prepared), dried over Na$_2$SO$_4$ and evaporated under reduced pressure to yield 1.08 g (90%) of a mixture of 4-((S)-2-oxo-tetrahydro-furan-3-yl)-1-(3-trifluoromethyl-phenyl)-[1,4]diazepan-5-one (ca 5-10%) and the title compound as white foam. MS: 375.2 (MH$^+$).

D) (S)-4-Oxo-2-[7-oxo-4-(3-trifluoromethyl-phenyl)-[1,4]diazepan-1-yl]-butyric acid methyl ester In analogy to the procedure described in example 1I, (S)-4-hydroxy-2-[7-oxo-4-(3-trifluoromethyl-phenyl)-[1,4]diazepan-1-yl]-butyric acid methyl ester gave a mixture of 4-((S)-2-oxo-tetrahydro-furan-3-yl)-1-(3-trifluoromethyl-phenyl)-[1,4]diazepan-5-one (ca 5-10%) and the title compound in 97% yield as orange oil. MS: 373.1 (MH$^+$).

E) (S)-4-((S)-4-Hydroxy-6-aza-spiro[2.5]oct-6-yl)-2-[7-oxo-4-(3-trifluoromethyl-phenyl)-[1,4]diazepan-1-yl]-butyric acid methyl ester In analogy to the procedure described in example 1K, (S)-4-oxo-2-[7-oxo-4-(3-trifluoromethyl-phenyl)-[1,4]diazepan-1-yl]-butyric acid methyl ester and (S)-6-aza-spiro[2.5]octan-4-ol hydrochloride (intermediate 2) gave the pure title compound in 70% yield as light yellow foam. MS: 484.4 (MH$^+$).

Example 6

4-[(S)-3-((S)-4-Hydroxy-6-aza-spiro[2.5]oct-6-yl)-1-hydroxymethyl-propyl]-1-(3-trifluoromethyl-phenyl)-[1,4]diazepan-5-one

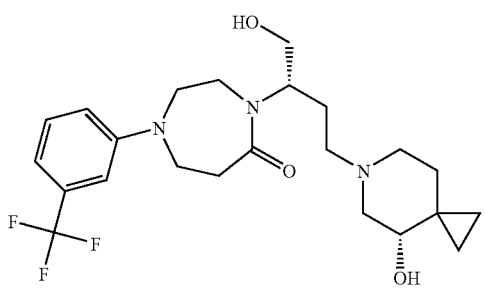

In analogy to the procedure described in example 2, (S)-4-((S)-4-hydroxy-6-aza-spiro[2.5]oct-6-yl)-2-[7-oxo-4-(3-trifluoromethyl-phenyl)-[1,4]diazepan-1-yl]-butyric acid methyl ester and LiBH$_4$ gave the title compound in 64% yield as a white foam. MS: 456.4 (MH$^+$).

Example 7

(S)-4-((3S,5S)-3-Hydroxy-5-methyl-piperidin-1-yl)-2-[7-oxo-4-(3-trifluoromethyl-phenyl)-[1,4]diazepan-1-yl]-butyric acid methyl ester

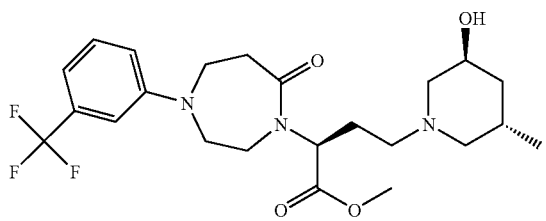

In analogy to the procedure described in example 1K, (S)-4-oxo-2-[7-oxo-4-(3-trifluoromethyl-phenyl)-[1,4]diazepan-1-yl]-butyric acid methyl ester, containing 4-((S)-2-oxo-tetrahydro-furan-3-yl)-1-(3-trifluoromethyl-phenyl)-[1,4]diazepan-5-one (ca 5-10%) (example 5D) and (3S,5S)-5-methyl-piperidin-3-ol hydrochloride (intermediate 4) gave 4-((S)-2-oxo-tetrahydro-furan-3-yl)-1-(3-trifluoromethyl-phenyl)-[1,4]diazepan-5-one, MS: 343.0 (MH+); and the title compound, (S)-4-((3S,5S)-3-hydroxy-5-methyl-piperidin-1-yl)-2-[7-oxo-4-(3-trifluoromethyl-phenyl)-[1,4]diazepan-1-yl]-butyric acid methyl ester as light yellow foam. MS: 472.1 (MH+).

Example 8

(R)-4-((S)-4-Hydroxy-6-aza-spiro[2.5]oct-6-yl)-2-[7-oxo-4-(3-trifluoromethyl-phenyl)-[1,4]diazepan-1-yl]-butyric acid methyl ester

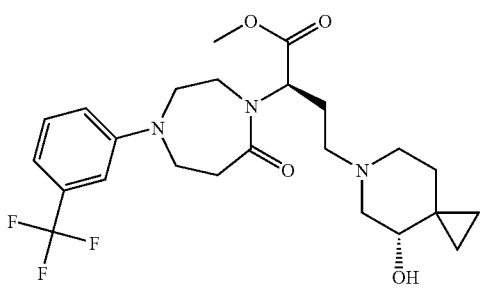

A) (R)-4-Benzyloxy-2-{2-[(2-tert-butoxycarbonyl-ethyl)-(3-trifluoromethyl-phenyl)-amino]-ethylamino}-butyric acid methyl ester In analogy to the procedure described in example 1E, 3-[(2-oxo-ethyl)-(3-trifluoromethyl-phenyl)-amino]-propionic acid tert-butyl ester (example 5A) and (R)-2-amino-4-benzyloxy-butyric acid methyl ester hydrochloride (intermediate 7) gave the title compound as yellow oil. MS: 539.4 (MH+).

B) (R)-4-Benzyloxy-2-[7-oxo-4-(3-trifluoromethyl-phenyl)-[1,4]diazepan-1-yl]-butyric acid methyl ester In analogy to the procedure described in example 1F and 1G, (R)-4-benzyloxy-2-{2-[(2-tert-butoxycarbonyl-ethyl)-(3-trifluoromethyl-phenyl)-amino]-ethylamino}-butyric acid methyl ester gave the title compound as light yellow oil. MS: 465.2 (MH+).

C) (R)-4-Hydroxy-2-[7-oxo-4-(3-trifluoromethyl-phenyl)-[1,4]diazepan-1-yl]-butyric acid methyl ester In analogy to the procedure described in example 5C, (R)-4-benzyloxy-2-[7-oxo-4-(3-trifluoromethyl-phenyl)-[1,4]diazepan-1-yl]-butyric acid methyl ester was hydrogenated to give the title compound in 97% yield as white oil. MS: 375.2 (MH+).

D) (R)-4-Oxo-2-[7-oxo-4-(3-trifluoromethyl-phenyl)-[1,4]diazepan-1-yl]-butyric acid methyl ester In analogy to the procedure described in example 1I, (R)-4-hydroxy-2-[7-oxo-4-(3-trifluoromethyl-phenyl)-[1,4]diazepan-1-yl]-butyric acid methyl ester gave the title compound in quantitative yield as orange oil. MS: 373.1 (MH+).

E) (R)-4-((S)-4-Hydroxy-6-aza-spiro[2.5]oct-6-yl)-2-[7-oxo-4-(3-trifluoromethyl-phenyl)-[1,4]diazepan-1-yl]-butyric acid methyl ester In analogy to the procedure described in example 1K, (R)-4-oxo-2-[7-oxo-4-(3-trifluoromethyl-phenyl)-[1,4]diazepan-1-yl]-butyric acid methyl ester and (S)-6-aza-spiro[2.5]octan-4-ol; hydrochloride (intermediate 2) gave the title compound in 77% as white foam. MS: 484.4 (MH+).

Example 9

4-[(R)-3-((S)-4-Hydroxy-6-aza-spiro[2.5]oct-6-yl)-1-hydroxymethyl-propyl]-1-(3-trifluoromethyl-phenyl)-[1,4]diazepan-5-one

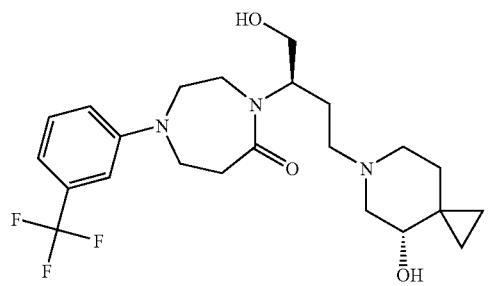

In analogy to the procedure described in example 2, (R)-4-((S)-4-hydroxy-6-aza-spiro[2.5]oct-6-yl)-2-[7-oxo-4-(3-trifluoromethyl-phenyl)-[1,4]diazepan-1-yl]-butyric acid methyl ester and LiBH4 gave the title compound in 60% yield as a white foam. MS: 456.4 (MH+).

Example 10

(S)-4-((S)-4-Hydroxy-6-aza-spiro[2.5]oct-6-yl)-2-(7-oxo-4-phenyl-[1,4]diazepan-1-yl)-butyric acid methyl ester

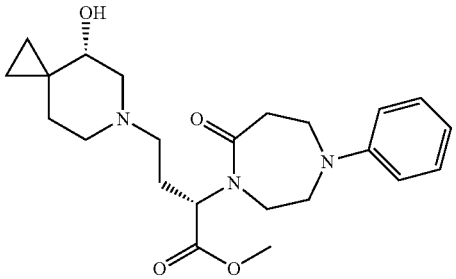

A) (S)-4-Hydroxy-2-(7-oxo-4-phenyl-[1,4]diazepan-1-yl)-butyric acid methyl ester In analogy to the procedure described in example 5C, (S)-4-benzyloxy-2-[4-(3-chloro-phenyl)-7-oxo-[1,4]diazepan-1-yl]-butyric acid methyl ester (example 3B) was hydrogenated to give the title compound in 66% yield as light yellow gum. MS: 307.2 (MH+).

B) (S)-4-Oxo-2-(7-oxo-4-phenyl-[1,4]diazepan-1-yl)-butyric acid methyl ester

In analogy to the procedure described in example 1I, (S)-4-hydroxy-2-(7-oxo-4-phenyl-[1,4]diazepan-1-yl)-butyric acid methyl ester gave the title compound in quantitative yield as light brown gum. MS: 305.2 (MH+).

C) (S)-4-((S)-4-Hydroxy-6-aza-spiro[2.5]oct-6-yl)-2-(7-oxo-4-phenyl-[1,4]diazepan-1-yl)-butyric acid methyl ester In analogy to the procedure described in example 1K, (S)-4-oxo-2-(7-oxo-4-phenyl-[1,4]diazepan-1-yl)-butyric acid methyl ester and (S)-6-aza-spiro[2.5]octan-4-ol hydrochloride (intermediate 2) gave the title compound in 50% as light yellow foam. MS: 416.3 (MH+).

Example 11

(S)-4-((S)-4-Hydroxy-6-aza-spiro[2.5]oct-6-yl)-2-[7-oxo-4-(4-trifluoromethoxy-phenyl)-[1,4]diazepan-1-yl]-butyric acid methyl ester

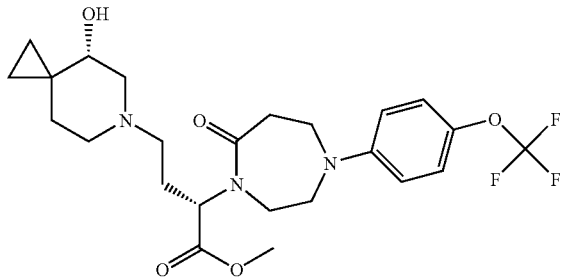

amino]-propionic acid tert-butyl ester

In analogy to the procedure described in example 1A to 1D, 4-trifluoromethoxy-phenylamine gave the title compound as orange oil. MS: 347 (M+).

B) (S)-4-Benzyloxy-2-[7-oxo-4-(4-trifluoromethoxy-phenyl)-[1,4]diazepan-1-yl]-butyric acid methyl ester In analogy to the procedure described in example 1E to 1G, 3-[(2-oxo-ethyl)-(4-trifluoromethoxy-phenyl)-amino]-propionic acid tert-butyl ester gave the title compound as light yellow oil. MS: 481.3 (MH+).

C) (S)-4-Hydroxy-2-[7-oxo-4-(4-trifluoromethoxy-phenyl)-[1,4]diazepan-1-yl]-butyric acid methyl ester In analogy to the procedure described in example 5C, (S)-4-benzyloxy-2-[7-oxo-4-(4-trifluoromethoxy-phenyl)-[1,4]diazepan-1-yl]-butyric acid methyl ester was hydrogenated to give the title compound in 98% yield as white oil. MS: 391.0 (MH+).

D) (S)-4-Oxo-2-[7-oxo-4-(4-trifluoromethoxy-phenyl)-[1,4]diazepan-1-yl]-butyric acid methyl ester In analogy to the procedure described in example 1I, (S)-4-hydroxy-2-[7-oxo-4-(4-trifluoromethoxy-phenyl)-[1,4]diazepan-1-yl]-butyric acid methyl ester gave the title compound in quantitative yield as brown oil. MS: 389.1 (MH+).

E) (S)-4-((S)-4-Hydroxy-6-aza-spiro[2.5]oct-6-yl)-2-[7-oxo-4-(4-trifluoromethoxy-phenyl)-[1,4]diazepan-1-yl]-butyric acid methyl ester In analogy to the procedure described in example 1K, (S)-4-oxo-2-[7-oxo-4-(4-trifluoromethoxy-phenyl)-[1,4]diazepan-1-yl]-butyric acid methyl ester and (S)-6-aza-spiro[2.5]octan-4-ol; hydrochloride (intermediate 2) gave the title compound in 63% yield as white foam. MS: 500.2 (MH+).

Example 12

4-[(S)-3-((S)-4-Hydroxy-6-aza-spiro[2.5]oct-6-yl)-1-hydroxymethyl-propyl]-1-(4-trifluoromethoxy-phenyl)-[1,4]diazepan-5-one

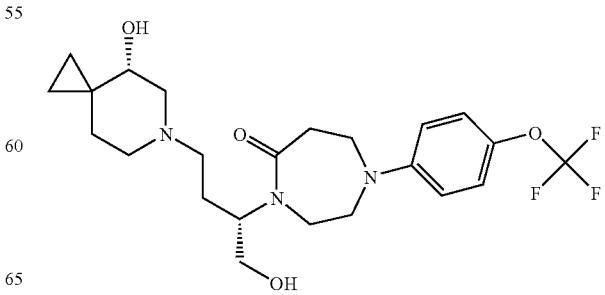

In analogy to the procedure described in example 2, (S)-4-((S)-4-hydroxy-6-aza-spiro[2.5]oct-6-yl)-2-[7-oxo-4-(4-trifluoromethoxy-phenyl)-[1,4]diazepan-1-yl]-butyric acid methyl ester and LiBH₄ gave the title compound in 79% yield as a white foam. MS: 472.3 (MH⁺).

Example 13

(S)-4-((S)-4-Hydroxy-6-aza-spiro[2.5]oct-6-yl)-2-[7-oxo-4-(3-trifluoromethoxy-phenyl)-[1,4]diazepan-1-yl]-butyric acid methyl ester

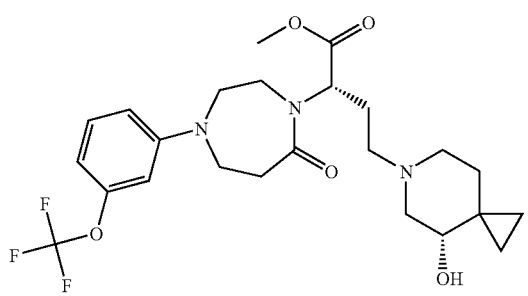

A) 3-[(2-Oxo-ethyl)-(3-trifluoromethoxy-phenyl)-amino]-propionic acid tert-butyl ester In analogy to the procedure described in example 1A to 1D, 3-trifluoromethoxy-phenylamine gave the title compound as orange oil. MS: 348.2 (MH⁺).

B) (S)-4-Benzyloxy-2-[7-oxo-4-(3-trifluoromethoxy-phenyl)-[1,4]diazepan-1-yl]-butyric acid methyl ester In analogy to the procedure described in example 1E to 1G, 3-[(2-oxo-ethyl)-(3-trifluoromethoxy-phenyl)-amino]-propionic acid tert-butyl ester gave the title compound as light brown oil. MS: 481.3 (MH⁺).

C) (S)-4-Hydroxy-2-[7-oxo-4-(3-trifluoromethoxy-phenyl)-[1,4]diazepan-1-yl]-butyric acid methyl ester In analogy to the procedure described in example 5C, (S)-4-benzyloxy-2-[7-oxo-4-(3-trifluoromethoxy-phenyl)-[1,4]diazepan-1-yl]-butyric acid methyl ester was hydrogenated to give the title compound in 98% yield as white foam. MS: 391.1 (MH⁺).

D) (S)-4-Oxo-2-[7-oxo-4-(3-trifluoromethoxy-phenyl)-[1,4]diazepan-1-yl]-butyric acid methyl ester In analogy to the procedure described in example 1I, (S)-4-hydroxy-2-[7-oxo-4-(3-trifluoromethoxy-phenyl)-[1,4]diazepan-1-yl]-butyric acid methyl ester gave the title compound in 98% yield as light red oil. MS: 389.1 (MH⁺).

E) (S)-4-((S)-4-Hydroxy-6-aza-spiro[2.5]oct-6-yl)-2-[7-oxo-4-(3-trifluoromethoxy-phenyl)-[1,4]diazepan-1-yl]-butyric acid methyl ester In analogy to the procedure described in example 1K, (S)-4-oxo-2-[7-oxo-4-(3-trifluoromethoxy-phenyl)-[1,4]diazepan-1-yl]-butyric acid methyl ester and (S)-6-aza-spiro[2.5]octan-4-ol hydrochloride (intermediate 2) gave the title compound in 60% yield as light yellow viscous oil. MS: 500.3 (MH⁺).

Example 14

4-[(S)-3-((S)-4-Hydroxy-6-aza-spiro[2.5]oct-6-yl)-1-hydroxymethyl-propyl]-1-(3-trifluoromethoxy-phenyl)-[1,4]diazepan-5-one

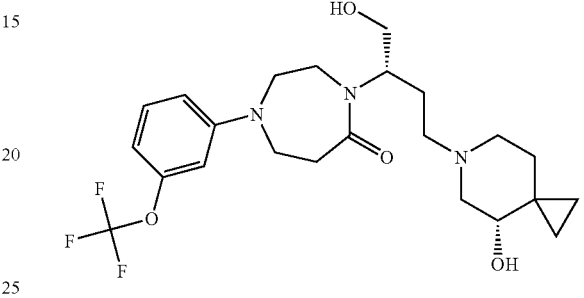

In analogy to the procedure described in example 2, (S)-4-((S)-4-hydroxy-6-aza-spiro[2.5]oct-6-yl)-2-[7-oxo-4-(3-trifluoromethoxy-phenyl)-[1,4]diazepan-1-yl]-butyric acid methyl ester and LiBH₄ gave the title compound in 73% yield as a white foam. MS: 472.3 (MH⁺).

Example 15

(R,S)-4-((S)-4-Hydroxy-6-aza-spiro[2.5]oct-6-yl)-2-[7-oxo-4-(3-trifluoromethyl-phenyl)-[1,4]diazepan-1-yl]-butyric acid methyl ester

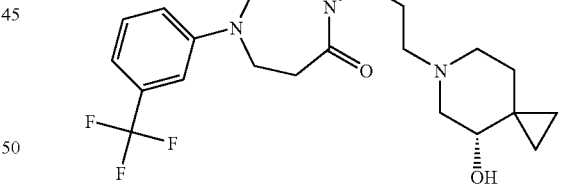

A) 1-(3-Trifluoromethyl-phenyl)-[1,4]diazepan-5-one

A mixture of 5.00 g (43.80 mmol) 1,4-diazepan-5-one, 16.64 g (87.61 mmol) of 3-(trifluoromethylphenyl)boronic acid, 11.94 g (65.70 mmol) of copper(II) acetate and 10 spoonful of molecular sieves (0.4 nm) were degassed (Argon) and the treated with 6.93 ml (87.61 mmol) of pyridine in 200 ml of CH₂Cl₂. The blue suspension became slowly green during stirring for 4 days. The mixture was filtered and evaporated. The residue was taken up in EtOAc and washed with sat. aq NaHCO₃ solution (4×) and dried over Na₂SO₄. After evaporation and purification by flash silica gel column (n-heptane:EtOAc gradient, then EtOAc:MeOH 95:5), 0.997 g (9%) of the title compound as light brown solid were received. MS: 258.9 (MH⁺).

B) (rac)-4-(tert-Butyl-dimethyl-silanyloxy)-2-[7-oxo-4-(3-trifluoromethyl-phenyl)-[1,4]diazepan-1-yl]-butyric acid methyl ester A solution of 1.60 g (1.94 mmol) of 1-(3-trifluoromethyl-phenyl)-[1,4]diazepan-5-one in 15 ml of DMF was treated at 0° C. with 0.33 g (7.44 mmol) of NaH (55% dispersion in oil). After 20 min at this temperature, the suspension was warmed to RT and added to a cooled solution (0° C.) of 2.33 g (6.50 mmol) of (rac)-4-(tert-butyl-dimethyl-silanyloxy)-2-iodo-butyric acid methyl ester (intermediate 1) in 15 ml of DMF. The solution was stirred 6 h at 0° C. and neutralized with cold 10% aq. KH$_2$PO$_4$ solution and extracted with Et$_2$O (3×). The organic phases were washed with 10% aq. KH$_2$PO$_4$ solution, dried over Na$_2$SO$_4$ evaporated and purified by flash silica gel column (CH$_2$Cl$_2$:Et$_2$O 4:1 to 2:1) to yield 2.06 g (68%) of the title compound as light yellow oil. MS: 489.2 (MH⁺)

C) (rac)-4-Bromo-2-[7-oxo-4-(3-trifluoromethyl-phenyl)-[1,4]diazepan-1-yl]-butyric acid methyl ester A solution of 1.03 g (2.12 mmol) of (rac)-4-(tert-butyl-dimethyl-silanyloxy)-2-[7-oxo-4-(3-trifluoromethyl-phenyl)-[1,4]diazepan-1-yl]-butyric acid methyl ester in 6 ml of CH$_2$Cl$_2$ was treated at 0° C. with 2.33 ml (2.33 mmol, 1M in CH$_2$Cl$_2$) of boron tribromide and kept 2.5 h at this temperature. The solution was warmed to RT cooled (0° C.) and treated again with 2.33 ml (2.33 mmol, 1M in CH$_2$Cl$_2$) of boron tribromide. After 1 h at this temperature, the reaction was extracted with cold sat. aq. NaHCO$_3$ and EtOAc solution (3×). The organic phases were washed with sat. aq. NaHCO$_3$ solution, dried over Na$_2$SO$_4$ and evaporated to give 1.14 g of the crude compound. Purification by flash silica gel column ((n-heptane:EtOAc 95:5, 1:1 to EtOAc) gave 0.086 g (11%) of the title compound as light yellow oil, MS: 437.1 (MH⁺, 1Br) and 0.28 g (39%) of (rac)-4-(2-oxo-tetrahydro-furan-3-yl)-1-(3-trifluoromethyl-phenyl)-[1,4]diazepan-5-one as a light yellow foam, MS: 443.1 (MH⁺).

D) (R,S)-4-((S)-4-Hydroxy-6-aza-spiro[2.5]oct-6-yl)-2-[7-oxo-4-(3-trifluoromethyl-phenyl)-[1,4]diazepan-1-yl]-butyric acid methyl ester A cold solution (0° C.) of 0.05 g (0.11 mmol) of (rac)-4-bromo-2-[7-oxo-4-(3-trifluoromethyl-phenyl)-[1,4]diazepan-1-yl]-butyric acid methyl ester in 0.4 ml of DMA was treated with 0.026 (0.16 mmol) of (S)-6-aza-spiro[2.5]octan-4-ol hydrochloride (intermediate 2), 0.19 g (0.57 mmol) of cesium carbonate and 0.07 g (0.46 mmol) of sodium iodide. After 16 h at RT, the reaction was extracted with cold sat. aq. NaHCO$_3$ solution and Et$_2$O (3×), 10% aq. NaCl solution, dried over Na$_2$SO$_4$ and purified by flash silica gel column (CH$_2$Cl$_2$:MeOH 99:1 to 95:5) to yield 0.027 g (49%) of the title compound as light yellow oil. MS: 484.3 (MH⁺).

Example 16

4-[(R,S)-3-((S)-4-Hydroxy-6-aza-spiro[2.5]oct-6-yl)-1-hydroxymethyl-propyl]-1-(3-trifluoromethyl-phenyl)-[1,4]diazepan-5-one

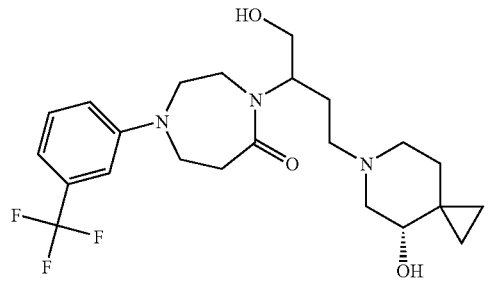

In analogy to the procedure described in example 2, (R,S)-4-((S)-4-hydroxy-6-aza-spiro[2.5]oct-6-yl)-2-[7-oxo-4-(3-trifluoromethyl-phenyl)-[1,4]diazepan-1-yl]-butyric acid methyl ester and LiBH$_4$ gave the title compound in 50% yield as off-white foam. MS: 456.4 (MH⁺).

Example 17

(R,S)-4-((S)-4-Hydroxy-6-aza-spiro[2.5]oct-6-yl)-N,N-dimethyl-2-[7-oxo-4-(3-trifluoromethyl-phenyl)-[1,4]diazepan-1-yl]-butyramide

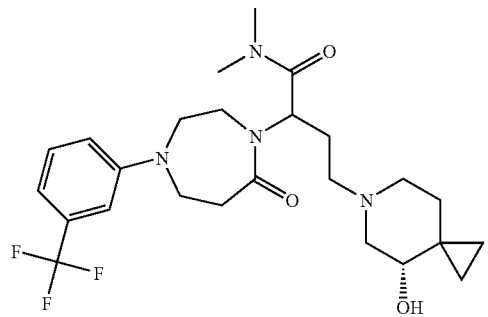

A) (rac)-4-Hydroxy-N,N-dimethyl-2-[7-oxo-4-(3-trifluoromethyl-phenyl)-[1,4]diazepan-1-yl]-butyramide 0.26 g (0.76 mmol) of (rac)-4-(2-oxo-tetrahydro-furan-3-yl)-1-(3-trifluoromethyl-phenyl)-[1,4]diazepan-5-one (example 15C) was dissolved in 3 ml of EtOH and treated with 2.71 ml (15.19 mmol) of a solution of dimethylamine (5.6 M in EtOH). The reaction was stirred 20 h at RT, evaporated and re-evaporated with toluene to afford 0.31 g (quantitative) of the title compound as yellow oil. MS: 388.1 (MH⁺).

B) (rac)-N,N-Dimethyl-4-oxo-2-[7-oxo-4-(3-trifluoromethyl-phenyl)-[1,4]diazepan-1-yl]-butyramide In analogy to the procedure described in example 1D, (rac)-4-hydroxy-N,N-dimethyl-2-[7-oxo-4-(3-trifluoromethyl-phenyl)-[1,4]diazepan-1-yl]-butyramide gave the title compound in 90% yield as an yellow gum. MS: 349.2 (MH⁺).

C) (R,S)-4-((S)-4-Hydroxy-6-aza-spiro[2.5]oct-6-yl)-N,N-dimethyl-2-[7-oxo-4-(3-trifluoromethyl-phenyl)-[1,4]diazepan-1-yl]-butyramide In analogy to the procedure described in example 1E, (rac)-N,N-dimethyl-4-oxo-2-[7-oxo-4-(3-trifluoromethyl-phenyl)-[1,4]diazepan-1-yl]-butyramide and (S)-6-aza-spiro[2.5]octan-4-ol hydrochloride (intermediate 2) gave the title compound in 67% yield as white foam. MS: 497.3 (MH$^+$).

Example 18

(R,S)-4-((3S,5S)-3-Hydroxy-5-methyl-piperidin-1-yl)-N,N-dimethyl-2-[7-oxo-4-(3-trifluoromethyl-phenyl)-[1,4]diazepan-1-yl]-butyramide

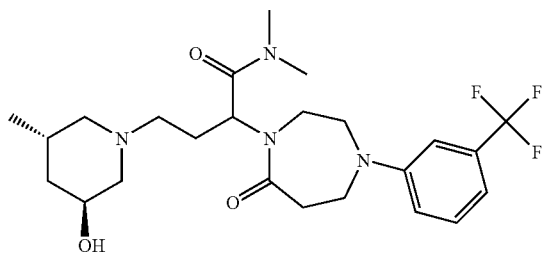

In analogy to the procedure described in example 1E, (rac)-N,N-dimethyl-4-oxo-2-[7-oxo-4-(3-trifluoromethyl-phenyl)-[1,4]diazepan-1-yl]-butyramide (example 17B) and (3S,5S)-5-methyl-piperidin-3-ol; hydrochloride (intermediate 4) gave the title compound in 60% yield as off-white foam. MS: 485.3 (MH$^+$).

Example 19

(S)-4-((S)-4-Hydroxy-6-aza-spiro[2.5]oct-6-yl)-2-[7-oxo-4-(4-trifluoromethyl-phenyl)-[1,4]diazepan-1-yl]-butyric acid methyl ester

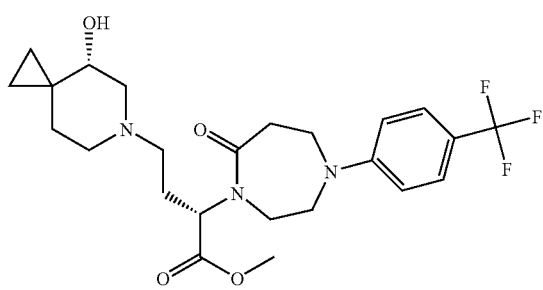

A) 3-[(2-Oxo-ethyl)-(4-trifluoromethyl-phenyl)-amino]-propionic acid tert-butyl ester In analogy to the procedure described in example 1A to 1D, 4-trifluoromethyl-phenylamine gave the title compound as light yellow solid. MS: 332.2 (MH$^+$).

B) (S)-4-Benzyloxy-2-[7-oxo-4-(4-trifluoromethyl-phenyl)-[1,4]diazepan-1-yl]-butyric acid methyl ester In analogy to the procedure described in example 1E to 1G, 3-[(2-oxo-ethyl)-(4-trifluoromethyl-phenyl)-amino]-propionic acid tert-butyl ester gave the title compound as white oil. MS: 465.2 (MH$^+$).

C) (S)-4-Hydroxy-2-[7-oxo-4-(4-trifluoromethyl-phenyl)-[1,4]diazepan-1-yl]-butyric acid methyl ester In analogy to the procedure described in example 5C, (S)-4-benzyloxy-2-[7-oxo-4-(4-trifluoromethyl-phenyl)-[1,4]diazepan-1-yl]-butyric acid methyl ester was hydrogenated to give the title compound in 94% yield as white foam. MS: 375.2 (MH$^+$).

D) (S)-4-Oxo-2-[7-oxo-4-(4-trifluoromethyl-phenyl)-[1,4]diazepan-1-yl]-butyric acid methyl ester In analogy to the procedure described in example 1I, (S)-4-hydroxy-2-[7-oxo-4-(4-trifluoromethyl-phenyl)-[1,4]diazepan-1-yl]-butyric acid methyl ester gave the title compound in quantitative yield as yellow oil. MS: 373.1 (MH$^+$).

E) (S)-4-((S)-4-Hydroxy-6-aza-spiro[2.5]oct-6-yl)-2-[7-oxo-4-(4-trifluoromethyl-phenyl)-[1,4]diazepan-1-yl]-butyric acid methyl ester In analogy to the procedure described in example 1K, (S)-4-oxo-2-[7-oxo-4-(4-trifluoromethyl-phenyl)-[1,4]diazepan-1-yl]-butyric acid methyl ester and (S)-6-aza-spiro[2.5]octan-4-ol hydrochloride (intermediate 2) gave the title compound in 75% yield as light yellow foam. MS: 484.4 (MH$^+$).

Example 20

4-[(S)-3-((S)-4-Hydroxy-6-aza-spiro[2.5]oct-6-yl)-1-hydroxymethyl-propyl]-1-(4-trifluoromethyl-phenyl)-[1,4]diazepan-5-one

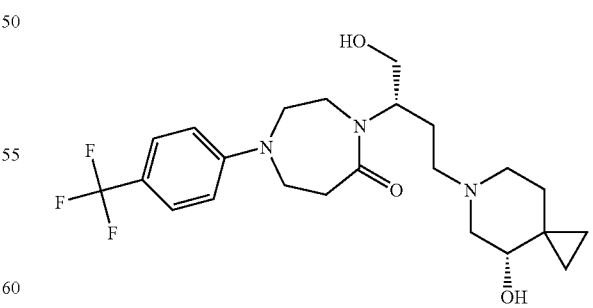

In analogy to the procedure described in example 2, (S)-4-((S)-4-hydroxy-6-aza-spiro[2.5]oct-6-yl)-2-[7-oxo-4-(4-trifluoromethyl-phenyl)-[1,4]diazepan-1-yl]-butyric acid methyl ester and LiBH$_4$ gave the title compound in 75% yield as a white foam. MS: 456.3 (MH$^+$).

Example 21

(R)-4-((S)-4-Hydroxy-6-aza-spiro[2.5]oct-6-yl)-N,N-dimethyl-2-[7-oxo-4-(3-trifluoromethyl-phenyl)-[1,4]diazepan-1-yl]-butyramide

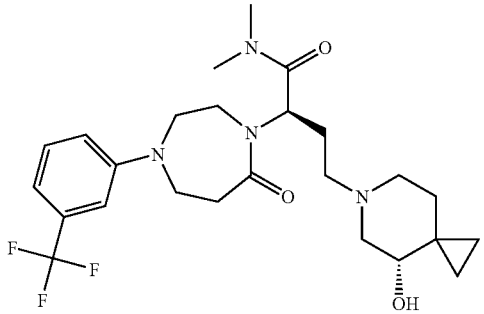

A) Lithium; (R)-4-((S)-4-hydroxy-6-aza-spiro[2.5]oct-6-yl)-2-[7-oxo-4-(3-trifluoromethyl-phenyl)-[1,4]diazepan-1-yl]-butyrate A solution of 0.22 g (0.45 mmol) of (R)-4-((S)-4-hydroxy-6-aza-spiro[2.5]oct-6-yl)-2-[7-oxo-4-(3-trifluoromethyl-phenyl)-[1,4]diazepan-1-yl]-butyric acid methyl ester (example 8) in 1.26 ml of THF/MeOH (1:1) was treated at 0° C. with 0.45 ml (0.45 mmol) of 1 M aq. LiOH solution, and kept 1¾ h at this temperature. The reaction was evaporated, dissolved in CH$_3$CN and evaporated again (3×) to give 0.21 g (97%) of the title compound as light yellow powder. MS: 468.1 (M–H$^-$).

B) (R)-4-((S)-4-Hydroxy-6-aza-spiro[2.5]oct-6-yl)-N,N-dimethyl-2-[7-oxo-4-(3-trifluoromethyl-phenyl)-[1,4]diazepan-1-yl]-butyramide 0.105 g (0.22 mmol) of Lithium; (R)-4-((S)-4-hydroxy-6-aza-spiro[2.5]oct-6-yl)-2-[7-oxo-4-(3-trifluoromethyl-phenyl)-[1,4]diazepan-1-yl]-butyrate was dissolved at RT in 1.2 ml of DMF followed by addition of 0.020 g (0.24 mmol) dimethylamine hydrochloride, 0.123 ml (0.88 mmol) of triethylamine and at 0° C. with 0.095 g (0.24 mmol) of HATU. The solution was stirred overnight and warmed up to RT. The reaction was poured on a sat. aq. NaHCO$_3$ solution followed by extraction with EtOAc (3 times). The organic phases were washed with a solution of sat. aq. NaHCO$_3$ solution and with a solution of NaCl 10%. The combined organic phases were dried over Na$_2$SO$_4$ and the solvent was removed under vacuum. The crude product was purified by flash chromatography (20 g amine-silica, AcOEt/n-heptane 9:1) to yield 0.095 g (87%) of the title compound as a white foam. MS: 497.3 (MH$^+$).

Example 22

(S)-4-((S)-4-Hydroxy-6-aza-spiro[2.5]oct-6-yl)-N,N-dimethyl-2-[7-oxo-4-(3-trifluoromethyl-phenyl)-[1,4]diazepan-1-yl]-butyramide

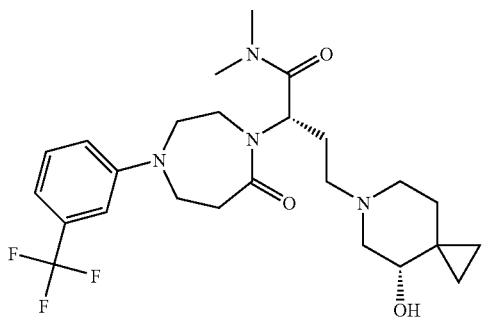

A) (S)-4-Hydroxy-N,N-dimethyl-2-[7-oxo-4-(3-trifluoromethyl-phenyl)-[1,4]diazepan-1-yl]-butyramide In analogy to the procedure described in example 17A, 4-((S)-2-oxo-tetrahydro-furan-3-yl)-1-(3-trifluoromethyl-phenyl)-[1,4]diazepan-5-one (example 7) and dimethylamine (5.6 M in EtOH) gave the title compound in quantitative yield as an yellow oil. MS: 388.1 (MH$^+$).

B) (S)—N,N-Dimethyl-4-oxo-2-[7-oxo-4-(3-trifluoromethyl-phenyl)-[1,4]diazepan-1-yl]-butyramide In analogy to the procedure described in example 11, (S)-4-hydroxy-N,N-dimethyl-2-[7-oxo-4-(3-trifluoromethyl-phenyl)-[1,4]diazepan-1-yl]-butyramide gave the title compound in 99% yield as yellow oil. MS: 386.1 (MH$^+$).

C) (S)-4-((S)-4-Hydroxy-6-aza-spiro[2.5]oct-6-yl)-N,N-dimethyl-2-[7-oxo-4-(3-trifluoromethyl-phenyl)-[1,4]diazepan-1-yl]-butyramide In analogy to the procedure described in example 1K, (S)—N,N-dimethyl-4-oxo-2-[7-oxo-4-(3-trifluoromethyl-phenyl)-[1,4]diazepan-1-yl]-butyramide and (S)-6-aza-spiro[2.5]octan-4-ol hydrochloride (intermediate 2) gave the title compound in 57% yield as white foam. MS: 497.3 (MH$^+$).

Example 23

4-[(S)-3-((S)-4-Hydroxy-6-aza-spiro[2.5]oct-6-yl)-1-methoxymethyl-propyl]-1-(3-trifluoromethyl-phenyl)-[4]diazepan-5-one

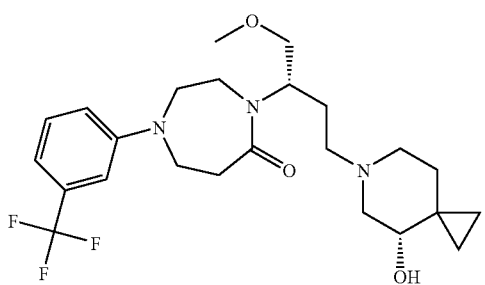

A) 4-((S)-3-Benzyloxy-1-hydroxymethyl-propyl)-1-(3-trifluoromethyl-phenyl)-[1,4]diazepan-5-one In analogy to the procedure described in example 2, (S)-4-benzyloxy-2-[7-oxo-4-(3-trifluoromethyl-phenyl)-[1,4]diazepan-1-yl]-butyric acid methyl ester (example 5B) and LiBH$_4$ gave the title compound in 94% yield as light yellow oil. MS: 437.2 (MH$^+$).

B) 4-((S)-3-Benzyloxy-1-methoxymethyl-propyl)-1-(3-trifluoromethyl-phenyl)-[1,4]diazepan-5-one 0.40 g (0.92 mmol) of the above prepared 4-((S)-3-benzyloxy-1-hydroxymethyl-propyl)-1-(3-trifluoromethyl-phenyl)-[1,4]diazepan-5-one and 0.29 ml (4.58 mmol) of methyl iodide were dissolved in 1.6 ml of DMF. After cooling (0° C.), 0.048 g (1.10 mmol) of NaH (55% dispersion in oil) was added. The reaction was stirred for 3 h at this temperature, then poured onto crashed ice/aq. 10% KHSO$_4$ solution and extracted with Et$_2$O (3×). The organic layers were washed with aq. 10% KHSO$_4$ solution and aq. 10% NaCl solution, dried over Na$_2$SO$_4$, evaporated and purified by flash silica gel column (n-heptane:EtOAc 1:1) to yield 0.42 g (quantitative) of the title compound as light yellow oil. MS: 451.2 (MH$^+$, 1Cl).

C) 4-((S)-3-Hydroxy-1-methoxymethyl-propyl)-1-(3-trifluoromethyl-phenyl)-[1,4]diazepan-5-one In analogy to the procedure described in example 5C, 4-((S)-3-benzyloxy-1-methoxymethyl-propyl)-1-(3-trifluoromethyl-phenyl)-[1,4]diazepan-5-one was hydrogenated to give the title compound in 92% yield as off-white gum. MS: 361.1 (MH$^+$).

D) (S)-4-Methoxy-3-[7-oxo-4-(3-trifluoromethyl-phenyl)-[1,4]diazepan-1-yl]-butyraldehyde In analogy to the procedure described in example 1I, 4-((S)-3-hydroxy-1-methoxymethyl-propyl)-1-(3-trifluoromethyl-phenyl)-[1,4]diazepan-5-one gave the title compound in 91% yield as light yellow oil. MS: 359.2 (MH$^+$).

E) 4-[(S)-3-((S)-4-Hydroxy-6-aza-spiro[2.5]oct-6-yl)-1-methoxymethyl-propyl]-1-(3-trifluoromethyl-phenyl)-[1,4]diazepan-5-one In analogy to the procedure described in example 1K, (S)-4-methoxy-3-[7-oxo-4-(3-trifluoromethyl-phenyl)-[1,4]diazepan-1-yl]-butyraldehyde and (S)-6-aza-spiro[2.5]octan-4-ol hydrochloride (intermediate 2) gave the title compound in 58% yield as light yellow foam. MS: 470.2 (MH$^+$).

Example 24

4-[(S)-3-((3S,5S)-3-Hydroxy-5-methyl-piperidin-1-yl)-1-methoxymethyl-propyl]-1-(3-trifluoromethyl-phenyl)-[1,4]diazepan-5-one

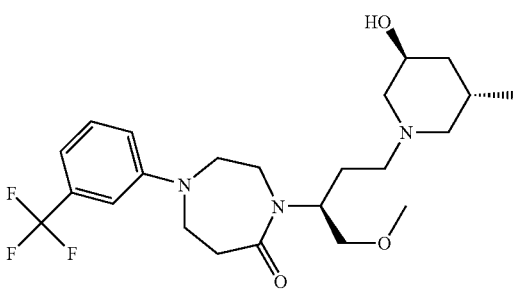

In analogy to the procedure described in example 1K, (S)-4-methoxy-3-[7-oxo-4-(3-trifluoromethyl-phenyl)-[1,4]diazepan-1-yl]-butyraldehyde (example 23D) and (3S,5S)-5-methyl-piperidin-3-ol hydrochloride (intermediate 4) gave the title compound in 63% yield as light yellow gum. MS: 458.3 (MH$^+$).

Example 25

(rac)-5-(4-Hydroxy-4-methyl-piperidin-1-yl)-2-[7-oxo-4-(3-trifluoromethyl-phenyl)-[1,4]diazepan-1-yl]-pentanoic acid dimethylamide

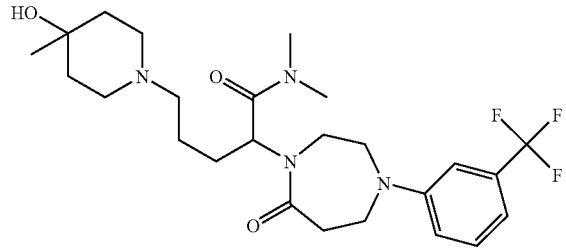

A) (rac)-5-Bromo-2-[7-oxo-4-(3-trifluoromethyl-phenyl)-[1,4]diazepan-1-yl]-pentanoic acid dimethylamide In analogy to the procedure described in example 15B, 1-(3-trifluoromethyl-phenyl)-[1,4]diazepan-5-one (example 15 A) and (rac)-2,5-dibromo-N,N-dimethyl-pentanamide (intermediate 9) gave the title compound in 73% yield as light yellow oil. MS: 466.2 (1Br, MH$^+$).

B) (rac)-5-(4-Hydroxy-4-methyl-piperidin-1-yl)-2-[7-oxo-4-(3-trifluoromethyl-phenyl)-[1,4]diazepan-1-yl]-pentanoic acid dimethylamide A solution of 107 mg (0.23 mmol) of (rac)-5-bromo-2-[7-oxo-4-(3-trifluoromethyl-phenyl)-[1,4]diazepan-1-yl]-pentanoic acid dimethylamide in 4 ml of CH$_3$CN was treated with 115 mg (0.28 mmol) of 4-methyl-piperidin-4-ol (intermediate 8) and 63 mg (0.46 mmol) of potassium carbonate. After 16 h at RT, the reaction mixture was diluted with AcOEt and a white solid was filtered off. The filtrate was evaporated and chromatographed by amine-silica gel column (AcOEt: MeOH 19:1) to yield 40 mg (35%) of the title compound as yellow oil. MS: 499.2 (MH+).

Example 26

(R,S)-5-((S)-4-Hydroxy-6-aza-spiro[2.5]oct-6-yl)-2-[7-oxo-4-(3-trifluoromethyl-phenyl)-[1,4]diazepan-1-yl]-pentanoic acid methyl ester

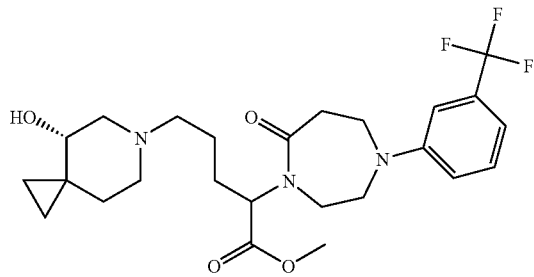

A) (rac)-5-Bromo-2-[7-oxo-4-(3-trifluoromethyl-phenyl)-[1,4]diazepan-1-yl]-pentanoic acid methyl ester In analogy to the procedure described in example 15B, 1-(3-trifluoromethyl-phenyl)-[1,4]diazepan-5-one (example 15 A) and (rac)-2,5-dibromo-pentanoic acid methyl ester gave the title compound in 97% yield as yellow oil. MS: 453.1 (1Br, MH+).

B) (R,S)-5-((S)-4-Hydroxy-6-aza-spiro[2.5]oct-6-yl)-2-[7-oxo-4-(3-trifluoromethyl-phenyl)-[1,4]diazepan-1-yl]-pentanoic acid methyl ester In analogy to the procedure described in example 25B, (rac)-5-bromo-2-[7-oxo-4-(3-trifluoromethyl-phenyl)-[1,4]diazepan-1-yl]-pentanoic acid methyl ester and (S)-6-aza-spiro[2.5]octan-4-ol hydrochloride (intermediate 2) gave the title compound in 82% yield as light yellow oil. MS: 498.0 (MH+).

Example 27

4-[(R,S)-4-((S)-4-Hydroxy-6-aza-spiro[2.5]oct-6-yl)-1-hydroxymethyl-butyl]-1-(3-trifluoromethyl-phenyl)-[1,4]diazepan-5-one

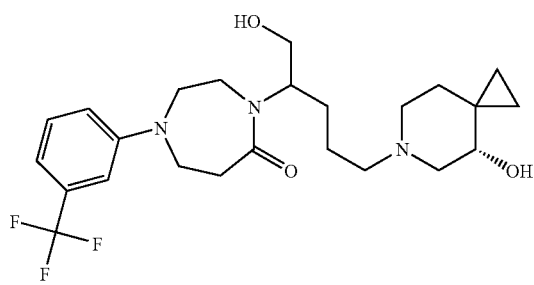

In analogy to the procedure described in example 2, (R,S)-5-((S)-4-hydroxy-6-aza-spiro[2.5]oct-6-yl)-2-[7-oxo-4-(3-trifluoromethyl-phenyl)-[1,4]diazepan-1-yl]-pentanoic acid methyl ester (example 26) was treated with LiBH4 to give the title compound in 73% yield as white foam. MS: 470.2 (MH+).

Example 28

4-[(R,S)-4-((S)-4-Hydroxy-6-aza-spiro[2.5]oct-6-yl)-t-methoxymethyl-butyl]-1-(3-trifluoromethyl-phenyl)-[1,4]diazepan-5-one

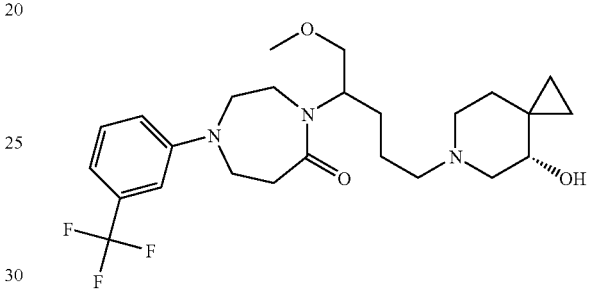

In analogy to the procedure described in example 23B, 4-[(R,S)-4-((S)-4-hydroxy-6-aza-spiro[2.5]oct-6-yl)-1-hydroxymethyl-butyl]-1-(3-trifluoromethyl-phenyl)-[1,4]diazepan-5-one (example 27) was treated with iodomethane and NaH to give the title compound in 21% yield as colorless oil. MS: 484.4 (MH+).

Example 29

(rac)-5-(4-Hydroxy-4-methyl-piperidin-1-yl)-2-[7-oxo-4-(3-trifluoromethyl-phenyl)-[1,4]diazepan-1-yl]-pentanoic acid methyl ester

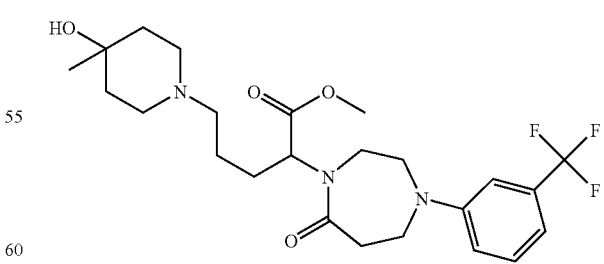

In analogy to the procedure described in example 25B, (rac)-5-bromo-2-[7-oxo-4-(3-trifluoromethyl-phenyl)-[1,4] diazepan-1-yl]-pentanoic acid methyl ester (example 26A) and 4-methyl-piperidin-4-ol (intermediate 8) gave the title compound in 73% yield as colorless oil. MS: 486.3 (MH+).

Example 30

(rac)-4-[1-Hydroxymethyl-4-(4-hydroxy-4-methyl-piperidin-1-yl)-butyl]-1-(3-trifluoromethyl-phenyl)-[1,4]diazepan-5-one

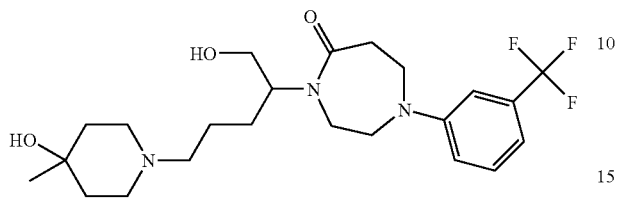

In analogy to the procedure described in example 2, the reduction of (rac)-5-(4-hydroxy-4-methyl-piperidin-1-yl)-2-[7-oxo-4-(3-trifluoromethyl-phenyl)-[1,4]diazepan-1-yl]-pentanoic acid methyl ester with SBH gave the title compound in 98% yield as white foam. MS: 458.3 (MH$^+$).

Example 31

(rac)-4-[4-(4-Hydroxy-4-methyl-piperidin-1-yl)-1-methoxymethyl-butyl]-1-(3-trifluoromethyl-phenyl)-[1,4]diazepan-5-one

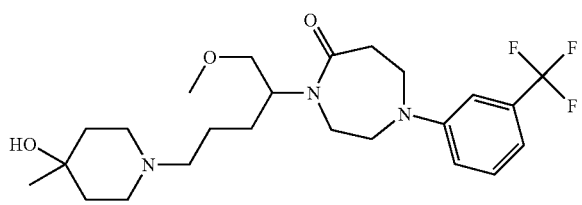

In analogy to the procedure described in example 23B, (rac)-4-[1-hydroxymethyl-4-(4-hydroxy-4-methyl-piperidin-1-yl)-butyl]-1-(3-trifluoromethyl-phenyl)-[1,4]diazepan-5-one was treated with iodomethane and NaH to give the title compound in 25% yield as colorless oil. MS: 472.4 (MH$^+$).

Example 32

4-[(R,S)-4-((S)-4-Hydroxy-6-aza-spiro[2.5]oct-6-yl)-1-hydroxymethyl-butyl]-1-(3-trifluoromethoxy-phenyl)-[1,4]diazepan-5-one

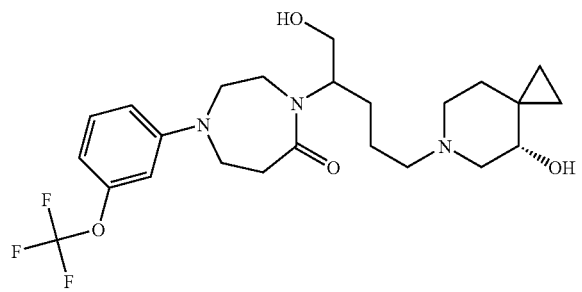

A) 1-(3-Trifluoromethoxy-phenyl)-[1,4]diazepan-5-one

In analogy to the procedure described in example 15A, 1,4-diazepan-5-one and 3-(trifluoromethoxyphenyl)boronic acid gave the title compound in 17% yield as white solid. MS: 275.0 (MH$^+$).

B) (rac)-5-Bromo-2-[7-oxo-4-(3-trifluoromethoxy-phenyl)-[1,4]diazepan-1-yl]-pentanoic acid methyl ester In analogy to the procedure described in example 15B, 1-(3-trifluoromethoxy-phenyl)-[1,4]diazepan-5-one and (rac)-2,5-dibromo-pentanoic acid methyl ester gave the title compound in 92% yield as colorless oil. MS: 469.1 (1Br, MH$^+$).

C) (R,S)-5-((S)-4-Hydroxy-6-aza-spiro[2.5]oct-6-yl)-2-[7-oxo-4-(3-trifluoromethoxy-phenyl)-[1,4]diazepan-1-yl]-pentanoic acid methyl ester In analogy to the procedure described in example 25B, (rac)-5-bromo-2-[7-oxo-4-(3-trifluoromethoxy-phenyl)-[1,4]diazepan-1-yl]-pentanoic acid methyl ester and (S)-6-aza-spiro[2.5]octan-4-ol hydrochloride (intermediate 2) gave the title compound in 52% yield as light yellow oil. MS: 514.3 (MH$^+$).

D) 4-[(R,S)-4-((S)-4-Hydroxy-6-aza-spiro[2.5]oct-6-yl)-1-hydroxymethyl-butyl]-1-(3-trifluoromethoxy-phenyl)-[1,4]diazepan-5-one In analogy to the procedure described in example 2, (R,S)-5-((S)-4-hydroxy-6-aza-spiro[2.5]oct-6-yl)-2-[7-oxo-4-(3-trifluoromethoxy-phenyl)-[1,4]diazepan-1-yl]-pentanoic acid methyl ester was treated with LiBH$_4$ to give the title compound in 92% yield as white foam. MS: 486.3 (MH$^+$).

Example 33

4-(3-Piperidin-1-yl-propyl)-1-(3-trifluoromethyl-phenyl)-[1,4]diazepan-5-one

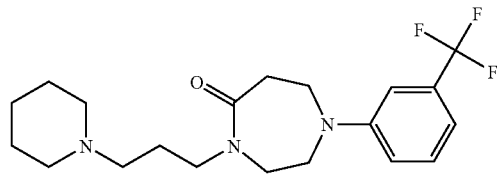

A) 5-Oxo-4-(3-piperidin-1-yl-propyl)-[1,4]diazepane-1-carboxylic acid tert-butyl ester A solution of 8.52 g (39.75 mmol) of 5-oxo-[1,4]diazepane-1-carboxylic acid tert-butyl ester in 200 ml of DMA was treated at 0° C. with 2.60 g (59.62 mmol) of NaH (55% dispersion in oil) in small portions. The reaction was stirred 1 h at this temperature, then the free 1-(3-chloropropyl)piperidine in 200 ml toluene was dropped in [49.62 g (250.42 mmol, 6.3 eq.) 1-(3-chloropropyl)piperidine hydrochloride were dissolved in 262 ml of 1 M aq. 1N NaOH solution and extracted with toluene (200 ml). The organic phase was dried over Na₂SO₄]. The reaction was warmed up to RT and stirred over night. After 2 h at 50° C. and cooling to RT, the reaction was neutralized with water (50 ml), evaporated and then dissolved in aq. sat. NaHCO₃ solution/Et₂O. After reextraction with Et₂O, the organic phase was dried (Na₂SO₄), evaporated and crystallized from pentane to yield 12.08 g (90%) of the title compound as white crystals. MS: 340.2 (MH⁺).

B) 4-(3-Piperidin-1-yl-propyl)-[1,4]diazepan-5-one

A solution of 7.3 g (21.50 mmol) of 5-oxo-4-(3-piperidin-1-yl-propyl)-[1,4]diazepane-1-carboxylic acid tert-butyl ester was in 140 ml CH₂Cl₂, cooled to 0° C. and treated with 54 ml (215 mmol) of HCl solution (4 M dioxane), then warmed to RT. After 3 h, 40 ml of MeOH were added to dissolve the precipitation and stirring was continued over night. The solution was evaporated, dissolved in aq. sat. NaHCO₃. solution, the water evaporated and the solid extracted with in CH₂Cl₂:MeOH 9:1. Concentration afforded the title compound 5.0 g (97%) as yellow oil. MS: 240.1 (MH⁺).

C) 4-(3-Piperidin-1-yl-propyl)-1-(3-trifluoromethyl-phenyl)-[1,4]diazepan-5-one

A suspension of 0.02 g (0.10 mmol) of 4-(3-piperidin-1-yl-propyl)-[1,4]diazepan-5-one, 3-iodobenzotrifluoride 0.03 g (0.12 mmol), Pd(OAc)₂ 0.01 g (0.05 mmol), racemic-2,2'-bis(diphenylphosphino)-1,1'-binaphthyl 0.03 g (0.05 mmol), cesium carbonate 0.16 g (0.5 mmol) in toluene (1 ml) was heated at 110° C. for 24 h. The reaction was then filtered, concentrated and the residue purified by preparative HPLC affording the title compound 0.1 g (26%) as a gum. MS: 384.2 (MH⁺).

Example 34

4-[3-(4-Hydroxy-4-phenyl-piperidin-1-yl)-propyl]-1-(3-trifluoromethyl-phenyl)-[1,4]diazepan-5-one

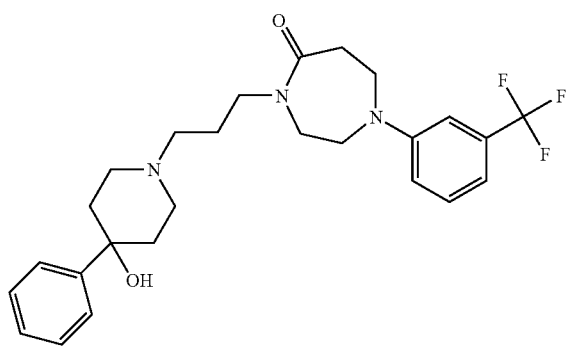

A) 1-(3-Trifluoromethyl-phenyl)-[1,4]diazepan-5-one

To a solution of Pd(OAc)₂ 0.1 g (0.5 mmol) and racemic-2,2'-bis(diphenylphosphino)-1,1'-binaphthyl (0.3 g, 0.5 mmol) in toluene:dioxane (2:1 30 ml) was added 1,4-diazepan-5-one 1.0 g (9.0 mmol), 3-iodobenzenetrifluoride 2.9 g (11 mmol) and cesium carbonate 14.3 g (44 mmol) and the mixture heated to 100° C. for 16 h. The reaction was then filtered and concentrated. The residue was purified by flash column chromatography (EtOAc→EtOAc:MeOH 9:1) to afford the title compound 0.29 g (12%) as a light brown solid. MS: 259.4 (MH⁺).

B) 4-But-3-enyl-1-(3-trifluoromethyl-phenyl)-[1,4]diazepan-5-one

To a solution of 1-(3-trifluoromethyl-phenyl)-[1,4]diazepan-5-one 0.29 g (1 mmol) and 4-bromobut-1-ene 0.3 g (2 mmol) in DMF (2 ml) was added NaH 0.1 g (2 mmol of 55% dispersion in oil) and the mixture stirred for 6 h. The reaction was then poured into water and extracted with EtOAc, dried (Na₂SO₄) and concentrated. Purification by flash column chromatography (EtOAc/n-heptane 1:1) afforded the title compound 0.09 g (25%) as a yellow gum. MS: 313.2 (MH⁺).

C) 3-[7-Oxo-4-(3-trifluoromethyl-phenyl)-[1,4]diazepan-1-yl]-propionaldehyde

To a solution of 4-but-3-enyl-1-(3-trifluoromethyl-phenyl)-[1,4]diazepan-5-one 0.09 g (0.03 mmol) in tBuOH:water (2 ml 1:1) was added potassium osmate dihydrate 0.001 g (0.001 mmol) and sodium periodate 0.13 g (0.1 mmol). The mixture was stirred for 1 h, then extracted with CH₂Cl₂, dried (Na₂SO₄) and concentrated. Purification by flash column chromatography (EtOAc:n-heptane 1:1→1:0) afforded the title compound 0.06 g (64%) as a brown gum. MS: 315.2 (MH⁺).

D) 4-[3-(4-Hydroxy-4-phenyl-piperidin-1-yl)-propyl]-1-(3-trifluoromethyl-phenyl)-[1,4]diazepan-5-one To a solution of 3-[7-oxo-4-(3-trifluoromethyl-phenyl)-[1,4]diazepan-1-yl]-propionaldehyde 0.016 g (0.05 mmol) and 4-phenyl-piperidin-4-ol 0.018 g (0.10 mmol) in DCE/EtOH 1:1 (0.5 ml) was added pyridine-borane complex (25 µL of 8 M solution in pyridine, 0.2 mmol) and AcOH (25 µL, 0.4 mmol) and the mixture stirred for 16 h. The mixture was then evaporated to dryness and purified by preparative HPLC, affording the title compound 0.01 g (44%) as a white solid. MS: 476.2 (MH⁺).

Example 35

4-[3-(4-Fluoro-piperidin-1-yl)-propyl]-1-(3-trifluoromethyl-phenyl)-[1,4]diazepan-5-one

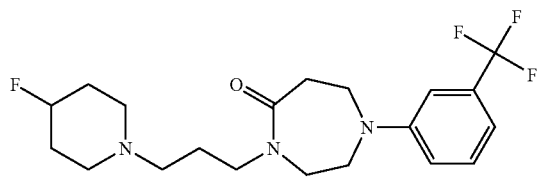

The title compound was prepared from 3-[7-oxo-4-(3-trifluoromethyl-phenyl)-[1,4]diazepan-1-yl]-propionaldehyde (Example 34C) and 4-fluoropiperidine in analogy to example 34D. MS: 402.2 (MH+).

Example 36

1-(3,4-Dichloro-phenyl)-4-(3-piperidin-1-yl-propyl)-[1,4]diazepan-5-one

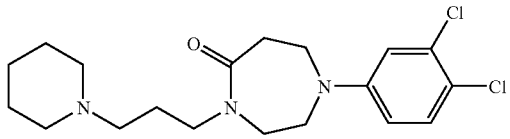

The title compound was prepared from 4-(3-piperidin-1-yl-propyl)-[1,4]diazepan-5-one (Example 33B) and 1,2-dichloro-4-iodo-benzene in analogy to example 33. MS: 384.4 (MH+, 2Cl).

Example 37

4-(3-Piperidin-1-yl-propyl)-1-(3-trifluoromethoxy-phenyl)-[1,4]diazepan-5-one

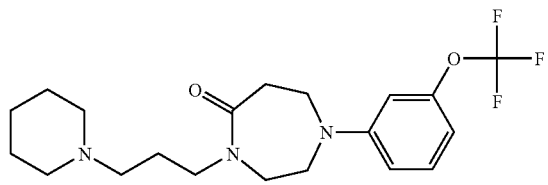

The title compound was prepared from 4-(3-piperidin-1-yl-propyl)-[1,4]diazepan-5-one (Example 33B) and 1-iodo-3-trifluoromethoxy-benzene in analogy to example 33. MS: 400.2 (MH+).

Example 38

4-[3-((S)-4-Hydroxy-6-aza-spiro[2.5]oct-6-yl)-propyl]-1-(3-trifluoromethoxy-phenyl)-[1,4]diazepan-5-one

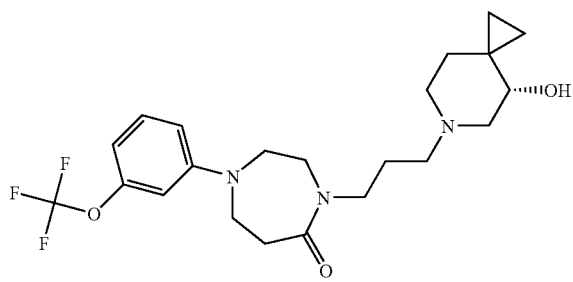

A) 4-[2-(Methoxy-methyl-carbamoyl)-ethyl]-5-oxo-[1,4]diazepane-1-carboxylic acid tert-butyl ester To a cooled (0° C.) solution of 5-oxo-[1,4]diazepane-1-carboxylic acid tert-butyl ester 5.9 g (28 mmol) and 4-bromo-N-methoxy-N-methyl-butyramide 5.4 g (28 mmol) in DMF (220 ml) was added NaH 1.3 g (30 mmol, 55% dispersion in oil), the mixture allowed to reach RT and the mixture stirred for a further 2 h. The reaction was then concentrated, the residue redissolved in EtOAc and washed with 10% aq. KHSO$_4$ solution, brine, dried (MgSO$_4$) and concentrated affording the title compound 9.1 g (quant) as white foam. MS: 330.3 (MH+).

B) 5-Oxo-4-(3-oxo-propyl)-[1,4]diazepane-1-carboxylic acid tert-butyl ester

To a cooled (−78° C.) solution of 4-[2-(methoxy-methyl-carbamoyl)-ethyl]-5-oxo-[1,4]diazepane-1-carboxylic acid tert-butyl ester 3 g (9 mmol) was added dropwise a solution of lithium aluminum hydride 9.1 ml (9 mmol, 1 M solution in THF). The mixture was quenched by addition of acetone and then AcOH. The reaction was allowed to reach RT after which time water and 10% aq. KHSO$_4$ solution were added and the mixture repeatedly extracted with TBME. The combined organic was washed with brine, dried (MgSO$_4$) and concentrated. Purification by flash column chromatography (EtOAc:MeOH 19:1) afforded the title compound 1.5 g (61%) as a colorless oil. MS: 271.5 (MH+).

C) 4-[3-((S)-4-Hydroxy-6-aza-spiro[2.5]oct-6-yl)-propyl]-[1,4]diazepan-5-one

To a suspension of (S)-6-aza-spiro[2.5]octan-4-ol hydrochloride (intermediate 2) 0.16 g (1 mmol) in CH$_2$Cl$_2$ (5 ml) was added Et$_3$N 0.14 ml (1 mmol) and AcOH 0.11 ml (2 mmol) followed by a solution of 5-oxo-4-(3-oxo-propyl)-[1,4]diazepane-1-carboxylic acid tert-butyl ester 0.34 g (1 mmol) in CH$_2$Cl$_2$ (5 ml) and finally sodium triacetoxyborohydride 0.25 g (1 mmol). The mixture was stirred for 1 h after which time sat. aq. NaHCO$_3$. solution was added, the reaction extracted with in CH$_2$Cl$_2$, dried (Na$_2$SO$_4$) and concentrated. The residue was taken up in 1 M HCl solution in dioxane (10 ml), stirred for 10 minutes before the solvent was evaporated. The residue was then dissolved in sat. aq. NaHCO$_3$. solution the water removed by evaporation, and the solid extracted with CH$_2$Cl$_2$:MeOH (9:1). Concentration afforded the title compound 0.2 g (71%) as yellow oil. MS: 282.1 (MH+).

D) 4-[3-((S)-4-Hydroxy-6-aza-spiro[2.5]oct-6-yl)-propyl]-1-(3-trifluoromethoxy-phenyl)-[1,4]diazepan-5-one The title compound was prepared from 4-[3-((S)-4-hydroxy-6-aza-spiro[2.5]oct-6-yl)-propyl]-[1,4]diazepan-5-one and 1-iodo-3-trifluoromethoxy-benzene in analogy to example 33. MS: 442.3 (MH+).

Example 39

(R)-2-Methyl-4-(3-piperidin-1-yl-propyl)-1-(3-trifluoromethyl-phenyl)-[1,4]diazepan-5-one

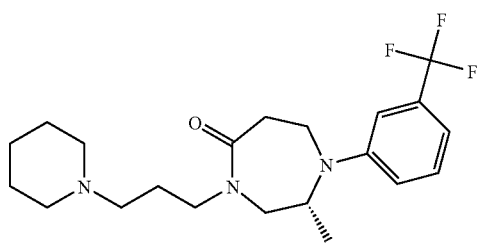

A) ((R)-2-Amino-propyl)-carbamic acid tert-butyl ester 2.0 g (14 mmol) of (R)-propane-1,2-diamine dihydrochloride were charged in the reactor followed by MeOH/H$_2$O (4/1 10 ml). To the resulting solution was added in one portion a solution of 3.8 g (17 mmol) of di-tert-butyl dicarbonate dissolved in MeOH (2 ml). The reaction was cooled to 5° C. 4.4 ml (18 mmol) of aq. 4 M NaOH solution were added dropwise over 2 h. The reaction was allowed to warm to RT. After 17 h, the organic solvents were removed under reduced pressure. 25 ml of EtOAc and 25 ml of water were added. The aqueous phase was adjusted to pH 2-3 with 1 M aq. HCl solution (ca 2 ml). The aqueous phase was separated and washed with 25 ml EtOAc. The organic phases were combined and water (25 ml) was added. The pH was adjusted to pH 2-3 (with 0.5 ml 1 M aq. HCl solution), the organic phase was separated and discarded. The aqueous phases were combined, adjusted to pH 14 by adding ca 2 ml aq NaOH 32% solution and extracted twice with 50 ml CH$_2$Cl$_2$. The organic phases were combined, dried (MgSO$_4$), filtered and concentrated under reduced to afford 1.6 g of the title product as a colorless oil (67% yield, 97% regioselectivity by GC). MS: 175.2 (MH$^+$).

B) 3-[Benzyloxycarbonyl-((R)-2-tert-butoxycarbonylamino-1-methyl-ethyl)-amino]-propionic acid methyl ester 72 g (413 mmol) ((R)-2-amino-propyl)-carbamic acid tert-butyl ester were dissolved in MeOH (350 ml) in a jacketed reactor. A solution of 40 ml (438 mmol) methyl acrylate in MeOH (50 ml) was added over 10 min. After 15 h reaction at RT, 108 g (413 mmol) of N-benzyloxycarbonyloxy-succinimide were added in one portion. After 18 h, the reaction mixture was concentrated under reduced pressure affording a yellow oil (ca 270 g). The oil was re-dissolved in 300 mL MeOH and concentrated under reduced pressure (45° C./160-200 mbar) until constant weight to give 219 g of crude titled product as a yellow oil used directly in the next step.

C) (R)-2-methyl-5-oxo-[1,4]diazepane-1-carboxylic acid benzyl ester 110 g of crude 3-[benzyloxycarbonyl-((R)-2-tert-butoxycarbonylamino-1-methyl-ethyl)-amino]-propionic acid methyl ester were dissolved in EtOAc (500 ml) and extracted twice with 0.1 M aq. HCl solution (200 ml), washed with) water (200 ml) and half-sat. aq. NaCl solution (200 ml). The organic phase was dried (Na$_2$SO$_4$), filtered and concentrated under reduced pressure to afford 88 g of a colorless viscous oil (78% HPLC, contains ca 10% w/w AcOEt), which was dissolved in MeOH (100 ml). This solution was added to a methanolic hydrogen chloride solution (prepared by adding 50 ml acetyl chloride to 300 ml MeOH-caution, highly exothermic). After 5 h stirring the reaction mixture was concentrated under reduced pressure and redissolved in MeOH (300 ml). The solution was concentrated under reduced pressure and redissolved in MeOH (350 ml). 30% NaOMe in MeOH (143 ml) were added over 15-20 min. After 30 min reaction, AcOH (27 ml) was added. The white suspension was stirred overnight (hold point) and filtered. The reactor was washed with MeOH 100 ml). The filtrate was concentrated under reduced pressure and the resulting oil was dissolved in ethyl acetate (300 ml). The solution was washed with water (200 ml), aq. NaHCO$_3$ (200 ml), dried (Na$_2$SO$_4$) and concentrated under reduced pressure to give 51 g of crude product as an oil. The product was crystallized from EtOAc/heptane (400 ml AcOEt/150 ml n-heptane) to provide 29 g of the titled product as a white powder. MS: 262.9 (MH$^+$).

D) (R)-2-Methyl-5-oxo-4-(3-piperidin-1-yl-propyl)-[1,4]diazepane-1-carboxylic acid benzyl ester The title compound could be prepared from (R)-2-methyl-5-oxo-[1,4]diazepane-1-carboxylic acid benzyl ester and 1-(3-chloropropyl)piperidine in analogy to example 33A. MS: 388.3 (MH$^+$).

E) (R)-2-Methyl-4-(3-piperidin-1-yl-propyl)-[1,4]diazepan-5-one

A solution of (R)-2-methyl-5-oxo-4-(3-piperidin-1-yl-propyl)-[1,4]diazepane-1-carboxylic acid benzyl ester 1.0 g (3 mmol) in MeOH (20 ml) was stirred with 10% palladium on charcoal under an atmosphere of hydrogen for 1 h. Filtration and concentrated afforded the title compound 0.6 g (83%) as a colorless oil. MS: 254.2 (MH$^+$).

F) (R)-2-Methyl-4-(3-piperidin-1-yl-propyl)-1-(3-trifluoromethyl-phenyl)-[1,4]diazepan-5-one The title compound was prepared from (R)-2-methyl-4-(3-piperidin-1-yl-propyl)-[1,4]diazepan-5-one and iodobenzotrifluoride in analogy to example 33. MS: 398.3 (MH$^+$).

Example 40

(R)-2-Methyl-4-(3-piperidin-1-yl-propyl)-1-(3-trifluoromethoxy-phenyl)-[1,4]diazepan-5-one

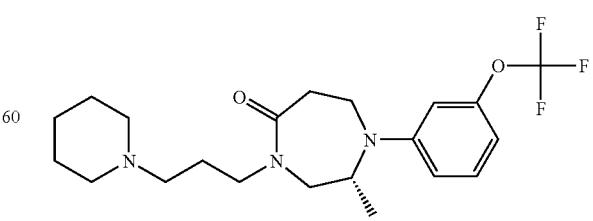

The title compound was prepared from (R)-2-methyl-4-(3-piperidin-1-yl-propyl)-[1,4]diazepan-5-one (Example 39E)

and 1-iodo-3-trifluoromethoxy-benzene in analogy to example 33. MS: 414.4 (MH+).

Example 41

3-Methyl-1-(3-piperidin-1-yl-propyl)-4-(3-trifluoromethoxy-phenyl)-piperazin-2-one

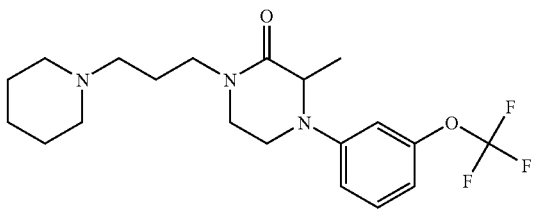

A) (3-Trifluoromethoxy-phenylamino)-acetonitrile

A mixture of 3-(trifluoromethoxy)aniline (1.00 g, 5.64 mmol), bromoacetonitrile (745 mg, 6.21 mmol), sodium iodide (1.86 g, 12.4 mmol), and sodium carbonate (858 mg, 6.21 mmol) in CH$_3$CN (15 mL) was heated at reflux for 18 h, then partitioned between water and EtOAc. The organic layer was washed with brine, dried (MgSO$_4$), filtered, and evaporated. Chromatography (SiO$_2$; heptane/EtOAc gradient) afforded the title compound (904 mg, 74%). Brown liquid, MS: 215.2 (M+H)+.

B) N$^1$-(3-Trifluoromethoxy-phenyl)-ethane-1,2-diamine

Borane-tetrahydrofuran complex solution (1 M in THF, 3.6 mL, 3.6 mmol) was added dropwise at 0° C. to a solution of (3-trifluoromethoxy-phenylamino)-CH$_3$CN (290 mg, 1.34 mmol) in THF (20 mL), then after 1 h the ice bath was removed and the solution heated at reflux for 4 h. After cooling, EtOH (2 mL) and 6 M aq. HCl solution (1 mL) were added, and the reaction mixture was concentrated in vacuo. The residue was partitioned between half-saturated aq. NaHCO$_3$ solution and TBME. The organic layer was washed with brine, dried (MgSO$_4$), filtered, and evaporated. Chromatography (IST Isolute® Flash NH$_2$; EtOAc/MeOH 95:5) afforded the title compound (222 mg, 75%). Colorless oil, MS: 221.2 (M+H)+.

C) 2-Chloro-N-[2-(3-trifluoromethoxy-phenylamino)-ethyl]-propionamide

A solution of 2-chloropropionic acid (103 mg, 0.95 mmol) in CH$_2$Cl$_2$ (10 mL) was added dropwise at −30° C. to a solution of N$^1$-(3-trifluoromethoxy-phenyl)-ethane-1,2-diamine (210 mg, 0.95 mmol) and N,N'-dicyclohexylcarbodiimide (226 mg, 1.10 mmol) in CH$_2$Cl$_2$ (20 mL), then after 1 h insoluble material was removed by filtration and the filtrate evaporated. Chromatography (SiO$_2$; heptane/EtOAc 3:2) afforded the title compound (272 mg, 92%). Colorless oil, MS: 309.3 (M−H)−.

D) 3-Methyl-4-(3-trifluoromethoxy-phenyl)-piperazin-2-one

Sodium iodide (64 mg, 0.43 mmol) and NaHCO$_3$ (86 mg, 1.03 mmol) were added to a solution of 2-chloro-N-[2-(3-trifluoromethoxy-phenylamino)-ethyl]-propionamide (266 mg, 0.86 mmol) in acetone (20 mL). The reaction mixture was heated at reflux for 72 h, then evaporated. The residue was partitioned between EtOAc and water. The organic layer was dried (MgSO$_4$), filtered, and evaporated. Chromatography (SiO$_2$; heptane/EtOAc gradient) afforded the title compound (156 mg, 66%). Yellow oil, MS: 275.1 (M+H)−.

E) 3-Methyl-1-(3-piperidin-1-yl-propyl)-4-(3-trifluoromethoxy-phenyl)-piperazin-2-one NaH (55% dispersion in mineral oil, 36 mg, 0.82 mmol) was added portionwise at RT to a solution of 3-methyl-4-(3-trifluoromethoxy-phenyl)-piperazin-2-one (150 mg, 0.55 mmol) in DMA (3 mL), then after 1 h a solution of 1-(3-chloropropyl)-piperidine in toluene [prepared from commercially available 1-(3-chloropropyl)-piperidine hydrochloride (542 mg, 2.74 mmol) by partitioning between toluene (4 ml) and 1 M aq. sodium hydroxide solution (4 ml) and drying of the organic layer with MgSO$_4$] was added. The reaction mixture was heated at 75° C. for 1 h, then partitioned between sat. aq. NaHCO$_3$ solution and CH$_2$Cl$_2$. The organic layer was dried (MgSO$_4$), filtered, and evaporated. Chromatography (IST Isolute® Flash NH$_2$; EtOAc) afforded the title compound (184 mg, 84%). Light yellow oil, MS: 400.3 (M+H)+.

Examples 42 and 43

(S)-3-Methyl-1-(3-piperidin-1-yl-propyl)-4-(3-trifluoromethoxy-phenyl)-piperazin-2-one and (R)-3-methyl-1-(3-piperidin-1-yl-propyl)-4-(3-trifluoromethoxy-phenyl)-piperazin-2-one

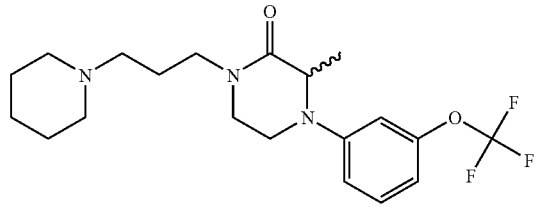

Example 42

(S)-Enantiomer

Example 43

(R)-Enantiomer

The racemate 3-methyl-1-(3-piperidin-1-yl-propyl)-4-(3-trifluoromethoxy-phenyl)-piperazin-2-one (example 42; 130 mg, 0.33 mmol) was separated by preparative HPLC on a Chiralpak® AD column using heptane/EtOH 85:15 as the eluent. This produced (S)-3-methyl-1-(3-piperidin-1-yl-propyl)-4-(3-trifluoromethoxy-phenyl)-piperazin-2-one (49 mg, 38%; light yellow oil, MS: 400.2 (M+H)+) and (R)-3-methyl-1-(3-piperidin-1-yl-propyl)-4-(3-trifluoromethoxy-phenyl)-piperazin-2-one (46 mg, 35%; light yellow oil, MS: 400.2 (M+H)+).

Example 44

1-[3-((S)-4-Hydroxy-6-aza-spiro[2.5]oct-6-yl)-propyl]-3-methyl-4-(3-trifluoromethoxy-phenyl)-piperazin-2-one

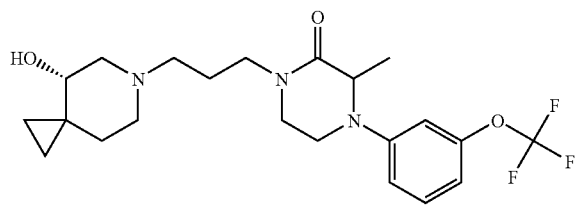

A) N-Methoxy-N-methyl-3-[3-methyl-2-oxo-4-(3-trifluoromethoxy-phenyl)-piperazin-1-yl]-propionamide NaH (55% dispersion in mineral oil, 24 mg, 0.56 mmol) was added at 0° C. to a solution of 3-methyl-4-(3-trifluoromethoxy-phenyl)-piperazin-2-one (example 41D; 127 mg, 0.46 mmol) in N,N-dimethylformamide (3 mL), then after 5 min a solution of 3-bromo-N-methoxy-N-methyl-propionamide (Patent Application US 2007249589; 100 mg, 0.51 mmol) was added. After 30 min the ice bath was removed and the reaction mixture was allowed to reach RT over 1 h, then partitioned between EtOAc and 10% aq. KHSO$_4$ solution. The organic layer was washed with brine, dried (MgSO$_4$), filtered, and evaporated to afford the title compound (189 mg) which was directly used in the next step. Light yellow oil, MS: 390.3 (M+H)$^+$.

B) 3-[3-Methyl-2-oxo-4-(3-trifluoromethoxy-phenyl)-piperazin-1-yl]-propionaldehyde Lithium aluminum hydride solution (1 M in THF (0.46 mL, 0.46 mmol) was added dropwise at −30° C. to a solution of N-methoxy-N-methyl-3-[3-methyl-2-oxo-4-(3-trifluoromethoxy-phenyl)-piperazin-1-yl]-propionamide (180 mg, 0.46 mmol) in THF (10 mL). The reaction mixture was cooled to −75° C., then acetone (0.59 g, 10 mmol) and AcOH (44 mg, 0.93 mmol) were added dropwise. The reaction mixture was then partitioned between TBME and 1 M aq. KHSO$_4$ solution. The organic layer was dried (MgSO$_4$), filtered, and evaporated to afford the title compound (122 mg, 80%). Light yellow oil, MS: 331.1 (M+H)$^+$.

C) 1-[3-((S)-4-Hydroxy-6-aza-spiro[2.5]oct-6-yl)-propyl]-3-methyl-4-(3-trifluoromethoxy-phenyl)-piperazin-2-one To a solution of 3-[3-methyl-2-oxo-4-(3-trifluoromethoxy-phenyl)-piperazin-1-yl]-propionaldehyde (117 mg, 0.35 mmol) in EtOH (1.6 mL) and CH$_2$Cl$_2$ (1.6 mL) were added (S)-6-aza-spiro[2.5]octan-4-ol hydrochloride (intermediate 2; 70 mg, 0.43 mmol) triethylamine (43 mg, 0.43 mmol), borane pyridine complex solution (8 M in pyridine, 0.093 mL, 0.74 mmol), then after 1 h the reaction mixture was partitioned between CH$_2$Cl$_2$ and sat. aq. NaHCO$_3$ solution. The organic layer was washed with brine, dried (MgSO$_4$), filtered, and evaporated. Chromatography (SiO$_2$; CH$_2$Cl$_2$, then CH$_2$Cl$_2$/MeOH 4:1) afforded the title compound (90 mg, 58%). Light yellow oil, MS: 442.3 (M+H)$^+$.

Examples 45 and 46

(S)-1-[3-((S)-4-Hydroxy-6-aza-spiro[2.5]oct-6-yl)-propyl]-3-methyl-4-(3-trifluoromethoxy-phenyl)-piperazin-2-one and (R)-1-[3-((S)-4-hydroxy-6-aza-spiro[2.5]oct-6-yl)-propyl]-3-methyl-4-(3-trifluoromethoxy-phenyl)-piperazin-2-one

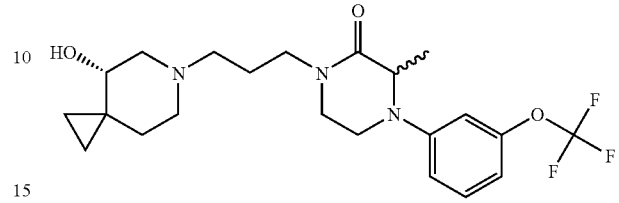

Example 45

(S)-Epimer

Example 46

(R)-Epimer

The epimeric mixture, 1-[3-((S)-4-hydroxy-6-aza-spiro[2.5]oct-6-yl)-propyl]-3-methyl-4-(3-trifluoromethoxy-phenyl)-piperazin-2-one (example 44; 85 mg, 0.19 mmol), was separated by preparative HPLC on a Chiralpak® AD column using heptane/EtOH 75:25 as the eluent. This produced (S)-1-[3-((S)-4-hydroxy-6-aza-spiro[2.5]oct-6-yl)-propyl]-3-methyl-4-(3-trifluoromethoxy-phenyl)-piperazin-2-one (27 mg, 32%; light yellow oil, MS: 442.4 (M+H)$^+$) and (R)-1-[3-((S)-4-hydroxy-6-aza-spiro[2.5]oct-6-yl)-propyl]-3-methyl-4-(3-trifluoromethoxy-phenyl)-piperazin-2-one (26 mg, 31%; light yellow oil, MS: 442.3 (M+H)$^+$).

Example 47

4-((S)-4-Hydroxy-6-aza-spiro[2.5]oct-6-yl)-2-[3-methyl-2-oxo-4-(3-trifluoromethoxy-phenyl)-piperazin-1-yl]-butyric acid methyl ester

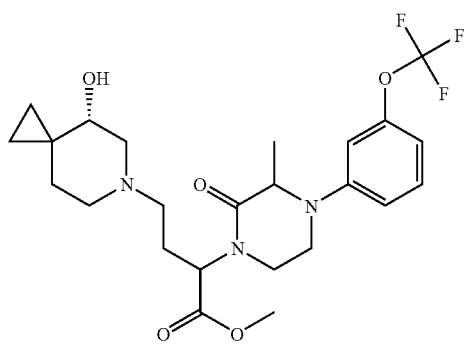

A) 4-(tert-Butyl-diphenyl-silanyloxy)-2-[3-methyl-2-oxo-4-(3-trifluoromethoxy-phenyl)-piperazin-1-yl]-butyric acid methyl ester The title compound was produced in analogy to example 15B from 3-methyl-4-(3-trifluoromethoxy-phenyl)-piperazin-2-one (example 41D) and 4-(tert-butyl-diphenyl-silanyloxy)-2-methanesulfonyloxy-butyric acid methyl ester (intermediate 10). Yellow oil, MS: 629.4 (M+H)$^+$.

B) 4-Hydroxy-2-[3-methyl-2-oxo-4-(3-trifluoromethoxy-phenyl)-piperazin-1-yl]-butyric acid methyl ester Boron trichloride solution (1 M in CH$_2$Cl$_2$, 1.33 mL, 1.33 mmol) was added at 0° C. to a solution of 4-(tert-butyl-diphenyl-silanyloxy)-2-[3-methyl-2-oxo-4-(3-trifluoromethoxy-phenyl)-piperazin-1-yl]-butyric acid methyl ester (430 mg, 0.68 mmol) in CH$_2$Cl$_2$ (6 mL), then the ice bath was removed and the solution stirred for 18 h. Another portion of boron trichloride solution (1 M in CH$_2$Cl$_2$, 0.70 mL, 0.70 mmol) was then added, then after 6 h the reaction mixture was partitioned between CH$_2$Cl$_2$ and sat. aq. NaHCO$_3$ solution. The organic layer was washed with brine, dried (MgSO$_4$), filtered, and evaporated. Chromatography (SiO$_2$; heptane/EtOAc 4:1) afforded the title compound (131 mg, 42%), which contained 15% of the lactonized side product, 3-methyl-1-(2-oxo-tetrahydro-furan-3-yl)-4-(3-trifluoromethoxy-phenyl)-piperazin-2-one. Light yellow oil, MS: 391.1 (M+H)$^+$.

C) 2-[3-Methyl-2-oxo-4-(3-trifluoromethoxy-phenyl)-piperazin-1-yl]-4-oxo-butyric acid methyl ester The title compound was produced in analogy to example 1D from 4-hydroxy-2-[3-methyl-2-oxo-4-(3-trifluoromethoxy-phenyl)-piperazin-1-yl]-butyric acid methyl ester. Colorless oil, MS: 389.1 (M+H)$^+$.

D) 4-((S)-4-Hydroxy-6-aza-spiro[2.5]oct-6-yl)-2-[3-methyl-2-oxo-4-(3-trifluoromethoxy-phenyl)-piperazin-1-yl]-butyric acid methyl ester The title compound was produced in analogy to example 44C from 2-[3-methyl-2-oxo-4-(3-trifluoromethoxy-phenyl)-piperazin-1-yl]-4-oxo-butyric acid methyl ester and (S)-6-aza-spiro[2.5]octan-4-ol hydrochloride (intermediate 2). Colorless oil, MS: 500.2 (M+H)$^+$.

Examples 48 and 49

4-((S)-4-Hydroxy-6-aza-spiro[2.5]oct-6-yl)-2-[3-methyl-2-oxo-4-(3-trifluoromethoxy-phenyl)-piperazin-1-yl]-butyric acid and 1-[3-((S)-4-hydroxy-6-aza-spiro[2.5]oct-6-yl)-1-hydroxymethyl-propyl]-3-methyl-4-(3-trifluoromethoxy-phenyl)-piperazin-2-one

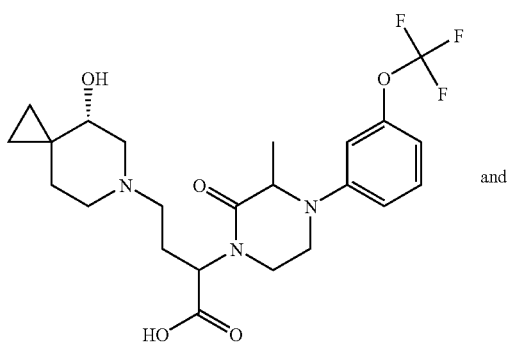

and

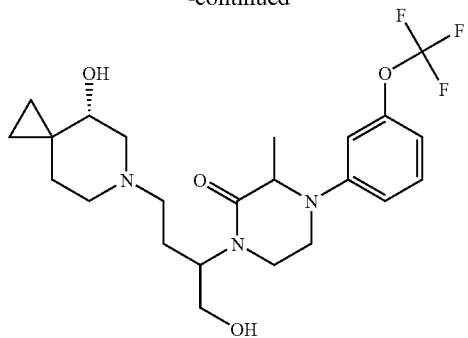

Sodium borohydride (11 mg, 0.28 mmol) was added at RT to a solution of 4-((S)-4-hydroxy-6-aza-spiro[2.5]oct-6-yl)-2-[3-methyl-2-oxo-4-(3-trifluoromethoxy-phenyl)-piperazin-1-yl]-butyric acid methyl ester (70 mg, 0.14 mmol) in EtOH (2 mL), then after 16 min another portion of sodium borohydride (11 mg, 0.28 mmol) was added. After 24 h another portion of sodium borohydride (30 mg, 0.80 mmol) was added and the reaction mixture heated at 60° C. for 6 h. After cooling 10% aq. KHSO$_4$ solution and CH$_2$Cl$_2$ were added to the reaction mixture, the organic layer washed with brine, dried (MgSO$_4$), filtered, and evaporated. Chromatography (SiO$_2$; CH$_2$Cl$_2$/MeOH 4:1, then CH$_2$Cl$_2$/MeOH/25% aq. ammonia solution 80:20:1) afforded 4-((S)-4-hydroxy-6-aza-spiro[2.5]oct-6-yl)-2-[3-methyl-2-oxo-4-(3-trifluoromethoxy-phenyl)-piperazin-1-yl]-butyric acid (41 mg, 60%; light yellow solid, MS: 484.2 (M–H)$^-$) and 1-[3-((S)-4-hydroxy-6-aza-spiro[2.5]oct-6-yl)-1-hydroxymethyl-propyl]-3-methyl-4-(3-trifluoromethoxy-phenyl)-piperazin-2-one (22 mg, 33%; colorless oil, MS: 472.2 (M+H)$^+$).

Example 50

4-((S)-4-Hydroxy-6-aza-spiro[2.5]oct-6-yl)-N,N-dimethyl-2-[3-methyl-2-oxo-4-(3-trifluoromethoxy-phenyl)-piperazin-1-yl]-butyramide

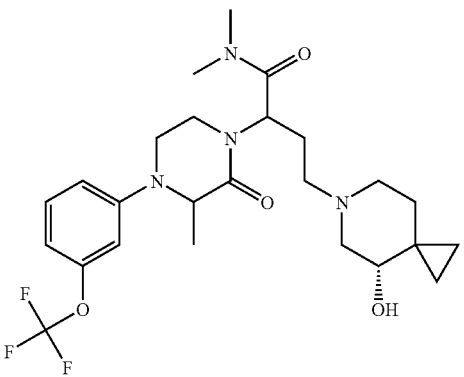

To a solution of 4-((S)-4-hydroxy-6-aza-spiro[2.5]oct-6-yl)-2-[3-methyl-2-oxo-4-(3-trifluoromethoxy-phenyl)-piperazin-1-yl]-butyric acid (example 48; 40 mg, 82 μmol) in N,N-dimethylformamide (1.5 mL) was added dimethylamine hydrochloride (10 mg, 0.12 mmol), triethylamine (33 mg, 0.33 mmol) and O-(7-azabenzotriazol-1-yl)-1,1,3,3-tetramethyluronium hexafluorophosphate (38 mg, 99 μmol), then after 1 h the reaction mixture was partitioned between EtOAc and sat. aq. NaHCO$_3$ solution. The organic layer was washed with brine, dried (MgSO$_4$), filtered, and evaporated. Chroma-

Example 51

3-Methyl-1-(3-piperidin-1-yl-propyl)-4-(3-trifluoromethyl-phenyl)-piperazin-2-one

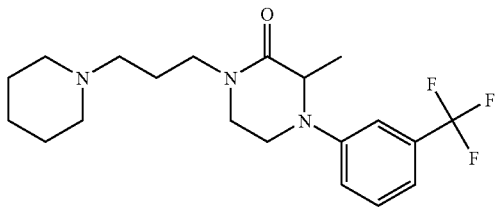

A) (3-Trifluoromethyl-phenylamino)-acetonitrile

The title compound was produced in analogy with example 41A from 3-(trifluoro-methyl)aniline and bromoacetonitrile. Yellow oil, MS: 199.1 (M–H)⁻.

B) N¹-(3-Trifluoromethyl-phenyl)-ethane-1,2-diamine

The title compound was produced in analogy with example 41B from (3-trifluoromethyl-phenylamino)-acetonitrile. Light yellow oil, MS: 205.1 (M+H)⁺.

C) 2-Chloro-N-[2-(3-trifluoromethyl-phenylamino)-ethyl]-propionamide

The title compound was produced in analogy with example 41C from 2-chloropropionic acid and N¹-(3-trifluoromethyl-phenyl)-ethane-1,2-diamine. Light yellow oil, MS: 295.1 (M+H)⁺.

D) 3-Methyl-4-(3-trifluoromethyl-phenyl)-piperazin-2-one

The title compound was produced in analogy with example 41D from 2-chloro-N-[2-(3-trifluoromethyl-phenylamino)-ethyl]-propionamide. Yellow solid, MS: 259.0 (M+H)⁺.

E) 3-Methyl-1-(3-piperidin-1-yl-propyl)-4-(3-trifluoromethyl-phenyl)-piperazin-2-one The title compound was produced in analogy with example 41E from 3-methyl-4-(3-trifluoromethyl-phenyl)-piperazin-2-one and 1-(3-chloropropyl)-piperidine. Light yellow oil, MS: 384.3 (M+H)⁺.

Examples 52 and 53

(S)-3-Methyl-1-(3-piperidin-1-yl-propyl)-4-(3-trifluoromethyl-phenyl)-piperazin-2-one and (R)-3-Methyl-1-(3-piperidin-1-yl-propyl)-4-(3-trifluoromethyl-phenyl)-piperazin-2-one

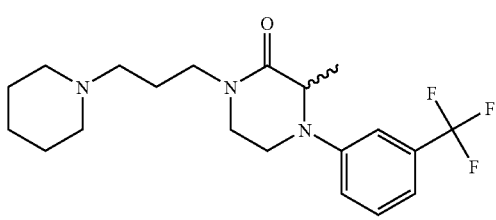

Example 52

(S)-Enantiomer

Example 53

(R)-Enantiomer

The racemate 3-methyl-1-(3-piperidin-1-yl-propyl)-4-(3-trifluoromethoxy-phenyl)-piperazin-2-one (example 51; 100 mg, 0.26 mmol) was separated by preparative HPLC on a Chiralpak® AD column using heptane/EtOH 80:20 as the eluent. This produced (S)-3-methyl-1-(3-piperidin-1-yl-propyl)-4-(3-trifluoromethoxy-phenyl)-piperazin-2-one (which was further purified by chromatography using a IST Isolute® Flash NH₂ and EtOAc as the eluent to yield 27 mg, 27%; colorless oil, MS: 384.3 (M+H)⁺) and (R)-3-methyl-1-(3-piperidin-1-yl-propyl)-4-(3-trifluoromethoxy-phenyl)-piperazin-2-one (33 mg, 33%; light yellow oil, MS: 384.2 (M+H)⁺).

Example 54

4-((S)-4-Hydroxy-6-aza-spiro[2.5]oct-6-yl)-2-[3-methyl-2-oxo-4-(3-trifluoromethyl-phenyl)-piperazin-1-yl]-butyric acid methyl ester

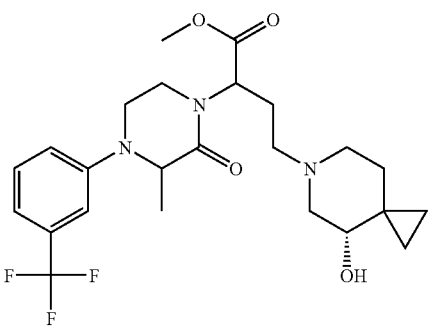

The title compound was produced in analogy to example 47, steps B-D. Thus, deprotection of 4-(tert-butyl-diphenyl-silanyloxy)-2-[3-methyl-2-oxo-4-(3-trifluoromethyl-phenyl)-piperazin-1-yl]-butyric acid methyl ester (example 56A) in step B, produced 4-hydroxy-2-[3-methyl-2-oxo-4-(3-trifluoromethyl-phenyl)-piperazin-1-yl]-butyric acid methyl ester. This was oxidized in step C to 2-[3-methyl-2-oxo-4-(3-trifluoromethyl-phenyl)-piperazin-1-yl]-4-oxo-butyric acid methyl ester, which was reacted in step D with (S)-6-aza-spiro[2.5]octan-4-ol hydrochloride (intermediate 2). Yellow oil, MS: 484.4 (M+H)⁺.

Example 55

1-[3-((S)-4-Hydroxy-6-aza-spiro[2.5]oct-6-yl)-1-hydroxymethyl-propyl]-3-methyl-4-(3-trifluoromethyl-phenyl)-piperazin-2-one

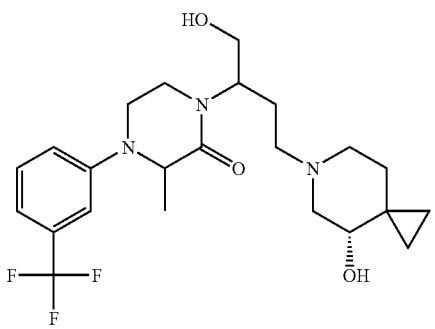

Sodium borohydride (63 mg, 1.7 mmol) was added at RT to a solution of 4-((S)-4-hydroxy-6-aza-spiro[2.5]oct-6-yl)-2-[3-methyl-2-oxo-4-(3-trifluoromethyl-phenyl)-piperazin-1-yl]-butyric acid methyl ester (example 54; 80 mg, 0.17 mmol) in EtOH (2 mL). The reaction mixture was heated at reflux for 2 h, then after cooling partitioned between $CH_2Cl_2$ and 10% aq. $KHSO_4$ solution. The organic layer was dried ($MgSO_4$), filtered, and evaporated. Chromatography (IST Isolute® Flash $NH_2$; EtOAc/MeOH 19:1) afforded the title compound (42 mg, 56%). Colorless oil, MS: 456.3 $(M+H)^+$.

Example 56

1-[3-((S)-4-Hydroxy-6-aza-spiro[2.5]oct-6-yl)-1-methoxymethyl-propyl]-3-methyl-4-(3-trifluoromethyl-phenyl)-piperazin-2-one

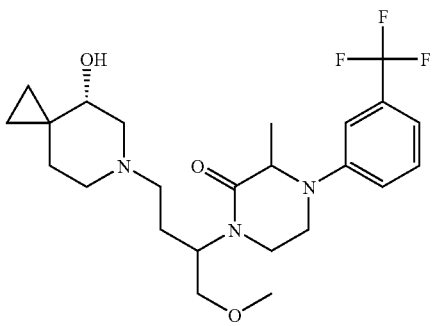

A) 4-(tert-Butyl-diphenyl-silanyloxy)-2-[3-methyl-2-oxo-4-(3-trifluoromethyl-phenyl)-piperazin-1-yl]-butyric acid methyl ester The title compound was produced in analogy to example 47A from 3-methyl-4-(3-trifluoromethyl-phenyl)-piperazin-2-one (example 51D) and 4-(tert-butyl-diphenyl-silanyloxy)-2-methanesulfonyloxy-butyric acid methyl ester (intermediate 10). Yellow oil, MS: 613.2 $(M+H)^+$.

B) 1-[3-(tert-Butyl-diphenyl-silanyloxy)-1-hydroxymethyl-propyl]-3-methyl-4-(3-trifluoromethyl-phenyl)-piperazin-2-one Sodium borohydride (59 mg, 1.6 mmol) was added at RT to a solution of 4-(tert-butyl-diphenyl-silanyloxy)-2-[3-methyl-2-oxo-4-(3-trifluoromethyl-phenyl)-piperazin-1-yl]-butyric acid methyl ester (480 mg, 0.78 mmol) in EtOH (7 mL), then after 20 h the reaction mixture was partitioned between 10% aq. $KHSO_4$ solution and $CH_2Cl_2$. The organic layer was dried ($MgSO_4$), filtered, and evaporated. Chromatography ($SiO_2$; heptane/EtOAc 4:1) afforded the title compound (224 mg, 49%). Light yellow oil, MS: 585.4 $(M+H)^+$.

C) 1-[3-(tert-Butyl-diphenyl-silanyloxy)-1-methoxymethyl-propyl]-3-methyl-4-(3-trifluoromethyl-phenyl)-piperazin-2-one NaH (55% dispersion in mineral oil, 20 mg, 0.45 mmol) was added at 0° C. to a solution of 1-[3-(tert-butyl-diphenyl-silanyloxy)-1-hydroxymethyl-propyl]-3-methyl-4-(3-trifluoromethyl-phenyl)-piperazin-2-one (224 mg, 0.38 mmol) in N,N-dimethylformamide (3.5 mL), then after 5 min a solution of iodomethane (54 mg, 0.45 mmol) in N,N-dimethylformamide (1.5 mL) was added, then after 3 h the reaction mixture was partitioned between EtOAc and sat. aq. $NaHCO_3$ solution. The organic layer was washed with brine, dried ($MgSO_4$), filtered, and evaporated. Chromatography ($SiO_2$; heptane/EtOAc 19:1) afforded the title compound (139 mg, 61%). Light yellow oil, MS: 599.3 $(M+H)^+$.

D) 1-(3-Hydroxy-1-methoxymethyl-propyl)-3-methyl-4-(3-trifluoromethyl-phenyl)-piperazin-2-one To a solution of 1-[3-(tert-butyl-diphenyl-silanyloxy)-1-methoxymethyl-propyl]-3-methyl-4-(3-trifluoromethyl-phenyl)-piperazin-2-one (139 mg, 0.23 mmol) in THF (3 mL) was added tetrabutylammonium fluoride solution (1 M in THF, 0.28 mL, 0.28 mmol) at 0° C., then after 2 h the reaction mixture was partitioned between sat. aq. $NaHCO_3$ solution and EtOAc. The organic layer was washed with brine, dried ($MgSO_4$), filtered, and evaporated. Chromatography ($SiO_2$; EtOAc/MeOH 19:1) afforded the title compound (44 mg, 52%) as a colorless oil.

E) 4-Methoxy-3-[3-methyl-2-oxo-4-(3-trifluoromethyl-phenyl)-piperazin-1-yl]-butyraldehyde The title compound was produced in analogy to example 1D from 1-(3-hydroxy-1-methoxymethyl-propyl)-3-methyl-4-(3-trifluoromethyl-phenyl)-piperazin-2-one. Yellow oil, MS: 359.2 $(M+H)^+$.

F) 1-[3-((S)-4-Hydroxy-6-aza-spiro[2.5]oct-6-yl)-1-methoxymethyl-propyl]-3-methyl-4-(3-trifluoromethyl-phenyl)-piperazin-2-one The title compound was produced in analogy to example 44C from 4-methoxy-3-[3-methyl-2-oxo-4-(3-trifluoromethyl-phenyl)-piperazin-1-yl]-butyraldehyde and (S)-6-aza-spiro[2.5]octan-4-ol hydrochloride (intermediate 2). Light yellow oil, MS: 470.4 $(M+H)^+$.

Example 57

1-(4-Benzyl-morpholin-2-ylmethyl)-3-methyl-4-(3-trifluoromethyl-phenyl)-piperazin-2-one

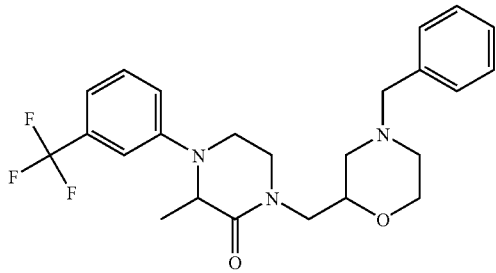

The title compound was produced in analogy to example 41E from 3-methyl-4-(3-trifluoromethyl-phenyl)-piperazin-2-one (example 51D) and 4-benzyl-2-(chloromethyl)morpholine. Yellow oil, MS: 448.2 (M+H)$^+$.

Example 58

3-Methyl-1-(1-methyl-piperidin-3-ylmethyl)-4-(3-trifluoromethyl-phenyl)-piperazin-2-one

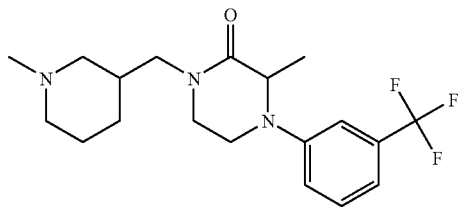

The title compound was produced in analogy to example 41E from 3-methyl-4-(3-trifluoromethyl-phenyl)-piperazin-2-one (example 51D) and 3-chloromethyl-1-methylpiperidine. Yellow oil, MS: 370.2 (M+H)$^+$.

Example 59

(S)-2-[4-(3,4-Dichloro-phenyl)-7-oxo-[1,4]diazepan-1-yl]-4-((S)-4-hydroxy-6-aza-spiro[2.5]oct-6-yl)-N,N-dimethyl-butyramide

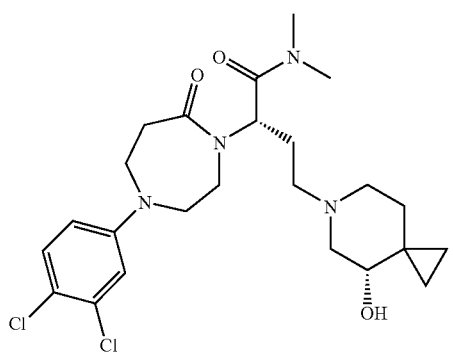

A) Lithium: (S)-2-[4-(3,4-dichloro-phenyl)-7-oxo-[1,4]diazepan-1-yl]-4-((S)-4-hydroxy-6-aza-spiro[2.5]oct-6-yl)-butyrate A solution of 0.369 g (0.76 mmol) of ((S)-2-[4-(3,4-dichloro-phenyl)-7-oxo-[1,4]diazepan-1-yl]-4-((S)-4-hydroxy-6-aza-spiro[2.5]oct-6-yl)-butyric acid methyl ester (example 1K) in 2 ml THF/MeOH (1:1) was treated at 0° C. with 0.762 ml (0.76 mmol) of 1 M aq. LiOH solution, and kept 3 h at this temperature. The reaction was evaporated, dissolved in CH$_3$CN and evaporated again (3×) to give 0.367 g (quantitative) of the title compound as light yellow solid. MS: 468.2 (M−H$^-$, 2Cl).

B) (S)-2-[4-(3,4-Dichloro-phenyl)-7-oxo-[1,4]diazepan-1-yl]-4-((S)-4-hydroxy-6-aza-spiro[2.5]oct-6-yl)-N,N-dimethyl-butyramide 0.080 g (0.17 mmol) of lithium; (S)-2-[4-(3,4-dichloro-phenyl)-7-oxo-[1,4]diazepan-1-yl]-4-((S)-4-hydroxy-6-aza-spiro[2.5]oct-6-yl)-butyrate was dissolved at RT in 0.88 ml of N,N-dimethylformamide followed by addition of 0.094 ml (0.67 mmol, 4 eq.) of triethylamine, 0.015 g (0.18 mmol, 1.1 eq.) of dimethylamine hydrochloride and at 0° C. with 0.072 g (0.18 mmol, 1.1 eq.) of O-(7-azabenzotriazol-1-yl)-1,1,3,3-tetramethyluronium hexafluorophosphate. The solution was stirred overnight and warmed up to RT. The reaction was poured on a solution of sat. aq. NaHCO$_3$ solution, followed by extraction with EtOAc (3 times). The organic phases were washed with a solution of sat. aq. NaHCO$_3$ solution and with 10% aq. NaCl solution. The combined organic phases were dried over Na$_2$SO$_4$ and the solvent was removed under vacuum. The crude product was purified by flash chromatography (20 g IST Isolute® Flash NH$_2$; EtOAc/n-heptane 9:1) to give 0.072 g (86%) of the title compound as white foam. MS: 497.3 (MH$^+$, 2Cl).

Example 60

1-(3,4-Dichloro-phenyl)-4-[(S)-3-((S)-4-hydroxy-6-aza-spiro[2.5]oct-6-yl)-1-(pyrrolidine-1-carbonyl)-propyl]-[1,4]diazepan-5-one

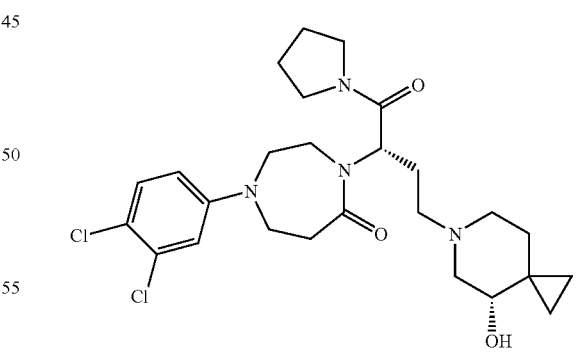

In analogy to the procedure described in example 59B, lithium; (S)-2-[4-(3,4-dichloro-phenyl)-7-oxo-[1,4]diazepan-1-yl]-4-((S)-4-hydroxy-6-aza-spiro[2.5]oct-6-yl)-butyrate (example 59A) and pyrrolidine (but with 1 eq. of triethylamine) gave after purification by flash chromatography (20 g amine-silica, CH$_2$Cl$_2$, then CH$_2$Cl$_2$/MeOH 19:1+0.25% NH$_3$) 0.040 g (52%) of the title compound as white foam. MS: 523.3 (MH$^+$, 2Cl).

Example 61

(S)-2-[4-(3,4-Dichloro-phenyl)-7-oxo-[1,4]diazepan-1-yl]-4-((S)-4-hydroxy-6-aza-spiro[2.5]oct-6-yl)-N-(2-hydroxy-ethyl)-N-methyl-butyramide

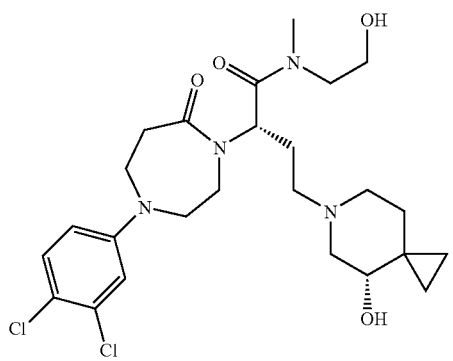

In analogy to the procedure described in example 59B, lithium; (S)-2-[4-(3,4-dichloro-phenyl)-7-oxo-[1,4]diazepan-1-yl]-4-((S)-4-hydroxy-6-aza-spiro[2.5]oct-6-yl)-butyrate (example 59A) and 2-methylamino-ethanol (but with 1 eq. of triethylamine) gave 0.060 g (68%) of the title compound as white foam. MS: 527.3 (MH+, 2Cl).

Example 62

(S)—N-Cyclopropyl-2-[4-(3,4-dichloro-phenyl)-7-oxo-[1,4]diazepan-1-yl]-4-((S)-4-hydroxy-6-aza-spiro[2.5]oct-6-yl)-N-methyl-butyramide

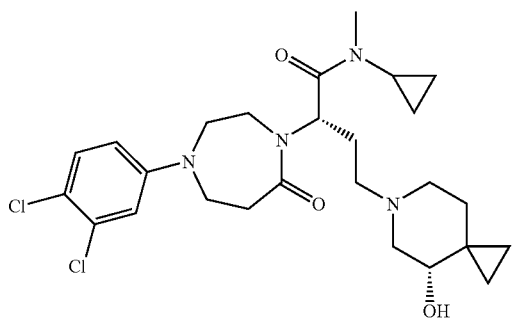

0.080 g (0.17 mmol) of lithium; (S)-2-[4-(3,4-dichloro-phenyl)-7-oxo-[1,4]diazepan-1-yl]-4-((S)-4-hydroxy-6-aza-spiro[2.5]oct-6-yl)-butyrate (example 59A) and 0.021 g (0.18 mmol, 1.1 eq.) of N-hydroxy-2-pyridone were suspended in 4 ml CH$_2$Cl$_2$ and treated at 0° C. with 0.036 g (0.18 mmol, 1.1 eq.) of N-(3-dimethylaminopropyl)-N'-ethylcarbodiimide hydrochloride. The cooling bath was allowed to come to RT and the reaction mixture became cloudier. After addition of 2.0 ml of N,N-dimethylformamide, this reaction mixture went into solution. The solution was stirred overnight at RT. 0.031 g (0.18 mmol, 1.1 eq.) of N-cyclopropylmethylamine oxalate salt was dissolved in 1.5 ml of dimethyl sulfoxide, treated with 0.026 ml (0.18 mmol, 1.1 eq.) of triethylamine and added to the activated ester intermediate. After 1 h at RT, the reaction was poured on a solution of sat. aq. NaHCO$_3$ solution and extracted with diethyl ether (3 times). The organic phases were washed with a solution of sat. aq. NaHCO$_3$ solution and with 10% aq. NaCl solution. The combined organic phases were dried over Na$_2$SO$_4$ and the solvent was removed under vacuum. The crude product was purified by flash chromatography (20 g IST Isolute® Flash NH$_2$; EtOAc/n-heptane 1:1, 2:1) to give 0.062 g (71%) of the title compound as white foam. MS: 523.2 (MH+, 2Cl).

Example 63

1-(3,4-Dichloro-phenyl)-4-[(S)-1-(3,3-difluoro-azetidine-1-carbonyl)-3-((S)-4-hydroxy-6-aza-spiro[2.5]oct-6-yl)-propyl]-[1,4]diazepan-5-one

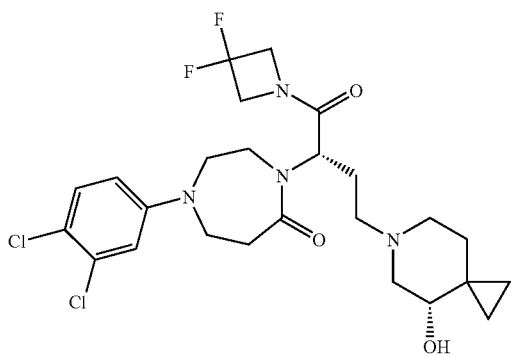

In analogy to the procedure described in example 59B, lithium; (S)-2-[4-(3,4-dichloro-phenyl)-7-oxo-[1,4]diazepan-1-yl]-4-((S)-4-hydroxy-6-aza-spiro[2.5]oct-6-yl)-butyrate (example 59A) and 3,3-difluoroazetidine hydrochloride gave 0.078 g (77%) of the title compound as white foam. MS: 545.3 (MH+, 2Cl).

Example 64

(S)-2-[4-(3,4-Dichloro-phenyl)-7-oxo-[1,4]diazepan-1-yl]-4-((S)-4-hydroxy-6-aza-spiro[2.5]oct-6-yl)-butyramide

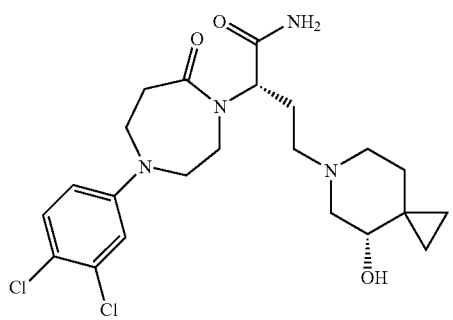

In analogy to the procedure described in example 59B, lithium; (S)-2-[4-(3,4-dichloro-phenyl)-7-oxo-[1,4]diazepan-1-yl]-4-((S)-4-hydroxy-6-aza-spiro[2.5]oct-6-yl)-butyrate (example 59A) and 1.2 eq. of ammonium bicarbonate

Examples 65, 66 and 67

(S)-2-[(R)-4-(3,4-dichloro-phenyl)-3-methyl-7-oxo-[1,4]diazepan-1-yl]-4-((S)-4-hydroxy-6-aza-spiro[2.5]oct-6-yl)-butyric acid methyl ester, (S)-2-[(S)-4-(3,4-dichloro-phenyl)-3-methyl-7-oxo-[1,4]diazepan-1-yl]-4-((S)-4-hydroxy-6-aza-spiro[2.5]oct-6-yl)-butyric acid methyl ester, and (S)-2-[(R,S)-4-(3,4-dichloro-phenyl)-3-methyl-7-oxo-[1,4]diazepan-1-yl]-4-((S)-4-hydroxy-6-aza-spiro[2.5]oct-6-yl)-butyric acid methyl ester (1:1 Diastereomeric Mixture)

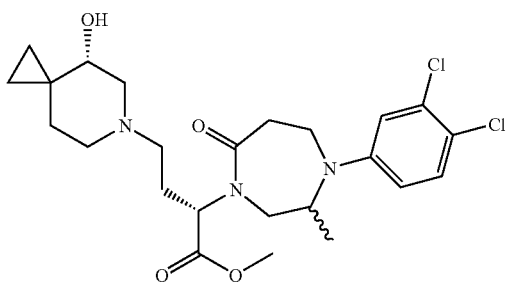

Example 65

(R)-Epimer

Example 66

(S)-Epimer

Example 67

1:1 Diastereomeric Mixture

A) 2-(3,4-Dichloro-phenylamino)-propan-1-ol 33.11 ml (33.11 mmol, 1 M in THF) of a borane-tetrahydrofuran complex solution was added dropwise at 0° C. to a solution of 3.10 g (13.24 mmol) 2-(3,4-dichloro-phenylamino)-propionic acid (synthesized in analogy to intermediate 11, with 3,4-dichloroiodobenzene, D-alanine and copper (I) iodide, 2-hydroxybenzaldehyde phenylhydrazone and tripotassium phosphate in N,N-dimethylformamide; enantiomeric ratio 71:29) in 50 ml THF, then after 10 min the ice bath was removed and the solution stirred for 2 h at RT. After cooling, 22 ml of MeOH and 1.1 ml of $H_2SO_4$ were added, and after 30 min at RT and 1 h at reflux the reaction mixture was concentrated in vacuo. The residue was partitioned between NaCl sat. 1 M aq. sodium hydroxide solution and EtOAc (3×). The organic layer was washed with brine, dried ($Na_2SO_4$), filtered, and evaporated. Flash silica gel column ($CH_2Cl_2$/MeOH 99:1→98:2) afforded 2.90 g (99%) of the title compound as a 71:29 mixture of the (R) and (S) stereoisomers. Yellow oil, MS: 220.0 ($MH^+$, 2Cl)

B) (S)-4-Benzyloxy-2-[2-(3,4-dichloro-phenylamino)-propylamino]-butyric acid methyl ester To a solution of 0.73 ml (8.36 mmol) of oxalyl chloride in 21 ml $CH_2Cl_2$ at −50 to −60° C. was added a solution of 1.24 ml (17.45 mmol) dimethylsulfoxide in 5 ml of $CH_2Cl_2$ within 10 min. The solution was stirred for 5 min and a solution of 1.600 (7.27 mmol) 2-(3,4-dichloro-phenylamino)-propan-1-ol in 21 ml of $CH_2Cl_2$ was added within 10 min. The mixture was stirred for 15 min and 5.07 ml (36.35 mmol) of triethylamine were added within 20 min. The suspension was stirred for 75 min and slowly warmed to 0° C. (complete oxidation followed by TLC, $SiO_2$, EtOAc:n-heptane 1:1). 1.88 g (7.27 mmol) of (S)-2-amino-4-benzyloxy-butyric acid methyl ester hydrochloride (intermediate 5) was added and 0.9 ml of acetic to adjust the pH to 5 followed by 1.75 g (8.00 mmol) of sodium triacetoxyborohydride. After 5 min at 0° C. and 1.5 h at RT, the reaction was poured on a solution of sat. aq. $NaHCO_3$ solution, followed by extraction with EtOAc (3 times). The organic phases were washed with a solution of 10% aq. NaCl solution. The combined organic phases were dried over $Na_2SO_4$ and the solvent was removed under vacuum to give 3.13 g (quantitative) of the title compound as a 71:29 mixture of the (R) and (S) diastereomers. Yellow oil, MS: 425.2 ($MH^+$, 2Cl).

C) (S)-4-Benzyloxy-2-[[2-(3,4-dichloro-phenylamino)-propyl]-(3,3-dimethoxy-propionyl)-amino]-butyric acid methyl ester A solution of 1.26 g (2.96 mmol) of (S)-4-benzyloxy-2-[2-(3,4-dichloro-phenylamino)-propylamino]-butyric acid methyl ester in 30 ml $CH_2Cl_2$ was treated with a solution of 0.91 g (3.55 mmol) of 2-chloro-1-methylpyridinium iodide and 0.48 g (3.55 mmol) of 3,3-dimethoxy-propionic acid (synthesized from methyl 3,3-dimethoxy-propionate by hydrolysis with LiOH) in 20 ml of $CH_2Cl_2$. The suspension was cooled and treated at 0° C. with 1.77 ml (7.41 mmol) of tributylamine. The cooling bath was removed after 10 min and stirring was continued over night. The reaction was extracted with 10% aq. $KHSO_4$ solution/diethyl ether (3×). The organic phases were washed with 10% aq. $KHSO_4$ solution (2×), sat. aq. $NaHCO_3$ solution, 10% aq. NaCl solution and dried over $Na_2SO_4$ to yield 1.53 g (96%) of the title compound as a 71:29 mixture of the (R) and (S) diastereomers. Yellow oil, MS: 541.2 ($MH^+$, 2Cl).

D) (S)-4-Benzyloxy-2-[4-(3,4-dichloro-phenyl)-3-methyl-7-oxo-[1,4]diazepan-1-yl]-butyric acid methyl ester A cooled solution (0° C.) of 1.75 g (3.23 mmol) of (S)-4-benzyloxy-2-[[2-(3,4-dichloro-phenylamino)-propyl]-(3,3-dimethoxy-propionyl)-amino]-butyric acid methyl ester in 30 ml $CH_2Cl_2$ was treated with 3.71 ml (48.48 mmol) of trifluoroacetic acid and after 2 h at RT with 2.57 ml (16.16 mmol) of triethylsilane. The reaction was stirred at RT for 16 h, cooled (0° C.) and neutralized with 6.76 ml (48.48 mmol) of triethylamine. The residue was dissolved in diethyl ether and cold water. The reaction was extracted with 10% aq. $KHSO_4$ solution/diethyl ether (3×). The organic phases were washed with sat. aq. $NaHCO_3$ solution, dried over $Na_2SO_4$ and evaporated. Flash silica gel column (n-heptane/EtOAc 4:1→1:1) afforded 0.79 g (46%) of the title compound as a 71:29 mixture of the (R) and (S) diastereomers. Orange oil, MS: 479.1 ($MH^+$, 2Cl).

E) (S)-2-[4-(3,4-Dichloro-phenyl)-3-methyl-7-oxo-[1,4]diazepan-1-yl]-4-hydroxy-butyric acid methyl ester In analogy to the procedure described in example 1H, (S)-4-benzyloxy-2-[4-(3,4-dichloro-phenyl)-3-methyl-7- oxo-[1,4]diazepan-1-yl]-butyric acid methyl ester and boron tribromide (after warming up the reaction to maximum to −5° C.) gave after precipitation CH$_2$Cl$_2$/n-pentane 78% of the title compound as a 71:29 mixture of the (R) and (S) diastereomers. Off-white foam, MS: 447.0 (M+OAc$^-$, 2Cl).

F) (S)-2-[4-(3,4-Dichloro-phenyl)-3-methyl-7-oxo-[1,4]diazepan-1-yl]-4-oxo-butyric acid methyl ester In analogy to the procedure described in example 1D, (S)-2-[4-(3,4-dichloro-phenyl)-3-methyl-7-oxo-[1,4]diazepan-1-yl]-4-hydroxy-butyric acid methyl ester gave the title compound in a yield of 87% as a 71:29 mixture of the (R) and (S) diastereomers. Light brown foam, MS: 387.1 (MH$^+$, 2Cl).

G) (S)-2-[(R)-4-(3,4-Dichloro-phenyl)-3-methyl-7-oxo-[1,4]diazepan-1-yl]-4-((S)-4-hydroxy-6-aza-spiro[2.5]oct-6-yl)-butyric acid methyl ester (Example 65), (S)-2-[(S)-4-(3,4-Dichloro-phenyl)-3-methyl-7-oxo-[1,4]diazepan-1-yl]-4-((S)-4-hydroxy-6-aza-spiro[2.5]oct-6-yl)-butyric acid methyl ester (Example 66), and (S)-2-[(R,S)-4-(3,4-Dichloro-phenyl)-3-methyl-7-oxo-[1,4]diazepan-1-yl]-4-((S)-4-hydroxy-6-aza-spiro[2.5]oct-6-yl)-butyric acid methyl ester (1:1 Diastereomeric Mixture) (Example 67)

In analogy to the procedure described in example 1E, (S)-2-[4-(3,4-dichloro-phenyl)-3-methyl-7-oxo-[1,4]diazepan-1-yl]-4-oxo-butyric acid methyl ester and (S)-6-aza-spiro[2.5]octan-4-ol hydrochloride (intermediate 2) gave after separation of the two diastereomers with flash chromatography (50 g silicycle SiO$_2$, CH$_2$Cl$_2$/MeOH 99:1→9:1):
28% of (S)-2-[(R)-4-(3,4-dichloro-phenyl)-3-methyl-7-oxo-[1,4]diazepan-1-yl]-4-((S)-4-hydroxy-6-aza-spiro[2.5]oct-6-yl)-butyric acid methyl ester (example 65), as light yellow foam, MS: 498.19 (MH$^+$, 2Cl),
8% of (S)-2-[(S)-4-(3,4-dichloro-phenyl)-3-methyl-7-oxo-[1,4]diazepan-1-yl]-4-((S)-4-hydroxy-6-aza-spiro[2.5]oct-6-yl)-butyric acid methyl ester (example 66), as yellow foam, MS: 498.19 (MH$^+$, 2Cl),
18% of (S)-2-[(R,S)-4-(3,4-dichloro-phenyl)-3-methyl-7-oxo-[1,4]diazepan-1-yl]-4-((S)-4-hydroxy-6-aza-spiro[2.5]oct-6-yl)-butyric acid methyl ester (1:1 diastereomeric mixture) (example 67), as light yellow foam, MS: 498.3 (MH$^+$, 2Cl).

Example 68

(R,S)-1-(3,4-Dichloro-phenyl)-4-[(S)-3-((S)-4-hydroxy-6-aza-spiro[2.5]oct-6-yl)-1-hydroxymethyl-propyl]-2-methyl-[1,4]diazepan-5-one

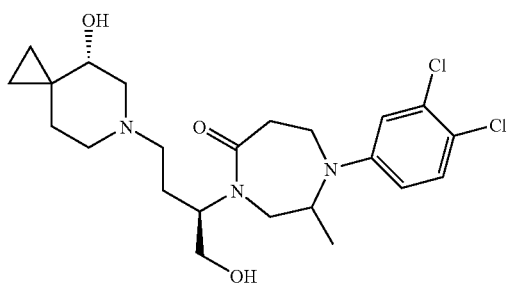

In analogy to the procedure described in example 2, reaction of (S)-2-[(R,S)-4-(3,4-dichloro-phenyl)-3-methyl-7-oxo-[1,4]diazepan-1-yl]-4-((S)-4-hydroxy-6-aza-spiro[2.5]oct-6-yl)-butyric acid methyl ester (example 67) with LiBH$_4$ gave the title compound in 39% yield as light yellow solid. MS: 470.2 (MH$^+$, 2Cl).

Example 69

(R)-1-(3,4-Dichloro-phenyl)-4-[(S)-3-((S)-4-hydroxy-6-aza-spiro[2.5]oct-6-yl)-1-hydroxymethyl-propyl]-2-methyl-[1,4]diazepan-5-one

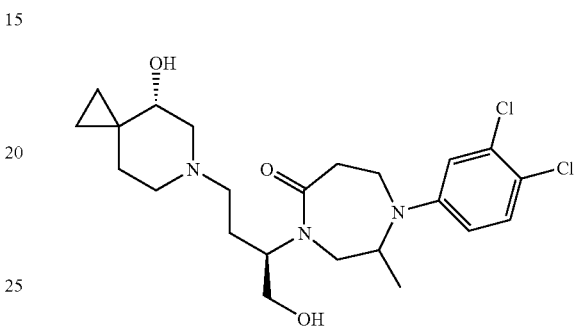

In analogy to the procedure described in example 2, (S)-2-[(R)-4-(3,4-dichloro-phenyl)-3-methyl-7-oxo-[1,4]diazepan-1-yl]-4-((S)-4-hydroxy-6-aza-spiro[2.5]oct-6-yl)-butyric acid methyl ester (example 65) and LiBH$_4$ gave the title compound in 61% yield as white solid. MS: 470.2 (MH$^+$, 2Cl).

Example 70

4-(4-Chloro-3-trifluoromethyl-phenyl)-3-methyl-1-(3-piperidin-1-yl-propyl)-piperazin-2-one

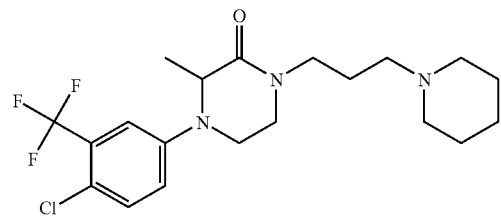

A) 3-Methyl-4-(4-nitro-3-trifluoromethyl-phenyl)-piperazin-2-one

A mixture of 3-methyl-2-ketopiperazine (200 mg, 1.75 mmol), 5-fluoro-2-nitrobenzo-trifluoride (366 mg, 1.75 mmol), N,N-diisopropylethylamine and N,N-dimethylformamide (1 mL) was heated at 140° C. for 10 min under microwave irradiation, then partitioned between sat. aq. ammonium chloride solution and EtOAc. The organic layer was washed with brine, dried (MgSO$_4$), filtered, and evaporated. Chromatography (SiO$_2$; heptane/EtOAc 4:1) produced the title compound (130 mg, 24%). Yellow solid, MS: 304.1 (M+H)$^+$.

B) 4-(4-Amino-3-trifluoromethyl-phenyl)-3-methyl-piperazin-2-one

A solution of 3-methyl-4-(4-nitro-3-trifluoromethyl-phenyl)-piperazin-2-one (118 mg, 0.39 mmol) in MeOH (2 mL) was stirred at RT under a hydrogen atmosphere (1 bar) in the presence of palladium (10% on activated charcoal, 20 mg), then after 45 min insoluble material was removed by filtration through diatomaceous earth. The filtrate was evaporated to afford the title compound (98 mg, 92%). Light yellow viscous oil, MS: 274.1 (M+H)$^+$.

C) 4-(4-Chloro-3-trifluoromethyl-phenyl)-3-methyl-piperazin-2-one

Tert-butyl nitrite (58 mg, 0.51 mmol) was added at RT to a suspension of copper(I) chloride (54 mg, 0.41 mmol) in CH$_3$CN (3.5 mL). The reaction mixture was heated at 65° C., then a solution of 4-(4-amino-3-trifluoromethyl-phenyl)-3-methyl-piperazin-2-one (93 mg, 0.34 mmol) in CH$_3$CN (2 mL) was added over 5 min. After 20 min the reaction mixture was partitioned between 20% aq. HCl solution and EtOAc. The organic layer was washed with 20% aq. HCl solution, dried (MgSO$_4$), filtered, and evaporated. Chromatography (SiO$_2$; heptane/EtOAc 4:1) produced the title compound (28 mg, 28%). Yellow viscous oil, MS: 293.1 (M+H)$^+$.

D) 4-(4-Chloro-3-trifluoromethyl-phenyl)-3-methyl-1-(3-piperidin-1-yl-propyl)-piperazin-2-one The title compound was produced in analogy with the procedure of example 33A from 4-(4-chloro-3-trifluoromethyl-phenyl)-3-methyl-piperazin-2-one and 1-(3-chloropropyl)piperidine. Yellow viscous oil, MS: 418.3 (M+H)$^+$.

Example 71

4-(3,4-Dichloro-phenyl)-3-methyl-1-(3-piperidin-1-yl-propyl)-piperazin-2-one

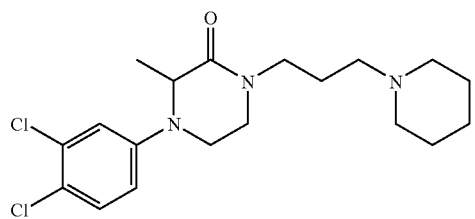

A) (2,2-Dimethoxy-ethyl)-(3-piperidin-1-yl-propyl)-amine

To a solution of 1-piperidinepropylamine (3.00 g, 21.1 mmol) in MeOH (60 mL) were added dimethoxyacetaldehyde (45% solution in TBME, 6.5 mL, 25 mmol) magnesium sulfate (22.8 g, 190 mmol), AcOH (5.07 g, 84.4 mmol), and sodium cyanoborohydride (1.99 g, 31.6 mmol) at 0° C. The ice bath was removed, then after 18 h the reaction mixture was partitioned between sat. aq. sodium hyrogencarbonate solution and EtOAc. The organic layer was washed with brine, dried (MgSO$_4$), and evaporated. Chromatography (SiO$_2$; CH$_2$Cl$_2$/MeOH/25% aq. ammonia solution 90:10:0.25) afforded the title compound (2.08 mg, 43%). Colorless liquid, 231.2 (M+H)$^+$.

B) 2-(3,4-Dichloro-phenylamino)-N-(2,2-dimethoxy-ethyl)-N-(3-piperidin-1-yl-propyl)-propionamide To a solution of (2,2-dimethoxy-ethyl)-(3-piperidin-1-yl-propyl)-amine (400 mg, 1.74 mmol) in N,N-dimethylformamide (4 mL) were added 2-(3,4-dichloro-phenylamino)-propionic acid (intermediate 11; 337 mg, 1.91 mmol), 4-methylmorpholine (527 mg, 5.21 mmol) and O-(7-azabenzotriazol-1-yl)-1,1,3,3-tetramethyluronium hexafluorophosphate (990 mg, 2.61 mmol) at RT, then after 2 h the reaction mixture was partitioned between EtOAc and sat. aq. NaHCO$_3$ solution. The organic layer was washed with brine, dried (MgSO$_4$), and evaporated. Chromatography (SiO$_2$; CH$_2$Cl$_2$/MeOH/25% aq. ammonia solution 90:10:0.25) afforded the title compound (545 mg, 70%). Yellow viscous oil, MS: 446.2 (M+H)$^+$.

C) 4-(3,4-Dichloro-phenyl)-3-methyl-1-(3-piperidin-1-yl-propyl)-piperazin-2-one Trifluoroacetic acid (1.15 g, 10.1 mmol) was added to a solution of 2-(3,4-dichloro-phenylamino)-N-(2,2-dimethoxy-ethyl)-N-(3-piperidin-1-yl-propyl)-propionamide (300 mg, 0.67 mmol) in CH$_2$Cl$_2$ (6 mL) at 0° C. After 30 min the ice bath was removed, then after 1 h triethylsilane (391 mg, 3.36 mmol) was added. After 16 h the reaction mixture was cooled to 0° C. and treated with triethylamine, then after 15 min partitioned between CH$_2$Cl$_2$ and sat. aq. NaHCO$_3$ solution. The organic layer was washed with brine, dried (MgSO$_4$), and evaporated. Chromatography (IST Isolute® Flash NH$_2$; EtOAc) afforded the title compound (184 mg, 71%). Yellow oil, MS: 384.2 (M+H)$^+$.

Examples 72 and 73

(S)-4-(3,4-Dichloro-phenyl)-3-methyl-1-(3-piperidin-1-yl-propyl)-piperazin-2-one and (R)-4-(3,4-dichloro-phenyl)-3-methyl-1-(3-piperidin-1-yl-propyl)-piperazin-2-one

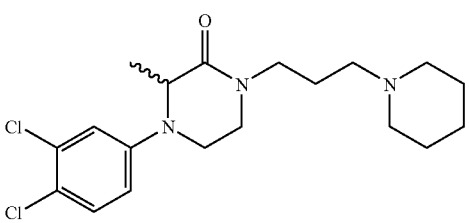

Example 72

(S)-Enantiomer

Example 73

(R)-Enantiomer

The racemate 4-(3,4-dichloro-phenyl)-3-methyl-1-(3-piperidin-1-yl-propyl)-piperazin-2-one (example 71; 131 mg, 0.34 mmol) was separated into its enantiomers by preparative HPLC using a Chiralpak® AD column as stationary phase and heptane/EtOH 3:1 as the eluent. This afforded the (S)-enantiomer (example 72; 42 mg, 32%; light yellow gum, MS: 384.2 (M+H)$^+$) and the (R)-enantiomer (example 73; 38 mg, 29%; light yellow gum, MS: 384.2 (M+H)$^+$).

Examples 74 and 75

(S)-4-(3,4-Dichloro-phenyl)-1-[3-((S)-4-hydroxy-6-aza-spiro[2.5]oct-6-yl)-propyl]-3-methyl-piperazin-2-one and (R)-4-(3,4-dichloro-phenyl)-1-[3-((S)-4-hydroxy-6-aza-spiro[2.5]oct-6-yl)-propyl]-3-methyl-piperazin-2-one

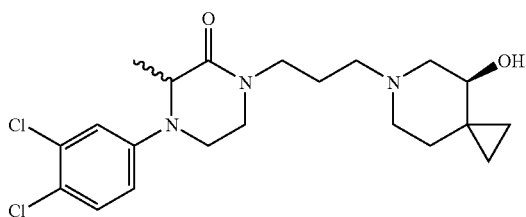

Example 74

(S)-Epimer

Example 75

(R)-Epimer

A) [3-((S)-4-Hydroxy-6-aza-spiro[2.5]oct-6-yl)-propyl]-carbamic acid benzyl ester To a solution of 3-[(benzyloxycarbonyl)amino]-1-propanal (300 mg, 1.45 mmol) in EtOH (2 mL) and CH$_2$Cl$_2$ (2 mL) were added (S)-6-aza-spiro[2.5]octan-4-ol hydrochloride (284 mg, 1.74 mmol), triethylamine (176 mg, 1.74 mmol), borane pyridine complex solution (8 M in pyridine 0.34 mL, 3.2 mmol), and AcOH (400 mg, 6.66 mmol) at RT, then after 1 h the reaction mixture was partitioned between CH$_2$Cl$_2$ and sat. aq. NaHCO$_3$ solution. The organic layer was washed with brine, dried (MgSO$_4$), and evaporated. Chromatography (SiO$_2$; EtOAc-MeOH gradient) produced the title compound (404 mg, 88%). Colorless gum, MS: 319.1 (M+H)$^+$.

B) (S)-6-(3-Amino-propyl)-6-aza-spiro[2.5]octan-4-ol

A solution of [3-((S)-4-hydroxy-6-aza-spiro[2.5]oct-6-yl)-propyl]-carbamic acid benzyl ester (590 mg, 1.85 mmol) in MeOH (14 mL) was stirred under a hydrogen atmosphere (1 bar) in the presence of palladium (10% on activated charcoal, 200 mg), then after 90 min insoluble material was removed by filtration and the filtrate evaporated to afford the title compound (303 mg, 89%). Yellow liquid, MS: 185.2 (M+H)$^+$.

C) (S)-6-[3-(2,2-Dimethoxy-ethylamino)-propyl]-6-aza-spiro[2.5]octan-4-ol

A mixture of (S)-6-(3-amino-propyl)-6-aza-spiro[2.5]octan-4-ol (200 mg, 1.09 mmol), bromoacetaldehyde (183 mg, 1.09 mmol), potassium carbonate (300 mg, 2.17 mmol), and EtOH (2.5 mL) was heated at 150° C. for 20 min under microwave irradiation, then insoluble material was removed by filtration and the filtrate evaporated to afford 224 mg of a 60:40 mixture of the title compound and the tertiary amine (S)-6-{3-[bis-(2,2-dimethoxy-ethyl)-amino]-propyl}-6-aza-spiro[2.5]octan-4-ol, which was directly used in the next step. Yellow gum, MS: 273.2 (M+H)$^+$.

D) 2-(3,4-Dichloro-phenylamino)-N-(2,2-dimethoxy-ethyl)-N-[3-((S)-4-hydroxy-6-aza-spiro[2.5]oct-6-yl)-propyl]-propionamide The title compound was produced in analogy with example 71B from 2-(3,4-dichloro-phenylamino)-propionic acid (intermediate 11) and (S)-6-[3-(2,2-dimethoxy-ethylamino)-propyl]-6-aza-spiro[2.5]octan-4-ol. Yellow gum, MS: 488.3 (M+H)$^+$.

E) 4-(3,4-Dichloro-phenyl)-1-[3-((S)-4-hydroxy-6-aza-spiro[2.5]oct-6-yl)-propyl]-3-methyl-piperazin-2-one The title compound was produced in analogy with example 71C from 2-(3,4-dichloro-phenylamino)-N-(2,2-dimethoxy-ethyl)-N-[3-((S)-4-hydroxy-6-aza-spiro[2.5]oct-6-yl)-propyl]-propionamide.

F) (S)-4-(3,4-Dichloro-phenyl)-1-[3-((S)-4-hydroxy-6-aza-spiro[2.5]oct-6-yl)-propyl]-3-methyl-piperazin-2-one and (R)-4-(3,4-dichloro-phenyl)-1-[3-((S)-4-hydroxy-6-aza-spiro[2.5]oct-6-yl)-propyl]-3-methyl-piperazin-2-one HPLC separation of the epimeric mixture 4-(3,4-dichloro-phenyl)-1-[3-((S)-4-hydroxy-6-aza-spiro[2.5]oct-6-yl)-propyl]-3-methyl-piperazin-2-one in analogy with examples 72 and 73 afforded the (S)-epimer (example 74; light yellow gum, MS: 426.2 (M+H)$^+$) and the (R)-epimer (example 75; yellow gum, MS: 426.2 (M+H)$^+$).

Examples 76 and 77

(S)-4-(4-Chloro-3-trifluoromethyl-phenyl)-1-[3-((S)-4-hydroxy-6-aza-spiro[2.5]oct-6-yl)-propyl]-3-methyl-piperazin-2-one and (R)-4-(4-chloro-3-trifluoromethyl-phenyl)-1-[3-((S)-4-hydroxy-6-aza-spiro[2.5]oct-6-yl)-propyl]-3-methyl-piperazin-2-one

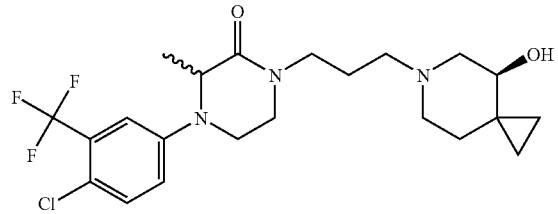

Example 76

(S)-Epimer

Example 77

(R)-Epimer

The title compounds were produced in analogy with examples 74 and 75, steps D-F. Thus, coupling of 2-(4-chloro-3-trifluoromethyl-phenylamino)-propionic acid (intermediate 12) with (S)-6-[3-(2,2-dimethoxy-ethylamino)-propyl]-6-aza-spiro[2.5]octan-4-ol (examples 74/75C) in step D led to 2-(4-chloro-3-trifluoromethyl-phenylamino)-N-(2,2-dimethoxy-ethyl)-N-[3-((S)-4-hydroxy-6-aza-spiro

[2.5]oct-6-yl)-propyl]-propionamide, which was cyclized in step E. Finally, HPLC separation of the epimeric mixture, 4-(4-chloro-3-trifluoromethyl-phenyl)-1-[3-((S)-4-hydroxy-6-aza-spiro[2.5]oct-6-yl)-propyl]-3-methyl-piperazin-2-one, in step F afforded the (S)-epimer (example 76; yellow gum, MS: 460.3 (M+H)$^+$), and the (R)-epimer (example 77; light yellow gum, MS: 460.3 (M+H)$^+$).

Example 78

(S)-4-(4-Fluoro-3-trifluoromethyl-phenyl)-1-[3-((S)-4-hydroxy-6-aza-spiro[2.5]oct-6-yl)-propyl]-3-methyl-piperazin-2-one

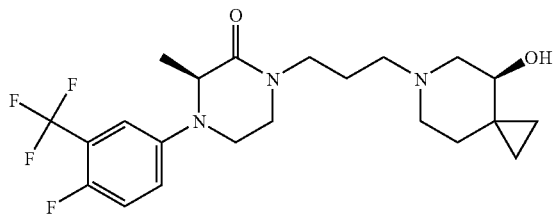

The title compound was produced in analogy with examples 74 and 75, steps D-F. Thus, coupling of 2-(4-fluoro-3-trifluoromethyl-phenylamino)-propionic acid (intermediate 13) with (S)-6-[3-(2,2-dimethoxy-ethylamino)-propyl]-6-aza-spiro[2.5]octan-4-ol (examples 74/75C) in step D led to 2-(4-fluoro-3-trifluoromethyl-phenylamino)-N-(2,2-dimethoxy-ethyl)-N-[3-((S)-4-hydroxy-6-aza-spiro[2.5]oct-6-yl)-propyl]-propionamide, which was cyclized in step E. Finally, HPLC purification of the epimeric mixture, 4-(4-fluoro-3-trifluoromethyl-phenyl)-1-[3-((S)-4-hydroxy-6-aza-spiro[2.5]oct-6-yl)-propyl]-3-methyl-piperazin-2-one, in step F afforded the title compound. Light yellow gum, MS: 444.3 (M+H)$^+$.

Example 79

(S)-4-(3-Chloro-4-fluoro-phenyl)-1-[3-((S)-4-hydroxy-6-aza-spiro[2.5]oct-6-yl)-propyl]-3-methyl-piperazin-2-one

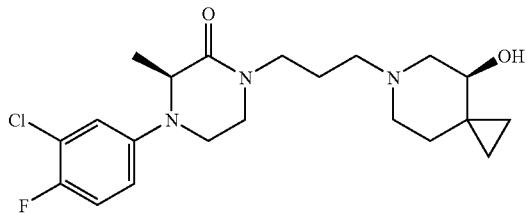

The title compound was produced in analogy with examples 74 and 75, steps D-F. Thus, coupling of 2-(3-chloro-4-fluoro-phenylamino)-propionic acid (intermediate 14) with (S)-6-[3-(2,2-dimethoxy-ethylamino)-propyl]-6-aza-spiro[2.5]octan-4-ol (examples 74/75C) in step D led to 2-(3-chloro-4-fluoro-phenylamino)-N-(2,2-dimethoxy-ethyl)-N-[3-((S)-4-hydroxy-6-aza-spiro[2.5]oct-6-yl)-propyl]-propionamide, which was cyclized in step E. Finally, HPLC purification of the epimeric mixture, 4-(3-chloro-4-fluoro-phenyl)-1-[3-((S)-4-hydroxy-6-aza-spiro[2.5]oct-6-yl)-propyl]-3-methyl-piperazin-2-one, in step F afforded the title compound. Light yellow gum, MS: 410.2 (M+H)$^+$.

Examples 80 and 81

(S)-4-Biphenyl-4-yl-1-[3-((S)-4-hydroxy-6-aza-spiro[2.5]oct-6-yl)-propyl]-3-methyl-piperazin-2-one and (R)-4-biphenyl-4-yl-1-[3-((S)-4-hydroxy-6-aza-spiro[2.5]oct-6-yl)-propyl]-3-methyl-piperazin-2-one

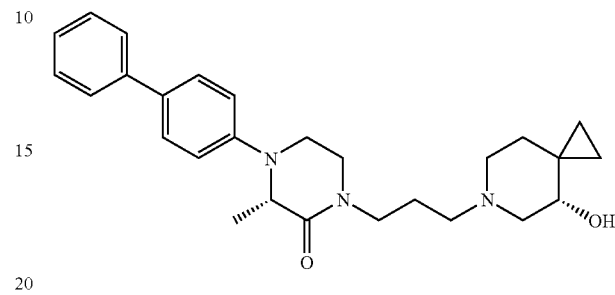

Example 80

(S)-Epimer

Example 81

(R)-Epimer

The title compounds were produced in analogy with examples 74 and 75, steps D-F. Thus, coupling of 2-(biphenyl-4-ylamino)-propionic acid (intermediate 15) with (S)-6-[3-(2,2-dimethoxy-ethylamino)-propyl]-6-aza-spiro[2.5]octan-4-ol (examples 74/75C) in step D led to 2-(biphenyl-4-ylamino)-N-(2,2-dimethoxy-ethyl)-N-[3-((S)-4-hydroxy-6-aza-spiro[2.5]oct-6-yl)-propyl]-propionamide, which was cyclized in step E. Finally, HPLC separation of the epimeric mixture, 4-biphenyl-4-yl-1-[3-((S)-4-hydroxy-6-aza-spiro[2.5]oct-6-yl)-propyl]-3-methyl-piperazin-2-one, in step F afforded the (S)-epimer (example 80; white solid, MS: 434.4 (M+H)$^+$), and the (R)-epimer (example 81; light yellow gum, MS: 434.4 (M+H)$^+$).

Example 82

(S)-1-[3-((S)-4-Hydroxy-6-aza-spiro[2.5]oct-6-yl)-propyl]-3-methyl-4-naphthalen-2-yl-piperazin-2-one

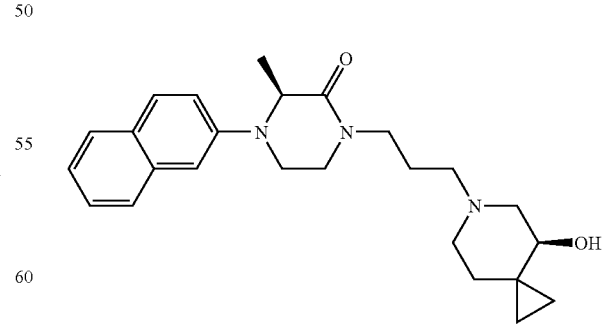

The title compound was produced in analogy with examples 74 and 75, steps D-F. Thus, coupling of 2-(naphthalen-2-ylamino)-propionic acid (intermediate 16) with (S)-6-[3-(2,2-dimethoxy-ethylamino)-propyl]-6-aza-spiro[2.5]

octan-4-ol (examples 74/75C) in step D led to N-(2,2-dimethoxy-ethyl)-N-[3-((S)-4-hydroxy-6-aza-spiro[2.5]oct-6-yl)-propyl]-2-(naphthalen-2-ylamino)-propionamide, which was cyclized in step E. Finally, HPLC purification of the epimeric mixture, 1-[3-((S)-4-hydroxy-6-aza-spiro[2.5]oct-6-yl)-propyl]-3-methyl-4-naphthalen-2-yl-piperazin-2-one, in step F afforded the title compound. Light yellow gum, MS: 408.4 (M+H)$^+$.

Example 83

(S)-4-(3-Chloro-4-trifluoromethyl-phenyl)-1-[3-((S)-4-hydroxy-6-aza-spiro[2.5]oct-6-yl)-propyl]-3-methyl-piperazin-2-one

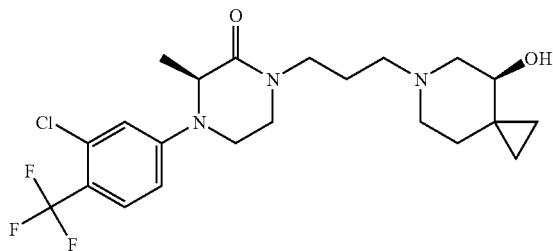

A) {3-[(S)-4-(tert-Butyl-dimethyl-silanyloxy)-6-aza-spiro[2.5]oct-6-yl]-propyl}-carbamic acid benzyl ester To a solution of [3-((S)-4-hydroxy-6-aza-spiro[2.5]oct-6-yl)-propyl]-carbamic acid benzyl ester (examples 74/75A; 3.90 g, 12.2 mmol in N,N-dimethylformamide (50 mL) was added tert-butyl-dimethylchlorosilane (2.77 g, 18.3 mmol), imidazole (2.08 g, 30.6 mmol), and 4-(dimethylamino)pyridine (14 mg, 0.12 mmol) at RT. The reaction mixture was heated at 60° C. for 24 h, then partitioned between sat. aq. NaHCO$_3$ solution and EtOAc. The organic layer was washed with brine, dried (MgSO$_4$), filtered, and evaporated. Chromatography (SiO$_2$; EtOAc/MeOH 19:1) afforded the title compound (4.34 g, 82%). Light yellow oil, MS: 433.4 (M+H)$^+$.

B) 3-[(S)-4-(tert-Butyl-dimethyl-silanyloxy)-6-aza-spiro[2.5]oct-6-yl]-propylamine The title compound was produced in analogy with examples 74/75B from {3-[(S)-4-(tert-butyl-dimethyl-silanyloxy)-6-aza-spiro[2.5]oct-6-yl]-propyl}-carbamic acid benzyl ester. Colourless liquid, MS: 299.3 (M+H)$^+$.

C) {3-[(S)-4-(tert-Butyl-dimethyl-silanyloxy)-6-aza-spiro[2.5]oct-6-yl]-propyl}-(2,2-dimethoxy-ethyl)-amine A solution of 3-[(S)-4-(tert-butyl-dimethyl-silanyloxy)-6-aza-spiro[2.5]oct-6-yl]-propylamine (234 mg, 0.78 mmol) and dimethoxyacetaldehyde (45% solution in TBME, 0.20 mL, 0.78 mmol) in MeOH (3 mL) was stirred for 5 h at RT, then sodium borohydride (47 mg, 1.25 mmol) was added, then after 15 min the reaction mixture was partitioned between EtOAc and sat. aq. NaHCO$_3$ solution. The organic layer was washed with brine, dried (MgSO$_4$), filtered, and evaporated. Chromatography (IST Isolute® Flash NH$_2$; EtOAc) afforded the title compound (210 mg, 69%). Light yellow gum, MS: 387.4 (M+H)$^+$.

D) (S)—N-{3-[(S)-4-(tert-Butyl-dimethyl-silanyloxy)-6-aza-spiro[2.5]oct-6-yl]-propyl}-2-(3-chloro-4-trifluoromethyl-phenylamino)-N-(2,2-dimethoxy-ethyl)-propionamide The title compound was produced in analogy with example 71B from (S)-2-(3-chloro-4-trifluoromethyl-phenylamino)-propionic acid (intermediate 18) and {3-[(S)-4-(tert-butyl-dimethyl-silanyloxy)-6-aza-spiro[2.5]oct-6-yl]-propyl}-(2,2-dimethoxy-ethyl)-amine. Colourless oil, MS: 636.3 (M+H)$^+$.

E) (S)-1-{3-[(S)-4-(tert-Butyl-dimethyl-silanyloxy)-6-aza-spiro[2.5]oct-6-yl]-propyl}-4-(3-chloro-4-trifluoromethyl-phenyl)-3-methyl-piperazin-2-one The title compound was produced in analogy with example 71C from (S)—N-{3-[(S)-4-(tert-butyl-dimethyl-silanyloxy)-6-aza-spiro[2.5]oct-6-yl]-propyl}-2-(3-chloro-4-trifluoromethyl-phenylamino)-N-(2,2-dimethoxy-ethyl)-propionamide. Yellow oil, MS: 574.3 (M+H)$^+$.

F) (S)-4-(3-Chloro-4-trifluoromethyl-phenyl)-1-[3-((S)-4-hydroxy-6-aza-spiro[2.5]oct-6-yl)-propyl]-3-methyl-piperazin-2-one A solution of (S)-1-{3-[(S)-4-(tert-butyl-dimethyl-silanyloxy)-6-aza-spiro[2.5]oct-6-yl]-propyl}-4-(3-chloro-4-trifluoromethyl-phenyl)-3-methyl-piperazin-2-one (65 mg, 0.11 mmol) and hydrogen fluoride pyridine complex (70% HF; 0.26 mL) in CH$_3$CN (3 mL) was heated at 50° C. for 16 h, then partitioned between EtOAc and sat. aq. NaHCO$_3$ solution. The organic layer was washed with brine, dried (MgSO$_4$), filtered, and evaporated. Chromatography (IST Isolute® Flash NH$_2$; EtOAc-MeOH gradient) afforded the title compound (29 mg, 56%) in a diastereomeric ratio of 97:3. Colourless gum, MS: 460.3 (M+H)$^+$.

Example 84

(S)-4-(4-Chloro-3-trifluoromethoxy-phenyl)-1-[3-((S)-4-hydroxy-6-aza-spiro[2.5]oct-6-yl)-propyl]-3-methyl-piperazin-2-one

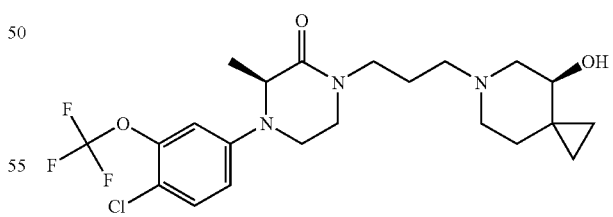

The title compound was produced in analogy with example 83, steps D-F. Thus, (S)-2-(4-chloro-3-trifluoromethoxy-phenylamino)-propionic acid (intermediate 19) was coupled with {3-[(S)-4-(tert-butyl-dimethyl-silanyloxy)-6-aza-spiro[2.5]oct-6-yl]-propyl}-(2,2-dimethoxy-ethyl)-amine (example 83C) in step D, leading to (S)—N-{3-[(S)-4-(tert-butyl-dimethyl-silanyloxy)-6-aza-spiro[2.5]oct-6-yl]-propyl}-2-(4-chloro-3-trifluoromethoxy-phenylamino)-N-(2,2-dimethoxy-ethyl)-propionamide. This was cyclized to (S)-1-

{3-[(S)-4-(tert-butyl-dimethyl-silanyloxy)-6-aza-spiro[2.5]oct-6-yl]-propyl}-4-(4-chloro-3-trifluoromethoxy-phenyl)-3-methyl-piperazin-2-one in step E. Finally, deprotection in step F afforded the title compound. Light yellow gum, MS: 476.2 (M+H)⁺.

Example 85

4-(3,4-Dichloro-phenyl)-1-[3-((S)-4-hydroxy-6-aza-spiro[2.5]oct-6-yl)-propyl]-piperazin-2-one

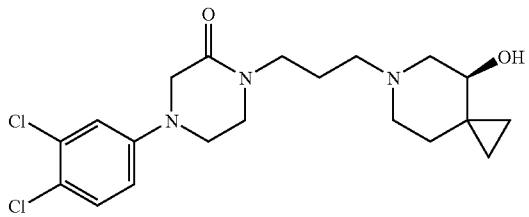

A) N-{3-[(S)-4-(tert-Butyl-dimethyl-silanyloxy)-6-aza-spiro[2.5]oct-6-yl]-propyl}-2-(3,4-dichloro-phenylamino)-N-(2,2-dimethoxy-ethyl)-acetamide The title compound was produced in analogy with example 71B from N-(3,4-dichlorophenyl)glycine (intermediate 20) and {3-[(S)-4-(tert-butyl-dimethyl-silanyloxy)-6-aza-spiro[2.5]oct-6-yl]-propyl}-(2,2-dimethoxy-ethyl)-amine (example 83C). Colourless gum, MS: 588.3 (M+H)⁺.

B) 4-(3,4-Dichloro-phenyl)-1-[3-((S)-4-hydroxy-6-aza-spiro[2.5]oct-6-yl)-propyl]-piperazin-2-one Trifluoroacetic acid (1.51 g, 13.3 mmol) was added to a solution of N-{3-[(S)-4-(tert-butyl-dimethyl-silanyloxy)-6-aza-spiro[2.5]oct-6-yl]-propyl}-2-(3,4-dichloro-phenylamino)-N-(2,2-dimethoxy-ethyl)-acetamide (142 mg, 0.24 mmol) in CH₂Cl₂ (1 mL) at RT, then after 3 h triethylsilane (140 mg, 1.21 mmol) was added. The solution was heated at 60° C. over 72 h, then partitioned between CH₂Cl₂ and sat. aq. NaHCO₃ solution. The organic layer was dried (MgSO₄), filtered, and evaporated. Chromatography (IST Isolute® Flash NH₂; EtOAc/MeOH 19:1) afforded the title compound (17 mg, 17%). Yellow gum, MS: 412.2 (M+H)⁺.

Example 86

(S)-4-(4-Fluoro-3-trifluoromethoxy-phenyl)-1-[3-((S)-4-hydroxy-6-aza-spiro[2.5]oct-6-yl)-propyl]-3-methyl-piperazin-2-one

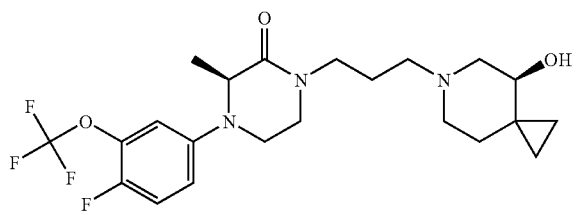

A) N-{3-[(S)-4-(tert-Butyl-dimethyl-silanyloxy)-6-aza-spiro[2.5]oct-6-yl]-propyl}-N-(2,2-dimethoxy-ethyl)-2-(4-fluoro-3-trifluoromethoxy-phenylamino)-propionamide The title compound was produced in analogy with example 71B from 2-(4-fluoro-3-trifluoromethoxy-phenylamino)-propionic acid (intermediate 21) and {3-[(S)-4-(tert-butyl-dimethyl-silanyloxy)-6-aza-spiro[2.5]oct-6-yl]-propyl}-(2,2-dimethoxy-ethyl)-amine (example 83C). Colourless gum, MS: 636.4 (M+H)⁺.

B) 4-(4-Fluoro-3-trifluoromethoxy-phenyl)-1-[3-((S)-4-hydroxy-6-aza-spiro[2.5]oct-6-yl)-propyl]-3-methyl-piperazin-2-one The title compound was produced in analogy with example 85B from N-{3-[(S)-4-(tert-butyl-dimethyl-silanyloxy)-6-aza-spiro[2.5]oct-6-yl]-propyl}-N-(2,2-dimethoxy-ethyl)-2-(4-fluoro-3-trifluoromethoxy-phenylamino)-propionamide. Yellow gum, MS: 460.3 (M+H)⁺.

C) (S)-4-(4-Fluoro-3-trifluoromethoxy-phenyl)-1-[3-((S)-4-hydroxy-6-aza-spiro[2.5]oct-6-yl)-propyl]-3-methyl-piperazin-2-one The title compound was produced in analogy with examples 72/73 by HPLC purification of the epimeric mixture, 4-(4-fluoro-3-trifluoromethoxy-phenyl)-1-[3-((S)-4-hydroxy-6-aza-spiro[2.5]oct-6-yl)-propyl]-3-methyl-piperazin-2-one. Yellow gum, MS: 460.3 (M+H)⁺.

Examples 87 and 88

(S)-4-(3,4-Dichloro-phenyl)-3-ethyl-1-[3-((S)-4-hydroxy-6-aza-spiro[2.5]oct-6-yl)-propyl]-piperazin-2-one

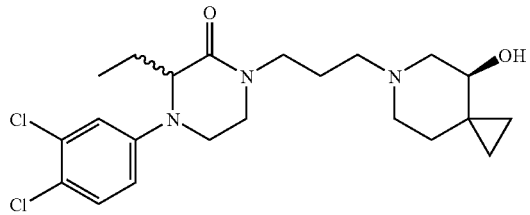

Example 87

(S)-Epimer

Example 88

(R)-Epimer

A) N-{3-[(S)-4-(tert-Butyl-dimethyl-silanyloxy)-6-aza-spiro[2.5]oct-6-yl]-propyl}-2-(3,4-dichloro-phenylamino)-N-(2,2-dimethoxy-ethyl)-butyramide The title compound was produced in analogy with example 71B from 2-(3,4-dichloro-phenylamino)-butyric acid (intermediate 22) and {3-[(S)-4-(tert-butyl-dimethyl-silanyloxy)-6-aza-spiro[2.5]oct-6-yl]-propyl}-(2,2-dimethoxy-ethyl)-amine (example 83C). Light yellow oil, MS: 616.5 (M+H)⁺.

B) 1-{3-[(S)-4-(tert-Butyl-dimethyl-silanyloxy)-6-aza-spiro[2.5]oct-6-yl]-propyl}-4-(3,4-dichloro-phenyl)-3-ethyl-piperazin-2-one The title compound was produced in analogy with example 71C from N-{3-[(S)-4-(tert-butyl-dimethyl-silanyloxy)-6-aza-spiro[2.5]oct-6-yl]-propyl}-2-(3,4-dichloro-phenyl-amino)-N-(2,2-dimethoxy-ethyl)-butyramide. Light yellow gum, MS: 554.2 (M+H)⁺.

C) 4-(3,4-Dichloro-phenyl)-3-ethyl-1-[3-((S)-4-hydroxy-6-aza-spiro-[2.5]oct-6-yl)-propyl]-piperazin-2-one The title compound was produced in analogy with example 83F from 1-{3-[(S)-4-(tert-butyl-dimethyl-silanyloxy)-6-aza-spiro[2.5]oct-6-yl]-propyl}-4-(3,4-dichloro-phenyl)-3-ethyl-piperazin-2-one. Light yellow gum, MS: 440.3 (M+H)⁺.

D) (S)-4-(3,4-Dichloro-phenyl)-3-ethyl-1-[3-((S)-4-hydroxy-6-aza-spiro[2.5]oct-6-yl)-propyl]-piperazin-2-one and (R)-4-(3,4-dichloro-phenyl)-3-ethyl-1-[3-((S)-4-hydroxy-6-aza-spiro[2.5]oct-6-yl)-propyl]-piperazin-2-one The title compounds were obtained in analogy with examples 72/73 by HPLC separation of the epimeric mixture, 4-(3,4-dichloro-phenyl)-3-ethyl-1-[3-((S)-4-hydroxy-6-aza-spiro[2.5]oct-6-yl)-propyl]-piperazin-2-one. This afforded the (S)-epimer (example 87; light yellow gum, MS: 440.1 (M+H)⁺) and the (R)-epimer (example 88; light yellow gum, MS: 440.3 (M+H)⁺)

Example 89

1-[3-((S)-4-Hydroxy-6-aza-spiro[2.5]oct-6-yl)-propyl]-4-(3-iodo-phenyl)-3-methyl-piperazin-2-one

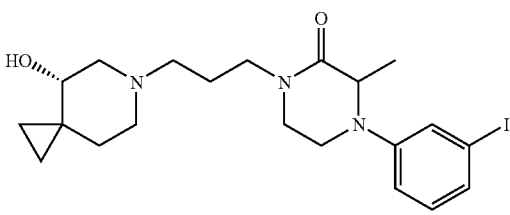

The title compound was produced in analogy with examples 87/88, steps A-C. Thus, 2-(3-iodo-phenylamino)-propionic acid (intermediate 23) was coupled with {3-[(S)-4-(tert-butyl-dimethyl-silanyloxy)-6-aza-spiro[2.5]oct-6-yl]-propyl}-(2,2-dimethoxy-ethyl)-amine (example 83C) in step A, leading to N-{3-[(S)-4-(tert-butyl-dimethyl-silanyloxy)-6-aza-spiro[2.5]oct-6-yl]-propyl}-N-(2,2-dimethoxy-ethyl)-2-(3-iodo-phenylamino)-propionamide. This was cyclized to 1-{3-[(S)-4-(tert-butyl-dimethyl-silanyloxy)-6-aza-spiro[2.5]oct-6-yl]-propyl}-4-(3-iodo-phenyl)-3-methyl-piperazin-2-one in step B. Finally, deprotection in step C afforded the title compound. Light yellow gum, MS: 484.3 (M+H)⁺)

Example 90

4-Biphenyl-3-yl-1-[3-((S)-4-hydroxy-6-aza-spiro[2.5]oct-6-yl)-propyl]-3-methyl-piperazin-2-one

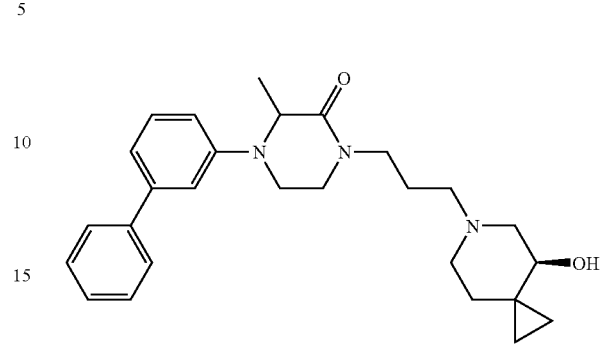

A mixture of 1-[3-((S)-4-hydroxy-6-aza-spiro[2.5]oct-6-yl)-propyl]-4-(3-iodo-phenyl)-3-methyl-piperazin-2-one (example 89; 60 mg, 0.12 mmol), phenylboronic acid (16 mg, 0.13 mmol), potassium carbonate (43 mg, 0.31 mmol), Pd(OAc)₂ (0.6 mg, 2 μmol), acetone (0.5 mL), and water (0.6 mL) was heated at 65° C. for 30 min, then partitioned between CH₂Cl₂ and sat. aq. NaHCO₃ solution. The organic layer was dried (MgSO₄), filtered, and evaporated. Chromatography (SiO₂; EtOAc/MeOH 19:1) afforded the title compound (51 mg, 95%). Colorless gum, MS: 434.4 (M+H)⁺.

Example 91

1-[3-((S)-4-Hydroxy-6-aza-spiro[2.5]oct-6-yl)-propyl]-3-methyl-4-(3-pyridin-3-yl-phenyl)-piperazin-2-one

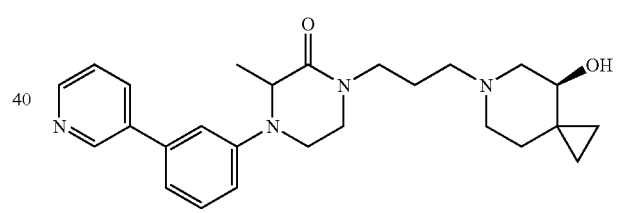

The title compound was produced in analogy with example 90 from 1-[3-((S)-4-hydroxy-6-aza-spiro[2.5]oct-6-yl)-propyl]-4-(3-iodo-phenyl)-3-methyl-piperazin-2-one (example 89) and 3-pyridineboronic acid. White foam, MS: 435.2 (M+H)⁺.

Example 92

1-[3-((S)-4-Hydroxy-6-aza-spiro[2.5]oct-6-yl)-propyl]-3-methyl-4-(3-pyridin-4-yl-phenyl)-piperazin-2-one

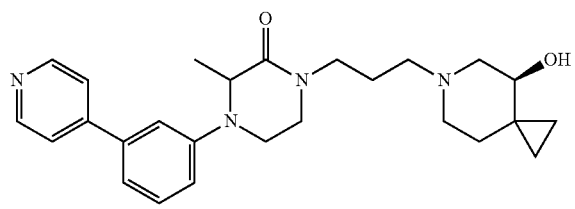

The title compound was produced in analogy with example 90 from 1-[3-((S)-4-hydroxy-6-aza-spiro[2.5]oct-6-yl)-propyl]-4-(3-iodo-phenyl)-3-methyl-piperazin-2-one (example 89) and 4-pyridineboronic acid. Light yellow gum, MS: 435.3 (M+H)+.

Example 93

1-[3-((S)-4-Hydroxy-6-aza-spiro[2.5]oct-6-yl)-propyl]-3-methyl-4-(3-pyridin-2-yl-phenyl)-piperazin-2-one

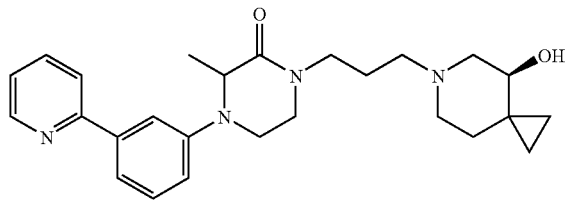

A mixture of 1-[3-((S)-4-hydroxy-6-aza-spiro[2.5]oct-6-yl)-propyl]-4-(3-iodo-phenyl)-3-methyl-piperazin-2-one (example 89; 80 mg, 0.17 mmol), 2-(tributylstannyl)pyridine (73 mg, 0.20 mmol), tetrakis(triphenylphosphine)palladium (0), lithium chloride (42 mg, 0.99 mmol) copper chloride (82 mg, 0.83 mmol), and N,N-dimethylformamide (3 mL) was heated at 100° C. for 16 h, then the reaction mixture was partitioned between CH$_2$Cl$_2$ and sat. aq. NaHCO$_3$ solution. The organic layer was washed with brine, dried (MgSO$_4$), filtered, and evaporated. Chromatography (SiO$_2$; EtOAc-MeOH gradient) afforded the title compound (3.5 mg, 5%). Colorless gum, MS: 435.3 (M+H)+.

Example 94

(S)-4-(3,4-Dichloro-phenyl)-1-[4-((S)-4-hydroxy-6-aza-spiro[2.5]oct-6-yl)-butyl]-3-methyl-piperazin-2-one

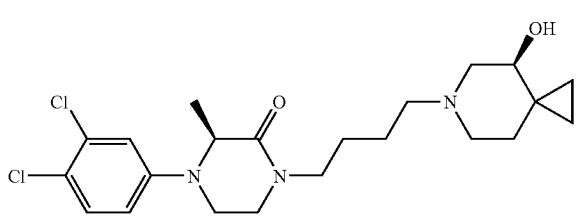

A) [4-((S)-4-Hydroxy-6-aza-spiro[2.5]oct-6-yl)-butyl]-carbamic acid benzyl ester A solution of dimethyl sulfoxide (4.50 g, 57.6 mmol) in CH$_2$Cl$_2$ (24 mL) was added dropwise at −70° C. to a solution of oxalyl chloride (3.94 g, 31.0 mmol) in CH$_2$Cl$_2$ (72 mL), then after 15 min a solution of (4-hydroxy-butyl)-carbamic acid benzyl ester (4.95 g, 22.2 mmol) in CH$_2$Cl$_2$ (36 mL) was added dropwise. After 60 min triethylamine (11.2 g, 111 mmol) was added, then after 20 min the reaction mixture was allowed to reach RT over 2 h. The reaction mixture was washed with water, dried (MgSO$_4$) and filtered to afford (4-oxo-butyl)-carbamic acid benzyl ester as CH$_2$Cl$_2$ solution.

This was added at RT to a mixture of (S)-6-aza-spiro[2.5]octan-4-ol hydrochloride (3.63 g, 22.2 mmol), sodium triacetoxyborohydride (5.17 g, 24.4 mmol), AcOH (2.66 g, 44.3 mmol), and triethylamine (2.24 g, 22.2 mmol), then after 16 h the reaction mixture was washed with 2 M aq. sodium carbonate solution. The organic layer was washed with water, dried (MgSO$_4$) and filtered, and evaporated. Chromatography (SiO$_2$; CH$_2$Cl$_2$→CH$_2$Cl$_2$/MeOH/25% aq. ammonia solution 90:10:0.25) afforded the title compound (4.54 g, 62%). Colorless gum, MS: 435.3 (M+H)+.

B) [4-((S)-4-Triethylsilanyloxy-6-aza-spiro[2.5]oct-6-yl)-butyl]-carbamic acid benzyl ester The title compound was produced in analogy with example 83A from [4-((S)-4-hydroxy-6-aza-spiro[2.5]oct-6-yl)-butyl]-carbamic acid benzyl ester and triethylchlorosilane. Light yellow oil, MS: 447.3 (M+H)+.

C) 4-((S)-4-Triethylsilanyloxy-6-aza-spiro[2.5]oct-6-yl)-butylamine

The title compound was produced in analogy with examples 74/75B from [4-((S)-4-triethylsilanyloxy-6-aza-spiro[2.5]oct-6-yl)-butyl]-carbamic acid benzyl ester. Colourless oil, MS: 313.1 (M+H)+.

D) (2,2-Dimethoxy-ethyl)-[4-((S)-4-triethylsilanyloxy-6-aza-spiro[2.5]oct-6-yl)-butyl]-amine The title compound was produced in analogy with example 83C from 4-((S)-4-triethylsilanyloxy-6-aza-spiro[2.5]oct-6-yl)-butylamine. Colourless liquid, MS: 401.5 (M+H)+.

E) (S)-2-(3,4-Dichloro-phenylamino)-N-(2,2-dimethoxy-ethyl)-N-[4-((S)-4-triethylsilanyloxy-6-aza-spiro[2.5]oct-6-yl)-butyl]-propionamide The title compound was produced in analogy with example 71B from (S)-2-(3,4-dichloro-phenylamino)-propionic acid (intermediate 24) and (2,2-dimethoxy-ethyl)-[4-((S)-4-triethylsilanyloxy-6-aza-spiro[2.5]oct-6-yl)-butyl]-amine. Light yellow gum, MS: 616.3 (M+H)+.

F) (S)-4-(3,4-Dichloro-phenyl)-1-[4-((S)-4-hydroxy-6-aza-spiro[2.5]oct-6-yl)-butyl]-3-methyl-piperazin-2-one Trifluoroacetic acid (255 mg, 2.24 mmol) was added at RT to a solution of (S)-2-(3,4-dichloro-phenylamino)-N-(2,2-dimethoxy-ethyl)-N-[4-((S)-4-triethylsilanyloxy-6-aza-spiro[2.5]oct-6-yl)-butyl]-propionamide (92 mg, 0.15 mmol), then after 30 min triethylsilane (87 mg, 0.75 mmol) was added. The reaction mixture was stirred for 16 h, then cooled to 0° C. and treated with triethylamine (226 mg, 2.24 mmol). The ice bath was removed, then after 15 min the reaction mixture was partitioned between CH$_2$Cl$_2$ and sat. aq. NaHCO$_3$ solution. The organic layer was dried (MgSO$_4$), filtered, and evaporated. Chromatography (SiO$_2$; CH$_2$Cl$_2$→CH$_2$Cl$_2$/MeOH/25% aq. ammonia solution 80:20:1) afforded the title compound (34 mg, 52%). Light yellow gum, MS: 440.3 (M+H)+.

Example 95

(S)-1-[4-((S)-4-Hydroxy-6-aza-spiro[2.5]oct-6-yl)-butyl]-3-methyl-4-(3-trifluoromethoxy-phenyl)-piperazin-2-one

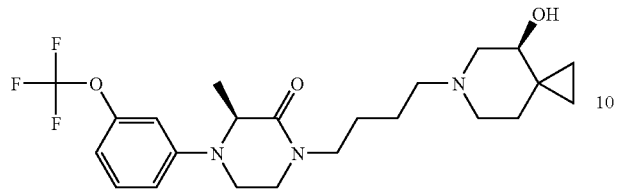

The title compound was produced in analogy with example 94, steps E and F. Thus, (S)-2-(3-trifluoromethoxy-phenylamino)-propionic acid (intermediate 25) was coupled in step E with (2,2-dimethoxy-ethyl)-[4-((S)-4-triethylsilanyloxy-6-aza-spiro[2.5]oct-6-yl)-butyl]-amine (example 94D), leading to (S)-2-(3-trifluoromethoxy-phenylamino)-N-(2,2-dimethoxy-ethyl)-N-[4-((S)-4-hydroxy-6-aza-spiro[2.5]oct-6-yl)-butyl]-propionamide, which was converted to the title compound in step F. Light yellow gum, MS: 456.4 (M+H)$^+$.

Examples 96 and 97

(S)-1-[3-((S)-4-Hydroxy-6-aza-spiro[2.5]oct-6-yl)-propyl]-3-methyl-4-(4-trifluoromethyl-phenyl)-piperazin-2-one and (R)-1-[3-((S)-4-hydroxy-6-aza-spiro[2.5]oct-6-yl)-propyl]-3-methyl-4-(4-trifluoromethyl-phenyl)-piperazin-2-one

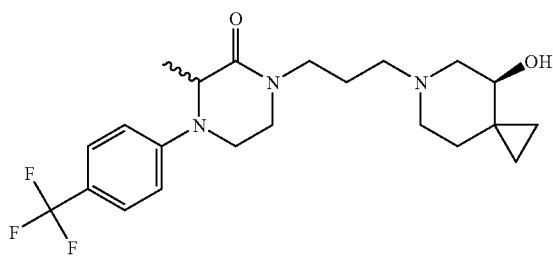

Example 96

(S)-Epimer

Example 97

(R)-Epimer

The title compounds were produced in analogy with examples 87/88, step A-D. Thus, 2-(4-trifluoromethyl-phenylamino)-propionic acid (intermediate 26) was coupled with {3-[(S)-4-(tert-butyl-dimethyl-silanyloxy)-6-aza-spiro[2.5]oct-6-yl]-propyl}-(2,2-dimethoxy-ethyl)-amine (example 83C) in step A, leading to N-{3-[(S)-4-(tert-butyl-dimethyl-silanyloxy)-6-aza-spiro[2.5]oct-6-yl]-propyl}-N-(2,2-dimethoxy-ethyl)-2-(4-trifluoromethyl-phenylamino)-propionamide. This was cyclized to 1-{3-[(S)-4-(tert-butyl-dimethyl-silanyloxy)-6-aza-spiro[2.5]oct-6-yl]-propyl}-4-(4-trifluoromethyl-phenyl)-3-methyl-piperazin-2-one in step B and deprotected in step C, leading to 1-[3-((S)-4-hydroxy-6-aza-spiro[2.5]oct-6-yl)-propyl]-3-methyl-4-(4-trifluoromethyl-phenyl)-piperazin-2-one as mixture of epimers. Finally, HPLC separation in step D afforded the (S)-epimer (example 96; light yellow gum, MS: 426.1 (M+H)$^+$) and the (R)-epimer (example 97; light yellow gum, MS: 426.1 (M+H)$^+$).

Examples 98 and 99

(R)-4-(3,4-Dichloro-phenyl)-1-[(S)-2-hydroxy-3-((S)-4-hydroxy-6-aza-spiro[2.5]oct-6-yl)-propyl]-3-methyl-piperazin-2-one and (S)-4-(3,4-dichloro-phenyl)-1-[(S)-2-hydroxy-3-((S)-4-hydroxy-6-aza-spiro[2.5]oct-6-yl)-propyl]-3-methyl-piperazin-2-one

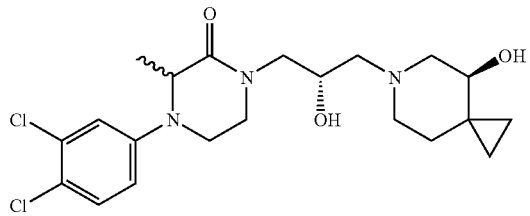

Example 98

(R)-Epimer

Example 99

(S)-Epimer

A) [(R)-2-Hydroxy-3-((S)-4-hydroxy-6-aza-spiro[2.5]oct-6-yl)-propyl]-carbamic acid benzyl ester The title compound was produced in analogy with examples 74/75A from ((R)-2-hydroxy-3-oxo-propyl)-carbamic acid benzyl ester (*J. Am. Chem. Soc.* 2007, 129, 14811) and (S)-6-aza-spiro[2.5]octan-4-ol hydrochloride. Yellow gum, MS: 335.2 (M+H)$^+$.

B) [(R)-2-Triethylsilanyloxy-3-((S)-4-triethylsilanyloxy-6-aza-spiro[2.5]oct-6-yl)-propyl]-carbamic acid benzyl ester Triethylchlorosilane (351 mg, 2.33 mmol) was added to a solution of [(R)-2-hydroxy-3-((S)-4-hydroxy-6-aza-spiro[2.5]oct-6-yl)-propyl]-carbamic acid benzyl ester (260 mg, 0.78 mmol), imidazole (264 mg, 3.89 mmol), and 4-(dimethylamino)pyridine (1.9 mg, 16 μmol) in N,N-dimethylformamide at RT, then after 90 min the reaction mixture was partitioned between EtOAc and sat. aq. NaHCO$_3$ solution. The organic layer was washed with brine, dried (MgSO$_4$), filtered, and evaporated. Chromatography (SiO$_2$; heptane/EtOAc 7:3) afforded the title compound (397 mg, 91%). Light yellow liquid, MS: 563.4 (M+H)$^+$.

C) (R)-2-Triethylsilanyloxy-3-((S)-4-triethylsilanyloxy-6-aza-spiro[2.5]oct-6-yl)-propylamine The title compound was produced in analogy with example 71/75B from [(R)-2-triethylsilanyloxy-3-((S)-4-triethylsilanyloxy-6-aza-spiro[2.5]oct-6-yl)-propyl]-carbamic acid benzyl ester. Light yellow liquid, MS: 429.4 (M+H)$^+$.

D) (2,2-Dimethoxy-ethyl)-[(R)-2-triethylsilanyloxy-3-((S)-4-triethylsilanyloxy-6-aza-spiro[2.5]oct-6-yl)-propyl]-amine The title compound was produced in analogy with example 83C from (R)-2-triethylsilanyloxy-3-((S)-4-triethylsilanyloxy-6-aza-spiro[2.5]oct-6-yl)-propylamine. Colourless liquid, MS: 517.4 (M+H)+.

E) 2-(3,4-Dichloro-phenylamino)-N-(2,2-dimethoxy-ethyl)-N—[(S)-2-hydroxy-3-((S)-4-triethylsilanyloxy-6-aza-spiro[2.5]oct-6-yl)-propyl]-propionamide The title compound was produced in analogy with example 71B from 2-(3,4-dichloro-phenylamino)-propionic acid (intermediate 11) and (2,2-dimethoxy-ethyl)-[(R)-2-triethylsilanyloxy-3-((S)-4-triethylsilanyloxy-6-aza-spiro[2.5]oct-6-yl)-propyl]-amine. Light yellow gum, MS: 732.5 (M+H)+.

F) 4-(3,4-Dichloro-phenyl)-1-[(S)-2-hydroxy-3-((S)-4-hydroxy-6-aza-spiro[2.5]oct-6-yl)-propyl]-3-methyl-piperazin-2-one The title compound was produced in analogy with example 94F from 2-(3,4-dichloro-phenylamino)-N-(2,2-dimethoxy-ethyl)-N—[(S)-2-hydroxy-3-((S)-4-triethylsilanyloxy-6-aza-spiro[2.5]oct-6-yl)-propyl]-propionamide. Light yellow gum, MS: 442.3 (M+H)+.

G) (R)-4-(3,4-Dichloro-phenyl)-1-[(S)-2-hydroxy-3-((S)-4-hydroxy-6-aza-spiro[2.5]oct-6-yl)-propyl]-3-methyl-piperazin-2-one and (S)-4-(3,4-dichloro-phenyl)-1-[(S)-2-hydroxy-3-((S)-4-hydroxy-6-aza-spiro[2.5]oct-6-yl)-propyl]-3-methyl-piperazin-2-one The epimeric mixture, 4-(3,4-dichloro-phenyl)-1-[(S)-2-hydroxy-3-((S)-4-hydroxy-6-aza-spiro[2.5]oct-6-yl)-propyl]-3-methyl-piperazin-2-one (51 mg, 0.12 mmol) was separated into its epimers by preparative HPLC using a Reprosil Chiral-NR column as stationary phase and heptane/EtOH 4:1 as the eluent. This afforded the (R)-epimer (example 98; 13.9 mg, 27%, light yellow solid, MS: 442.3 (M+H)+), and the (S)-epimer (example 99; 8.6 mg, 17%, light yellow foam, MS: 442.2 (M+H)+).

Examples 100 and 101

(R)-4-(3,4-Dichloro-phenyl)-1-[(R)-2-hydroxy-3-((S)-4-hydroxy-6-aza-spiro[2.5]oct-6-yl)-propyl]-3-methyl-piperazin-2-one and (S)-4-(3,4-dichloro-phenyl)-1-[(R)-2-hydroxy-3-((S)-4-hydroxy-6-aza-spiro[2.5]oct-6-yl)-propyl]-3-methyl-piperazin-2-one

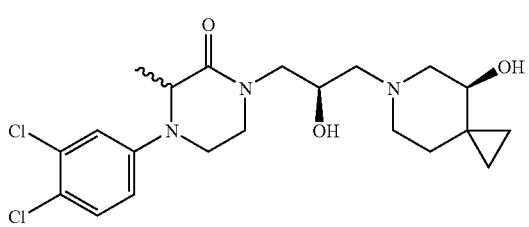

Example 100

(R)-Epimer

Example 101

(S)-Epimer

The title compounds were produced in analogy with examples 98/99, steps A-G. Thus, reductive amination of ((S)-2-hydroxy-3-oxo-propyl)-carbamic acid benzyl ester (*J. Am. Chem. Soc.* 2007, 129, 14811) with (S)-6-aza-spiro[2.5]octan-4-ol hydrochloride (intermediate 2) in step A led to [(S)-2-hydroxy-3-((S)-4-hydroxy-6-aza-spiro[2.5]oct-6-yl)-propyl]-carbamic acid benzyl ester. This was silylated to [(S)-2-triethylsilanyloxy-3-((S)-4-triethylsilanyloxy-6-aza-spiro[2.5]oct-6-yl)-propyl]-carbamic acid benzyl ester in step B, followed by hydrogenation in step C, upon which (S)-2-triethylsilanyloxy-3-((S)-4-triethylsilanyloxy-6-aza-spiro[2.5]oct-6-yl)-propylamine was obtained. This underwent reductive alkylation to (2,2-dimethoxy-ethyl)-[(S)-2-triethylsilanyloxy-3-((S)-4-triethylsilanyloxy-6-aza-spiro[2.5]oct-6-yl)-propyl]-amine in step D, followed by coupling with 2-(3,4-dichloro-phenylamino)-propionic acid (intermediate 11) in step E, leading to 2-(3,4-dichloro-phenylamino)-N-(2,2-dimethoxy-ethyl)-N—[(R)-2-hydroxy-3-((S)-4-triethylsilanyloxy-6-aza-spiro[2.5]oct-6-yl)-propyl]-propionamide. Reductive cyclization and concomitant desilylation in step F then gave 4-(3,4-dichloro-phenyl)-1-[(R)-2-hydroxy-3-((S)-4-hydroxy-6-aza-spiro[2.5]oct-6-yl)-propyl]-3-methyl-piperazin-2-one. Finally, HPLC separation of this epimeric mixture in step G afforded (R)-4-(3,4-dichloro-phenyl)-1-[(R)-2-hydroxy-3-((S)-4-hydroxy-6-aza-spiro[2.5]oct-6-yl)-propyl]-3-methyl-piperazin-2-one (example 100; white solid, MS: 442.3 (M+H)+) and (S)-4-(3,4-dichloro-phenyl)-1-[(R)-2-hydroxy-3-((S)-4-hydroxy-6-aza-spiro[2.5]oct-6-yl)-propyl]-3-methyl-piperazin-2-one (example 101; white foam, MS: 442.3 (M+H)+).

Examples 102 and 103

(S)-4-(3-Fluoro-4-trifluoromethyl-phenyl)-1-[3-((S)-4-hydroxy-6-aza-spiro[2.5]oct-6-yl)-propyl]-3-methyl-piperazin-2-one and (R)-4-(3-fluoro-4-trifluoromethyl-phenyl)-1-[3-((S)-4-hydroxy-6-aza-spiro[2.5]oct-6-yl)-propyl]-3-methyl-piperazin-2-one

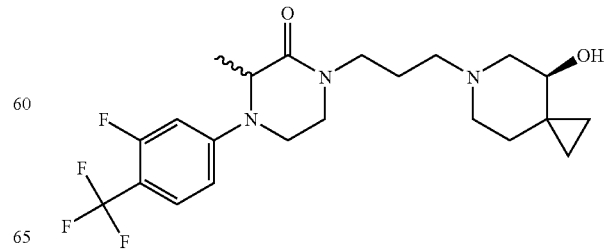

Example 102

(S)-Epimer

Example 103

(R)-Epimer

A) [3-((S)-4-Triethylsilanyloxy-6-aza-spiro[2.5]oct-6-yl)-propyl]-carbamic acid benzyl ester The title compound was produced in analogy with example 83A from [3-((S)-4-hydroxy-6-aza-spiro[2.5]oct-6-yl)-propyl]-carbamic acid benzyl ester (examples 74/75A) and triethylsilane. Yellow oil, MS: 433.3 (M+H)⁺.

B) 3-((S)-4-Triethylsilanyloxy-6-aza-spiro[2.5]oct-6-yl)-propylamine

The title compound was produced in analogy with examples 74/75B from [3-((S)-4-triethylsilanyloxy-6-aza-spiro[2.5]oct-6-yl)-propyl]-carbamic acid benzyl ester. Yellow oil, MS: 299.3 (M+H)⁺.

C) (2,2-Dimethoxy-ethyl)-[3-((S)-4-triethylsilanyloxy-6-aza-spiro[2.5]oct-6-yl)-propyl]-amine The title compound was produced in analogy with example 83C from 3-((S)-4-triethylsilanyloxy-6-aza-spiro[2.5]oct-6-yl)-propylamine. Yellow oil, MS: 387.4 (M+H)⁺.

D) N-(2,2-Dimethoxy-ethyl)-2-(3-fluoro-4-trifluoromethyl-phenylamino)-N-[3-((S)-4-triethylsilanyloxy-6-aza-spiro[2.5]oct-6-yl)-propyl]-propionamide The title compound was produced in analogy with example 71B from 2-(3-fluoro-4-trifluoromethyl-phenylamino)-propionic acid (intermediate 27) and (2,2-dimethoxy-ethyl)-[3-((S)-4-triethylsilanyloxy-6-aza-spiro[2.5]oct-6-yl)-propyl]-amine. Yellow gum, MS: 620.5 (M+H)⁺.

E) 4-(3-Fluoro-4-trifluoromethyl-phenyl)-1-[3-((S)-4-hydroxy-6-aza-spiro[2.5]oct-6-yl)-propyl]-3-methyl-piperazin-2-one The title compound was produced in analogy with example 94F from N-(2,2-dimethoxy-ethyl)-2-(3-fluoro-4-trifluoromethyl-phenylamino)-N-[3-((S)-4-triethylsilanyloxy-6-aza-spiro[2.5]oct-6-yl)-propyl]-propionamide. Light yellow gum.

F) (S)-4-(3-Fluoro-4-trifluoromethyl-phenyl)-1-[3-((S)-4-hydroxy-6-aza-spiro[2.5]oct-6-yl)-propyl]-3-methyl-piperazin-2-one and (R)-4-(3-fluoro-4-trifluoromethyl-phenyl)-1-[3-((S)-4-hydroxy-6-aza-spiro[2.5]oct-6-yl)-propyl]-3-methyl-piperazin-2-one HPLC separation of the epimeric mixture, 4-(3-fluoro-4-trifluoromethyl-phenyl)-1-[3-((S)-4-hydroxy-6-aza-spiro[2.5]oct-6-yl)-propyl]-3-methyl-piperazin-2-one, in analogy with examples 72/73, afforded the (S)-epimer (example 102; light grey solid, MS: 444.3 (M+H)⁺), and the (R)-epimer (example 103; light yellow gum, MS: 444.3 (M+H)⁺).

Example 104

(S)-4-(3,4-Dichloro-phenyl)-1-[(R)-2-hydroxy-4-((S)-4-hydroxy-6-aza-spiro[2.5]oct-6-yl)-butyl]-3-methyl-piperazin-2-one

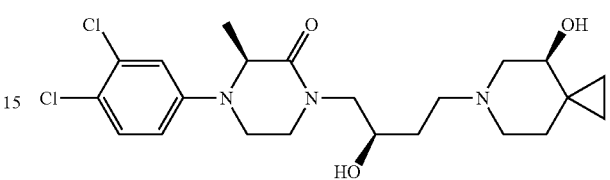

A) ((R)-2-Hydroxy-pent-4-enyl)-carbamic acid benzyl ester

To a solution of 2-allyl-oxirane (*Synthesis* 1986, 309; 918 mg, 10.9 mmol) in TBME (12 mL) were added benzyl carbamate (750 mg, 4.96 mmol), 4-nitrobenzoic acid (146 mg, 0.87 mmol) and (1S,2S)-(+)-N—N'-bis(3,5-di-tert-butylsalicylidene)-1,2-cyclohexanediaminocobalt(II) 264 mg, 0.44 mmol) at RT, then after 72 h the reaction mixture was partitioned between TBME and sat. aq. NaHCO₃ solution. The organic layer was washed with brine, dried (MgSO₄), filtered, and evaporated. Chromatography (SiO₂; heptane-EtOAc gradient) produced the title compound (694 mg, 48%). Brown oil, MS: 236.2 (M+H)⁺.

B) ((R)-2-Hydroxy-4-oxo-butyl)-carbamic acid benzyl ester

A mixture of ((R)-2-hydroxy-pent-4-enyl)-carbamic acid benzyl ester (690 mg, 2.35 mmol), osmium(VIII) oxide (4% solution in water, 0.22 mL, 35 μmol), and 4-methyl-morpholine-4-oxide (50% solution in water, 0.27 mL, 1.29 mmol) in acetone/THF/water 6:2:1 (6 mL) was stirred for 45 min at RT, then sodium metaperiodate (1.51 g, 7.04 mmol) was added, then after 16 h 10% aq. sodium sulfite solution (5.5 mL) was added. The reaction mixture was partitioned between EtOAc and water, the organic layer was washed with brine, dried (MgSO₄), filtered, and evaporated. Chromatography (SiO₂; heptane-EtOAc gradient) produced the title compound (407 mg, 73%) as a brown gum.

C) [(R)-2-Hydroxy-4-((S)-4-hydroxy-6-aza-spiro[2.5]oct-6-yl)-butyl]-carbamic acid benzyl ester The title compound was produced in analogy with example 83A from ((R)-2-hydroxy-4-oxo-butyl)-carbamic acid benzyl ester and (S)-6-aza-spiro[2.5]octan-4-ol hydrochloride (intermediate 2). Light yellow gum, MS: 349.4 (M+H)⁺.

D) [(R)-2-Triethylsilanyloxy-4-((S)-4-triethylsilanyloxy-6-aza-spiro[2.5]oct-6-yl)-butyl]-carbamic acid benzyl ester The title compound was produced in analogy with examples 98/99B from [(R)-2-hydroxy-4-((S)-4-hydroxy-6-aza-spiro[2.5]oct-6-yl)-butyl]-carbamic acid benzyl ester and triethylsilane. Light yellow gum, MS: 577.5 (M+H)⁺.

E) (R)-2-Triethylsilanyloxy-4-((S)-4-triethylsilanyloxy-6-aza-spiro[2.5]oct-6-yl)-butylamine The title compound was produced in analogy with examples 74/75B from [(R)-2-triethylsilanyloxy-4-((S)-4-triethylsilanyloxy-6-aza-spiro[2.5]oct-6-yl)-butyl]-carbamic acid benzyl ester. Colourless gum, MS: 443.6 (M+H)$^+$.

F) (2,2-Dimethoxy-ethyl)-[(R)-2-triethylsilanyloxy-4-((S)-4-triethylsilanyloxy-6-aza-spiro[2.5]oct-6-yl)-butyl]-amine The title compound was produced in analogy with example 83C from (R)-2-triethylsilanyloxy-4-((S)-4-triethylsilanyloxy-6-aza-spiro[2.5]oct-6-yl)-butylamine. Light yellow gum, MS: 531.3 (M+H)$^+$.

G) (S)-2-(3,4-Dichloro-phenylamino)-N-(2,2-dimethoxy-ethyl)-N—[(R)-2-triethylsilanyloxy-4-((S)-4-triethylsilanyloxy-6-aza-spiro[2.5]oct-6-yl)-butyl]-propionamide The title compound was produced in analogy with example 71B from (S)-2-(3,4-dichloro-phenylamino)-propionic acid (intermediate 24) and (2,2-dimethoxy-ethyl)-[(R)-2-triethylsilanyloxy-4-((S)-4-triethylsilanyloxy-6-aza-spiro[2.5]oct-6-yl)-butyl]-amine. Light yellow gum, MS: 746.4 (M+H)$^+$.

H) (S)-4-(3,4-Dichloro-phenyl)-1-[(R)-2-hydroxy-4-((S)-4-hydroxy-6-aza-spiro[2.5]oct-6-yl)-butyl]-3-methyl-piperazin-2-one The title compound was produced in analogy with example 94F from (S)-2-(3,4-dichloro-phenylamino)-N-(2,2-dimethoxy-ethyl)-N—[(R)-2-triethylsilanyloxy-4-((S)-4-triethylsilanyloxy-6-aza-spiro[2.5]oct-6-yl)-butyl]-propionamide Light yellow gum, MS: 456.3 (M+H)$^+$.

Example 105

(S)-4-(3,4-Dichloro-phenyl)-1-[(S)-2-hydroxy-4-((S)-4-hydroxy-6-aza-spiro[2.5]oct-6-yl)-butyl]-3-methyl-piperazin-2-one

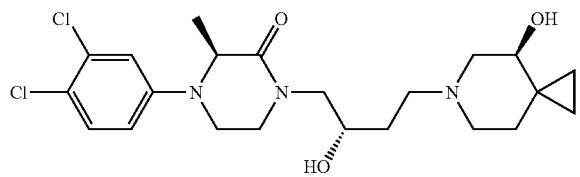

The title compound was produced in analogy with example 104, steps A-H. Thus, reaction of 2-allyl-oxirane with benzyl carbamate in the presence of (1R,2R)-(−)-N—N'-bis(3,5-di-tert-butylsalicylidene)-1,2-cyclohexanediaminocobalt(II) in step A led to ((S)-2-hydroxy-pent-4-enyl)-carbamic acid benzyl ester, which was converted to ((S)-2-hydroxy-4-oxo-butyl)-carbamic acid benzyl ester in step B. This underwent a reductive amination reaction with (S)-6-aza-spiro[2.5]octan-4-ol hydrochloride in step C, leading to [(S)-2-hydroxy-4-((S)-4-hydroxy-6-aza-spiro[2.5]oct-6-yl)-butyl]-carbamic acid benzyl ester. Silylation in step D gave [(S)-2-triethylsilanyloxy-4-((S)-4-triethylsilanyloxy-6-aza-spiro[2.5]oct-6-yl)-butyl]-carbamic acid benzyl ester, which was hydrogenated to (S)-2-triethylsilanyloxy-4-((S)-4-triethylsilanyloxy-6-aza-spiro[2.5]oct-6-yl)-butylamine in step E. This was converted to (2,2-dimethoxy-ethyl)-[(S)-2-triethylsilanyloxy-4-((S)-4-triethylsilanyloxy-6-aza-spiro[2.5]oct-6-yl)-butyl]-amine in step F, followed by coupling with (S)-2-(3,4-dichloro-phenylamino)-propionic acid (intermediate 24) in step G, leading to (S)-2-(3,4-dichloro-phenylamino)-N-(2,2-dimethoxy-ethyl)-N—[(S)-2-triethylsilanyloxy-4-((S)-4-triethylsilanyloxy-6-aza-spiro[2.5]oct-6-yl)-butyl]-propionamide. Finally, reductive cyclization and concomitant desilylation in step H afforded (S)-4-(3,4-dichloro-phenyl)-1-[(S)-2-hydroxy-4-((S)-4-hydroxy-6-aza-spiro[2.5]oct-6-yl)-butyl]-3-methyl-piperazin-2-one. Colourless gum, MS: 456.3 (M+H)$^+$.

Example 106

4-(3,4-Dichloro-phenyl)-1-[(R)-3-hydroxy-4-((S)-4-hydroxy-6-aza-spiro[2.5]oct-6-yl)-butyl]-3-methyl-piperazin-2-one

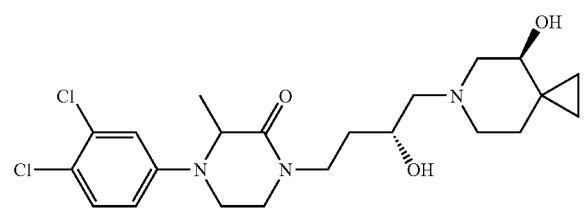

A) (R)-4-Benzyloxycarbonylamino-2-hydroxy-butyric acid ethyl ester

A solution of (R)-4-benzyloxycarbonylamino-2-hydroxy-butyric acid (2.42 g, 9.56 mmol) and sulfuric acid (94 mg, 0.96 mmol) in EtOH (6 mL) was heated at reflux for 18 h, then partitioned between EtOAc and sat. aq. NaHCO$_3$ solution. The organic layer was washed with brine, dried (MgSO$_4$), filtered, and evaporated to afford the title compound (2.18 g, 81%). Light yellow liquid, MS: 304.2 (M+Na)$^+$.

B) ((R)-3,4-Dihydroxy-butyl)-carbamic acid benzyl ester

A solution of (R)-4-benzyloxycarbonylamino-2-hydroxy-butyric acid ethyl ester (2.17 g, 7.71 mmol) in EtOH (6 mL) was added dropwise at <15° C. to a suspension of sodium borohydride (583 mg, 15.4 mmol) in EtOH (4 mL). The reaction mixture was stirred at RT for 16 h, then cooled to 5° C. and treated with MeOH (3 mL), then after 30 min acidified to pH 1-2 with conc. aq. HCl solution. The reaction mixture was stirred for 1 h, then diluted with CH$_2$Cl$_2$, dried (MgSO$_4$), filtered, and evaporated. Chromatography (SiO$_2$; CH$_2$Cl$_2$/MeOH gradient) afforded the title compound (1.76 g, 96%). Light yellow solid, MS: 262.1 (M+Na)$^+$.

C) (R)-4-Amino-butane-1,2-diol

The title compound was produced in analogy with examples 74/75B from ((R)-3,4-dihydroxy-butyl)-carbamic acid benzyl ester. Light yellow gum, MS: 106.1 (M+H)$^+$.

D) (R)-4-(2,2-Dimethoxy-ethylamino)-butane-1,2-diol

The title compound was produced in analogy with example 83C from (R)-4-amino-butane-1,2-diol. Light yellow foam, MS: 194.3 (M+H)$^+$.

E) 2-(3,4-Dichloro-phenylamino)-N—((R)-3,4-dihydroxy-butyl)-N-(2,2-dimethoxy-ethyl)-propionamide The title compound was produced in analogy with example 71B from 2-(3,4-dichloro-phenylamino)-propionic acid (intermediate 11) and (R)-4-(2,2-dimethoxy-ethylamino)-butane-1,2-diol. Colourless gum, MS: 431.2 (M+Na)$^+$.

F) 4-(3,4-Dichloro-phenyl)-1-((R)-3,4-dihydroxy-butyl)-3-methyl-piperazin-2-one The title compound was produced in analogy with example 94F from 2-(3,4-dichloro-phenylamino)-N—((R)-3,4-dihydroxy-butyl)-N-(2,2-dimethoxy-ethyl)-propionamide. Light yellow gum, MS: 347.1 (M+H)$^+$.

G) 4-(3,4-Dichloro-phenyl)-1-[(R)-3-hydroxy-4-((S)-4-hydroxy-6-aza-spiro[2.5]oct-6-yl)-butyl]-3-methyl-piperazin-2-one A solution of methanesulfonyl chloride (53 mg, 0.46 mmol) in DMA (0.5 mL) was added at 0° C. to a solution of 4-(3,4-dichloro-phenyl)-1-((R)-3,4-dihydroxy-butyl)-3-methyl-piperazin-2-one (160 mg, 0.46 mmol) and 2,4,6-trimethylpyridine (279 mg, 2.30 mmol) in DMA (2 mL), then after 2½ h the reaction mixture was partitioned between EtOAc and sat. aq. NaHCO$_3$ solution. The organic layer was washed with brine, dried (MgSO$_4$), filtered, and evaporated to afford crude methanesulfonic acid (R)-4-[4-(3,4-dichloro-phenyl)-3-methyl-2-oxo-piperazin-1-yl]-2-hydroxy-butyl ester (254 mg) as a light yellow gum. This was dissolved in DMA (2 mL), cooled to 0° C., and treated with NaH (55% dispersion in mineral oil, 41 mg, 0.94 mmol). After 15 min, as the methanesulfonate intermediate had disappeared, with mass spectrometry confirming the formation of the epoxide intermediate, 4-(3,4-dichloro-phenyl)-3-methyl-1-((R)-2-oxiranyl-ethyl)-piperazin-2-one [m/e=329, (M+H)$^+$)], cesium carbonate (184 mg, 0.56 mmol) and a solution of (S)-6-aza-spiro[2.5]octan-4-ol hydrochloride (intermediate 2; 77 mg, 0.47 mmol) and N,N-diisopropylethylamine (152 mg, 1.2 mmol) in DMA (1 mL) were added. The reaction mixture was heated at 80° C. for 20 h, then diluted with EtOAc/MeOH 4:1 and filtered through diatomaceous earth. The filtrate was chromatographed (IST Isolute® Flash NH$_2$; EtOAc/MeOH gradient) to produce the title compound (101 mg, 47%). Light yellow foam, MS: 456.2 (M+H)$^+$.

Example 107

4-(3,4-Dichloro-phenyl)-1-[(S)-3-hydroxy-4-((S)-4-hydroxy-6-aza-spiro[2.5]oct-6-yl)-butyl]-3-methyl-piperazin-2-one

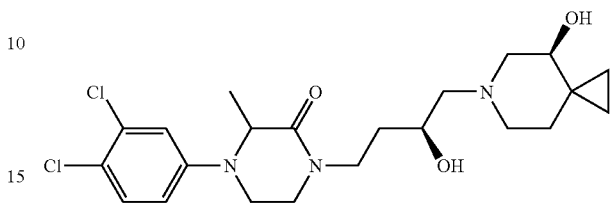

The title compound was produced in analogy with example 106, steps A-G. Thus, esterification of (S)-4-benzyloxycarbonylamino-2-hydroxy-butyric acid gave (S)-4-benzyloxycarbonylamino-2-hydroxy-butyric acid ethyl ester, which was reduced in step B, leading to ((S)-3,4-dihydroxy-butyl)-carbamic acid benzyl ester. Hydrogenation in step C led to (S)-4-amino-butane-1,2-diol, followed by reductive alkylation in step D, thus producing (S)-4-(2,2-dimethoxy-ethylamino)-butane-1,2-diol. This was coupled with 2-(3,4-dichloro-phenylamino)-propionic acid (intermediate 11) to 2-(3,4-dichloro-phenylamino)-N—((S)-3,4-dihydroxy-butyl)-N-(2,2-dimethoxy-ethyl)-propionamide in step E, followed by reductive cyclization in step F, leading to 4-(3,4-dichloro-phenyl)-1-((S)-3,4-dihydroxy-butyl)-3-methyl-piperazin-2-one. Finally, mesylation and intramolecular cyclization, followed by reaction with (S)-6-aza-spiro[2.5]octan-4-ol hydrochloride (intermediate 2) in step G afforded 4-(3,4-dichloro-phenyl)-1-[(S)-3-hydroxy-4-((S)-4-hydroxy-6-aza-spiro[2.5]oct-6-yl)-butyl]-3-methyl-piperazin-2-one. Light yellow foam, MS: 456.2 (M+H)$^+$.

Example A

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Polyvinylpyrrolidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene glycol 400 | 150.0 mg |
| Acetic acid | q.s. ad pH 5.0 |
| Water for injection solutions | Ad 1.0 ml |

The active ingredient is dissolved in a mixture of polyethylene glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavouring additives and filled into sachets.

Unless stated to the contrary, all compounds in the examples were prepared and characterized as described. All ranges recited herein encompass all combinations and subcombinations included within that range limit. All patents and publications cited herein are hereby incorporated by reference in their entirety.

The invention claimed is:

1. A compound of formula (I):

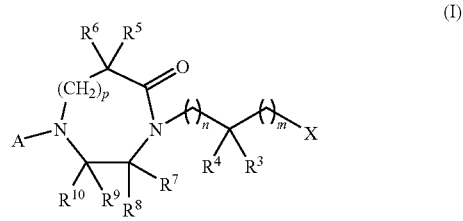

or a pharmaceutically acceptable salt thereof, wherein:
A is phenyl or napthyl, which is optionally substituted by one to three substituents independently selected from the group consisting of halogen, aryl, halo $C_{1-6}$ alkyl, and halo $C_{1-6}$ alkoxy;
X is $—N(R^1)(R^2)$;
$R^1$ and $R^2$ are independently selected from the group consisting of:
(1) hydrogen,
(2) $C_{1-6}$ alkyl,
(3) $C_{3-6}$ alkenyl,
(4) $C_{3-6}$ alkynyl,
(5) hydroxy $C_{2-6}$ alkyl,
(6) $C_{1-6}$ alkoxy $C_{2-6}$ alkyl,
(7) $C_{3-7}$ cycloalkyl, which is optionally substituted one to three times by $R^d$,
(8) $C_{3-7}$ cycloalkyl $C_{1-6}$ alkyl, wherein the $C_{3-7}$ cycloalkyl portion of said $C_{3-7}$ cycloalkyl $C_{1-6}$ alkyl is optionally substituted one to three times by $R^d$,
(9) $C_{7-10}$ bicycloalkyl,
(10) phenyl $C_{1-3}$ alkyl, wherein the phenyl portion of said phenyl $C_{1-3}$ alkyl is optionally substituted one to three times by $R^d$,
(11) heteroaryl $C_{1-3}$ alkyl, wherein the heteroaryl portion of said heteroaryl $C_{1-3}$ alkyl is optionally substituted one to three times by $R^d$,
(12) heterocyclyl, which is optionally substituted one to three times by $R^d$, and
(13) heterocyclyl $C_{1-6}$ alkyl, wherein the heterocyclyl portion of said heterocyclyl $C_{1-6}$ alkyl is optionally substituted one to three times by $R^d$;
provided that at least one of $R^1$ and $R^2$ is not hydrogen; or alternatively, $R^1$ and $R^2$, together with the nitrogen atom to which they are attached, form a heterocyclyl optionally substituted one to three times by $R^d$, and wherein: (a) one of the ring carbon atoms of said heterocyclyl formed by $R^1$ and $R^2$ is optionally replaced with a carbonyl group; and/or (b) one of the ring carbon atoms of said heterocyclyl formed by $R^1$ and $R^2$ is also a ring carbon atom of another ring which is a $C_{3-7}$ cycloalkyl or heterocyclyl, which is optionally substituted by a $C_{1-6}$ alkyl, and wherein one or two ring carbon atoms of said $C_{3-7}$ cycloalkyl or heterocyclyl is optionally replaced by a carbonyl group;

$R^3$ and $R^4$ are independently selected from the group consisting of:
(1) hydrogen,
(2) hydroxy,
(3) $C_{1-6}$ alkyl,
(4) $C_{1-6}$ alkoxy,
(5) $C_{3-7}$ cycloalkyl,
(6) $C_{3-7}$ cycloalkyl $C_{1-6}$ alkyl,
(7) $C_{1-6}$ alkoxycarbonyl,
(8) carboxyl,
(9) carbamoyl,
(10) mono or di-$C_{1-6}$ alkyl substituted carbamoyl,
(11) $C_{1-6}$ alkoxycarbonyloxy,
(12) mono or di-$C_{1-6}$ alkyl substituted aminocarbonyloxy,
(13) hydroxy-$C_{1-6}$ alkyl,
(14) $C_{1-6}$ alkoxy-$C_{1-6}$ alkyl,
(15) halogen or halo $C_{1-6}$ alkyl,
(16) optionally substituted heterocyclyl-carbonyl, and
(17) $R^{aa}R^{bb}N$—C(O)— wherein $R^{aa}$ and $R^{bb}$ are independently selected from the group consisting of hydrogen, $C_{1-6}$ alkyl, hydroxy-$C_{1-6}$ alkyl and $C_{3-7}$ cycloalkyl; or alternatively, $R^3$ and $R^4$, together with the carbon atom to which they are attached, form $C_{3-7}$ cycloalkyl or heterocyclyl optionally substituted by one to three substituents independently selected from the group consisting of $C_{1-4}$ alkyl, halo $C_{1-4}$ alkyl and halogen;

$R^5$ and $R^6$ are independently hydrogen, $C_{1-6}$ alkyl or $C_{3-7}$ cycloalkyl, wherein said $C_{1-6}$ alkyl and said $C_{3-7}$ cycloalkyl are optionally substituted by one to three substituents independently selected from the group consisting of: (1) amino, (2) hydroxy, (3) carboxyl, (4) carbamoyl, (5) mono or di-$C_{1-6}$ alkyl substituted carbamoyl and (6) $C_{1-6}$ alkoxycarbonyl; or alternatively $R^5$ and $R^6$, together with the carbon atom to which they are attached, form $C_{3-7}$ cycloalkyl or heterocyclyl;

$R^7$, $R^8$, $R^9$ and $R^{10}$ are independently hydrogen, $C_{1-6}$ alkyl, $C_{3-7}$ cycloalkyl, or aryl; wherein said $C_{1-6}$ alkyl is optionally substituted by one to three substituents independently selected from the group consisting of:
(1) hydroxy,
(2) $C_{1-6}$ alkoxy,
(3) carboxyl,
(4) carbamoyl,
(5) mono or di-$C_{1-6}$ alkyl substituted carbamoyl,
(6) $C_{1-6}$ alkoxycarbonyl,
(7) aryl, optionally substituted by one to three substituents independently selected from the group consisting of halogen, $C_{1-6}$ alkyl, halo $C_{1-6}$ alkyl, $C_{1-6}$ alkoxy and halo $C_{1-6}$ alkoxy, and
(8) heteroaryl, optionally substituted by one to three substituents independently selected from the group consisting of halogen, $C_{1-6}$ alkyl, halo $C_{1-6}$ alkyl, $C_{1-6}$ alkoxy and halo $C_{1-6}$ alkoxy;

$R^d$ is selected from the group consisting of:
(1) hydroxy,
(2) cyano,
(3) $NR^aR^b$,
(4) halogen,
(5) $C_{1-6}$ alkyl,
(6) halo $C_{1-6}$ alkyl,
(7) hydroxy $C_{1-6}$ alkyl,
(8) $C_{1-6}$ alkoxy,
(9) $C_{1-6}$ alkoxy $C_{1-6}$ alkyl,
(10) $C_{3-7}$ cycloalkyl,
(11) $C_{1-6}$ alkoxycarbonyl,
(12) acyl,
(13) —C(O)$NR^aR^b$,
(14) —$NR^a$—C(O)—$R^b$,
(15) —$NR^a$—C(O)—$OR^b$,
(16) —$NR^a$—C(O)—$NR^b$,
(17) —$NR^a$—$SO_2$—$R^b$,
(18) —$NR^a$—$SO_2$—$NR^bR^c$,
(19) —OC(O)$NR^aR^b$,
(20) —OC(O)$OR^a$,
(21) $C_{1-6}$ alkylsulfonyl,
(22) $C_{1-6}$ alkylsulfinyl,
(23) $C_{1-6}$ alkylthio,
(24) phenyl or phenyl $C_{1-3}$ alkyl, wherein the phenyl or phenyl portion of said phenyl $C_{1-3}$ alkyl is optionally substituted one to three times by a substituent independently selected from the group consisting of hydroxy, cyano, $NR^aR^b$, halogen, $C_{1-6}$ alkyl, halo $C_{1-6}$ alkyl, hydroxy $C_{1-6}$ alkyl, $C_{1-6}$ alkoxycarbonyl, acyl, —C(O)$NR^aR^b$, —$NR^a$—C(O)—$R^b$, —$NR^a$—C(O)—$OR^b$, —$NR^a$—C(O)—$NR^b$, —$NR^a$—$SO_2$—$R^b$, —$NR^a$—$SO_2$—$NR^bR^c$, —OC(O)$NR^aR^b$, —OC(O)$OR^a$, $C_{1-6}$ alkylsulfonyl, $C_{1-6}$ alkylsulfinyl, and $C_{1-6}$ alkylthio;
(25) heteroaryl or heteroaryl $C_{1-3}$ alkyl, wherein the heteroaryl or heteroaryl portion of said heteroaryl $C_{1-3}$ alkyl is optionally substituted one to three times by a substituent independently selected from the group consisting of hydroxy, cyano, $NR^aR^b$, halogen, $C_{1-6}$ alkyl, halo $C_{1-6}$ alkyl, hydroxy $C_{1-6}$ alkyl, $C_{1-6}$ alkoxycarbonyl, acyl, —C(O)$NR^aR^b$, —$NR^a$—C(O)—$R^b$, —$NR^a$—C(O)—$OR^b$, —$NR^a$—C(O)—$NR^b$, —$NR^a$—$SO_2$—$R^b$, —$NR^a$—$SO_2$—$NR^bR^c$, —OC(O)$NR^aR^b$, —OC(O)$OR^a$, $C_{1-6}$ alkylsulfonyl, $C_{1-6}$ alkylsulfinyl, and $C_{1-6}$ alkylthio; and
(26) heterocyclyl, which is optionally substituted one to three times by a substituent independently selected from the group consisting of hydroxy, cyano, $NR^aR^b$, halogen, $C_{1-6}$ alkyl, halo $C_{1-6}$ alkyl, hydroxy $C_{1-6}$ alkyl, $C_{1-6}$ alkoxycarbonyl, acyl, —C(O)$NR^aR^b$, —$NR^a$—C(O)—$R^b$, —$NR^a$—C(O)—$OR^b$, —$NR^a$—C(O)—$NR^b$, —$NR^a$—$SO_2$—$R^b$, —$NR^a$—$SO_2$—$NR^bR^c$, —OC(O)$NR^aR^b$, —OC(O)$OR^a$, $C_{1-6}$ alkylsulfonyl, $C_{1-6}$ alkylsulfinyl, and $C_{1-6}$ alkylthio, and wherein one or two ring carbon atoms of the heterocyclyl is optionally replaced with a carbonyl group;

$R^a$, $R^b$ and $R^c$ are independently hydrogen or $C_{1-6}$ alkyl;
m is an integer of 0 to 3; n is an integer of 0 to 3; m+n is an integer of 1 to 5; and
p is 1.

2. A compound of according to claim 1, wherein $R^3$ and $R^4$ are independently selected from the group consisting of:
(1) hydrogen,
(2) hydroxy,
(3) $C_{1-6}$ alkyl, (4) $C_{1-6}$ alkoxy,
(5) $C_{3-7}$ cycloalkyl,
(6) $C_{3-7}$ cycloalkyl $C_{1-6}$ alkyl,
(7) $C_{1-6}$ alkoxycarbonyl,
(8) carboxyl,
(9) carbamoyl,
(10) mono or di-$C_{1-6}$ alkyl substituted carbamoyl,
(11) $C_{1-6}$ alkoxycarbonyloxy,
(12) mono or di-$C_{1-6}$ alkyl substituted aminocarbonyloxy,
(13) hydroxy-$C_{1-6}$ alkyl,
(14) $C_{1-6}$ alkoxy-$C_{1-6}$ alkyl, and
(15) halogen or halo $C_{1-6}$ alkyl, or alternatively,
$R^3$ and $R^4$, together with the carbon atom to which they are attached, form $C_{3-7}$ cycloalkyl or heterocyclyl optionally substituted by one to three substituents independently selected from the group consisting of $C_{1-4}$ alkyl, halo $C_{1-4}$ alkyl and halogen.

3. A compound according to claim 1, wherein A is phenyl substituted by one or two substituents independently selected from the group consisting of halogen, halo $C_{1-6}$ alkyl and halo $C_{1-6}$ alkoxy.

4. A compound according to claim 1, wherein A is phenyl substituted by one or two substituents independently selected from the group consisting of chloro, trifluoromethyl, and trifluoromethoxy.

5. A compound according to claim 1, wherein A is 3,4-dichlorophenyl, 3-chlorophenyl, 3-trifluoromethylphenyl, 3-Chloro-4 trifluoromethylphenyl, or 3-trifluoromethoxylphenyl.

6. A compound according to claim 1, wherein X is —N($R^1$)($R^2$) and $R^1$ and $R^2$, together with the nitrogen atom to which they are attached, form heterocyclyl optionally substituted by one to three substituents independently selected from the group consisting of hydroxy, $C_{1-6}$ alkyl and hydroxy $C_{1-6}$ alkyl; and one of the ring carbon atoms of the heterocyclyl formed by $R^1$ and $R^2$ may also be a ring carbon atom of another ring which is a $C_{3-7}$ cycloalkyl.

7. A compound according to claim 1, wherein X is a mono spiro-heterocyclyl, wherein the spiro-heterocyclyl ring is optionally substituted by one to three substituents independently selected from the group consisting of hydroxy, oxo, alkoxy, fluoro, and $C_{1-6}$ alkyl.

8. A compound according to claim 1, wherein X is -aza-spiro[2,5]oct-6-yl, 5-azaspiro[2.5]oct-5-yl, 7-aza-spiro[3.5]non-7-yl, 8-aza-spiro[4.5]dec-8-yl, 1,8-diaza-spiro[4.5]dec-8-yl, 1,3,8-triaza-spiro[4.5]dec-8-yl, 2,8-diaza-spiro[4.5]dec-8-yl, 1-oxa-3,8-diaza-spiro[4.5]dec-8-yl, 1-oxa-8-aza-spiro[4.5]dec-8-yl, 2-oxa-8-aza-spiro[4.5]dec-8-yl, 2-oxa-7-aza-spiro[3.5]non-7-yl, 1-oxa-7-aza-spiro[3.5]non-7-yl, 9-aza-spiro[5.5]undec-9-yl, or 1-oxa-4,9-diaza-spiro[5.5]undec-9-yl, wherein the spiro-heterocyclyl ring is optionally substituted by one to three substituents independently selected from the group consisting of hydroxy, oxo, alkoxy, fluoro, and $C_{1-6}$ alkyl.

9. A compound according to claim 1, wherein the heterocyclyl formed by $R^1$ and $R^2$, together with the nitrogen atom to which they are attached, is piperidyl or pyrrolidinyl, and said piperidyl or pyrrolidinyl is optionally substituted by one or two substituents independently selected from the group consisting of hydroxy, $C_{1-6}$ alkyl, and hydroxy $C_{1-6}$ alkyl; and wherein one of the ring carbon atoms of said piperidyl or pyrrolidinyl is optionally shared by a cyclopropyl ring.

10. A compound according to claim 1, wherein X is (S)-4-Hydroxy-6-aza-spiro[2.5]oct-6-yl.

11. A compound according to claim 1, wherein m+n is an integer of 1, 2 or 3.

12. A compound according to claim 1, wherein one of $R^3$ and $R^4$ is hydrogen and the other is hydrogen, hydroxy, $C_{1-6}$ alkoxycarbonyl, di-$C_{1-6}$ alkyl substituted carbamoyl, hydroxy-$C_{1-6}$ alkyl, $C_{1-6}$ alkoxy-$C_{1-6}$ alkyl, N,N, hydroxy-$C_{1-6}$ alkyl-$C_{1-6}$ alkyl-carbamoyl, or N,N—$C_{3-7}$ cycloalkyl, $C_{1-6}$ alkyl-carbamoyl.

13. A compound according to claim 1, wherein n is 0, m is 2 and one of $R^3$ and $R^4$ is hydrogen, and the other is selected from the group consisting of hydrogen, $C_{1-6}$ alkoxycarbonyl, hydroxy-$C_{1-6}$ alkyl, $C_{1-6}$ alkoxy-$C_{1-6}$ alkyl, carboxyl, and mono or di-$C_{1-6}$ alkyl substituted carbamoyl.

14. A compound according to claim 1, wherein one or two of $R^5$, $R^6$, $R^7$, $R^8$, $R^9$ and $R^{10}$ are independently hydrogen, $C_{1-6}$ alkyl, phenyl, and phenyl-$C_{1-6}$ alkyl optionally substituted by trifluoromethyl; and the others are hydrogen.

15. A compound according to claim 1, wherein one of $R^5$ and $R^6$ is hydrogen or $C_{1-6}$ alkyl, and the other is hydrogen; one of $R^9$ and $R^{10}$ is hydrogen or $C_{1-6}$ alkyl, and the other is hydrogen; and $R^7$ and $R^8$ are hydrogen.

16. A compound according to claim 1, wherein one of $R^5$ and $R^6$ is hydrogen or $C_{1-6}$ alkyl, and the other is hydrogen; one of $R^9$ and $R^{10}$ is hydrogen or methyl, and the other is hydrogen, and $R^7$ and $R^8$ are hydrogen.

17. A compound according to claim 1, wherein one of $R^5$ and $R^6$ is hydrogen or $C_{1-6}$ alkyl, and the other is hydrogen; and $R^7$, $R^8$, $R^9$ and $R^{10}$ are hydrogen.

18. A compound according to claim 1, wherein one of $R^5$ and $R^6$ is methyl, and the other is hydrogen; and $R^7$, $R^8$, $R^9$ and $R^{10}$ are hydrogen.

19. A compound according to claim 1, selected from the group consisting of:
  1-(3,4-Dichloro-phenyl)-4-[(S)-3-((S)-4-hydroxy-6-aza-spiro[2.5]oct-6-yl)-1-hydroxymethyl-propyl]-[1,4]diazepan-5-one,
  1-(3-Chloro-phenyl)-4-[(S)-3-((S)-4-hydroxy-6-aza-spiro[2.5]oct-6-yl)-1-hydroxymethyl-propyl]-[1,4]diazepan-5-one,
  4-[(S)-3-((S)-4-Hydroxy-6-aza-spiro[2.5]oct-6-yl)-1-hydroxymethyl-propyl]-1-(3-trifluoromethyl-phenyl)-[1,4]diazepan-5-one,
  (S)-4-((S)-4-Hydroxy-6-aza-spiro[2.5]oct-6-yl)-N,N-dimethyl-2-[7-oxo-4-(3-trifluoromethyl-phenyl)-[1,4]diazepan-1-yl]-butyramide,
  4-[(S)-3-((S)-4-Hydroxy-6-aza-spiro[2.5]oct-6-yl)-1-methoxymethyl-propyl]-1-(3-trifluoromethyl-phenyl)-[1,4]diazepan-5-one,
  (S)-1-[3-((S)-4-Hydroxy-6-aza-spiro[2.5]oct-6-yl)-propyl]-3-methyl-4-(3-trifluoromethoxy-phenyl)-piperazin-2-one,
  4-((S)-4-Hydroxy-6-aza-spiro[2.5]oct-6-yl)-2-[3-methyl-2-oxo-4-(3-trifluoromethoxy-phenyl)-piperazin-1-yl]-butyric acid,
  1-[3-((S)-4-Hydroxy-6-aza-spiro[2.5]oct-6-yl)-1-hydroxymethyl-propyl]-3-methyl-4-(3-trifluoromethoxy-phenyl)-piperazin-2-one,
  4-((S)-4-Hydroxy-6-aza-spiro[2.5]oct-6-yl)-N,N-dimethyl-2-[3-methyl-2-oxo-4-(3-trifluoromethoxy-phenyl)-piperazin-1-yl]-butyramide,
  1-[3-((S)-4-Hydroxy-6-aza-spiro[2.5]oct-6-yl)-1-methoxymethyl-propyl]-3-methyl-4-(3-trifluoromethyl-phenyl)-piperazin-2-one,
  (R)-1-(3,4-Dichloro-phenyl)-4-[(S)-3-((S)-4-hydroxy-6-aza-spiro[2.5]oct-6-yl)-1-hydroxymethyl-propyl]-2-methyl-[1,4]diazepan-5-one,
  (S)-4-(3,4-Dichloro-phenyl)-1-[3-((S)-4-hydroxy-6-aza-spiro[2.5]oct-6-yl)-propyl]-3-methyl-piperazin-2-one, (S)-4-(3-Chloro-4-trifluoromethyl-phenyl)-1-[3-((S)-4-hydroxy-6-aza-spiro[2.5]oct-6-yl)-propyl]-3-methyl-piperazin-2-one, and (S)-4-(3,4-Dichloro-phenyl)-1-[4-((S)-4-hydroxy-6-aza-spiro[2.5]oct-6-yl)-butyl]-3-methyl-piperazin-2-one.

20. A process for manufacturing a compound of formula (I):

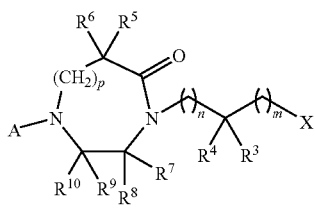
(I)

comprising a step of reacting a compound of formula 1:

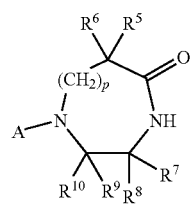
1 with a compound of formula 2:

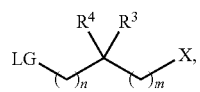
2 wherein A, X, $R^3$, $R^4$, $R^5$, $R^6$, $R^7$, $R^8$, $R^9$, $R^{10}$, m, n and p are as defined in claim 1 and LG refers to a leaving group.

21. A process for manufacturing a compound of formula (I):

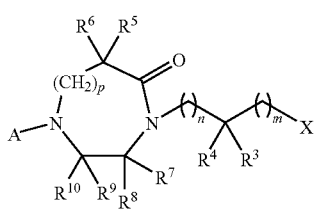
(I)

comprising a step of reacting a compound of formula 6:

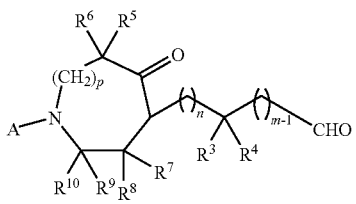
6 with $HN(R^1)(R^2)$, wherein A, X, $R^1$, $R^2$, $R^3$, $R^4$, $R^5$, $R^6$, $R^7$, $R^8$, $R^9$, $R^{10}$, m, n and p are as defined in claim 1.

22. A process for manufacturing a compound of formula (I):

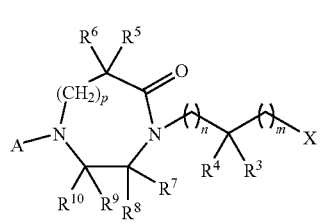
(I)

comprising a step of reacting a compound of formula 9:

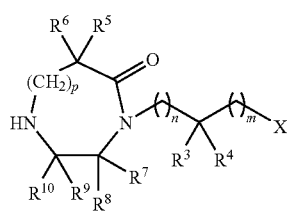
9 with $A\text{-}LG^2$, $A\text{-}B(OH)_2$ or $A'\text{-}CHO$, wherein A, X, $R^3$, $R^4$, $R^5$, $R^6$, $R^7$, $R^8$, $R^9$, $R^{10}$, m, n and p are as defined in claim 1, A' is aryl or heteroaryl, and $LG^2$ is a leaving group.

23. A pharmaceutical composition comprising a compound of claim 1 and a pharmaceutically acceptable excipient.

* * * * *